US012577254B2

(12) United States Patent
Morales et al.

(10) Patent No.: US 12,577,254 B2
(45) Date of Patent: Mar. 17, 2026

(54) THIENOPYRANONES AND FURANOPYRANONES AS KINASE, BROMODOMAIN, AND CHECKPOINT INHIBITORS

(71) Applicant: SignalRx Pharmaceuticals, Inc., Cumming, GA (US)

(72) Inventors: Guillermo A. Morales, Oro Valley, AZ (US); Joseph R. Garlich, Cape Coral, FL (US); Donald L. Durden, Charlotte, NC (US)

(73) Assignee: Signal Rx Pharmaceuticals, Inc.

( * ) Notice: Subject to any disclaimer, the term of this patent is extended or adjusted under 35 U.S.C. 154(b) by 0 days.

(21) Appl. No.: 18/451,918

(22) Filed: Aug. 18, 2023

(65) Prior Publication Data

US 2024/0043445 A1 Feb. 8, 2024

Related U.S. Application Data

(62) Division of application No. 16/481,220, filed as application No. PCT/US2018/015454 on Jan. 26, 2018, now Pat. No. 11,760,762.

(60) Provisional application No. 62/451,367, filed on Jan. 27, 2017.

(51) Int. Cl.

| | |
|---|---|
| ***C07D 471/04*** | (2006.01) |
| ***A61K 31/4375*** | (2006.01) |
| ***A61K 31/519*** | (2006.01) |
| ***A61K 31/5377*** | (2006.01) |
| ***A61K 31/541*** | (2006.01) |
| ***A61K 45/06*** | (2006.01) |
| ***A61P 1/16*** | (2006.01) |
| ***A61P 3/04*** | (2006.01) |
| ***A61P 3/10*** | (2006.01) |
| ***A61P 29/00*** | (2006.01) |
| ***A61P 35/00*** | (2006.01) |
| ***A61P 35/02*** | (2006.01) |
| ***C07D 493/04*** | (2006.01) |
| ***C07D 495/04*** | (2006.01) |
| ***C07D 519/00*** | (2006.01) |

(52) U.S. Cl.

CPC .......... *C07D 495/04* (2013.01); *A61K 31/519* (2013.01); *A61K 31/5377* (2013.01); *A61K 31/541* (2013.01); *A61K 45/06* (2013.01); *A61P 35/00* (2018.01); *A61P 35/02* (2018.01); *C07D 519/00* (2013.01)

(58) Field of Classification Search

CPC .. C07D 471/04; C07D 493/04; C07D 495/04; C07D 519/00; A61K 31/4375; A61K 31/519; A61K 31/5377; A61K 45/06; A61K 2300/00; A61P 1/16; A61P 3/04; A61P 3/10; A61P 29/00; A61P 35/00; A61P 35/02

See application file for complete search history.

(56) References Cited

U.S. PATENT DOCUMENTS

| | | | |
|---|---|---|---|
| 8,557,807 | B2 | 10/2013 | Morales et al. |
| 9,505,780 | B2 | 11/2016 | Morales et al. |
| 9,550,790 | B2 | 1/2017 | Morales et al. |
| 9,981,983 | B2 | 5/2018 | Morales et al. |
| 10,174,032 | B2 | 1/2019 | Morales et al. |
| 10,308,662 | B2 | 6/2019 | Morales et al. |

FOREIGN PATENT DOCUMENTS

| | | |
|---|---|---|
| WO | WO 2018/226739 | 12/2018 |
| WO | WO 2018/236971 | 12/2018 |

*Primary Examiner* — Brenda L Coleman

(74) *Attorney, Agent, or Firm* — TDW Patents & Consulting; Thomas D. Webster

(57) ABSTRACT

The invention relates to compounds and methods of treating diseases including but not limited to, cancer, non-cancer proliferative disease, sepsis, autoimmune disease, viral infection, atherosclerosis, Type 1 or 2 diabetes, obesity, inflammatory disease, or Myc-dependent disorder including by modulating biological processes by the inhibition of cell cycle checkpoint targets CDKs, and/or PI3 kinase, and/or bromodomain protein binding to substrates, comprising the administration of a compound(s) of Formula 1-V1 (or pharmaceutically acceptable salts thereof) as defined herein.

6 Claims, 9 Drawing Sheets

THIENOPYRANONES AND FURANOPYRANONES AS KINASE, BROMODOMAIN, AND CHECKPOINT INHIBITORS

FIELD OF THE INVENTION

The present invention relates to thieno- and furanopyranone compounds and methods of using the compounds as inhibitors of immune-oncology checkpoints and independently kinases and/or bromodomain proteins, for treating diseases in mammals.

BACKGROUND

The need for better treatments for cancer and other diseases has led to combination therapies using multiple anticancer agents. Recently, multitargeting single drug agents have been developed that block more than one target (see D. Melisi et al., Curr. Opin. Pharm., 2013, 13, 536-542; and L. Carlino et al., J. Med. Chem., 2016, 59, 9305-9320). The combined simultaneous inhibition of multiple key signaling pathways regulating, for example, survival, cell cycle, and epigenetic adaptation by a single molecule represents a new and promising approach to treating cancer and other diseases. Noteworthy pathways of interest in this regard include kinases, bromodomains, and checkpoint inhibitors.

The inhibition of cyclin-dependent kinase 4 and 6 (CDK4/6) is an important therapeutic strategy for hormone positive breast cancers when combined with Fulvestrant (Faslodex®). Unfortunately, the combinations of such drugs are compromised by resistance build-up. New evidence indicates that concurrent PI3 kinase (PI3K) inhibitors can prevent resistance to CDK4/6 inhibition, but once resistance is acquired PI3K inhibitors do not resensitize the cells. Thus, combined CDK4/6 and PI3K inhibition represents an important synthetic lethality for a number of cancer types including breast cancer (BrCA), mantle cell lymphoma (MCL), and neuroblastoma (NB). In addition, blocking the BRD4-chromatin reader protein blocks MYC from regulating cyclin D transcription thus enhancing the cell cycle in G1.

Thus, an emerging strategy for treating cancers and other diseases involves simultaneous inhibition of CDK4/6, PI3K and BRD4. This would ideally be performed with a single molecule as described below which greatly expands the breadth of patients that could benefit from CDK4/6 inhibition.

Protein kinases play an important role in regulating most cellular functions including proliferation, cell cycle, cell metabolism, survival/apoptosis, DNA damage repair, cell motility, and response to the microenvironment. Not surprisingly kinases have been identified as oncogenes. For example, kinases such as c-Src, c-Abl, mitogen activad protein (MAP) kinase, phosphotidylinositol-3-kinase (PI3-K, PI3K, PI-3 kinase), AKT (also known as PKB), and the epidermal growth factor (EGF) receptor are commonly activated in cancer cells and are known to contribute to tumorigenesis. Many of these mutations occur in the same signaling pathway. For example, HER-kinase family members (HER1 [EGFR], HER3, and HER4) transmit signals through MAP kinase and PI-3 kinase to promote cell proliferation.

PI3 kinases are a large family of lipid kinases comprising roughly 16 members divided into 3 classes based on sequence homology and the particular product formed by enzyme catalysis. The class I PI3 kinases are composed of 2 subunits: a 110 kd catalytic subunit and an 85 kd regulatory subunit. Class I PI-3 kinases are involved in important signal transduction events downstream of cytokines, integrins, growth factors and immunoreceptors, and control of this pathway may lead to important therapeutic effects. Inhibition of class I PI3 kinase induces apoptosis, blocks tumor induced angiogenesis in vivo, and increases radiosensitivity in certain tumors.

Molecular and genetic studies have demonstrated a strong correlation between the PI3 kinase pathway (also known as PI3K-AKT pathway) and a variety of diseases in humans such as inflammation, autoimmune conditions, and cancers (P. Workman et al., Nat. Biotechnol. 2006, 24, 794-796). The PI3 kinase pathway controls a number of cellular functions including cell growth, metabolism, differentiation, and apoptosis. Many types of cancer are thought to arise in response to abnormalities in signal transduction pathways of which the PI-3 kinase pathway is a major example.

The PI3 kinase pathway comprises a number of enzymes including PI3 kinase, PTEN (Phosphatase and Tensin homolog deleted on chromosome 10), and AKT (a serine/threonine kinase) all of which are involved in producing and maintaining intracellular levels of second messenger molecule PtdIns(3,4,5)P3 (Phosphatidylinositol (3,4,5)-trisphosphate or PIP3). Homeostasis in the levels of this important second messenger is maintained by the interaction between PI3 kinase and PTEN. When either PI3 kinase or PTEN are mutated and/or reduced in activity PIP3 levels are perturbed which may act as a trigger in the development of cancer. Indeed, both PI3 kinase and PTEN have been found to be mutated in multiple cancers including glioblastoma, ovarian, breast, endometrial, hepatic, melanoma, gut, lung, renal cell, thyroid and lymphoid cancer. Multiple studies have now shown that p110α, which is a Class IA isoform of the regulatory subunit of PI-3 kinase, is frequently over-expressed and mutated in many cancers including gliomas, colon, brain, breast, lung, prostate, gynecological and other tumor types (Y. Samuels et al., Science 2004, 304, 554). Thus, a rational approach to treating cancer relates to developing drugs that act on kinases including those of the PI3 kinase pathway.

Another putative mechanism for cancer involving kinase dependency is through loss of a negative regulator. Perhaps the best example of this comes from tumors with mutations in the PTEN tumor suppressor gene. This gene, which is mutated or deleted in a number of different cancers, encodes a lipid phosphatase that regulates signaling through the PI3 kinase pathway. Specifically, PTEN dephosphorylates PIP3, the product of PI3 kinase (for review see L. C. Cantley et al., Proc. Natl. Acad. Sci. 1999, 96, 4240-4245). As a consequence of PTEN loss and the resultant increase in PIP3 levels, signal propagation through downstream kinases such as AKT is constitutively elevated. Preclinical studies suggest that this indirect mode of constitutive kinase activation in tumor cells (i.e., through loss of the PTEN suppressor gene), creates a kinase dependency analogous to that seen in tumors with direct, activating mutations in the kinase itself.

Genetic and biochemical evidence from several model systems has established that constitutive levels of AKT can regulate TOR (mTOR in mammalian systems) through phosphorylation of the tuberous sclerosis complex (K. Inoki et al., Nat. Cell Biol. 2002, 4, 648-657). Hence, tumors with loss-of-function mutations in PTEN exhibit constitutive activation of AKT, as well as other downstream kinases such as mTOR. Many such tumors in murine models have been shown to be sensitive to mTOR inhibitors (M. S. Neshat et al., Proc. Natl. Acad. Sci. 2001, 98, 10314-10319).

At the cytocellular level, the induction and/or progression of cancer appears to involve a sub-population of cells within a tumor known as cancer stem cells. Within a population of cancer cells there exist a small number of cells that are capable of fully re-establishing a tumor. These cells are called cancer stem cells and are thought to be responsible for the inability to cure cancer with current drugs. Cancer stem cells are characterized as having enhanced drug efflux properties, lacking in cell cycle progression (quiescent), and possessing resistance to anoikis (apoptosis upon experiencing loss of anchorage). Cancer stem cells have been described in the literature in solid tumor types, for example, see the review and references incorporated therein by J. E. Visvader et al., Nat. Rev. Cancer 2008, 8, 755-768: "Cancer Stem Cells in Solid Tumors: accumulating evidence and unresolved questions". Non-solid tumor cancer stem cells have also been reviewed recently, for example, see the review and references incorporated therein by J. E. Dick et al., Blood 2008, 112, 4793-4807: "Stem cell concepts renew cancer research". To date the only approved cancer therapeutic drug that decreases cancer stem cells is Lapatinib which was shown to decrease the number of breast cancer stem cells in biopsies of women with breast tumors possessing high levels of HER2 protein (decreased from 11% down to 5% of cells) [C. Schmidt et al., J. Natl. Cancer I. 2008, 100, 694-695: "Lapatinib Study Supports Cancer Stem Cell Hypothesis, Encourages Industry Research"]. PI3K inhibitors have been shown to preferentially target cancer stem cells (PI3K/mTOR Dual Inhibitor VS-5584 Preferentially Targets Cancer Stem Cells, Vihren N. Kolev, Quentin G. Wright, Christian M. Vidal, Jennifer E. Ring, Irma M. Shapiro, Jill Ricono, David T. Weaver, Mahesh V. Padval, Jonathan A. Pachter and Qunli Xu, Cancer Res. Jan. 14, 2015, 75(2), 446-455. Thus, inhibition of PI3K is desirable to inhibit cancer stem cells.

While therapeutic agents that act as modulators of signaling pathways are of clear therapeutic interest as agonists or antagonists of particular enzymes within a signaling pathway, e.g., inhibitors of PI3 kinase, recent evidence indicates that independent mechanisms exist for providing therapeutic efficacy including, for example, oxidative stress. The generation of oxidative stress in cancer cells is a recent but well described cancer treatment approach. Examples of agents that induce oxidation stress include clinically evaluated compounds such as buthionine sulfoximine/melphalan, imexon, arsenic trioxide, and motexafin gadolinium, and the like [see for example the review and references incorporated therein by R. H. Engel et al., Front. Biosci 2006, 11, 300-312: "Oxidative Stress and Apoptosis: a new treatment paradigm in cancer"]. Cromenones such as LY294002 and the related analog LY3035111 have been reported to induce apoptosis in tumor cells due to intracellular hydrogen peroxide production independent of their PI3 kinase inhibition activity [T. W. Poh et al., Cancer Res. 2005, 65, 6264-6274: "LY294002 and LY303511 Sensitize Tumor Cells to Drug-Induced Apoptosis via Intracellular Hydrogen Peroxide Production Independent of the Phosphoinositide 3-Kinase-Akt Pathway"]. This ability to induce oxidative stress in cancer cells is a positive attribute for an anticancer agent. Oxidative stress induction has also been demonstrated to enhance sensitivity of prostate cancer cells to non-apopototic concentrations of the chemotherapeutic agent vincristine.

LY294002 [2-(4-morpholinyl)-8-phenyl-4H-1-benzopyran-4-one] is a potent, non-selective inhibitor of PI3 kinases with an $IC_{50}$ of 1.4 μM (C. J. Vlahos et al., J. Biol. Chem. 1994, 269, 5241-5248). While LY294002 is an effective inhibitor of PI3 kinase it has several undesirable attributes for clinical use including lack of aqueous solubility, poor pharmacokinetics, unacceptable toxicity, lack of tissue specificity, rapid metabolism in animals, and a synthetic route that involves the use of carbon disulfide, a highly toxic compound. As such, LY294002 has never been developed for clinical use.

In addition to defects in one or more kinase pathways, a growing list of diseases including cancer can arise by epigenetically-induced changes in gene expression and cellular phenotype by mechanisms other than changes in DNA nucleotide sequence. Epigenetic effects can be controlled by three types of proteins: the writers (i.e., DNA methyltransferase which adds methyl groups to DNA), the erasers (i.e., histone deacetylase, HDAC, which removes acetyl groups from histones), and the readers (i.e., BET bromodomain proteins such as BRD2, BRD3, BRD4 and BRDT). Bromodomain proteins serve as "readers" to recruit regulatory enzymes such as writers and erasers leading to regulation of gene expression. Inhibitors of bromodomain proteins are potentially useful in the treatment of diseases including obesity, inflammation, and cancer (A. C. Belkina et al., Nat. Rev. Cancer 2012, 12, 465-477). The BET bromodomain protein BRD4 is a current target to inhibit in cancer and a number of inhibitors are known and in development (Wadhwa E. Nicolaides T. Bromodomain Inhibitor Review: "Bromodomain and Extra-terminal Family Protein Inhibitors as a Potential New Therapy in Central Nervous System Tumors". Muacevic A, Adler J R, eds. Cureus. 2016, 8(5), e620. doi:10.7759/cureus.620)

BET inhibitors act as acetylated lysine mimetics that disrupt the binding interaction of BET proteins with acetylated lysine residues on histones (D. S. Hewings et al., J. Med. Chem. 2012, 55, 9393-9413). This leads to suppression of transcription of some key genes involved in cancer including c-MYC, MYCN, BCL-2, and some NF-kB-dependent genes (J. E. Delmore et al., Cell 2011, 146, 904-917) (A. Puissant et al., Cancer Discov. 2013, 3, 308-323). Most B-cell malignancies are associated with the activation of the c-MYC gene which is partially controlled by the PI3 kinase-AKT-GSK3beta signaling axis (J. E. Delmore et al., Cell 2011, 146, 904-917). MYC (encompassing c-MYC and MYCN) is an oncoprotein that has been difficult to inhibit using small molecule approaches (E. V. Prochownik et al., Genes Cancer 2010, 1, 650-659). Recently, it has been shown that BET inhibition prevents the transcription of MYCN (A. Puissant et al., Cancer Discov. 2013, 3, 308-323), and blocking PI3K enhances MYC degradation (L. Chesler et al., Cancer Res. 2006, 66, 8139-8146). Therefore, a single molecule that inhibits both PI3K and bromodomain proteins would provide a more effective way to inhibit MYC activity. Several reported BET inhibitors contain the 3,5-dimethylisoxazole chemotype as the acetyl-lysine mimetic moiety (D. S. Hewings, J. Med. Chem. 2011, 54, 6761-6770) (D. S. Hewings et al., J. Med. Chem. 2012, 55, 9393-9413) (D. S. Hewings et al., J. Med. Chem. 2013, 56, 3217-3227).

Another important point of regulation in human cells involves mitosis. Enzymes called cyclin dependent kinases (CDKs) play an important role in mitosis of normal human cells and cancer cells. The cell cycle has four basic phases: S phase where DNA replication occurs; M phase (mitosis) where DNA and cellular components are divided to form two daughter cells; G2 phase, between S and M, where cells prepare for mitosis; and the G1 phase after mitosis and before S phase, where cells commit and prepare for another round of DNA and cellular replication. To date, 21 CDKs have been identified in the human genome of which the following seven have a demonstrated role in cell cycle progression: CDK1-4, CDK6, CDK10, and CDK11. Cyclins are proteins that associate with CDKs (forming holoenzymes) to promote activity of the CDKs. Cyclin D is one of the major cyclins having three homologues (Cyclin D1, D2, and D3). Cyclin D interacts with four CDKs: CDK2, CDK4, CDK5, and CDK6. When cells are proliferating the accumulation of the cyclin D-CDK4/6 complex is of great importance for cell cycle progression. The cyclin D-CDK4/6 complex partially phosphorylates retinoblastoma tumor suppressor protein (Rb) to form phosphorylated retinoblastoma tumor suppressor protein (pRb). Rb functions to prevent excessive cell growth by inhibiting cell cycle progression until a cell is ready to divide. When a cell is ready to divide, Rb is phosphorylated and thereby inactived thus allowing the cell cycle to proceed. Rb inhibits cell cycle progression by binding to the E2F family of transcription factors which suppresses their activity and blocks proliferation. Phosphorylation (pRb) blocks the E2F binding relieving suppression and allowing expression of the genes needed for cell cycling. Phosphorylated Rb can also induce expression of some genes such as Cyclin E needed for S phase progression of the cell cycle. It has been estimated that the Rb pathway is deregulated in greater than 80% of human tumors (S. Ortega et al., Biochim. Biophys. Acta 2002, 1602, 73). Thus, CDK inhibitors have therapeutic potential for several diseases including cancer, diabetes, renal, neurodegenerative and infectious diseases. For cancer cyclin-dependent kinase 4 and 6 (CDK4/6) inhibition has emerged as an important therapy for breast cancer as illustrated by the FDA approval of Ibrance (Palbociclib, Pfizer) in 2015 followed by approval of (Ribociclib, Novartis) in 2016 and Verzenio (Abemaciclib, Eli Lilly) in September 2017. However, these drugs were approved to use in combinations because they suffer from being cytostatic in nature requiring combinations to be more effective and also face quick resistance build-up (References: Herrera-Abreu M T, Palafox M, Asghar U, Rivas M A, Cutts R J, Garcia-Murillas I, et al. "Early Adaptation and Acquired Resistance to CDK4/6 Inhibition in Estrogen Receptor-Positive Breast Cancer". Cancer Research 2016, 76(8), 2301-2313 and Sherr C J, Beach D, Shapiro G I. "Targeting CDK4 and CDK6: From Discovery to Therapy". Cancer Discovery 2016, 6(4), 353-367). Thus, a need exists for more effective agents that provide multiple anticancer mechanisms in a single drug.

Recently, it has been shown that some kinase inhibitors also inhibit bromodomain proteins. For example, PI3 kinase inhibitor LY294002 was found to modestly inhibit BET bromodomains (A. Dittmann et al., ACS Chem. Biol. 2014, 9, 495-502). Replacement of the morpholine group of LY294002 with a piperazine group (LY303511) causes it to lose PI3K inhibition activity but retain BET bromodomain inhibition. The morpholine ring is critical for binding in the PI3K catalytic pocket and cannot be replaced even by the structurally similar thiomorpholine (C. J. Vlahos et al., J. Biol. Chem. 1994, 269, 5241-5248). Other kinases have also been shown to have BET inhibition activity. For example, the PLK1 inhibitor B12536 and the JAK2 inhibitor TG101209 also potently inhibit the BET protein BRD4-1 (S. W. J. Ember, ACS Chem. Biol. 2014, 9, 1160-1171). However, the ability of kinase inhibitors to inhibit bromodomain proteins is not a general property of kinase inhibitors. As demonstrated by a recent study, of 628 kinase inhibitors tested only 7 inhibitors, namely B12536, B16727 (volasertib), the RSK inhibitor NI-F1870, the JAK inhibitor TG-101348, the FAK inhibitor PF-431396, the beta-isoform selective PI3K inhibitor GSK2636771, and the mTOR kinase inhibitor PP-242, showed some degree of BRD4-1 inhibitory activity (P. Ciceri et al., Nat. Chem. Biol. 2014, 10, 305-312). Thienopyranones that are drug-like molecules (i.e., conform to Lipinski's Rule of Five such as molecular weight less than 500 Daltons—see Lipinski C A "Lead- and drug-like compounds: the rule-of-five revolution". Drug Discovery Today. Technologies 2014, 1(4), 337-341) such as Compound 0 shown below have been disclosed as PI3K inhibitors as well as dual PI3K/BRD4 inhibitors (U.S. Pat. Nos. 8,557,807, 9,505,780, and Morales et al., J. Med. Chem. 2013, the entire contents of which are herein incorporated by reference).

Compound 0

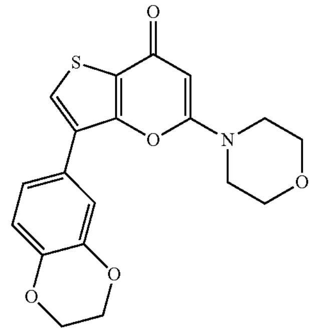

Single, dual, and triple inhibitors of PI3K, BRD4, and CDK4/6 of the invention are molecularly distinct but all belong to the general thienopyranone scaffold (See Formula I) These multi-target inhibitors are not simply conjugates of two inhibitors connected by a covalent linkage but are single molecules designed to fit tightly into specific sites (usually the enzymatic or catalytic site) on different proteins and thus can interfere or inhibit with the protein's function. A number of single and dual inhibitors of PI3K and PI3K/BRD4 belonging to the general thienopyranone scaffold have been described in U.S. Pat. Nos. 8,557,807 and 9,505,780, the entire contents of which is herein incorporated by reference.

There is growing interest in combining checkpoint inhibitors of CDK4 and CDK6 with inhibitors of the PI3K pathway. For example, Vora et al. (Cancer Cell 2014, 26, 136-149) describe how CDK4/6 inhibitors sensitize PIK3CA mutant (PI3K alpha gene) breast cancer to PI3K inhibitors such as BLY719 (selective PI3K alpha inhibitor). They note that "CDK4/6 inhibitors can prevent the emergence as well as overcome resistance" to PI3K inhibitors. Another study published recently in the journal Nature (O. De Henau et al., Nature 2016, 539, 443-447) showed that the selective PI3K gamma inhibitor IPI-549 could overcome resistance to checkpoint blockage.

Multiple advantages are realized with multi-targeted single molecule inhibitors over combinations of inhibitors including: a) reduced development costs; b) lower toxicity; c) lower non-target side effects due to less non-target drug interactions; d) simultaneous target inhibition in each cancer cell providing greater efficacy (combinations suffer from differing metabolism, distribution and pharmacokinetics/dynamics); e) lower financial costs to patients and the healthcare system; f) offering more sophisticated therapeutic combinations for patients aimed at increasing efficacy and longer durations of response; g) accelerated clinical drug development. Single-molecule dual inhibition can avoid problems with differing PK, adsorption, distribution, and metabolism that can arise when administering separate PI3K, CDK4/6, and/or BRD4 inhibitors. Moreover, a significant limitation in using drug combinations in oncology is dose limiting toxicity which results from additive off-target toxicities from the individual drugs. This is proven by the recent clinical evaluation of the PI3K inhibitor BKM120 in combination with a PARP inhibitor (Olaparib) where, due to the toxicity of the 2 drugs, the maximum tolerated dose of the PI3K inhibitor was limited to half that as a single agent. For reference see Matulonis U W G, Barry W, Birrer M, Westin S, Spagnoletti T, et al. "Phase I of oral BLK120 or BLY719 and olaparib for high-grade serous ovarian cancer or triple-negative breast cancer: final results of the BMK120 plus olaparib cohort". 106th Annual Meeting of the American Association for Cancer Research; April 18-22: AACR; 2015. From the patient's perspective, a triple inhibitor could dramatically simplify taking medications and improve patient compliance. For example, a patient requiring the inhibition of PI3K, BRD4, CDK4/6 and RAF kinase would have to take four separate medicines to achieve such inhibition whereas the triple inhibitors of the invention would allow the patient to take two medications such as Sorafinib (RAF Kinase inhibitor) plus our triple inhibitor agent. This would also improve patient compliance which is a developing impediment to cancer patients getting their full scheduled doses resulting in less effective treatment. Thus, there clearly is a need for more mechanisms of inhibition to be designed into new agents to enhance effectiveness of treating cancer patients. These needs can be met by the potent single molecule, multi-targeted inhibitors of the combinations depicted graphically in FIG. 1 including inhibitors of PI3K and CDK4/6 (region II), as well as BRD4 and CDK4/6 (region III), as well as CDK4/6 and PI3K and BRD4 (region IV).

SUMMARY OF THE INVENTION

The present invention relates to thienopyranone and furanopyranone compounds that are useful as inhibitors of protein combinations depicted in FIG. 1 including PI3K and CDK4/6 (region II), as well as BRD4 and CDK4/6 (region III), as well as triple inhibitors of CDK4/6 and PI3K and BRD4 (region IV).

In particular, the invention relates to new thienopyranone and/or furanopyranone compounds and conjugates thereof, pharmaceutical compositions containing the compounds or conjugates thereof as active ingredients, and use of the compounds for therapeutic purposes, for example, in the manufacture of a medicament to treat diseases, and as therapeutic agents such as antitumor agents in methods for treating disorders including but not limited to cancer. Some of the compounds disclosed in this application have been prepared by methods previously described in U.S. Pat. Nos. 8,557,807, 9,505,780, and Morales et al., J. Med. Chem. 2013, the entire contents of which are herein incorporated by reference.

The present invention relates further to methods of treating diseases in mammals using CDK inhibiting thienopyranone (7H-thieno[3,2-b] pyran-7-ones) or furanpyranone compounds of the general Formula I or a pharmaceutically acceptable salt thereof.

Formula I

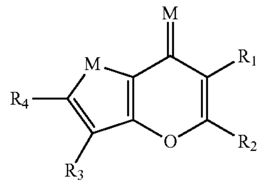

wherein M is independently oxygen (O) or sulfur (S);

R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1 or

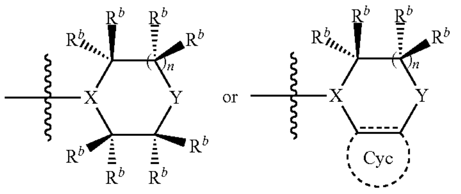

where X is C, N, P, P(O), $SiR^b$;

n is 0, 1, or 2;

Y is C—R1, O, S, $NR^a$, —C(O)($NH_2$), —$P(Z)_mR^a$, $SiR^aR^b$, $BR^b$;

Z is O or S;

m=0 or 1;

$R^a$ is hydrogen (H) or independently at each instance any group defined in R1;

$R^b$ is hydrogen (H) or independently at each instance any group defined in R1;

R3 is selected from R1;

R4 is selected from R1; and

Cyc is an aryl, substituted aryl, heterocycle, substituted heterocycle, carbocycle, or substituted carbocycle.

Compounds of region IV in FIG. 1 (i.e., triple inhibitors of BRD4, PI3K, and CDK) are those compounds of the invention, for example, Formula I wherein R2 preferably is an unsubstituted morpholine and there are no sterically bulky ortho substituents on the R3 group such that the R3 group can fit into the hydrophobic pocket of BRD4 formed by protein residues V87 and L92 (upper hydrophobic lobe) and W81 and P82 (lower hydrophobic lobe). While not wishing to be bound by theory it is believed that this provides a molecule that maintains the morpholine oxygen interaction with PI3K, the chromone carbonyl oxygen interaction with BRD4 Asp140, and allows hydrophobic-hydrophobic interactions with the hydrophobic region of BRD4, and lastly allows for the R3 group to provide binding interactions with CDK4 and CDK6 proteins.

Compound 1 provides potent triple inhibition of PI3K, BRD4 and CDK4 and CDK6 at the enzymatic level (see Examples). Compound 1 also provides potent anticancer activity at the cellular level and is less toxic on normal non-cancer cells than a combination of three separate individual inhibitors.

As used herein, the expression "a compound of Formula X" (e.g., Formulas I, II, III, IV, IVa, IVb, IVc, V, and VI, i.e., Formulas I-VI), or the expression "a compound of the invention" includes the compound, conjugates thereof, and any conventional prodrug thereof, as well as a pharmaceutically acceptable salt of said compound, conjugate, or prodrug. The compounds of the present invention also encompass polymorphic forms, solvates, hydrates, salts and complexes thereof.

Compounds of the invention, Formulas I-VI, are useful as multitarget double and triple inhibitors of proteins including, but not limited to the regions shown in FIG. 1, i.e., PI3K and CDK4/6 (region II), BRD4 and CDK4/6 (region III), and CDK4/6, PI3K, and BRD4 (region IV).

Compounds of Formulas I-VI are useful for therapeutic purposes including, but not limited to, as inhibitors of tumor growth and for the treatment of cancer as well as for treating inflammation, obesity, and acting as antiviral agents.

Accordingly, it is an object of the present invention to provide compounds, compositions, and methods for inhibiting CDK proteins in vitro and/or in vivo, for example CDKs, and/or bromodomain proteins, and their associated epigenetic mechanisms, and/or PI3Ks. It is a further object to provide methods for inhibiting cancerous tumor growth and for treating cancer and other diseases and conditions that may be related to defective activity of one or more of CDKs, bromodomain protein, and PI3Ks.

Compounds (or salts thereof) of the present invention can be used for the manufacture of a medicament for use in inhibiting CDK protein activity, e.g., CDKs and/or bromodomain protein(s) and/or PI3Ks for purposes of therapeutic treatment. The compounds of the invention were characterized by their ability to inhibit the target proteins using third party vendors offering such services. PI3K-alpha, PI3K-beta, PI3K-gamma, and PI3K-delta inhibition activity was determined by Thermo Fisher Scientific-Biosciences Life Sciences Solutions, Madison, WI. The bromodomain protein inhibition (binding domain 1 and 2 of BRD2, BRD3, BRD4, and BRDT) was determined by Reaction Biology Corp., Malvern, PA. Further analysis of compounds against a larger 40-bromodomain protein selection (Bromoscan) was performed by DiscoverX, San Diego, CA. The cyclin dependent kinase inhibition on proteins such as CDK2, CDK4, CDK6, and CDK9 was determined by Reaction Biology Corp., Malvern, PA. To obtain selectivity data a large collection of 468 human kinases was screened for inhibition using the KINOMEscan™ Profiling Service at DiscoverX, San Diego, CA. Lastly, pharmacokinetic parameters (PK) and other adsorption, distribution, metabolism, and excretion data (ADME) were obtained by the third-party service provider Quintara Discovery (Hayward, CA). Additional information on each of the above testing procedures and services is available at each company's website on the internet.

The present invention also relates to a method of inhibiting protein activity including but not limited to kinase activity in a mammal including a human comprising administering to a mammal in need of treatment, a kinase inhibiting dose of a compound of Formulas I-VI or conjugate or prodrug thereof having any of the definitions herein.

The present invention further relates to a method of inhibiting CDK and/or bromodomain protein and/or PI3Ks in vivo comprising administering to a mammal in need of treatment, including a human, a protein inhibiting dose of a compound of Formulas I-VI or conjugate or prodrug thereof having any of the definitions herein. The present invention further relates to a method of inhibiting CDKs and/or bromodomain proteins and/or PI3Ks comprising administering to insects or fungi for agricultural uses.

The present invention further relates to a method of inhibiting tumor growth comprising administering to a mammal in need of treatment, including a human, an effective dose of a compound of Formulas I-VI, or conjugate or prodrug thereof, having any of the definitions herein.

In another aspect the invention relates to a method of regulating gene transcription in a cell comprising exposing a bromodomain containing protein to a compound of Formulas I-VI.

In another aspect the present invention relates to a method of inhibiting bromodomain-mediated recognition of an acetyl lysine region of a bromodomain protein comprising exposing the bromodomain to a compound of Formula I-VI.

As an additional feature of the invention there is provided a pharmaceutical formulation comprising in association with a pharmaceutically acceptable carrier, diluent or excipient, a compound of Formulas I-VI or conjugate thereof (or of a pharmaceutically acceptable salt thereof) as provided in any of the descriptions herein.

In another aspect, the present invention relates to treating a disease, including but not limited to, cancer, non-cancer proliferative disease, sepsis, autoimmune disease, viral infection, atherosclerosis, Type 2 diabetes, obesity, inflammatory disease, and Myc-dependent disorder by administering a compound of the invention.

These and other objects of the invention are evidenced by the summary of the invention, the description of the preferred embodiments and the claims.

DETAILED DESCRIPTION

A. Definitions

Figure 1:
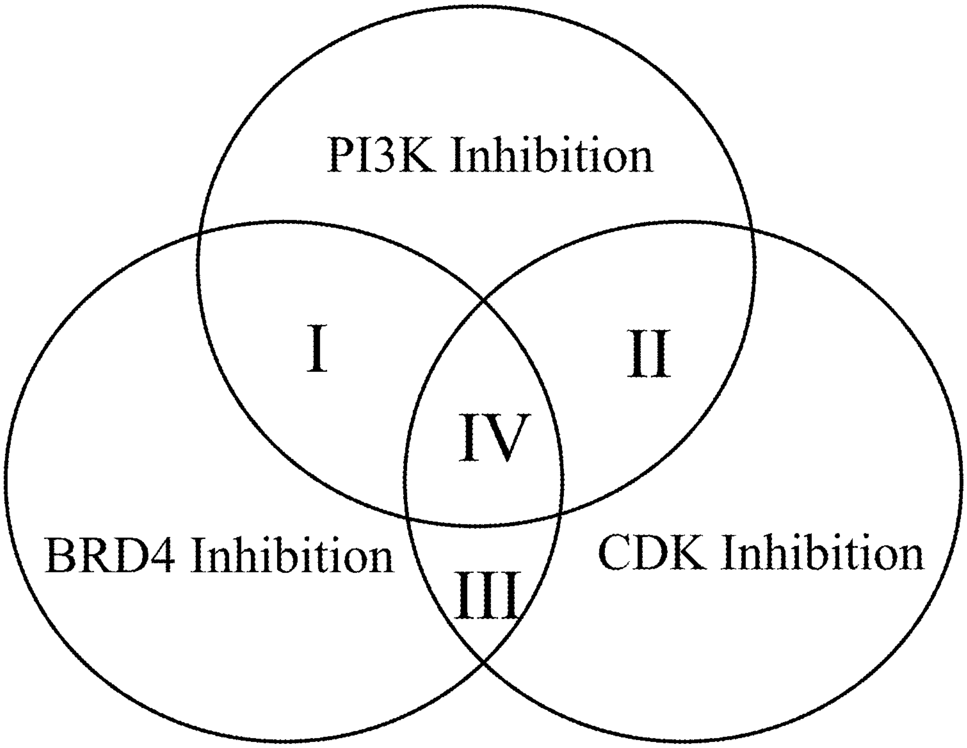
FIG. 1 provides a schematic representation of proteins targeted by single molecule multi-targeted inhibitors of the invention.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast cancer.

The term "cancerous cell" as provided herein, includes a cell affected by any one of the above-identified cancers. The term "cancer stem cell" refers to a subpopulation of cells in a solid or non-solid tumor that demonstrate enhanced drug efflux properties, are lacking in cell cycle progression, and are resistant to anoikis.

As used herein, the term "branched" refers to a group containing from 1 to 24 backbone atoms wherein the backbone chain of the group contains one or more subordinate branches from the main chain. Preferred branched groups herein contain from 1 to 12 backbone atoms. Examples of branched groups include, but are not limited to, isobutyl, t-butyl, isopropyl, $—CH_2CH_2CH(CH_3)CH_2CH_3$, $—CH_2CH(CH_2CH_3)CH_2CH_3$, $—CH_2CH_2C(CH_3)_2CH_3$, $—CH_2CH_2C(CH_3)_3$ and the like.

The term "unbranched" as used herein refers to a group containing from 1 to 24 backbone atoms wherein the backbone chain of the group extends in a direct line. Preferred unbranched groups herein contain from 1 to 12 backbone atoms.

The term "cyclic" or "cyclo" as used herein alone or in combination refers to a group having one or more closed rings, whether unsaturated or saturated, possessing rings of from 3 to 12 backbone atoms, preferably 3 to 7 backbone atoms.

The term "lower" as used herein refers to a group with 1 to 6 backbone atoms.

The term "saturated" as used herein refers to a group where all available valence bonds of the backbone atoms are attached to other atoms. Representative examples of saturated groups include, but are not limited to, butyl, cyclohexyl, piperidine and the like.

The term "unsaturated" as used herein refers to a group where at least one available valence bond of two adjacent backbone atoms is not attached to other atoms. Representative examples of unsaturated groups include, but are not limited to, $—CH_2CH_2CH{=}CH_2$, phenyl, pyrrole and the like.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "aromatic" as used herein refers to an unsaturated cyclic hydrocarbon group which may be substituted or unsubstituted having 4n+2 delocalized $\pi$(pi) electrons, The term aromatic further includes aromatic groups, which comprise a nitrogen atom replacing one or more carbons of the hydrocarbon backbone. Examples of aromatic groups include, but are not limited to, phenyl, naphthyl, thienyl, furanyl, pyridinyl, (is)oxazoyl and the like.

The term "substituted" as used herein refers to a group having one or more hydrogens or other atoms removed from a carbon or suitable heteroatom and replaced with a further group. Preferred substituted groups herein are substituted with one to five, most preferably one to three substituents. An atom with two substituents is denoted with "di," whereas an atom with more than two substituents is denoted by "poly." Representative examples of such substituents include, but are not limited to aliphatic groups, aromatic groups, alkyl, alkenyl, alkynyl, aryl, alkoxy, halo, aryloxy, carbonyl, acryl, cyano, amino, amide, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl", "optionally substituted alkenyl", "optionally substituted alkynyl", "optionally substituted carbocyclic", "optionally substituted aryl", "optionally substituted heteroaryl", "optionally substituted heterocyclic", and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, alkoxy, oxo, thiooxo, —NO2, —CN, —CF3, —N3, —$NH_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —CONH2, —CONH-alkyl, —CONH-alkenyl, —CONH-alkynyl, —CONH-cycloalkyl, —CONH-aryl, —CONH-heteroaryl, —CONH-heterocycloalkyl, —OCO2-alkyl, —OCO2-alkenyl, —OCO2-alkynyl, —OCO2-cycloalkyl, —OCO2-aryl, —OCO2-heteroaryl, —OCO2-heterocycloalkyl, —OCONH2, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —NHCO2-alkyl, —NHCO2-alkenyl, —NHCO2-alkynyl, —NHCO2-cycloalkyl, —NHCO2-aryl, —NHCO2-heteroaryl, —NHCO2-heterocycloalkyl, —NHC(O)$NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, —NHC(S)$NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)$NH_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl-SO2$NH_2$, —SO2NH-alkyl, —SO2NH-alkenyl, —SO2NH-alkynyl, —SO2NH-cycloalkyl, —SO2NH-aryl, —SO2NH-heteroaryl, —SO2NH-heterocycloalkyl, —NHSO2-alkyl, —NHSO2-alkenyl, —NHSO2-alkynyl, —NHSO2-cycloalkyl, —NHSO2-aryl, —NHSO2-heteroaryl, —NHSO2-heterocycloalkyl, —CH2NH2, —CH2SO2CH3, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

The term "unsubstituted" as used herein refers to a group that does not have any further groups attached thereto or substituted therefore.

The term "alkyl" as used herein, alone or in combination, refers to a branched or unbranched, saturated aliphatic group. The alkyl radical may be optionally substituted independently with one or more substituents described herein. Lower alkyl refers to alkyl groups of from one to six carbon atoms. Examples of lower alkyl groups include methyl, ethyl, propyl, isopropyl, butyl, s-butyl, t-butyl, isobutyl, pentyl, and the like. Higher alkyl refers to alkyl groups containing more than seven carbon atoms. A "Co" alkyl (as in "Co-$C_6$-alkyl") is a covalent bond. Exemplary alkyl groups are those of $C_{20}$ or below. In this application, alkyl refers to alkanyl, alkenyl, and alkynyl residues (and combinations thereof); it is intended to include vinyl, allyl, isoprenyl, and the like. Thus, when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetracosyl and the like. The terms "alkyl" or "alk" as used herein refer to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)_2$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, 1-heptyl, 1-octyl, and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. The cycloalkyl radical may be optionally substituted independently with one or more substituents described herein. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "alkenyl" as used herein alone or in combination refers to a branched or unbranched, unsaturated aliphatic group containing at least one carbon-carbon double bond which may occur at any stable point along the chain. The alkenyl radical may be optionally substituted independently with one or more substituents described herein, and includes radicals having "cis" and "trans" orientations, or alternatively, "E" and "Z" orientations. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain. The alkynyl radical may be optionally substituted independently with one or more substituents described herein. Representative examples of alkynyl groups include, but are not limited to, ethynyl, propynyl, propargyl, butynyl, hexynyl, decynyl and the like.

The term "aryl" as used herein alone or in combination refers to a substituted or unsubstituted aromatic group, which may be optionally fused to other aromatic or non-aromatic cyclic groups. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heteroaryl" and "heteroar-", used alone or as part of a larger moiety, e.g., "heteroaralkyl", or "heteroaralkoxy", refer to groups having 5 to 18 ring atoms, preferably 5, 6, 7, 9, or 14 ring atoms; having 6, 10, or 14 (pi) electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

The term "alkoxy" as used herein alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

The term "aryloxy" as used herein alone or in combination refers to an aryl group bound through a single terminal ether linkage.

The terms "halogen", "halo" and "hal" as used herein refer to monovalent atoms of fluorine, chlorine, bromine, iodine and astatine.

The term "hetero" or "heteroatom" as used herein combination refers to a group that includes one or more atoms of any element other than carbon or hydrogen. Representative examples of hetero groups include, but are not limited to, those groups that contain heteroatoms including, but not limited to, nitrogen, oxygen, sulfur and phosphorus.

The term "heterocycle" or "heterocyclyl" or "heterocyclic ring" or "heterocyclic" as used herein refers to a cyclic group containing one or more heteroatoms. The heterocyclic radical may be optionally substituted independently with one or more substituents described herein. Representative examples of heterocycles include, but are not limited to, pyridine, piperadine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical" are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "substituent" means any group selected from H, F, Cl, Br, I, alkyl, alkenyl, alkynyl, carbocycle, aryl, heterocycle, heteroaryl, formyl, nitro, cyano, amino, amide, carboxylic acid, carboxylic ester, carboxyl amide, reverse caboxyamide, halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally'substituted aryl, optionally substituted heteroaryl, alkylaminoalkyl, dialkylaminoalkyl, carboxy, carboxy ester, —C(O)$NR^5R''$ (where $R^5$ is hydrogen or alkyl and R" is hydrogen, alkyl, aryl, or heterocyclyl), —$NR^5C$(O)R" (where $R^5$ is hydrogen or alkyl and R" is alkyl, aryl, or heterocyclyl), amino, alkylamino, dialkylamino, and —$NHS(O)_2R'$ (where R' is alkyl, aryl, or heteroaryl).

The term "carbonyl" or "carboxy" as used herein alone or in combination refers to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

The term "carbamate" as used herein alone or in combination refers to an ester group represented by the general structure —NH(CO)O—. Carbamate esters may have alkyl or aryl groups substituted on the nitrogen, or the amide function.

term "cyanate" "isocyanate", "thiocyanate", or "isothiocyanate" as used herein alone or in combination refers to an oxygen- or sulfur-carbon double bond carbon-nitrogen double bond.

Representative examples of cyano groups include, but are not limited to, isocyanate, isothiocyanate and the like.

The term "cyano", "cyanide", "isocyanide", "nitrile", or "isonitrile" as used herein alone or in combination refers to a carbon-nitrogen triple bond.

The term "amino" as used herein alone or in combination refers to a group containing a backbone nitrogen atom. Representative examples of amino groups include, but are not limited to, alkylamino, dialkylamino, arylamino, diarylamino, alkylarylamino, alkylcarbonylamino, arylcarbonylamino, carbamoyl, ureido and the like.

The term "phosphate-containing group" as used herein refers to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphoranylidenes, phosphorosos and the like.

The term "sulfur-containing group" as used herein refers to a group containing a sulfur atom. Representative examples include, but are not limited to, sulfhydryls, sulfenos, sulfinos, sulfinyls, sulfos, sulfonyls, thios, thioxos and the like.

The term "optional" or "optionally" as used herein means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and substituted alkyl.

The term "targeting agent" as used herein means any moiety attached to a compound of the invention allowing an increase in concentration of the compound at a site of treatment, for example, a tumor site. Exemplary targeting agents include but are not limited to carbohydrates, peptides, vitamins, and antibodies.

As used herein, the term "multi-target inhibitor" or "multi-target agent" refers to a single molecule having the capacity to interact with at least two different protein targets in vitro or in vivo including the capacity to inhibit the activity or normal function of said targets, e.g., to inhibit binding or enzymatic activity. As used herein, multi-target inhibitors have the capacity to interact with at least one CDK and also one or two of PI3K and bromo domain proteins.

As used herein, the term "dual inhibitor" refers to the capacity of a single molecule to interact with and/or inhibit the activity or normal function of two different target proteins such as PI3K, bromodomain protein, CDK4 or CDK6, for example, to inhibit enzymatic activity or to prevent the interaction of the target protein with other proteins or molecules in vivo.

As used herein, the term "triple inhibitor" refers to the capacity of a single molecule to interact with and/or inhibit the activity or normal function of three different classes of target proteins, namely PI3K, bromodomain protein, and a CDK (such as CDK4 and/or CDK6), for example to inhibit enzymatic activity or to prevent the interaction of the target proteins with other proteins or molecules in vivo. Thus, by inhibiting two or three different classes of target proteins a dual or triple inhibitor would be displaying two or more mechanisms of anticancer activity.

The term "effective amount" or "effective concentration" when used in reference to a compound, product, or composition as provided herein, means a sufficient amount of the compound, product or composition to provide the desired pharmaceutical or therapeutic result. The exact amount required will vary depending on the particular compound, product or composition used, its mode of administration and the like. Thus, it is not always possible to specify an exact "effective amount." However, an appropriate effective amount may be determined by one of ordinary skill in the art informed by the instant disclosure using only routine experimentation.

The term "hydrolyzable" as used herein refers to whether the group is capable of or prone to hydrolysis (i.e., splitting of the molecule or group into two or more new molecules or groups).

The term "pharmaceutically acceptable salt" of a compound of the instant invention (e.g., Formula I) is one which is the acid addition salt of a basic compound of the invention with an inorganic or organic acid which affords a physiologically acceptable anion or which is the salt formed by an acidic compound of the invention with a base which affords a physiologically acceptable cation.

The term "prodrug" or "procompound" as used in this application refers to a precursor or derivative form of a compound of the invention that may be less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "conjugate" as used herein refers to a compound that has been formed by the joining of two or more compounds via either a covalent or non-covalent bond.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "metabolite" is a product produced through metabolism in the body of a specified compound or salt thereof metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the terms "treatment", "treat", and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (i.e., in light of a history of symptoms and/or in light of genetic or other susceptibility factors). Treatment may also be continued after symptoms have resolved, for example to prevent or delay their recurrence.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" include compounds of Formulas I-VI and stereoisomers, geometric isomers, tautomers, solvates, metabolites, and pharmaceutically acceptable salts, prodrugs, and conjugates thereof.

The term "TP scaffold" or "Thienopyranone scaffold" refers to a compound of general Formula I as described herein where M of the fused 5-membered ring is S. The term "Furanopyranone scaffold" refers to a compound of Formula I where M of the fused 5-membered ring is O.

As used herein, the term "CDK inhibiting" as applied to a compound of the invention means that a compound inhibits a normal or wild-type function of a CDK protein, in vivo and/or in vitro (e.g., CDK4 and/or CDK6) with an $IC_{50}$ value of less than or equal to 50 μM in an appropriate in vitro assay.

As used herein, the term "PI3K inhibiting" as applied to a compound of the invention means that a compound inhibits the normal or wild-type function of PI3K, i.e., enzymatic activity, in vivo and/or in vitro (e.g., PI3Kα, PI3Kβ, PI3Kγ) with an $IC_{50}$ value of less than or equal to 50 μM in an appropriate in vitro assay.

As used herein, the term "Bromodomain inhibiting" as applied to a compound of the invention means that a compound inhibits the normal or wild-type function of a Bromodomain protein, in vivo and/or in vitro (e.g., BRD4) with an $IC_{50}$ value of less than or equal to 50 μM in an appropriate in vitro assay.

B. Compounds

The present invention relates in part to compounds and therapeutic methods of use of compounds of the Formula I.

Formula I

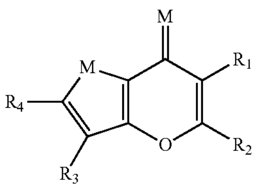

wherein M is independently O or S;

R1 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thimoether, carbamate, substituted carbamate;

R2 is selected from R1 or

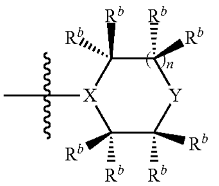

or

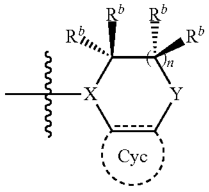

Where X is C, N, P, P(O), $SiR^b$;

n is 0, 1, or 2;

Y is C—R1, O, S, $NR^a$, —$C(O)(NH_2)$, —$P(Z)_mR^a$, $SiR^aR^b$, $BR^b$;

Z is O or S;

m=0 or 1;

$R^a$ is hydrogen (H) or independently at each instance any group defined in R1;

$R^b$ is hydrogen (H) or independently at each instance any group defined in R1;

R3 is selected from R1;

R4 is selected from R1; and

Cyc is an aryl, substituted aryl, heterocycle, substituted heterocycle, carbocycle, and substituted carbocycle.

In one embodiment of a compound of Formula I the R1 substituent includes a bone directing group such as, for example, amino phosphonic acid, bisphsphonate, or the like.

In another embodiment, compounds of Formula I include those wherein the substitutent R3 binds and potently ($IC_{50}$<1000 nM) inhibits cyclin dependent kinases such as but not limited to CDK4 and/or CDK6.

In another aspect, the present invention relates to compounds and methods of use for compounds of Formula II.

Formula II

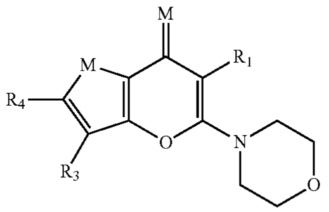

wherein M is independently selected from O or S;

R1 is selected from H, F, Cl, Br, I, alkyl, alkenyl, alkynyl, carbocycle, aryl, heterocycle, heteroaryl, formyl, nitro, cyano, amino, carboxylic acid, carboxylic ester, amide, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R3 is independently, at each instance, R1 preferably wherein R1 contains an aromatic group directly attached to the thiophene or furan ring; and R4 is independently, at each instance, R1.

In one aspect, a compound of Formula II provides a substitutent at R1 comprising a bone directing group such as, for example, amino phosphonic acid, bisphosphonate, or the like.

A particular subset of compounds of Formula II include those wherein the substituent R3 binds and potently ($IC_{50}$<1000 nM) inhibits cyclin dependent kinases including but not limited to CDK4 and/or CDK6.

Representative compounds of Formula II include but are not limited to Compound 1 and Compound 15:

Compound 1

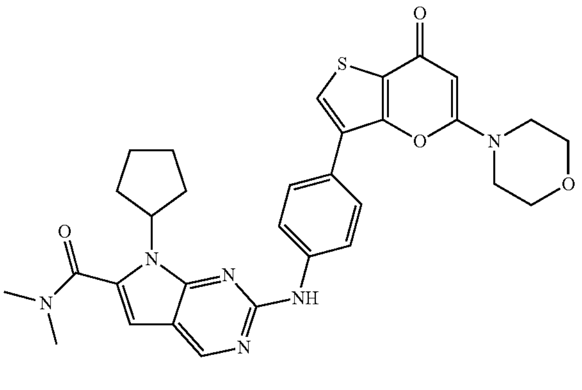

Compound 15

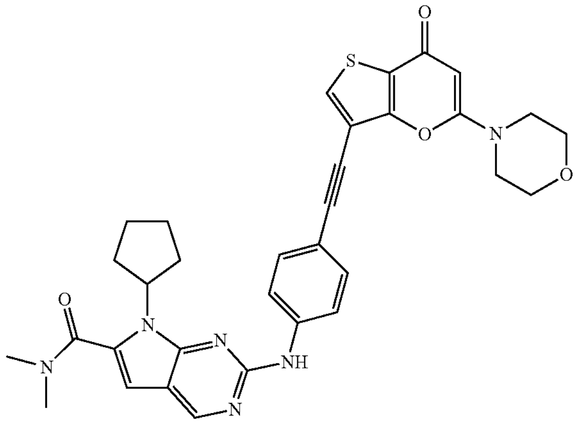

Additional compounds of Formula II include the following:

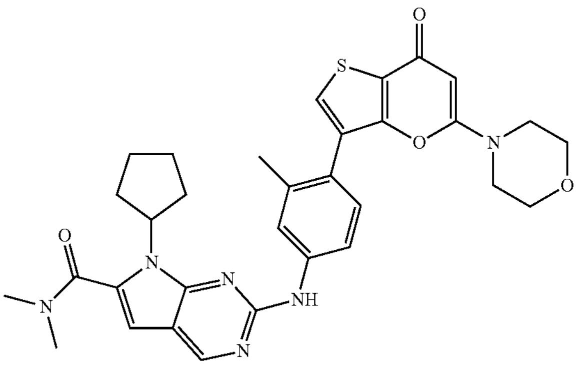

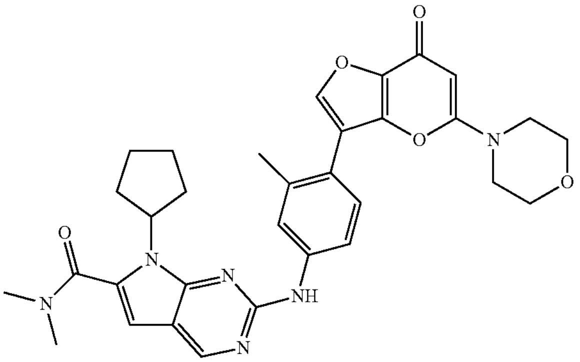

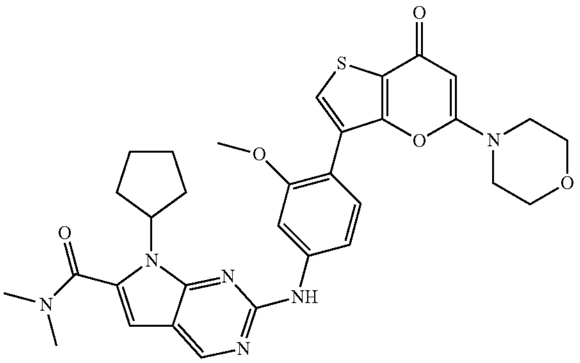

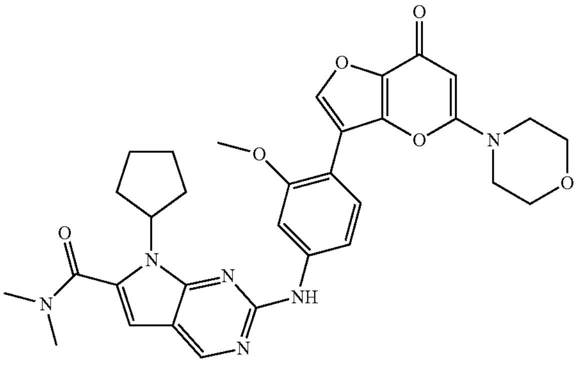

-continued

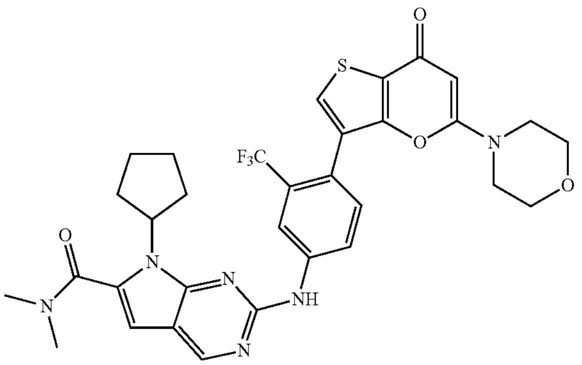

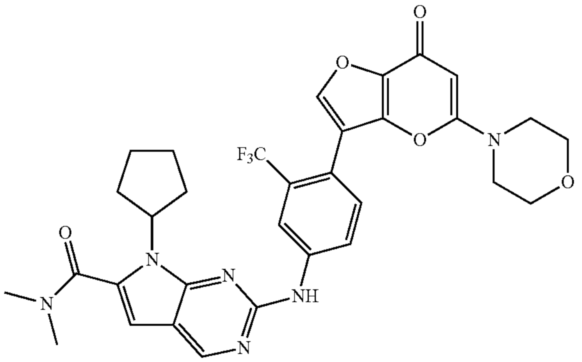

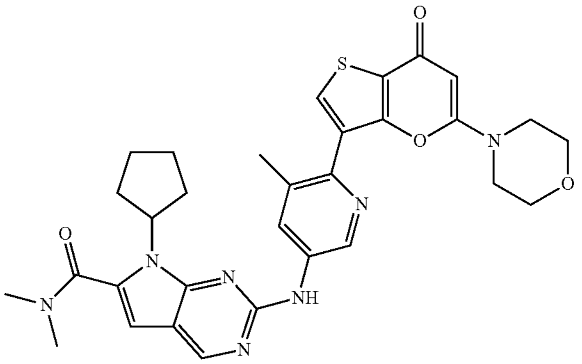

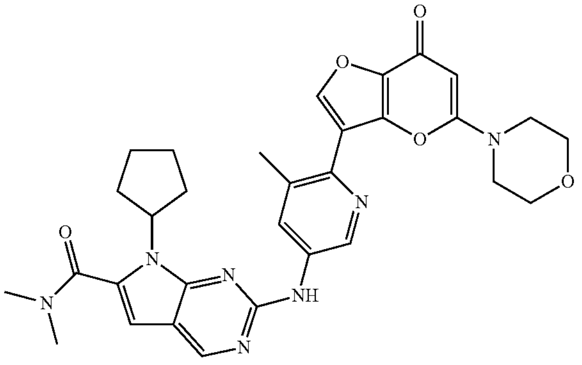

-continued

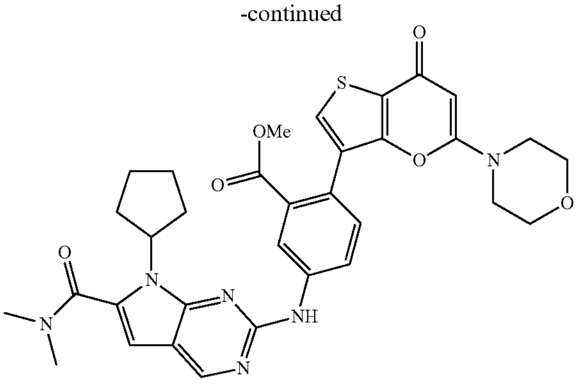

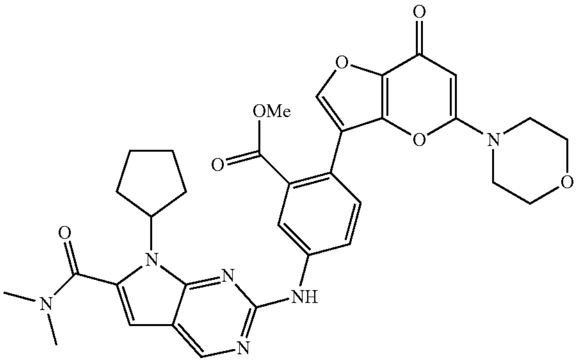

The present invention also relates to compounds and methods of use for compounds of Formulas III wherein R2 is as described for Formula I except that R2 excludes morpholino substituents, and R1 and R3 and R4 are as described for Formula II:

Formula III

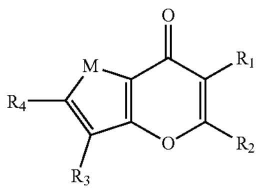

A particular subset of compounds of Formula III includes those in which the substituent R3 binds and potently ($IC_{50}$<1000 nM) inhibits cyclin dependent kinases such as but not limited to CDK4 and/or CDK6.

A representative example of a compound of Formula III that is a dual inhibitor of BRD4 and CDK (CDK4 and/or CDK6) include but is not limited to the following (note nonmorpholine substituents at R2):

Compound 2
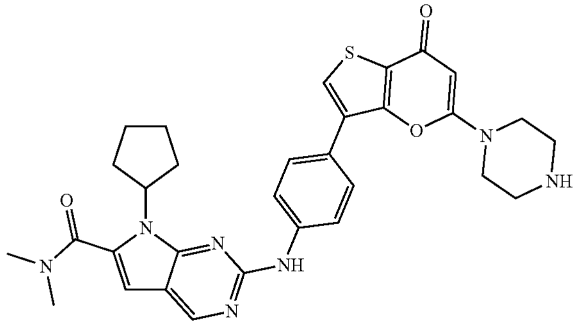
Additional compounds of Formula III include the following:
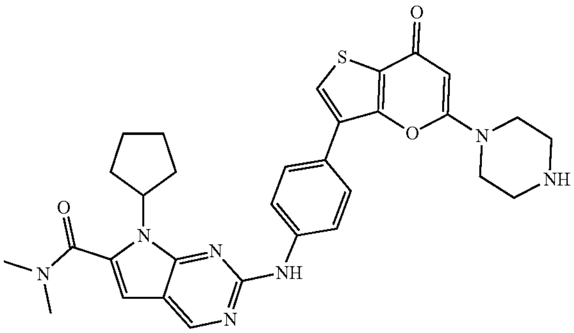
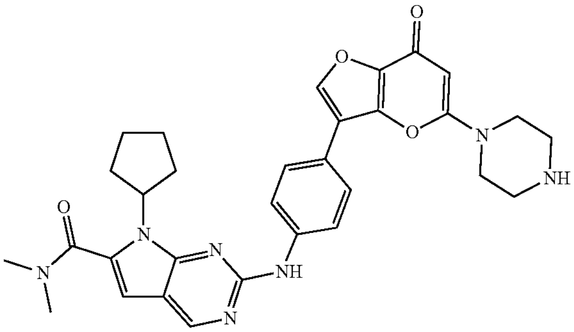
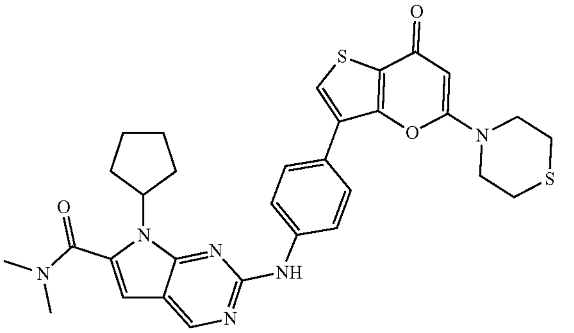
-continued
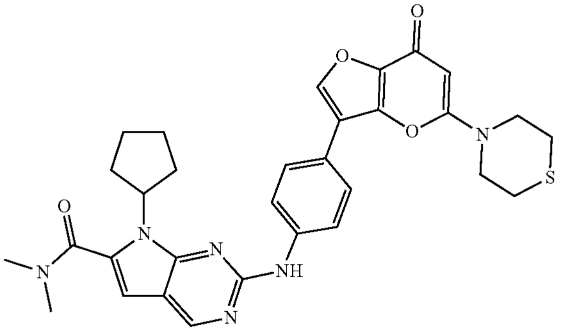
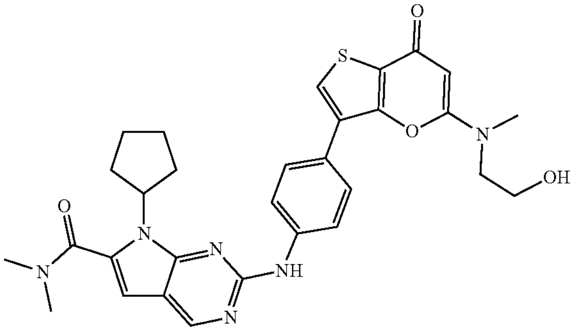
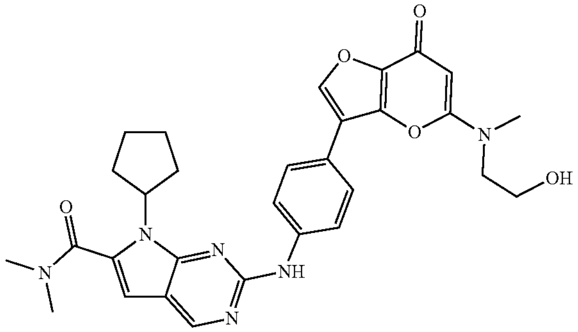
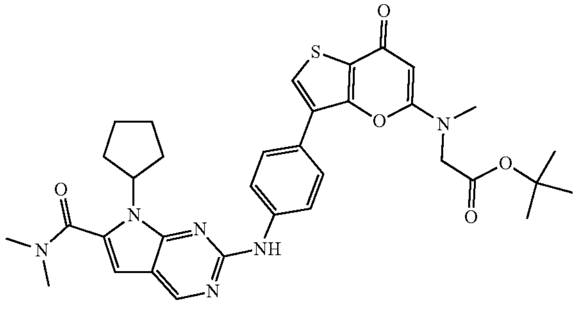
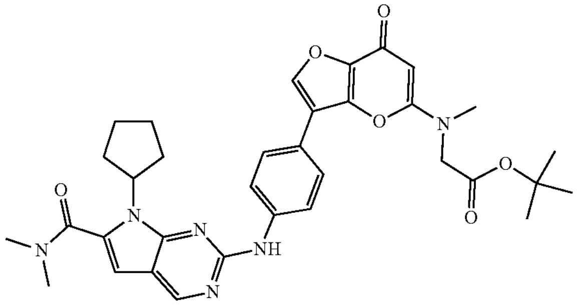
The present invention also relates to compounds and methods of use for compounds of Formula IV:

Formula IV

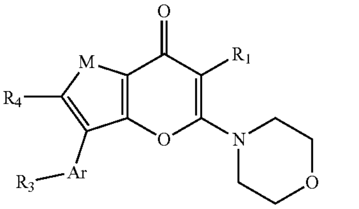

wherein M is S or O; R1, R3, and R4 are as described above for Formula I and Ar is defined as an aryl, heterocycle, or heteroaryl group unsubstituted beyond the attachment to thiophene (or furan) ring and the R3 substituent is in the meta- or para-positions.

A particular subset of compounds of Formula IV is wherein the substituent Ar—R3 binds and potently ($IC_{50}$<1000 nM) inhibits cyclin dependent kinases such as but not limited to CDK4 and/or CDK6.

Compounds of formula IV contain a morpholine substituent at position R2. The observation that morpholine is critical for maximum PI3K activity but not for BRD4 inhibition is observed with the triple inhibitor compound 1 when compared to its piperazine analog compound 2.

Triple inhibitors are generally characterized as having morpholine in the R2 position and a hydrophobic aromatic group at R3 attached to the furan or thiophene to bind BRD4 in the hydrophobic region (upper lobe V87/L92 and lower lobe W81/P82), and also containing the CDK inhibiting moiety in the R3 position.

Representative examples of compounds of Formula IV include but are not limited to:

Compound 3

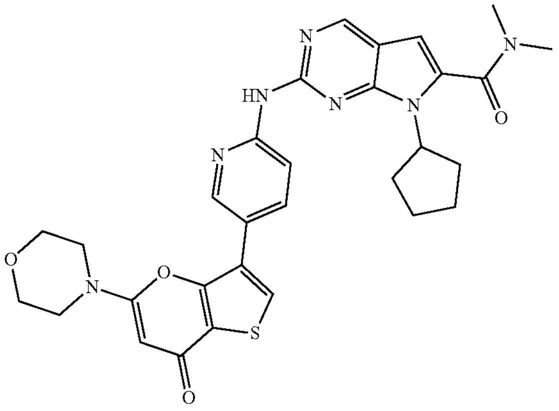

-continued

Compound 14

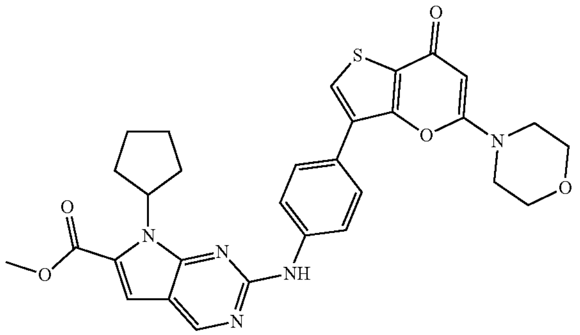

Additional compounds of Formula IV include the following:

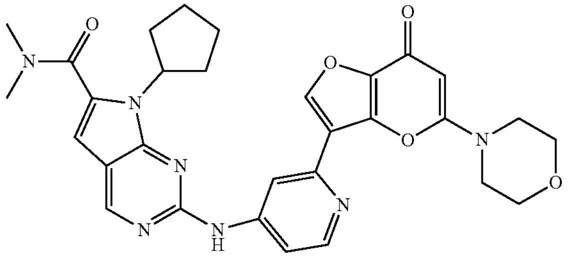

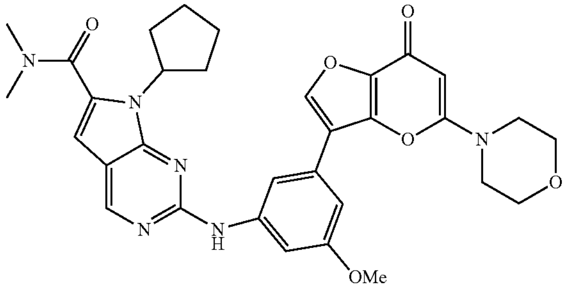

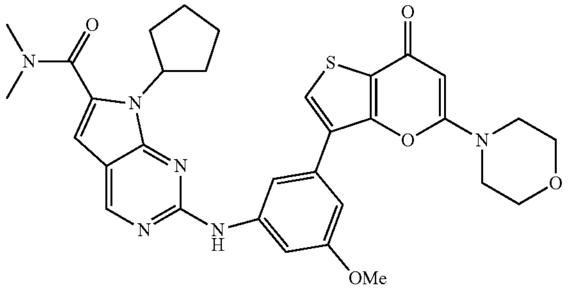

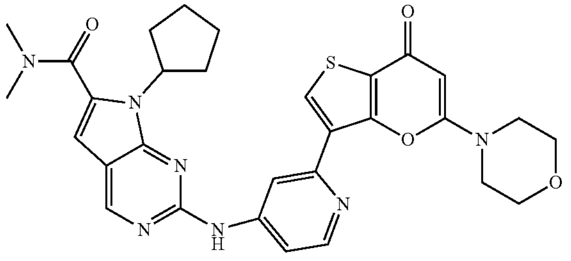

-continued

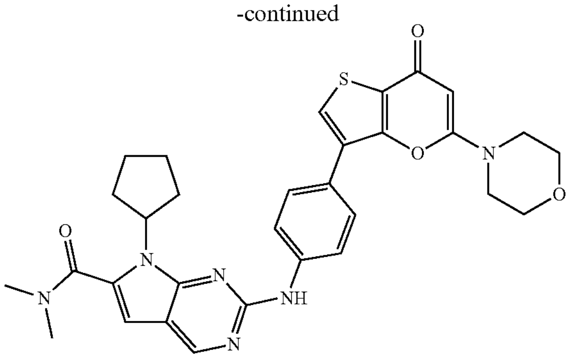

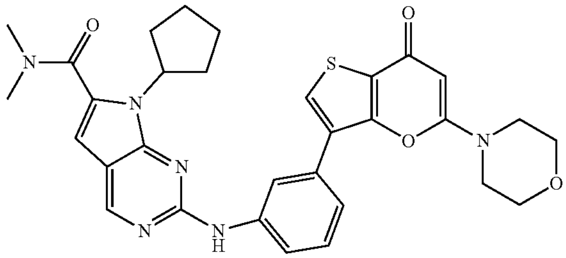

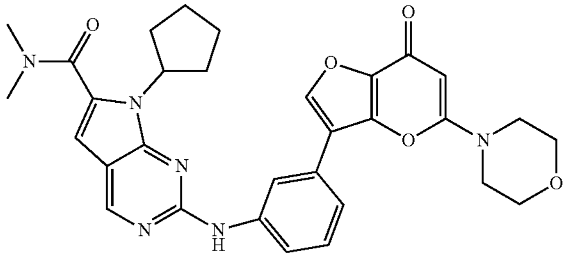

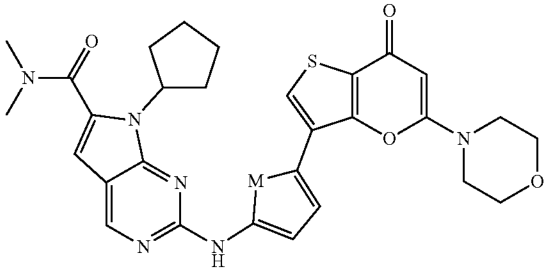

M = O or S

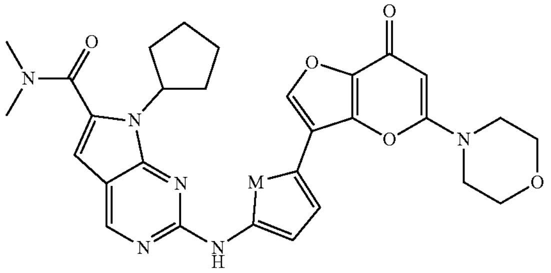

M = O or S

In another aspect the present invention also relates to compounds and methods of use for compounds of Formula IVa:

Formula IVa

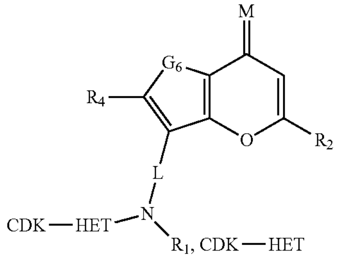

M, $R_4$ and $R_2$ are as defined in Formula I

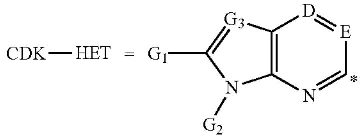

* = Point of attachment $G_1$ =

$NJ_1J_2$ $J_1$ = H, OH, $OCH_3$, $CH_3$, CHO
$J_2$ = H, $CH_3$

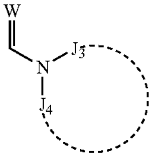

W = O, S
$J_3$ = H, OH, $OCH_3$, $CH_3$
$J_4$ = H, $CH_3$

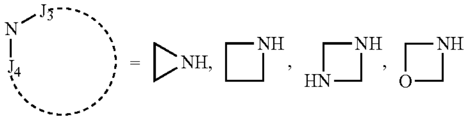

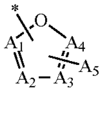

$A_1$ = C, N
$A_2$ = C, N
$A_3$ = C, N
$A_4$ = C, N
$A_5$ = H or $CH_3$ when $A_1$ or $A_2$ or $A_3$ or $A_4$ = C
* = link when $A_1$ or $A_2$ or $A_3$ or $A_4$ = C $G_2$ = $R_1$ ($R_1$ is as defined in Formula I)
$G_3$ = C, N
D = C, N
E = C, N

L = nothing,

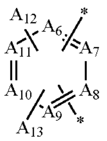

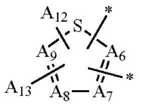

$A_6$ = C, N
$A_7$ = C, N
$A_8$ = C, N
$A_9$ = C, N
$A_{10}$ = C, N
$A_{11}$ = C, N
$A_{12}$ = H, OH, $OCH_3$, $CO_2CH_3$, $CO_2CH_2CH_3$, $CO_2H$, $NH_2$, $NHCH_3$, $N(CH_3)_2$
$A_{13}$ = H, OH, $OCH_3$, $CO_2CH_3$, $CO_2CH_2CH_3$, $CO_2H$, $NH_2$, $NHCH_3$, $N(CH_3)_2$
* = link to N or C $G_6$ = O, S Representative examples of compounds of Formula IVa include but are not limited to:

Compound 4
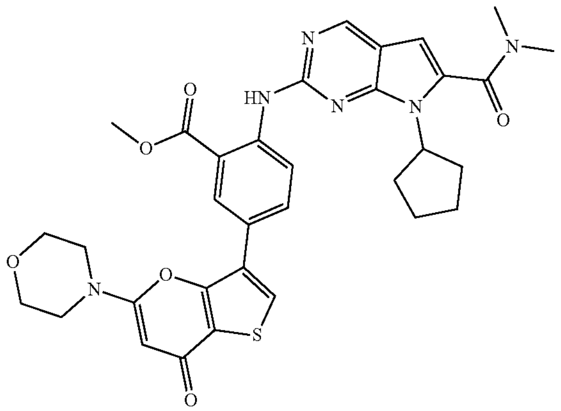
Compound 7
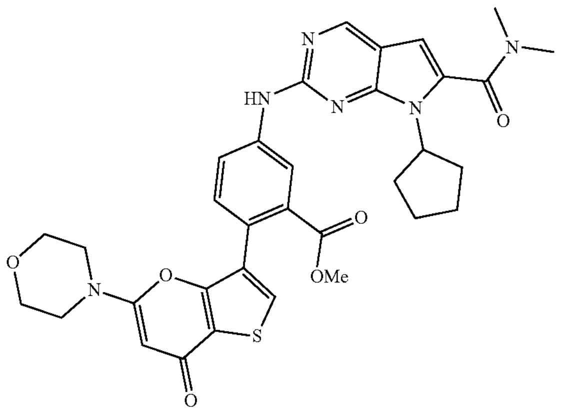
Compound 9
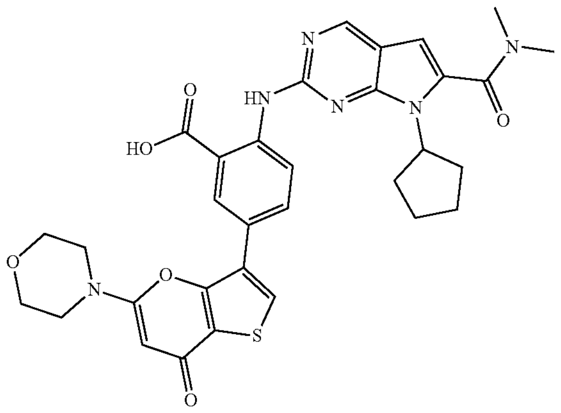
-continued
Compound 10
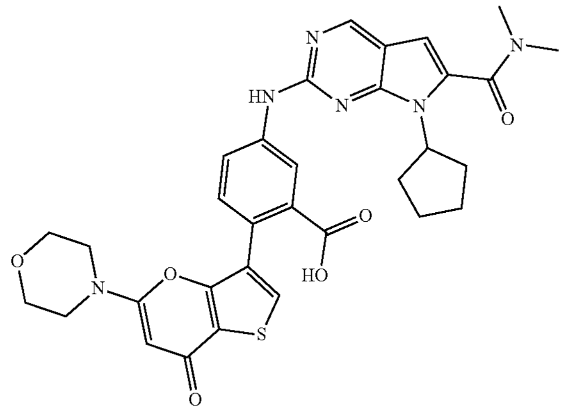
Compound 11
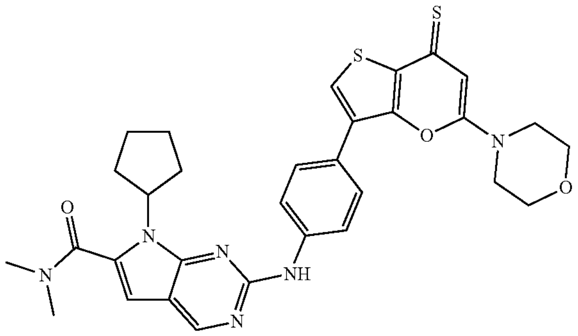
Compound 12
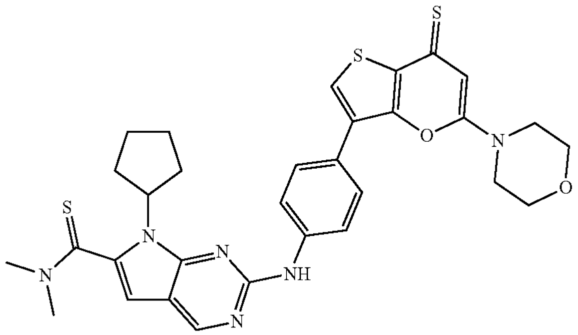
Compound 13
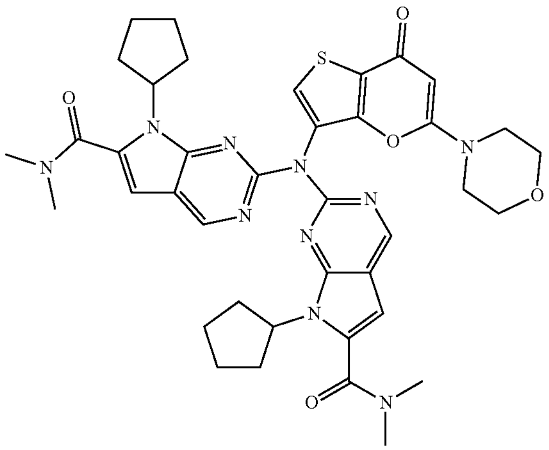

-continued

Compound 16

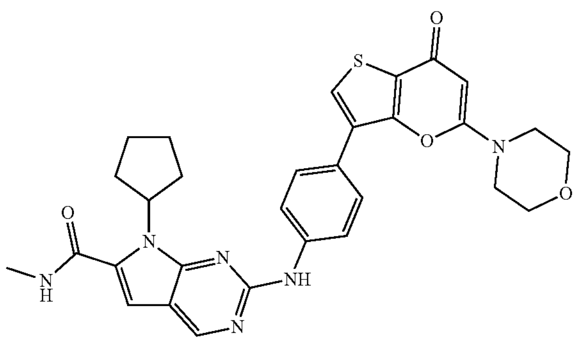

Compound 17

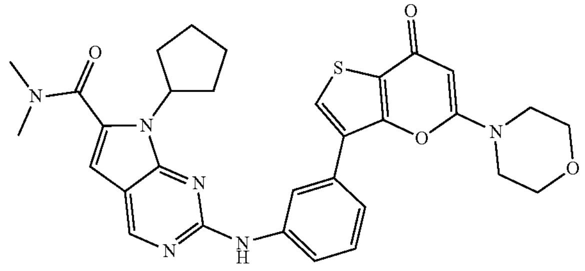

In another aspect the present invention also relates to compound and methods of use for compounds of Formula IVb:

Formula IVb

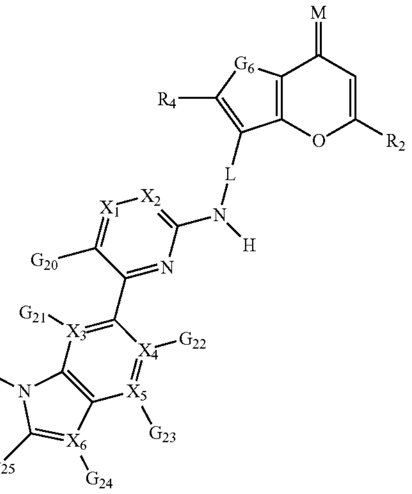

M, $R_4$ and $R_2$ are as defined in Formula I wherein $X_1$=C, N $X_2$=C, N $X_3$=C, N $X_4$=C, N $X_5$=C, N $X_6$=C, N $G_{20}$=H, F, Cl, Br, $CF_3$, $CH_3$ $G_{21}$=null (when $X_3$=N), H, F, Cl, Br, $CF_3$, $CH_3$ $G_{22}$=null (when $X_4$=N), H, F, Cl, Br, $CF_3$, $CH_3$ $G_{23}$=null (when $X_6$=N), H, F, Cl, Br, $CF_3$, $CH_3$ $G_{24}$=H, $CH_3$, $CH_2CH_3$, $CH(CH_3)_2$, $CF_3$, $G_{26}$ and the like $G_{25}$=H, $CH_3$, $CH_2CH_3$, $CH(CH_3)_2$, $CF_3$, $G_{26}$ and the like $G_{26}$=alkyl,

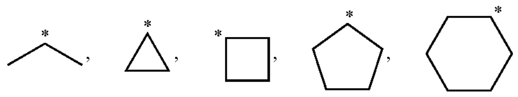

where *=point of attachment

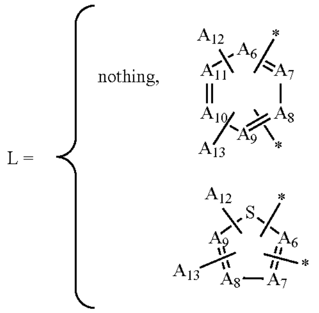

$A_6$ = C, N $A_7$ = C, N $A_8$ = C, N $A_9$ = C, N $A_{10}$ = C, N $A_{11}$ = C, N $A_{12}$ = H, OH, $OCH_3$, $CO_2CH_3$, $CO_2CH_2CH_3$, $CO_2H$, $NH_2$, $NHCH_3$, $N(CH_3)_2$ $A_{13}$ = H, OH, $OCH_3$, $CO_2CH_3$, $CO_2CH_2CH_3$, $CO_2H$, $NH_2$, $NHCH_3$, $N(CH_3)_2$

* = link to N or C

A representative example of a compound of Formula IVb includes but is not limited to:

Compound 5

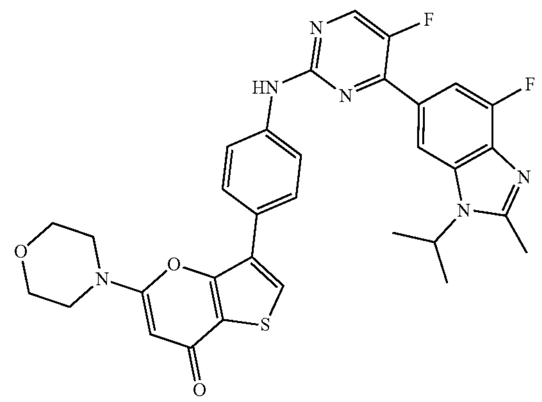

In another aspect the present invention also relates to compound and methods of use for compounds of Formula IVc:

Formula IVc

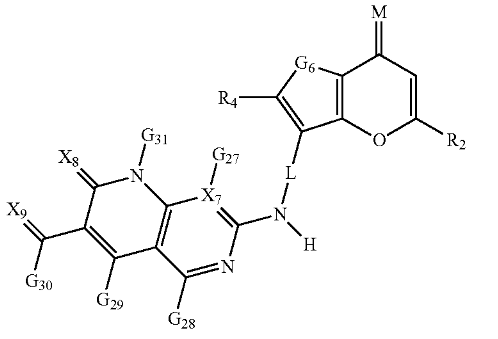

M, $R_4$ and $R_2$ are as defined in Formula I

Wherein $X_7$=C, N $X_8$=O, S $X_9$=O, S $G_{27}$=null (when $X_7$=N), H, F, Cl, Br, $CF_3$, $CH_3$, $CH_2CH_3$, $CH(CH_3)_2$ $G_{28}$=H, F, Cl, Br, $CF_3$, $CH_3$, $CH_2CH_3$, $CH(CH_3)_2$ $G_{29}$=H, F, Cl, Br, $CF_3$, $CH_3$, $CH_2CH_3$, $CH(CH_3)_2$ $G_{30}$=H, $CF_3$, $CH_2CH_3$, $CH(CH_3)_2$, $CF_3$, $NH_2$, $NHCH_3$, $N(CH_3)_2$, $G_{31}$ and the like $G_{31}$=alkyl,

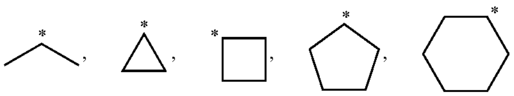

where *=point of attachment

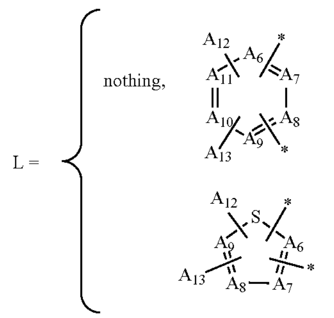

$A_6$ = C, N
$A_7$ = C, N
$A_8$ = C, N
$A_9$ = C, N
$A_{10}$ = C, N
$A_{11}$ = C, N
$A_{12}$ = H, OH, $OCH_3$, $CO_2CH_3$, $CO_2CH_2CH_3$, $CO_2H$, $NH_2$, $NHCH_3$, $N(CH_3)$;
$A_{13}$ = H, OH, $OCH_3$, $CO_2CH_3$, $CO_2CH_2CH_3$, $CO_2H$, $NH_2$, $NHCH_3$, $N(CH_3)$;
* = link to N or C Representative examples of compounds of Formula IVc include but are not limited to:

Compound 6

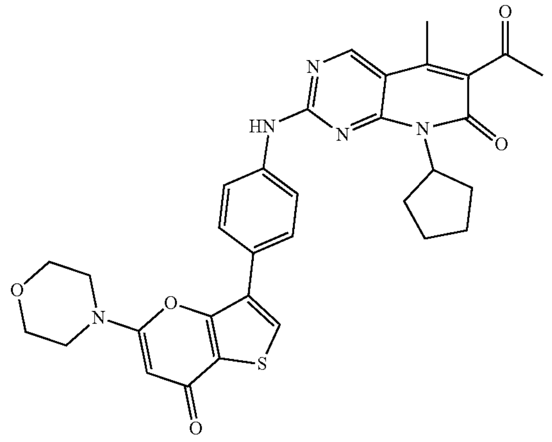

Compound 8

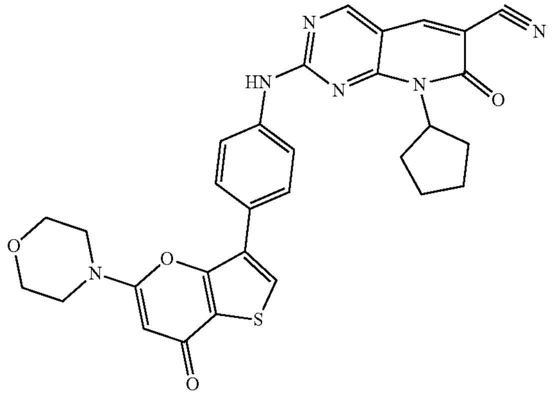

In some aspects a compound of the invention includes compounds of Formulas I, II, III, IVa, IVb, and IVc having a molecular weight of greater than 500 Daltons.

C. Conjugates

The present invention also provides methods of use for conjugates of Formula I-IV wherein R2 is a morpholino group. In one embodiment conjugates are formed by alkylating a compound of Formula I-IV wherein R2 is a morpholino group or substituted morpholino group with a linker group (L), the linker group optionally being substituted with a targeting agent (T). Methods for producing conjugates for this aspect of the invention include alkylation procedures disclosed in U.S. Pat. Nos. 6,949,537 and 7,396,828 the entire contents of which is herein incorporated by reference. In one embodiment of this aspect of the invention a compound of Formula I-IV is reacted with a halomethyl ester compound of Formula Q:

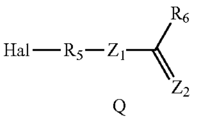

Q wherein Hal is a halogen; R5 is $CH_2$, $CH(CH_3)$, CH(Ph), $C(CH_3)(COOH)$, or $CH(CH(CH_3)2)$;

Z1 and Z2 are independently S or O;

R6 is hydrogen, optionally substituted aliphatic, optionally substituted aryl, alkoxy, carboxy, amino, heterocycle, aryloxy, and optionally substituted therewith a targeting agent (T) to form R6-T.

Targeting Agent.

In another embodiment, conjugates of the present invention are those compounds wherein, R6 further comprises one or more targeting agents (T) covalently attached thereto. Targeting agents allow the conjugates of the present invention to be delivered selectively to specific types of cells, tissues, organs or extracellular structures such as receptors. In some applications it may be desirable to limit the location of a drug or prodrug to the area of treatment or at least prevent it from reaching tissues where it can cause undesirable side effects, and to ensure that at any particular time effective, but not excessive, amounts of the drug are used. The use of targeting agents may allow the conjugates of the present invention to be concentrated at the site of treatment. Once delivered to a site of treatment, the linker may be enzymatically cleaved or hydrolyzed to yield a compound of formula I. Moreover, the use of a targeting agent may limit the dosage required to achieve an effective concentration of a drug at the site of treatment. The use of targeting agents may also reduce the frequency of dosages required.

Suitable targeting agents are preferentially attached to compounds of the present invention via a covalent bond which may be formed by methods including, but not limited to, a nucleophilic or electrophilic group of the targeting agent that is covalently reacted with an electrophilic or nucleophilic group, respectively, on the linker. In one embodiment, suitable targeting agents are those disclosed in U.S. Pat. No. 6,949,537, the entire contents of which is herein incorporated by reference.

In one embodiment of the present invention, conjugates of the present invention are those compounds wherein, R6-T is selected from the group consisting of the following:

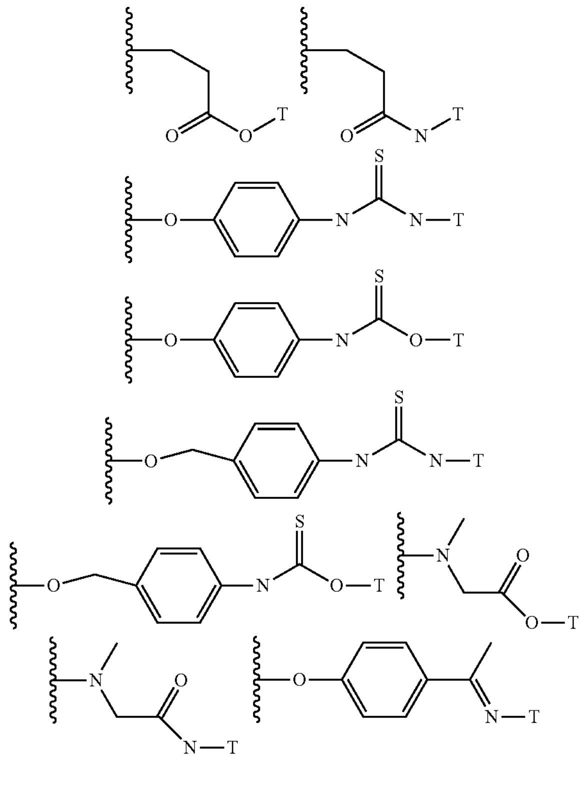

-continued

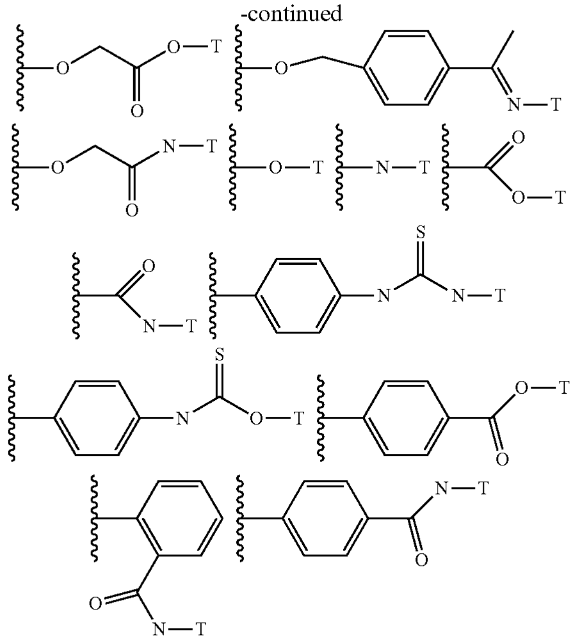

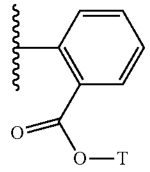

and

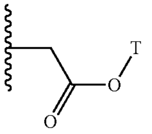

Targeting agents which may be reacted with the conjugates of the present invention include, but are not limited to, carbohydrates, vitamins, peptides, proteins, nucleosides, nucleotides, nucleic acids, liposomes, lipids, bone-seeking agents and cartilage-seeking agents. The targeting agent may also be a molecule which is bound by a receptor in a desired tissue and optionally transported into a cell by a receptor-mediated process. Representative examples of such targeting agents include, but are not limited to, diazepines that bind to peripheral benzodiazepine receptors (PBRs) present in glial cells in the brain. Representative examples of such diazepines are discussed in G. Trapani et al. Bioconjugate Chem. 2003, 14, 830-839 titled "Peripheral Benzodiazepine Receptor Ligand-Melphalan Conjugates for Potential Selective Drug Delivery to Brain Tumors," the contents of which are incorporated by reference.

Representative vitamins that may be used as targeting agents include, but are not limited to, folate, vitamin B12 or vitamin C. The term "folate" encompasses folic acid derivatives with capacity to bind with folate-receptors. Representative examples of folates that may be used as targeting agents include, but are not limited to, folic acid, folinic acid, pteropolyglutamic acid, and folate receptor-binding pteridines such as tetrahydropterins, dihydrofolates, tetrahydrofolates and their deaza and dideaza analogs. Other suitable folates are folate analogs including, but not limited to, aminopterin, amethopterin (methotrexate), $N_{10}$-methylfolate, 2-deamino-hydroxyfolate, deaza analogs such as 1-deazamethopterin or 3-deazamethopterin, and 3'5'-dichloro4-amino-4-deoxy-$N_{10}$-methylpteroyl-glutamic acid (dichloromethotrexate). Methods of conjugating molecules to folates that are suitable for covalent attachment to compounds of the present invention are disclosed in U.S. Pat. Nos. 6,576,239, 5,820,847, 5,688,488, 5,108,921, 5,635, 382, and 5,416,016 the contents of which are incorporated herein by reference. Methods of conjugating molecules to vitamin C that are suitable for covalent attachment of compounds of the present invention are disclosed in S. Manfrdini et al. J. Med. Chem. 2002, 45, 559-562, the contents of which are incorporated herein by reference.

Representative peptides and peptidomimetics that may be used as targeting agents include, but are not limited to, an RGD-containing peptide selected from the group consisting of RGDs, c(RGDfK), vitronectin, fibronectin, somatostatin-receptor agonists and somatostatin-receptor antagonists. Molecules that bind to the $\alpha_v\beta_3$ integrin receptor and act as antagonists may be used as targeting agents are described in U.S. Pat. Nos. 6,552,079, 6,426,353B, WO 2002/40505A2, and U.S. Patent Publications 2002/0055499, 2002/0061885, 2002/0065291, 2002/0072500, U.S. 2002/0072518; W. Arap et al. Science 1998, 279, 377-380; R. J. Kok et al. Biojonjugate Chem. 2002, 13, 128-135; D. A. Sipkins et al. Nat. Med. 1998, 4, 623-626; P. M. Winter et al. Cancer Res. 2003, 63, 5838-5843; and J. D. Hood et al. Science 2002, 296, 2404-2407; the contents of which are incorporated herein by reference. Representative proteins that may be used as targeting agents include, but are not limited to, antibodies or fragments thereof, such as a tumor-specific monoclonal antibody or fragment thereof. Representative bone-seeking agents that may be used as targeting agents include, but are not limited to, phosphonate, phosphonic acid, aminomethylphosphonic acid, phosphate, polyphosphate, and hydroxyapatite-binding polypeptides. Other peptides include chlorotoxin (U.S. Pat. No. 6,429,187B1) and tissue factor (G. M. Lanza et al. Circulation 2002, 106, 2842-2847).

Other suitable targeting agents include antibodies. The antibodies may be of classes IgG, IgM, IgA, IgD or IgE, or fragments or derivatives thereof, including Fab, $F(ab')_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibodies may also be a chimeric antibody. The antibodies may be directed against a variety of antigenic determinants including those associated with tumors, histocompatibility and other cell surface antigens, bacteria, fungi, viruses, enzymes, toxins, drugs and other biologically active molecules. Antigens associated with tumors for which antibodies may be specifically reactive include, but are not limited to, such antigens as are and include, but are not limited to, carcinoembryonic antigen (CEA), mucins such as TAG-72, human milk fat globule antigens, prostate serum antigen (PSA), prostate specific membrane antigen (PSMA), PS (phosphatidyl serine), and receptors including, but not limited to, the IL-2, EGF, VEGF and transferrin receptors. Other representative antigens associated with tumors include, but are not limited to, those tumor-associated antigens described in J. R. Zalcberg et al. J. Clin. Oncology 1985, 3, 876-882, World Patent WO 01/68709A1, and U.S. Patent Publication US2004/0009122A1, the contents of which are incorporated herein by reference.

Other suitable targeting agents include glucose, galactose, mannose, mannose 6-phosphate, hormones (e.g., insulin, growth hormone, and the like), growth factors or cytokines (e.g., TGF-beta, EGF, insulin-like growth factor, and the like), $YEE(GalNAcAH)_3$ or derivatives, cobalamin, alpha-2 macroglobulins, asialoglycoprotein, albumin, texaphyrin, metallotexaphyrin, antibodies, antibody fragments (e.g., Fab), single-chain antibody variable region (scFv), transferrin, any vitamin and any coenzyme.

The targeting agent may also be an agent that delivers a compound of the invention to bones. Bone targeting agents include, but are not limited to, bisphosphonates, EDTMP DOTMP, and ABEDTMP, which are disclosed in U.S. Pat. Nos. 4,937,333, 4,882,142, 5,064,633 and World Patent WO-94/00143, the contents of which are incorporated herein by reference. DOTMP and EDTMP may be attached to the linker moiety by any suitable coupling method including, but not limited to, coupling chemistry where the R group can have an appropriate electrophilic or nucleophilic group that reacts with the nucleophilic or electrophilic (respectively) group of the linker moiety. Further details of the coupling chemistry are provided in Tetrahedron 1999, 55, 12997-13010, the contents of which are incorporated by reference. Further details of bone-targeted prodrugs and coupling chemistry are provided in Proc. SPIE-Int. Soc. Opt. Eng. 1999, 3600 (Biomedical Imagn. Reporters Dyes & Instrumental, 99-106; U.S. Pat. No. 5,177,054; J. Med. Chem. 1994, 37, 498-511; Tetrahedron Lett. 1989, 30. 7141-7144; T. J. Houghton et al. J. Med. Chem. 2008, 51, 6955-6969; and U.S. Pat. No. 5,955,453, the contents of which are incorporated by reference.

The targeting agent may be used to deliver a conjugate of the invention (or salt thereof) to bones as a slow release reservoir site for the compounds of the present invention. The targeting agent may be a bone seeking (osteotropic) moiety attached to the compounds of the present invention via an acid cleavable linker. Examples of an acid cleavable linker include, but are not limited to, an ortho acid-amide linkage. Under acidic conditions the protein-ACL-3 amide linkage is readily cleaved freeing the native amino group of the amide functionality as described in WO-94/00143 the contents of which are incorporated by reference. During osteoclastic bone resorption, which involves an acidic mediated mechanism, the attachment tethering the prodrug to bone may be cleaved releasing the compounds of the present invention. Methods and particular bone-targeting agents are disclosed in U.S. Pat. No. 6,949,537, the entire contents of which are herein incorporated by reference.

The targeting agent may also comprise an RGD peptide moiety. As discussed in F. Curnis et al. Cancer Res. 2004, 64, 565-571, RGD moieties target RGD fusion proteins to vasculature by interacting with cell adhesion receptors, including $\alpha_v\beta_3$ integrin.

Conjugate compounds according to this aspect of the invention are depicted by Formula V or Formula VI wherein a hydrolyzable linker Rc is in either of two positions (as shown).

Formula V

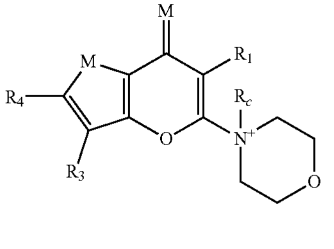

-continued

Formula VI

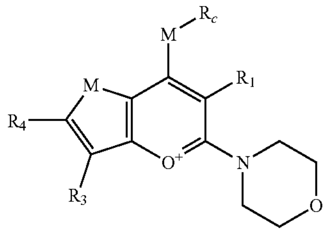

Wherein M is independently O or S and R1, R3, and R4 independently represent H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

Rc comprises a hydrolyzable linker group (L) which is optionally substituted with a targeting agent (T).

In one embodiment, a targeted conjugate used in the methods of the invention of Formula V or VI is one in which Rc has the structure:

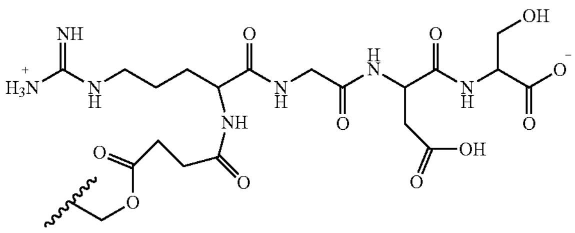 [SMILES: *COC(=O)CCC(=O)NC(CCCNC(=N)N)C(=O)NCC(=O)NC(CC(=O)O)C(=O)NC(CO)C(=O)O]

A pharmaceutically acceptable salt of a compound used in the methods of the instant invention is one which is the acid addition salt of a basic compound of formula I-VI with an inorganic or organic acid which affords a physiologically acceptable anion or which is the salt formed by an acidic compound of Formula I-VI with a base which affords a physiologically acceptable cation and provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a compound of formula I-VI (or a pharmaceutically acceptable salt thereof) as provided in any of the descriptions herein.

In addition, compounds (or salts thereof) of the present invention are useful as an active ingredient in the manufacture of a medicament for use in inhibiting kinase activity, e.g., PI-3 kinase activity and/or bromodomain activity, and/or CDK4/6 activity.

The present invention also provides a method for treating a disease in a human or other mammal including, but not limited to, cancer, non-cancer proliferative disease, sepsis, autoimmune disease, viral infection, atherosclerosis, Type 1 or 2 diabetes, obesity, inflammatory disease, and Myc-dependent disorder by administering a therapeutically effective amount of a compound(s) of Formula I-VI or conjugate or prodrug thereof having any of the definitions herein.

The present invention further provides a method of inhibiting CDKs by providing a compound of Formula I-VI, including administering to a human in need of such treatment, an effective dose of a compound of Formula I-VI or conjugate or prodrug thereof having any of the definitions herein.

Further, the present invention provides a method of inhibiting tumor growth comprising administering to a mammal in need of treatment, an effective dose of a compound of Formula I-VI, or conjugate or prodrug thereof, having any of the definitions herein.

Also, there is provided a compound of Formula I-VI (or conjugate, prodrug, or salt thereof) having any of the definitions herein for use as an anticancer agent.

As an additional feature of the invention there is provided a pharmaceutical formulation comprising in association with a pharmaceutically acceptable carrier, diluent or excipient, a compound or conjugate of a compound of Formula I-VI (or of a pharmaceutically acceptable salt thereof) as provided in any of the descriptions herein.

The present invention also includes methods of use of isotopically-labeled compounds, and pharmaceutically acceptable salts thereof, which are identical to those recited in Formulas I through VI, but replace one or more atoms by a corresponding isotope. Examples of isotopes that can be incorporated into compounds of the invention include isotopes of hydrogen, carbon, nitrogen, oxygen, phosphorous, fluorine and chlorine. Compounds of the present disclosure, conjugates thereof, and pharmaceutically acceptable salts of said compounds or of said conjugates which contain the aforementioned isotopes and/or other isotopes of other atoms are within the scope of this disclosure. Certain isotopically-labeled compounds of the present disclosure, for example those into which radioactive isotopes, such as 2H, 3H, 14C, 15N, 32P and 131I are incorporated, are useful in drug and/or substrate tissue distribution assays for example when imaging tumors. Fluorine-18 (18F) is particularly preferred for ease of preparation and detectability. Isotopically labeled compounds of the invention can generally be prepared by carrying out the procedures disclosed in the Schemes and/or in the Examples and Preparations below, by substituting a readily available isotopically labeled reagent for a non-isotopically labeled reagent.

It will be appreciated that certain compounds of Formula I-VI (or salts, procompounds, conjugates, etc.) and methods using such compounds may exist in, and be isolated in, isomeric forms, including tautomeric forms, cis- or trans-isomers, as well as optically active, racemic, enantiomeric or diastereomeric forms. It is to be understood that the present invention encompasses a compound of Formula I-VI in any of the tautomeric forms or as a mixture thereof; or as a mixture of diastereomers, as well as in the form of an individual diastereomer, and that the present invention encompasses a compound of Formula I-VI as a mixture of enantiomers, as well as in the form of an individual enantiomer, any of which mixtures or form possesses inhibitory properties against kinases including PI3 kinase, it being well known in the art how to prepare or isolate particular forms and how to determine inhibitory properties against kinases by standard tests including those described herein below.

In addition, a compound of Formula I-VI (or salt, pro-compound, conjugate thereof, etc.) used in the methods of the invention may exhibit polymorphism or may form a solvate with water or an organic solvent. The present invention also encompasses any such polymorphic form, any solvate or any mixture thereof.

Methods of the invention include use of a pharmaceutically acceptable salt of a compound defined by the above Formula I-VI. A basic compound used in methods of this invention possess one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzene-sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

D.1. Synthesis of Compounds and Conjugates

The compounds of the present invention may be prepared according to the examples provided herein as well as processes known in the chemical arts and described in U.S. Pat. No. 8,557,807 and references cited therein as well as G. A. Morales et al., J. Med. Chem. 2013, 56, 1922-1939 the entire contents of which are herein incorporated by reference. Starting materials and intermediates used to prepare a compound of the invention are either commercially available or can be easily prepared by one of ordinary skill in the art. Compounds and conjugates described herein and used in the methods of the invention can be made, for example, by the procedures disclosed in U.S. Pat. Nos. 6,949,537; 7,662,977; 7,396,828; 8,557,807; and 9,505,780; and in U.S. patent application Ser. Nos. 14/702,816, and 15/297,293, the entire contents of which are herein incorporated by reference. Compounds of the present invention may also be prepared by methods described in for example US20100160340 (LY2835219/Abemaciclib), WO2010020675 (PD-0332991/Palbociclib), WO2010020675 (LEE-011/Ribociclib), WO200803215 (Palbociclib) and U.S. Pat. No. 7,781,583 (Palbociclib) which are herein incorporated by reference. Thio compounds can be made as described in the art from oxygen analogs, for example by using Lawesson's reagent as described in Morales et al., J. Med. Chem. 2013. Furan analogs of the thiophene-pyranone compounds (termed thienopyranones) can be made for example by the general schemes outlined below where the key intermediate "g" is prepared and utilized. The intermediate "g" is then further elaborated to the oxygen analog of "compound 6" as described in Morales et al., J. Med. Chem. 2013 (reference incorporated herein) which is designated compound "i". Compound "i" can then be reacted via couplings with boronates to make final substituted furanopyranones of the invention. Alternatively, the bromine atom in compound "i" can be converted to a boron derivative and then coupled with aryl or heteroaryl bromides or iodides to make furanopyranones of the invention.

A reaction scheme is shown below for preparing furanopyranones of the invention via the key furan intermediate "g" and subsequent conversion to "i" which is then further reacted to produce compounds of the invention:

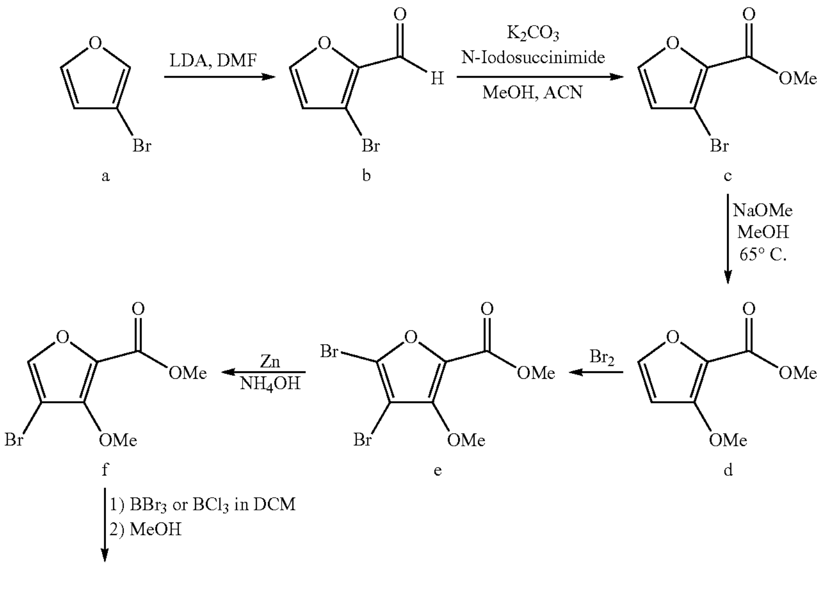

-continued

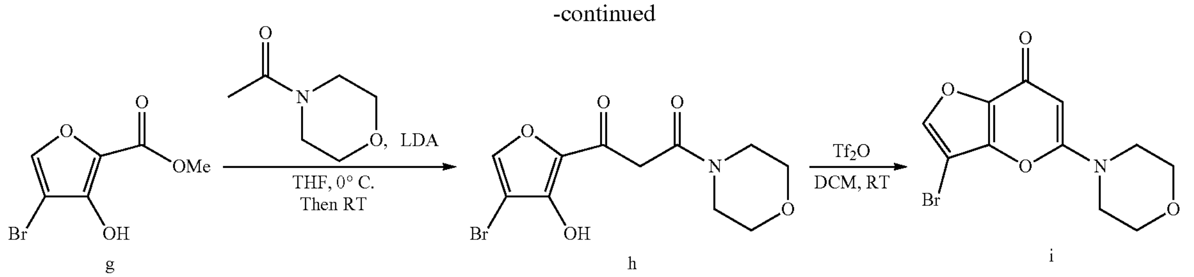

g h i

Expanded Reaction Scheme for Introducing Substituents at R4:

And to add $R_4$ groups

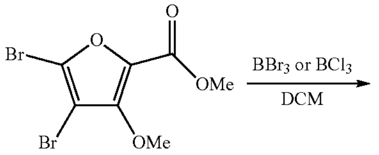

e

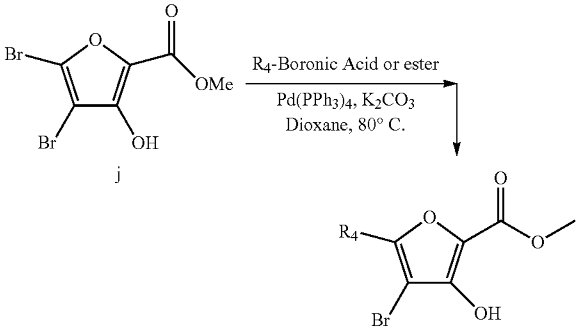

j k
US Patent
US-20120022059-A1

Scheme for Introducing Substituents at R4 of TP Scaffold Core

The selective introduction of substituents at the R4 position is based on the synthesis of molecule "m" (R4 is pyrazole) starting from molecule "1" as disclosed in US Patent US 2016/0287561, the entire contents of which is herein incorporated by reference.

And to add $R_4$ groups

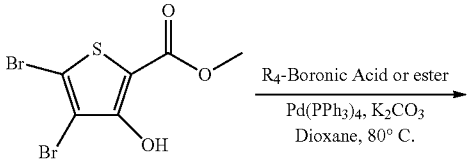

l
Commercially available
CAS 96232-71-2
U.S. Pat. No. 4,824,958

-continued

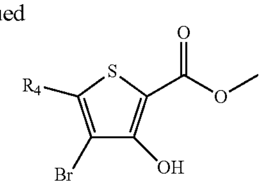

m
US Patent Application
US 2016/0287561

An additional scheme to obtain furanopyranones is shown below using $NaN_3$ to arrive at the key bromo-hydroxy-furan "g" which can then be used to make intermediate "i" and subsequent elaboration to compounds of the invention:

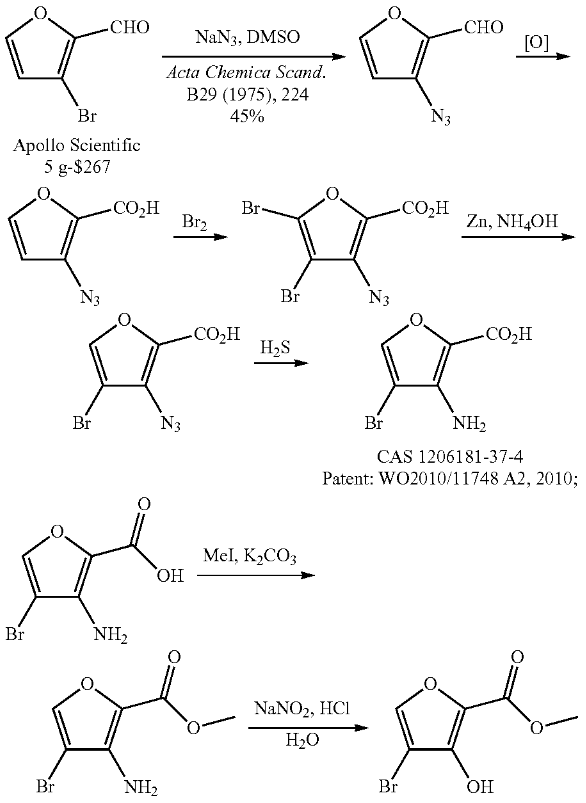

Compounds of the invention with various R2 substituents other than morpholine are made using for example acetylated amines, acetylated alcohols or other methyl ketones in place of the acetyl morpholine. For example, use of acetone in the reaction scheme would give R2=methyl group. Also, compounds of the invention with various R1 substituents are made using substituted ketones or substituted acetyl morpholine for example use of propionylmorpholine would yield R1=methyl group.

The compounds used in the methods of the invention, or their pharmaceutically acceptable salts, may have asymmetric carbon atoms or quaternized nitrogen atoms in their structure. It will be appreciated that certain compounds of Formula I (or salts, conjugates, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as a mixture thereof; or as a mixture of diastereomers, as well as in the form of an individual diastereomer, and that the present invention encompasses a compound of Formula I as a mixture of enantiomers, as well as in the form of an individual enantiomer, any of which mixtures or form possesses inhibitory properties against kinases, for example PI-3 kinases. The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of the invention.

Additional synthetic methodologies to prepare the compounds of the invention are described in the compound preparations described in the Examples.

E. Formulations

As an additional aspect of the invention there is provided a pharmaceutical formulation or composition comprising in association with a pharmaceutically acceptable carrier, diluent or excipient, a compound of the invention, e.g., Formula I (or a pharmaceutically acceptable salt or procompound or conjugate thereof) as provided in any of the descriptions herein. Compositions of the present invention may be in the form of tablets, capsules, or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions of the present invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions of the present invention may also be formulated as suppositories, which may contain suppository bases including, but not limited to, cocoa butter or glycerides. Compositions of the present invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of the present invention may also be formulated transdermal formulations comprising aqueous or nonaqueous vehicles including, but not limited to, creams, ointments, lotions, pastes, medicated plaster, patch, or membrane.

Compositions of the present invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of the present invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of the present invention may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh et al., U.S. Pat. No. 4,621,023 of Redziniak et al. or U.S. Pat. No. 4,508,703 of Redziniak et al. can be used. Other suitable formulations can employ niosomes. Niosomes are lipid vesicles similar to liposomes, with membranes consisting largely of non-ionic lipids, some forms of which are effective for transporting compounds across the stratum corneum.

The following formulation examples are illustrative only and are not intended to limit the scope of the compounds, or formulations, or methods of the invention in any way. The phrase "active ingredient" refers herein to a compound according to Formula I-VI or a pharmaceutically acceptable salt, procompound, conjugate, or solvate thereof.

Formulation 1:
Tablet containing the following components:

| Ingredient | Amount (mg/tablet) |
|---|---|
| Active ingredient | 250 |
| Dried starch | 200 |
| Magnesium stearate | 10 |
| Total | 460 mg |

| Formulation 2: Capsules containing the following components: | |
|---|---|
| Ingredient | Amount (mg/tablet) |
| Active ingredient | 60 |
| Dried starch | 44 |
| Magnesium stearate | 1.5 |
| Microcrystalline cellulose | 44 |
| Total | 150 mg |

Parenteral dosage forms for administration to patients by various routes including, but not limited to, subcutaneous, intravenous (including bolus injection), intramuscular, and intra-arterial are also contemplated by the present invention. Parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

An example parenteral composition used in a method of the invention would be intended for dilution with aqueous solution(s) comprising for example 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8.

F. Therapeutic Use

Compounds and compositions described herein are generally useful for treating diseases and disorders including, but not hinted to, cancer, non-cancer proliferative disease, sepsis, autoimmune disease, viral infection, atherosclerosis, Type 2 diabetes, obesity, inflammatory disease, or Myc-dependent disorder by administering a therapeutically effective dose of a compound of Formula I-VI. Without intending to be bound by theory, it is believed that the therapeutic effect of compounds and compositions of the invention in treating a mammal, including a human, may relate to the capacity of such compounds and compositions to inhibit Checkpoint proteins such as CDK4 and CDK6, and/or to the inhibition of PI3K, and/or to the inhibition of one or more proteins involved in epigenetic regulation mediated by bromodomain proteins.

In one embodiment the invention provides a therapeutic method in which the PI3K pathway is modulated by inhibiting PI3K.

In another aspect, the invention provides a method to modulate epigenetic regulation involving bromodomain proteins (e.g., BET proteins, such as BRD2, BRD3, BRD4, and/or BRDT, and non-BET proteins, such as CBP, ATAD2A, GCN5L, BAZ2B, FALZ, TAF1, and/or BRPF1), by administering a compound as described herein. In some embodiments, the compounds described herein are capable of inhibiting the activity of a bromodomain-containing protein, such as a BET protein (e.g., BRD2, BRD3, BRD4 and/or BRDT), non-BET proteins (e.g., CBP, ATAD2A, GCN5L, BAZ2B, FALZ, TAF1, and/or BRPF1) or a mutant thereof, in a biological sample useful for purposes including, but are not limited to, blood transfusion, organ-transplantation, biological specimen storage, and biological assays.

In other aspects, the present invention provides a method of inhibiting the activity of a bromodomain-containing protein, such as a BET protein (e.g., BRD2, BRD3, BRD4 and/or BRDT), non-BET proteins (e.g., CBP, ATAD2A, GCN5L, BAZ2B, FALZ, TAF1, and/or BRPF1) or a mutant thereof, in a patient comprising the step of administering to said patient a compound or composition of the invention having bromodomain inhibitory activity.

The present invention also encompasses methods of treatment comprising administration of a compound(s) of Formula I-VI including methods of treatment of a patient suffering from a condition or disease associated with aberrant kinase activity including PI-3 kinase, or associated with MYC (c-MYC or MYCN) driven disease, or any disease abated by a bromodomain inhibitor. In one aspect, kinase activity may be abnormal, excessive, or constitutively active in a patient in need of such treatment.

The present invention also relates to a method for treating an inflammatory disease comprising administering to a patient in need thereof a therapeutically effective amount of compound(s) of Formula I-VI. Exemplary, but non-exclusive inflammatory diseases and adverse health conditions attributable to kinase activity, in particular inappropriate PI-3 kinase signaling activity, have been disclosed in the art, for example U.S. 2002/0150954A1; U.S. Pat. Nos. 5,504,103; 6,518,277B1; 6,403,588; 6,482,623; 6,518,277; 6,667,300; US 20030216389; US 20030195211; U.S. 20020037276 and U.S. Pat. No. 5,703,075 the contents of which are herein incorporated by reference.

Treatment methods of the invention also include administration of a therapeutically effective amount of a compound of Formulas I-VI to treat CNS disorders, including schizophrenia, episodic paroxysmal anxiety (EPA) disorders such as obsessive compulsive disorder (OCD), post-traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; and attention deficit/hyperactivity disorder (ADHD).

In another aspect, the present invention provides a method for treating Alzheimer's Disease comprising administering to a patient in need thereof a therapeutically effective amount of a compound of Formula I-VI. It has been reported that increasing PIP2 concentrations by, for example, inhibiting PI-3 kinase decreases levels of neurotoxins associated with Alzheimer's Disease (US 2008/0312187; incorporated herein by reference).

In another aspect, the present invention provides a method for enhancing the chemosensitivity of tumor cells comprising administering to a patient in need thereof a therapeutically effective amount of a compound of Formula I-VI.

In another aspect, the present invention provides a method for enhancing the radiosensitivity of tumor cells comprising administering to a patient in need thereof a therapeutically effective amount of a compound of Formula I-VI.

In another aspect, the present invention provides a method for inhibiting or reducing tumor growth comprising administering to a patient in need thereof a therapeutically effective amount of a compound of a compound of Formula I-VI.

In another aspect, the present invention provides a method for inducing oxidative stress in tumor cells comprising administering to a patient in need thereof a therapeutically effective amount of a compound of Formula I-VI.

In another aspect, the present invention provides a method for inhibiting or reducing tumor growth by inhibiting cancer stem cell growth and/or proliferation comprising administering to a patient in need thereof a therapeutically effective amount of a compound of Formula I-VI.

In another aspect, the present invention provides a method for inhibiting tumor induced angiogenesis comprising administering to a patient in need thereof a therapeutically effective amount of a compound of Formula I-VI.

Further, the present invention provides a method for inhibiting angiogenesis associated with non-cancer diseases comprising administering to a patient in need thereof a therapeutically effective amount of a compound of Formula I-VI.

In yet another aspect, the present invention provides a therapeutic method for increasing apoptosis in cancer cells and cancerous tumors comprising administering to a patient in need thereof a therapeutically effective amount of a compound of Formula I-VI.

The present invention also provides a method of treating cancer comprising administering to a patient in need thereof a therapeutically effective amount of a compound of Formula I-VI.

Kinase, bromodomain, and cyclin-dependent kinase inhibitory activity of a compound of the invention can be determined routinely by methods known to the skilled artisan. For example, in vitro kinase inhibition (e.g., PI3K inhibition) can be detected by a standard kinase inhibition assay using labeled ATP to determine if a test compound inhibits the transfer of phosphate from ATP to the kinase substrate. In vivo, PI3K inhibition can be determined from target tissue biopsies by standard tissue processing to disrupt cells and then performing Western Blot analysis to determine the presence or absence of pAKT (substrate of PI3K) relative to a control sample. The activity of a compound of the invention as an inhibitor of a bromodomain-containing protein, such as a BET protein, such as BRD2, BRD3, BRD4, and/or BRDT, or an isoform or mutant thereof, may be determined in vitro, in vivo, or in a cell line. In vitro assays include assays that determine inhibition of bromodomain-containing proteins. Alternatively, inhibitor binding may be determined by running a competition experiment where a provided compound is incubated with a bromodomain-containing protein, such as a BET protein bound to known ligands, labeled or unlabeled. For example, bromodomain inhibition can be determined in vitro using Alpha Screen Technology (Perkin Elmer Life and Analytical Sciences, Shelton, CT). In vivo bromodomain inhibition can be determined indirectly by evaluating the amount of a protein whose gene' transcription is influenced or controlled by the bromodomain protein, for example, the MYCN protein transcription is controlled by BRD4 (J. E. Delmore et al., Cell 2011, 146, 904-917; A. Puissant, Cancer Discov. 2013, 3, 308-323). Bromodomain inhibition may also be predicted by in silico modeling as described below in the Examples.

Representative compounds of the invention were characterized for their ability to inhibit the target proteins using third party vendors offering such services. PI3K-alpha, PI3K-beta, PI3K-gamma, and PI3K-delta inhibition activity was determined by Thermo Fisher Scientific-Biosciences Life Sciences Solutions, Madison, WI. Bromodomain protein inhibition (binding domain 1 and 2 of BRD2, BRD3, BRD4, and BRDT) was determined by Reaction Biology Corp., Malvern, PA. Further analysis of compounds against a larger 40-bromodomain protein selection (Bromoscan) was performed by DiscoverX, San Diego, CA. The cyclin dependent kinase inhibition on proteins such as CDK2, CDK4, CDK6, and CDK9 was determined by Reaction Biology Corp., Malvern, PA. To obtain selectivity data, a large collection of 468 human kinases was screened for inhibition using the KINOMEscan™ Profiling Service at DiscoverX, San Diego, CA. Lastly, pharmacokinetic parameters (PK) and other adsorption, distribution, metabolism, and excretion data (ADME) were determined by the third-party service provider Quintara Discovery (Hayward, CA). Additional information on each of the above testing procedures and services is available at each company's website on the internet.

In certain embodiments, the invention provides a method for treating a disorder (as described above) in a subject in need thereof, comprising administering a therapeutically effective amount of a compound of the invention. The identification of those patients who are in need of treatment for the disorders described herein is within the ability and knowledge of one skilled in the art. Certain of the methods for identification of patients who are at risk of developing the above disorders which can be treated by the subject method are appreciated in the medical arts, such as through family history, and the presence of risk factors associated with the development of that disease state in the subject patient.

Assessing the efficacy of a treatment in a patient includes determining the pre-treatment extent of a disorder by methods known in the art (i.e., determining tumor size or screening for tumor markers where the cell proliferative disorder is cancer), then administering a therapeutically effective amount of a compound of the invention, to the patient. After an appropriate period of time after administration (e.g., 1 day, 1 week, 2 weeks, one month, six months), the extent of the disorder is again determined. Modulation (e.g., decrease) of the extent or invasiveness of the disorder (i.e., reduced tumor size) would indicate efficacy of the treatment. The extent or invasiveness of the disorder may be determined periodically throughout treatment. For example, the extent or invasiveness of the disorder may be assessed every few hours, days, weeks, or months to assess the further efficacy of the treatment. A decrease in extent or invasiveness of the disorder indicates that the treatment is efficacious. The methods described may be used to screen or select patients that may benefit from treatment with a compound of the invention.

A variety of cancers may be treated according to the methods of the present invention including, but not limited to: carcinoma of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma. The methods of the invention may also be used to treat accelerated or metastatic cancers of the bladder, pancreatic cancer, prostate cancer, non-small cell lung cancer, colorectal cancer, and breast cancer.

A method for treating cancer according to the invention may be administered simultaneously or metronomically with other anti-cancer treatments such as chemotherapy and radiation therapy. The term "simultaneous" or "simultaneously" as used herein, means that the other anti-cancer treatment and the compound of the present invention are administered within 48 hours, preferably 24 hours, more preferably 12 hours, yet more preferably 6 hours, and most preferably 3 hours or less, of each other. The term "metronomically" as used herein means the administration of the compounds at times different from the chemotherapy and at a certain frequency relative to repeat administration and/or the chemotherapy regimen.

Chemotherapy treatment may comprise administration of a cytotoxic agent or cytostatic agent, or combination thereof. Cytotoxic agents prevent cancer cells from multiplying by: (1) interfering with the cell's ability to replicate DNA, and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include but are not limited to the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-.alpha.), etoposide, and teniposide. Other proliferative cytotoxic agents are navelbene, CPT-11, anastrazole, letrazole, capecitabine, reloxafine, yclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see R. F. Service, Science 1996, 274, 2009) estramustine, nocodazole, MAP4, and the like. Examples of such agents are also described in J. C. Bulinski et al., J. Cell Sci. 1997, 110, 3055-3064; D. Panda et al., Proc. Natl. Acad. Sci. USA 1997, 94, 10560-10564; P. F. Muhlradt et al., Cancer Res. 1997, 57, 3344-3346; K. C. Nicolaou et al., Nature 1997, 387, 268-272; R. J. Vasquez et al., Mol. Biol. Cell. 1997, 8, 973-985; and D. Panda et al., J. Biol. Chem. 1996, 271, 29807-29812.

Other suitable cytotoxic agents include but are not limited to epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used according to the methods of the invention include, but are not limited to, hormones and steroids (including synthetic analogs): 17 alpha-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, zoladex. Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and Src inhibitors. Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include but are not limited to epidermal growth factor inhibitors, Her-2 inhibitors, MEK-1 kinase inhibitors, MAPK kinase inhibitors, PI3K inhibitors, Src kinase inhibitors, and PDGF inhibitors.

The present invention also encompasses a method for treating pancreatitis comprising administering to a patient in need thereof a therapeutically effective amount of a compound or compounds of Formula I-VI. As discussed in I. Gukovsky et al., Gastroenterology 2004, 126, 554-566, inhibition of PI-3 kinase may prevent pancreatitis.

The present invention also encompasses a method for treating ulcers comprising administering to a patient in need thereof a therapeutically effective amount of a compound of Formula I-VI. The present invention also encompasses a method for treating gastric cancer, such as stomach cancer, comprising administering to a patient in need thereof a therapeutically effective amount of a compound of the present invention. As discussed in Bacon et al., Digestive Disease Week Abstracts and Itinerary Planner, Vol. 2003, Abstract Number M921 (2003) and Rokutan et al., Digestive Disease Week Abstracts and Itinerary Planner, Vol. 2003, Abstract Number 354 (2003), PI-3 kinase is involved in the adhesion of *Helicobacter pylori* to gastric cells.

The present invention also encompasses a method for treating age-related macular degeneration (AMD) comprising administering to a patient in need thereof a therapeutically effective amount of a compound of Formula I-VI. As discussed in M. R. Barakat et al., Expert Opin. Investig. Drugs 2009, 18, 637-646, inhibition of VEGF inhibits blood vessel overgrowth associated with AMD. The methods of the invention may also treat AMD by inhibiting angiogenesis.

The present invention also encompasses a method for treating conditions associated with a mutant PTEN comprising administering to a patient in need thereof a therapeutically effective amount of a compound of Formula I-VI. PTEN is a tumor suppressor gene located on chromosome 10q23, in which mutations have been identified in patients with Cowden disease. As discussed in A. Vega et al., J. Invest. Dermatol. 2003, 121, 1356-1359, mutations in PTEN have reduced ability to inhibit the activation of the proto-oncogene AKT. Inhibitors of PI-3 kinase may inhibit phosphorylation of AKT, thereby reducing the deleterious effect of mutant PTEN.

Tat is the human immunodeficiency virus type 1 (HIV-1) trans-activator protein and is known to be tightly regulated by lysine acetylation (R. E. Kiernan et al., EMBO Journal 1999, 18, 6106-6118). It is also known that HIV-1 Tat transcriptional activity is absolutely required for productive HIV viral replication (K. T. Jeang et al., Curr. Top. Microbiol. Immunol. 1994, 188, 123-144). Thus, the interaction of the acetyl-lysine of the protein Tat with one or more bromodomain-containing proteins (which are associated with chromatin remodeling) could mediate gene transcription allowing viral replication. Blocking bromodomain-containing proteins can thus serve to inhibit HIV viral replication and act as a therapeutic treatment for diseases involving HIV viral replication such as AIDS. The present invention encompasses a method for treating diseases involving HIV viral replication such as but not limited to AIDS comprising administering to a patient in need thereof a therapeutically effective amount of a compound of Formula I-VI. The methods of this invention comprised of administering one or more compounds of Formula I-VI are useful for treating viral infections such as but not limited to human papillomavirus, Herpesvirus, Epstein-Barr virus, human immunodeficiency virus, hepatitis B virus, and hepatitis C virus.

In another aspect, the invention provides a method for inhibiting activity of a bromodomain-containing protein in a patient comprising the step of administering to said patient a compound or compounds of Formula I-VI either alone or in combination with other treatment agents.

In another aspect, the invention provides a method for treating bromodomain-containing protein-mediated disorders in a patient in need thereof, comprising administering to said patient a compound of Formula I-VI.

The methods of the invention also include treating a subject with a MYC-dependent cancer, comprising administration of a compound of Formula I-VI. Subjects with MYC-dependent cancer can be determined by several ways including but not limited to determining MYC mRNA expression levels in the tumor and/or MYC protein expression in the tumor. Preferred subjects for treatment with the methods of the invention can be identified by historical experience or known prevalence of MYC activation in certain cancers such as multiple myeloma (J. E. Delmore, Cell 2011, 146, 904-917), CLL (J. R. Brown et al., Clin. Cancer Res. 2012, 18, 3791-3802), leukaemia (M. A. Dawson et al., Nature 2013, 478, 529-533), neuroblastoma (A. Puissant et al., Cancer Discov. 2013, 3, 308-323), or medulloblastoma (Y. J. Cho et al., J. Clin. Oncol. 2010, 29, 1424-1430).

Other diseases and conditions treatable according to the methods of this invention include, but are not limited to, other proliferative disorders, sepsis, autoimmune disease, and viral infection. Diseases such as atherosclerosis and Type 2 diabetes (V. A. DeWaskin et al., Nature Rev. Drug Disc. 2013, 12, 661-662) and obesity and inflammation (A. C. Belkina et al., Nature Rev. Cancer 2012, 12, 465-474) are also treatable according to the methods of the invention.

The invention further provides methods for treating or ameliorating cancer or other proliferative disorder by administration of an effective amount of a compound of Formula I-VI to a mammal including a human in need of such treatment. Examples of cancers treatable using an effective amount of a compound of Formula I-VI include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangio sarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

The methods of this invention further include administering one or more compounds of Formula I-VI for treating benign proliferative disorders such as, but are not limited to, meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

The methods of this invention further comprise administering one or more compounds of Formula I-VI for treating infectious and noninfectious inflammatory events and autoimmune and other inflammatory diseases. Examples of autoimmune and inflammatory diseases, disorders, and syndromes treated using the compounds and methods described herein include but are not limited to: appendicitis, pancreatitis, cholecystitis, agammaglobulinemia, psoriasis, allergy, Crohn's disease, irritable bowel syndrome, ulcerative colitis, inflammatory pelvic disease, urethritis, skin sunburn, sinusitis, pneumonitis, encephalitis, meningitis, myocarditis, nephritis, osteomyelitis, myositis, asthma, allergic rhinitis, chronic obstructive pulmonary disease, autoimmune polyglandular disease/syndrome, autoimmune alopecia, pernicious anemia, glomerulonephritis, dermatomyositis, multiple sclerosis, scleroderma, hepatitis, gastritis, enteritis, dermatitis, gingivitis, Sjogren's disease, tissue graft rejection, hyperacute rejection of transplanted organs, vasculitis, autoimmune hemolytic and thrombocytopenic states, Goodpasture's syndrome, atherosclerosis, Addison's disease, Parkinson's disease, Alzheimer's disease, Type I or 2 diabetes, septic shock, systemic lupus erythematosus, rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Graves' disease, Guillain-Barre syndrome, Behcet's disease, scleracierma, mycosis fungoides, acute respiratory distress syndrome and ischemia/reperfusion injury. In some embodiments, the present invention provides a method of treating systemic inflammatory response syndromes such as LPS-induced endotoxic shock and/or bacteria-induced sepsis by administration of an effective amount of a compound of Formula I-VI to a mammal in need of such treatment.

Administration and Dosage

Compounds of Formula I-VI for use in a method of the present invention can be administered in any manner including but not limited to orally, parenterally, sublingually, transdermally, rectally, transmucosally, topically, pulmonarily, nasally, or bucally. Parenteral administration includes but is not limited to intravenous, intraarterial, intraperitoneal, subcutaneous, intramuscular, intrathecal, and intraarticular. Compounds or compositions of the invention may also be administered via slow controlled i.v. infusion or by release from an implant device.

A therapeutically effective amount of a compound of Formula I to VI for use in a method of the invention varies with the nature of the condition being treated, the length of treatment time desired, the age and the condition of the patient, and is ultimately determined by the attending physician. In general, however, doses employed for adult human treatment typically are in the range of 0.001 mg/kg to about 200 mg/kg per day. The dose may be about 1 μg/kg to about 100 μg/kg per day. The desired dose may be conveniently administered in a single dose, or as multiple doses administered at appropriate intervals, for example as two, three, four or more sub-doses per day. Multiple doses often are desired, or required.

A number of factors may lead to the compounds of Formula I-VI being administered according to the methods of the invention over a wide range of dosages. When given in combination with other therapeutic agents, the dosage of the compounds of the present invention may be given at relatively lower dosages. In addition, the use of targeting agents on a conjugate is expected to lower the effective dosage required for treatment. As a result, the daily dosage of a targeted compound administered according to the methods of the present invention may be from about 1 ng/kg to about 100 mg/kg. The dosage of a compound of Formula I-VI according to the methods of the present invention may be at any dosage including, but not limited to, about 1 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

TABLE 1
| Representative compounds of the invention. | | | |
|---|---|---|---|
| Compound Number | Formula Number | Structure | Molecular Weight |
| 0 | I | 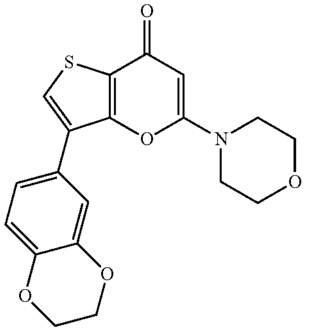 [SMILES: O=c1cc(N2CCOCC2)oc2c(-c3ccc4c(c3)OCCO4)csc12] | 371.41 |
| 1 | II | 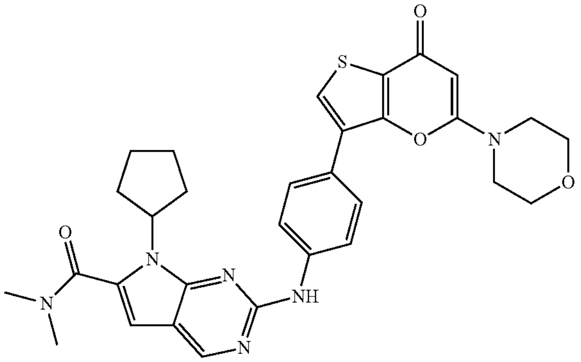 | 584.69 |
| 2 | III | 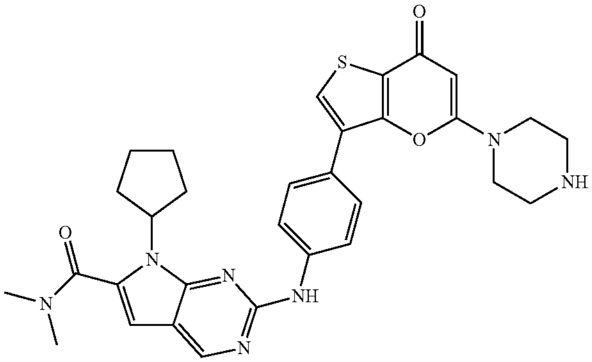 [SMILES: CN(C)C(=O)c1cc2cnc(Nc3ccc(-c4csc5c(=O)cc(N6CCNCC6)oc45)cc3)nc2n1C1CCCC1] | 583.70 |
| 3 | IV | 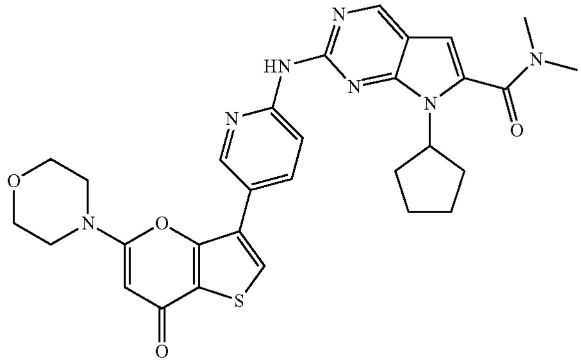 [SMILES: CN(C)C(=O)c1cc2cnc(Nc3ccc(-c4csc5c(=O)cc(N6CCOCC6)oc45)cn3)nc2n1C1CCCC1] | 585.68 |

TABLE 1-continued
| Representative compounds of the invention. | | | |
|---|---|---|---|
| Compound Number | Formula Number | Structure | Molecular Weight |
| 4 | IVa | 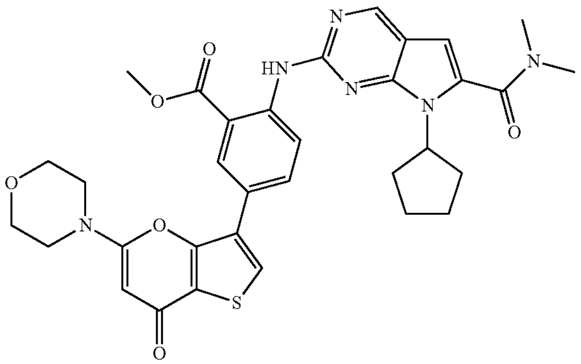 [SMILES: COC(=O)c1cc(-c2csc3c(=O)cc(N4CCOCC4)oc23)ccc1Nc1ncc2cc(C(=O)N(C)C)n(C3CCCC3)c2n1] | 642.72 |
| 5 | IVb | 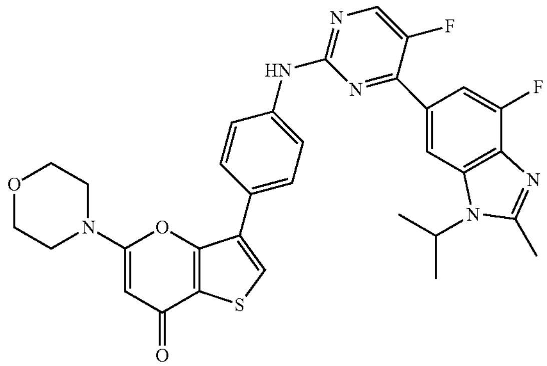 [SMILES: Cc1nc2c(F)cc(-c3nc(Nc4ccc(-c5csc6c(=O)cc(N7CCOCC7)oc56)cc4)ncc3F)cc2n1C(C)C] | 614.66 |
| 6 | IVc | 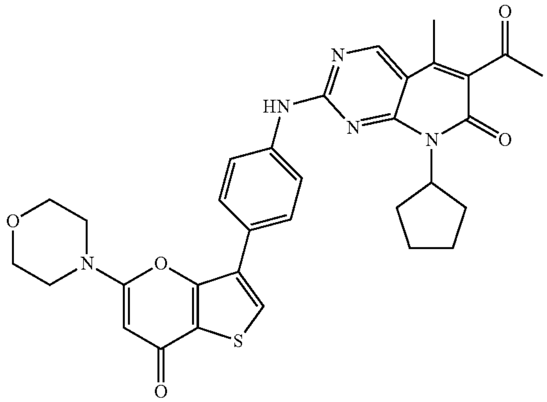 [SMILES: CC(=O)c1c(C)c2cnc(Nc3ccc(-c4csc5c(=O)cc(N6CCOCC6)oc45)cc3)nc2n(C2CCCC2)c1=O] | 597.68 |
| 7 | IVa | 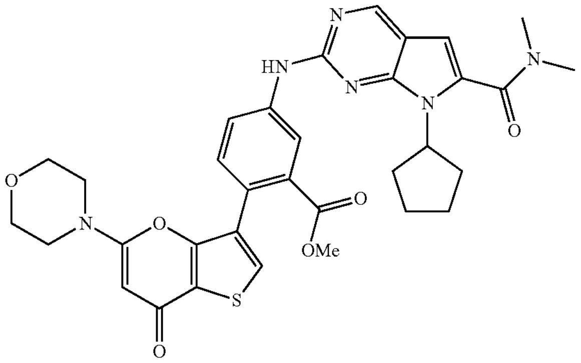 [SMILES: COC(=O)c1cc(Nc2ncc3cc(C(=O)N(C)C)n(C4CCCC4)c3n2)ccc1-c1csc2c(=O)cc(N3CCOCC3)oc12] | : 642.72 |

TABLE 1-continued
| Representative compounds of the invention. | | | |
|---|---|---|---|
| Compound Number | Formula Number | Structure | Molecular Weight |
| 8 | IVc | 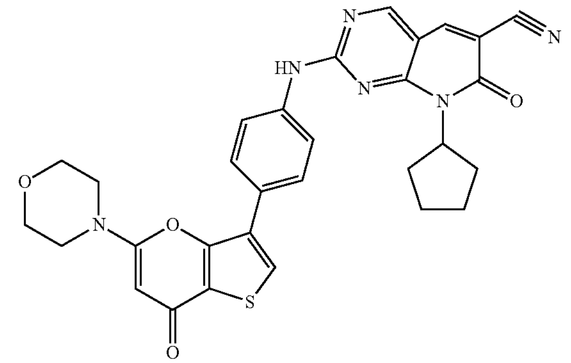 [SMILES: N#Cc1cc2cnc(Nc3ccc(-c4csc5c(=O)cc(N6CCOCC6)oc45)cc3)nc2n(C2CCCC2)c1=O] | 566.63 |
| 9 | IVa | 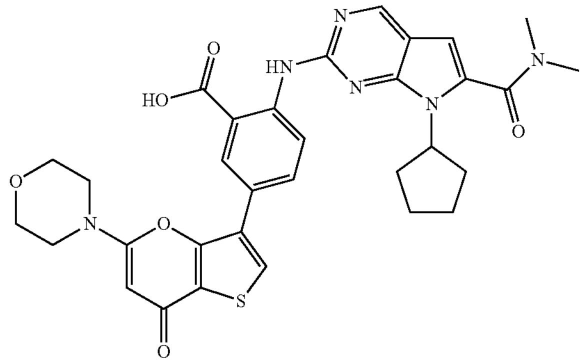 [SMILES: CN(C)C(=O)c1cc2cnc(Nc3ccc(-c4csc5c(=O)cc(N6CCOCC6)oc45)cc3C(=O)O)nc2n1C1CCCC1] | 628.70 |
| 10 | IVa | 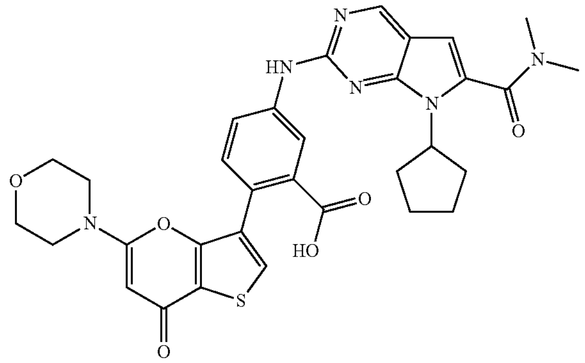 [SMILES: CN(C)C(=O)c1cc2cnc(Nc3ccc(-c4csc5c(=O)cc(N6CCOCC6)oc45)c(C(=O)O)c3)nc2n1C1CCCC1] | 628.70 |
| 11 | IVa | 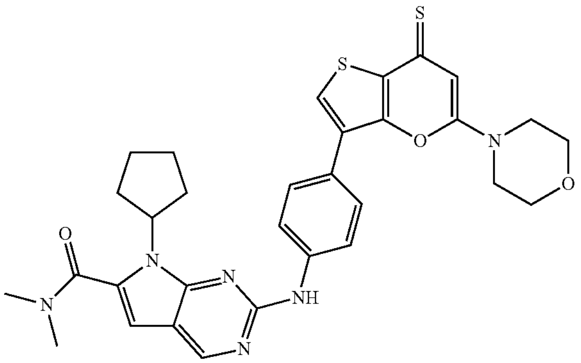 | 600.75 |

TABLE 1-continued
Representative compounds of the invention.
| Compound Number | Formula Number | Structure | Molecular Weight |
|---|---|---|---|
| 12 | IVa | 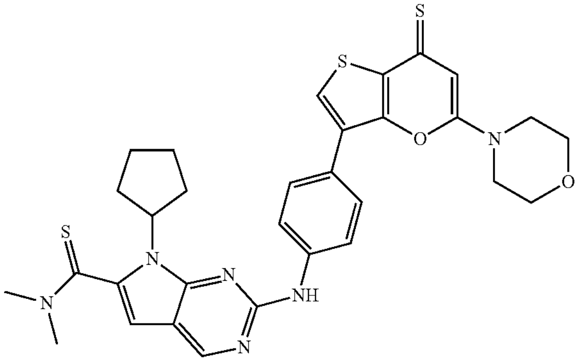 [SMILES: CN(C)C(=S)c1cc2cnc(Nc3ccc(-c4csc5c(=S)cc(N6CCOCC6)oc45)cc3)nc2n1C1CCCC1] | 616.82 |
| 13 | UVa | 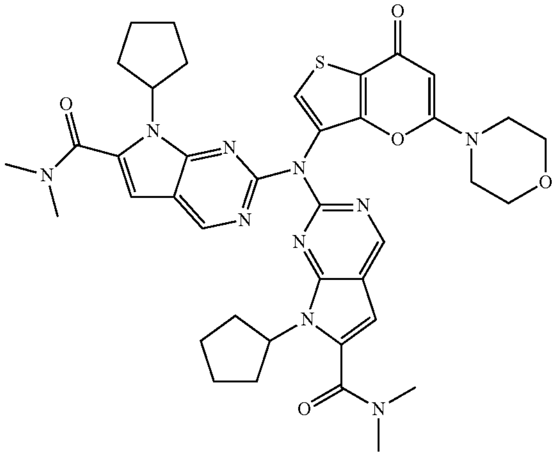 [SMILES: CN(C)C(=O)c1cc2cnc(N(c3ncc4cc(C(=O)N(C)C)n(C5CCCC5)c4n3)c3csc4c(=O)cc(N5CCOCC5)oc34)nc2n1C1CCCC1] | 764.90 |
| 14 | IV | 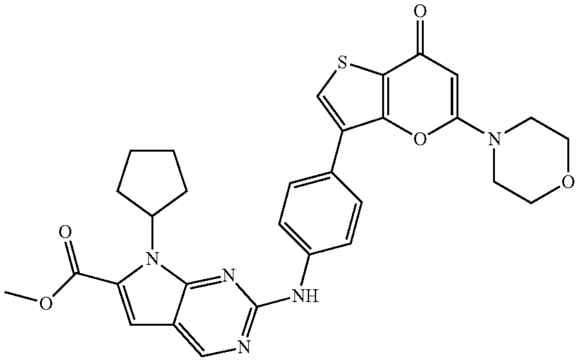 [SMILES: COC(=O)c1cc2cnc(Nc3ccc(-c4csc5c(=O)cc(N6CCOCC6)oc45)cc3)nc2n1C1CCCC1] | 571.65 |

TABLE 1-continued
Representative compounds of the invention.
| Compound Number | Formula Number | Structure | Molecular Weight |
|---|---|---|---|
| 15 | II | 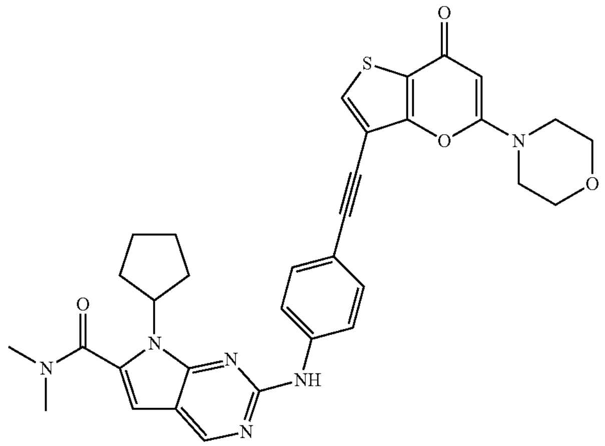 [SMILES: CN(C)C(=O)c1cc2cnc(Nc3ccc(C#Cc4csc5c(=O)cc(N6CCOCC6)oc45)cc3)nc2n1C1CCCC1] | 608.71 |
| 16 | IVa | 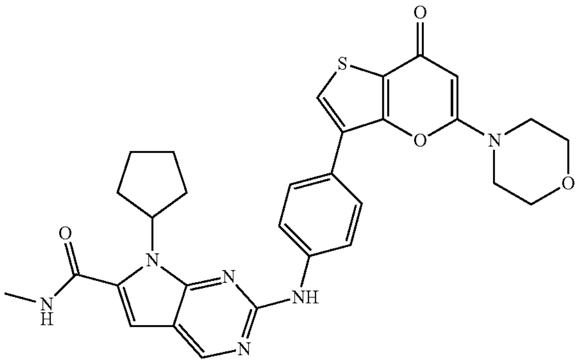 [SMILES: CNC(=O)c1cc2cnc(Nc3ccc(-c4csc5c(=O)cc(N6CCOCC6)oc45)cc3)nc2n1C1CCCC1] | 570.66 |
| 17 | IVa | 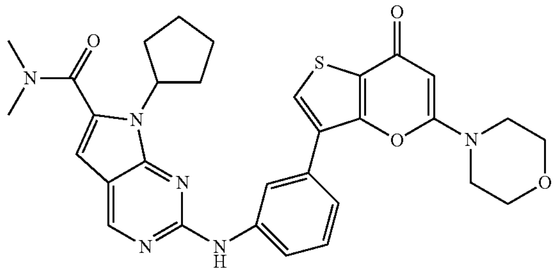 [SMILES: CN(C)C(=O)c1cc2cnc(Nc3cccc(-c4csc5c(=O)cc(N6CCOCC6)oc45)c3)nc2n1C1CCCC1] | 584.69 |
| 18 | IVa | 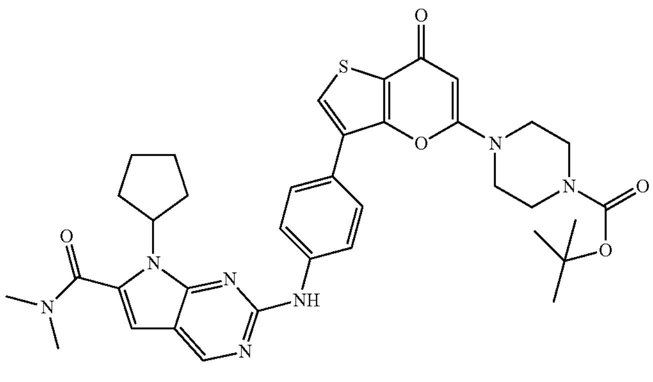 [SMILES: CN(C)C(=O)c1cc2cnc(Nc3ccc(-c4csc5c(=O)cc(N6CCN(C(=O)OC(C)(C)C)CC6)oc45)cc3)nc2n1C1CCCC1] | 683.82 |

TABLE 1-continued

| Representative compounds of the invention. | | | |
|---|---|---|---|
| Compound Number | Formula Number | Structure | Molecular Weight |
| 19 | IVa | 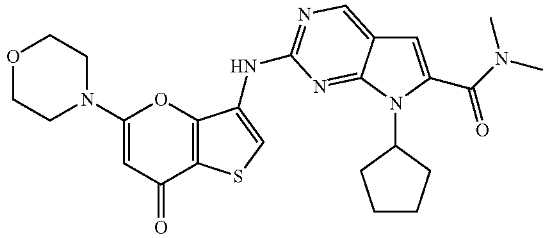 [SMILES: CN(C)C(=O)c1cc2cnc(Nc3csc4c(=O)cc(N5CCOCC5)oc34)nc2n1C1CCCC1] | 508.59 |

The present invention has multiple aspects, illustrated by the following non-limiting examples. The examples are merely illustrative and do not limit the scope of the invention in any way.

HPLC traces for example compounds synthesized were recorded using a HPLC consisting of Shimadzu or Agilent HPLC pumps, degasser and UV detector, equipped with an Agilent 1100 series auto-sampler. The UV detection provided a measure of purity by percent peak area. A MS detector (APCI) PE Sciex API 150 EX was incorporated for purposes of recording mass spectral data providing compound identification. HPLC/mass traces were obtained using one of three chromatographic methods. If a method is not specifically listed in the example then method A was utilized. The three methods are listed below:

Method A: Column SunFire™ (Waters) C18, size 2.1 mm×50 mm;

Solvent A: 0.05% TFA in water, Solvent B: 0.05% TFA in acetonitrile;

Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.

Method B: Column Aquasil™ (Thermo) C18, size 2.1 mm×150 mm; particle size 5μ. Solvent A: 0.05% TFA in water, Solvent B: 0.05% TFA in acetonitrile;

Flow rate—0.3 mL/min; Gradient: 10% B to 95% B in 2.4 min, hold at 95% B for 6.25 min and 95% B to 10% B in 0.2 min, hold at 10% B for 1.5 min.; UV detector—channel 1=220 nm, channel 2=254 nm.

Method C: Column Phenomenex C18, size 2 mm×50 mm; particle size 5μ. Solvent A: 0.05% TFA in water, Solvent B: 0.05% TFA in acetonitrile; Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.

Example 1. Preparation of Compound 1

Step 1: (6-Chloro-1-cyclopentyl-1,5,7-triaza-1H-inden-2-yl)(dimethylamino)formaldehyde A stirring solution of 6-chloro-1-cyclopentyl-1,5,7-triaza-1H-indene-2-carboxylic acid (199 mg, 0.75 mmol) and triethylamine (631 μL, 4.5 mmol) in DMF (4 mL) was treated with HBTU (427 mg, 1.13 mmol) in one portion. The resulting mixture was stirred at room temperature for 30 minutes. Dimethylamine hydrochloride salt (122 mg, 1.50 mmol) was added in one portion and the resulting solution was stirred at room temperature overnight. Next morning, LCMS analysis indicated clean conversion to product (m/z=293.4). The reaction mixture was diluted with EtOAc, transferred to a separatory funnel and washed with 0.1 N HCl aqueous and brine. The organics were dried over anhydrous $MgSO_4$, filtered and concentrated to yield the crude product. This was purified on a $SiO_2$ column using a hexanes/EtOAc gradient eluent. The fractions containing the product were concentrated to yield 215 mg (0.74 mmol, 99%). LC/MS—HPLC (254 nm)—Rt 2.90 min. MS (ESI) m/z 293.4 [M++H+].

Step 2: 3-(p-Aminophenyl)-5-morpholino-4-oxa-1-thia-7-indenone

3-Bromo-5-morpholino-7H-thieno[3,2-b]pyran-7-one (500 mg, 1.58 mmol), 4-aminophenyl boronic acid hydrochloride (284 mg, 2.07 mmol) dissolved in 1,4-dioxane (6 mL) was treated with 2M $Na_2CO_3$ (2.6 mL) and degassed under $N_2$ for 10 minutes. $Pd[Ph_3P]_4$ (38 mg, 0.03 mmol) was added and the mixture was heated at about 85-90° C. for 16 h under stirring. Then the reaction mixture was cooled to room temperature and diluted with EtOAc (50 mL). Then it was filtered, washed with water and dried ($Na_2SO_4$), filtered and concentrated to yield crude 3-(4-aminophenyl)-5-morpholino-7H-thieno[3,2-b]pyran-7-one (470 mg). The crude was purified on $SiO_2$ column using $CH_2Cl_2$/MeOH gradient. The fractions containing the product were concentrated to yield 282 mg (0.86 mmol, 54%) of pure 3-(p-aminophenyl)-5-morpholino-4-oxa-1-thia-7-indenone. LC/MS—HPLC (254 nm)—Rt 2.06 min. MS (ESI) m/z 329.3 [M++H+]. Purity=>96% by UV (254 nm).

Step 3: SYNTHESIS OF Compound 1: {1-Cyclopentyl-6-[p-(5-morpholino-7-oxo-4-oxa-1-thia-3-indenyl)phenylamino]-1,5,7-triaza-1H-inden-2-yl}(dimethylamino) formaldehyde In an 8 mL vial, (6-chloro-1-cyclopentyl-1,5,7-triaza-1H-inden-2-yl) (dimethylamino)formaldehyde (29 mg, 0.1 mmol), 3-(p-aminophenyl)-5-morpholino-4-oxa-1-thia-7-indenone (33 mg, 0.1 mmol), $Cs_2CO_3$ (47 mg, 0.144 mmol), BINAP (3 mg, 0.005 mmol) and $Pd(OAc)_2$ (1 mg, 0.005 mmol) were degassed under $N_2$ for 10 minutes. Degassed 1,4-dioxane (600 μL) was added and the resulting mixture was stirred at 110° C. for 4 hours. LCMS indicated complete consumption of starting material and formation of product. The reaction was cooled, diluted with EtOAc (50 mL) and washed with $H_2O$ (50 mL) and brine. The organic layer was dried over anhydrous $MgSO_4$, filtered and concentrated in vacuo. The crude residue was purified by preparative TLC plate (20×20 cm) on silica-gel, eluting with a EtOAc/MeOH (98:2 v/v). The product compound 1 was obtained as a yellow solid. Yield=24 mg (0.04 mmol, 41%). LC/MS—HPLC (254 nm)—Method B—Rt 6.40 min. MS (ESI) m/z 585.4 [M++H+]. Purity=>95% by UV (254 nm).

$^1$HNMR (400 MHz-DMSO-d6) δ9.73 (s, 1H); 8.79 (s, 1H); 8.08 (s, 1H); 7.99 (d, J=7.2 Hz, 2H); 7.66 (d, J=7.2 Hz, 2H); 6.61 (s, 1H); 5.54 (s, 1H); 4.76 (m, 1H); 3.73 (t, J=3.6 Hz, 4H); 3.47 (t, J=3.6 Hz, 4H); 3.06 (br, 6H); 2.00 (br, 6H); 1.69 (br, 2H).

Example 2. Enzymatic Activity of Compound 1

Samples of compound 1 were sent out to vendors for enzymatic activity against human BRD4 isoforms, human PI3K isoforms alpha, gamma, and delta, and against human CDK4/6. PI3K-alpha, PI3K-beta, PI3K-gamma, and PI3K-delta inhibition activity was determined by Thermo Fisher Scientific-Biosciences Life Sciences Solutions, Madison, WI. The bromodomain protein inhibition (binding domain 1 and 2 of BRD4) was determined by Reaction Biology Corp., Malvern, PA. The cyclin dependent kinase inhibition on proteins such as CDK2, CDK4, CDK6, and CDK9 was determined by Reaction Biology Corp., Malvern, PA.

Figure 2A:
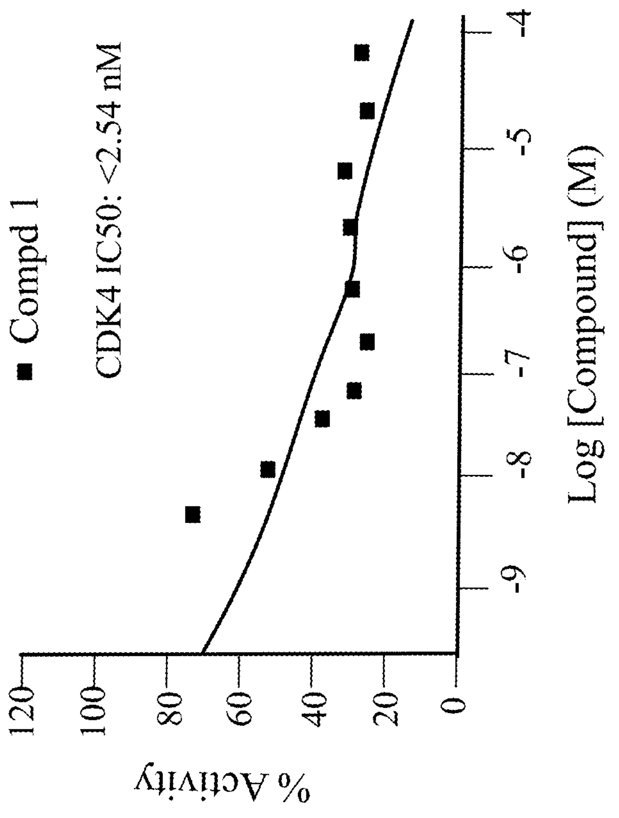
FIG. 2A shows the inhibitory activity of triple inhibitor Compound 1 against CDK4.
Figure 2B:
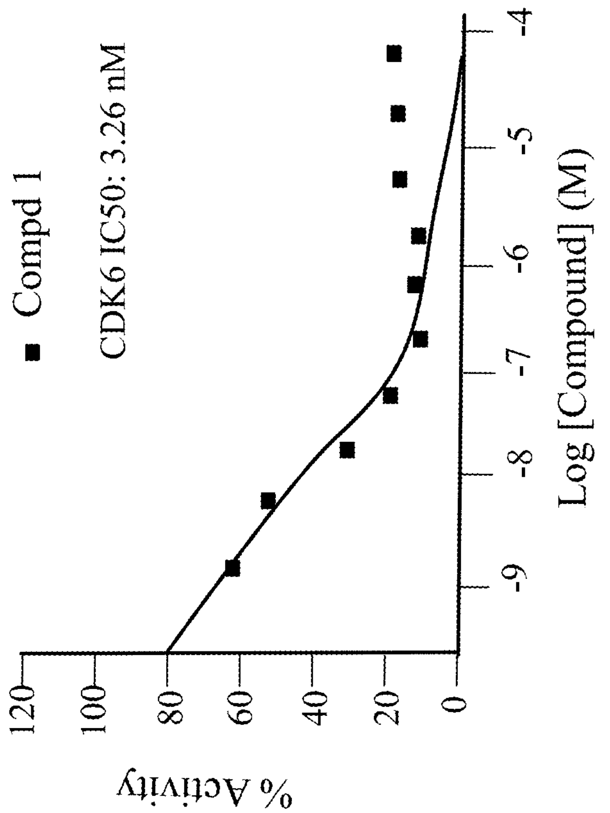
FIG. 2B shows the inhibitory activity of triple inhibitor Compound 1 against CDK6.

The inhibition of compound 1 towards CDK4 and CDK 6 ($IC_{50}$) was found to be <2.54 nM and 3.26 nM, respectively, as shown in FIGS. 2A and 2B, respectively. Moreover, compound 1 was also found to potently inhibit CDK9 ($IC_{50}$=2 nM) but much less potently against CDK2 ($IC_{50}$=500 nM).

To obtain selectivity data a large collection of 468 human kinases was screened for inhibition by compound 1 using the KINOMEscan™ Profiling Service by DiscoverX, San Diego, CA. The kinome scan data showed excellent selectivity towards kinases with a DiscoverX calculated selectivity index of <0.1 which is more selective than FDA approved blockbuster drugs like Gefitinib, Imatinib, and Erlotinib whose selectivity indexes are less selective and run between 0.1 and 0.2. Separately, compound 1 was tested and found to potently inhibit DNA-PK ($IC_{50}$=21 nM) and PIM1 ($IC_{50}$=35 nM).

The BRD4 and PI3K inhibition $IC_{50}$ values of compound 1 are tabulated in example 21 and demonstrate high potency as a triple inhibitor of BRD4/PI3K/CDK4-6.

Lastly an oral formulation for compound 1 (Hot Rod Formulation Kit #8 from Pharmatek/Catalent) was used for an oral pharmacokinetic (PK) study (performed by Quintara Discovery, Hayward, CA). The PK parameter results for compound 1 dosed by oral gavage at 30 mg/kg are as follows: Tmax=30 minutes, Cmax=1.4 μM, AUCinf=3520 hr*ng/mL, and $T_{1/2}$ (half-life)=10.4 hours. It should be noted that the Cmax is well above the $IC_{50}$ values for the targets to inhibit and, at 24 hours, plasma concentration was 63 nM which is within range to inhibit all targets. This data surprisingly indicates that drug-like properties such as suitable PK (half-life, Cmax, and area under the curve-exposure) can be found in compounds like compound 1 despite being over 500 molecular weight in contrast to Lipinski's rule of 5. The in vivo anticancer activity displaying drug like properties also bears this out as shown in FIG. 9 and the corresponding example.

Example 3. Signaling Activity of Compound 1 on Huh7 Cells In Vitro Showing PI3K Pathway Inhibition (pAkt) and CDK4/6 Inhibition (pRB S780)

Figure 3:
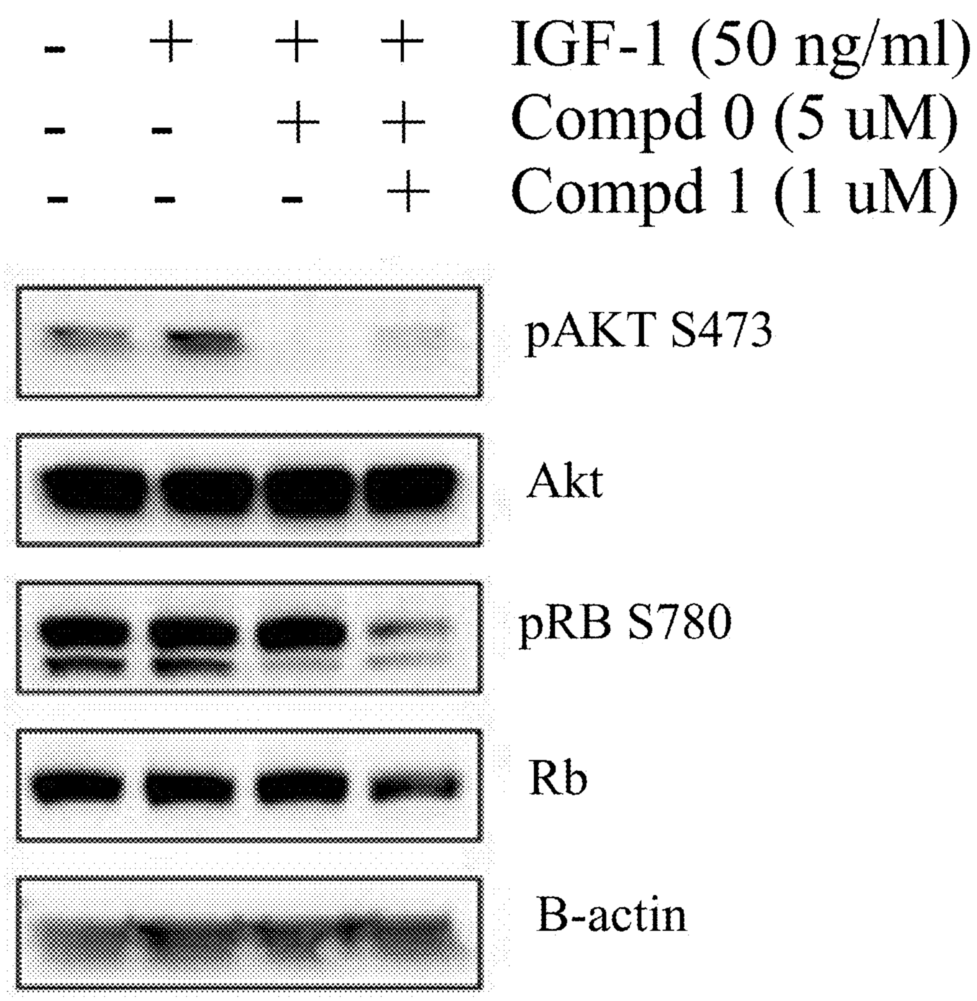
FIG. 3 provides Western blot data showing that Compound 1 inhibits phosphorylation of RB and Akt in Huh7 cells.

The hepatocellular carcinoma cell line, Huh7 was serum starved overnight in serum free medium. Cells were seeded into a 96 well tissue culture plate at 1×10$^4$ cells/well and pulsed with IGF-1 stimulation for 30 min at 37° C. at which time lysates were generated for SDS PAGE analysis. Western blot analysis was performed for p-AKT, AKT, pRB, RB and beta actin as loading control. The Western blot is shown in FIG. 3 and demonstrate that compound 1 blocks phosphorylation of CDK target, RB as well as the PI3K target AKT in cell-based assay model. Thus, compound 1 blocks signaling activity of the PI3K pathway and also the cyclin dependent kinase pathway to cancer cell reproduction.

Example 4. Inhibition of Neuroblastoma Cell Lines by Compound 1

Figure 4:
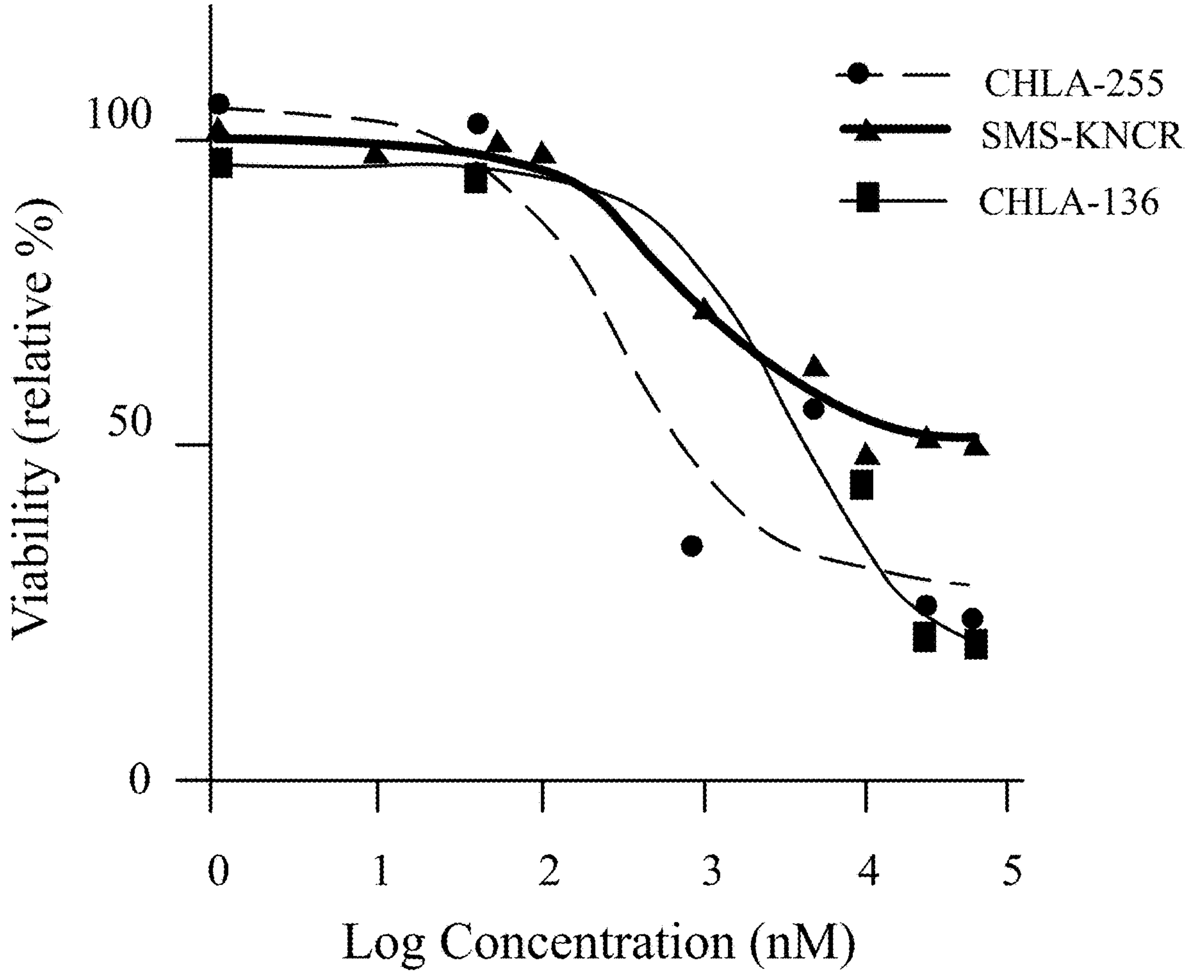
FIG. 4 shows the inhibitory activity of Compound 1 in three different neuroblastoma cell lines.

Human neuroblastoma cell lines, CHLA-255, CHLA-136 and SMS-KNCR were seeded into a 96 well tissue culture plate and cultivated in complete medium containing 10% FBS for 24 hours prior to the addition of compound 1 at different concentrations ranging from 50 μM to 50 nM and incubated for an additional 24 hours at which time viable cells were quantitated after incubation with Alamar Blue® detection reagent for 6 hours. $IC_{50}$ for each cell line was determined using Graphpad Prism software module. The sigmoidal viability versus concentration curves are shown in FIG. 4. The calculated $IC_{50}$ values for the three cell lines were 385 nM, 4496 nM, and 962 nM for CHLA-255, CHLA-136 and SMS-KNCR, respectively. These results clearly show that compound 1 is potently cytotoxic to multiple neuroblastoma cell lines in vitro.

Example 5. Inhibition of Mantle Cell Lymphoma Cell Lines by Compound 1

Mantle cell lymphoma cell lines Granta, Mino and Jeko-1 were seeded at a density of 2500 cells/0.1 mL per well in a 96-well plate. Compounds 1 or Palbociclib were added post-plating at 50 μM-50 nM concentrations for 48 hours followed by addition of AlamarBlue® and incubation of plates at 37° C. in 5% $CO_2$ for 6 hours. Fluorescence signals were read as emission at 590 nm after excitation at 560 nm. $IC_{50}$ for each cell line was determined using Graphpad Prism software module. As shown in Table 2 below, compound 1 is 17.7, 82.1, and 8.7 times more potent against the lymphoma cancer cell lines Granta, Mino, and Jeko-1, respectively, than is FDA approved CDK4/6 inhibitor drug Palbociclib.

TABLE 2

Inhibition of Mantle cell lymphoma lines by Compound 1 and Palbociclib

| | Mantle Cell Line $IC_{50}$ Values (nM) | | |
|---|---|---|---|
| Compound | Granta | Mino | Jeko-1 |
| Compound 1 | 579.9 | 583.1 | 851.4 |
| Palbociclib | 10,177 | 47,886 | 7430 |

Example 6. Inhibition of Hepatocellular Carcinoma Cell Lines by Triple Inhibitor PI3K/BRD4/CDK4-6 Compound 1 Versus Dual PI3K/BRD4 Inhibitor Compound 0

Human hepatocellular carcinoma cell lines, Huh7, Hep3B and HepG2 were tested for comparable sensitivity to triple inhibitor Compound 1 and dual inhibitor Compound 0 in vitro. Cells were seeded into 96-well plate at $1\times10^4$ cell per well in complete medium+10% FCS and incubated for 24 hours prior to the addition of compounds at concentrations ranging from 50 μM to 50 nM. Cell viability was quantitated 24 hours after the addition of compounds using AlamarBlue® viable cell detection reagent. $IC_{50}$ curves were determined using Graphpad Prism software. Table 3 below shows the $IC_{50}$ values for these two compounds against the three hepatocarcinoma cell lines. The results clearly show that the triple inhibition of PI3K/BRD4 and CDK4/6 by Compound 1 had greater potency to kill hepatocellular carcinoma cell lines as compared to the double inhibitor of PI3K/BRD4 Compound 0.

TABLE 3

Inhibition of hepatocarcinoma cell lines by Compound 1 versus Compound 0

| Compound | Hepatocarcinoma Cell Line $IC_{50}$ Values (μM) | | |
|---|---|---|---|
| | Huh7 | Hep3B | HepG2 |
| Compound 1 | 0.55 | 1.1 | 4.2 |
| Compound 0 | 14.3 | 6.6 | 5.0 |

Example 7. Triple Inhibitor Compound 1 is Less Toxic to Normal Cells than a Combination of Cognate Inhibitors Approximately 10,000 epithelial cells from normal tonsil (RRP-008) were grown in human Epilife medium with growth supplement and growth factors in 96-well plate with DMSO, and either Compound 1 or a 1:1:1 combination of a BRD4 inhibitor (JQ1) plus a PI3K inhibitor (BKM120) plus an FDA-approved CDK4/6 inhibitor (Palbociclib) at different concentrations (50 μM-50 nM). After 48 hr, AlamarBlue® was added and plates were incubated at 37° C. in 5% $CO_2$ for 4 hours. Fluorescence signals were read as emission at 590 nm after excitation at 560 nm. Graphpad Prism 5 was used to determine $IC_{50}$ values.

Figure 5:
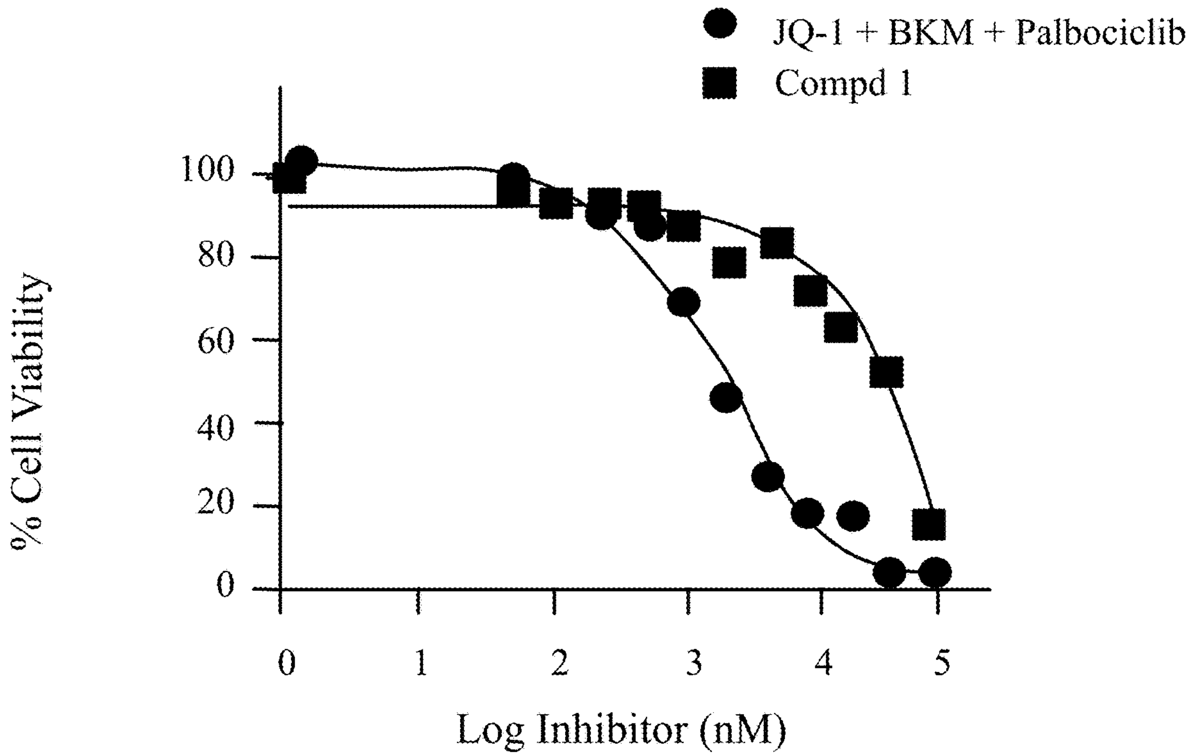
FIG. 5 shows that Compound 1 is less toxic to normal cells than a combination of three individual cognate inhibitors.

The results of this experiment show that the triple inhibitor Compound 1 is approximately 52-fold less toxic to normal epithelial cells than the combination of three different inhibitors JQ1+BKM120+Palbociclib which interact with the same three protein targets. As shown in FIG. 5, Compound 1 as a single, triple targeted small molecule is dramatically less toxic to normal epithelial cells as compared to exposure to 3 individual cognate inhibitors of equal individual potency.

Example 8. Inhibition of PI3K and CDK4/Cyclin D/R$^b$ Signaling Pathway by Compound 1

Figure 6A:
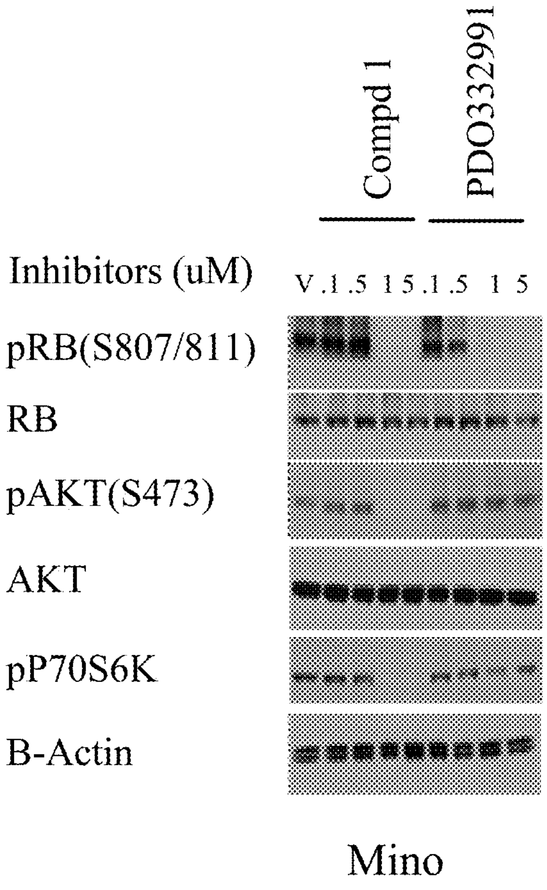
FIG. 6A provides Western blot data for Mantle cell lymphoma cell line Mino treated with Compound 1 and PDO 332991.
Figure 6B:
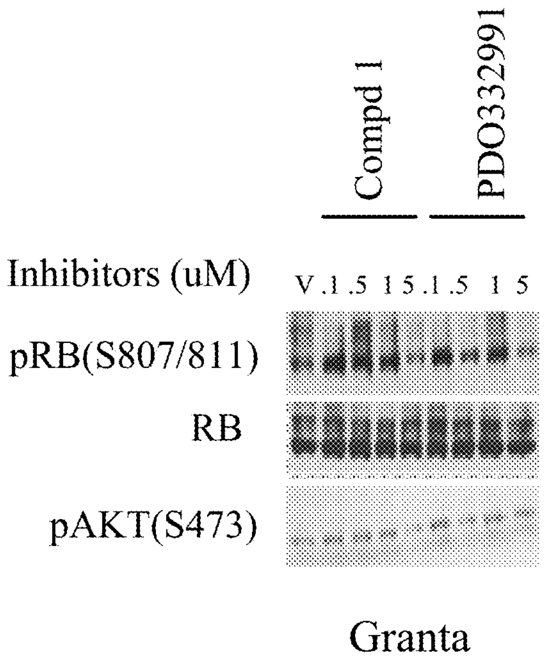
FIG. 6B provides Western blot data for Mantle cell lymphoma cell line Granta treated with Compound 1 and PDO 332991.

Mino and Granta cells (mantle cell lymphoma) were treated with different concentrations of Compound 1 or PD-0332991 (FDA-approved CDK4/6 inhibitor Palbociclib) for 24 hours. Cells were lysed in RIPA buffer and equal protein was loaded on SDS-PAGE gel followed by western blotting using p-AKT-Ser473, AKT, pRB-S780/811, RB, pP70S6K. β-actin served as loading control. As shown in FIGS. 6A-6B, the triple PI3K/BRD4/CDK4-6 inhibitor Compound 1 desirably inhibits two important targets involved in mantle cell lymphoma pathogenesis namely PI3K-AKT and cyclin D/RB signaling (by monitoring the inhibition of phosphorylation of RB) whereas the single inhibitor Palbociclib (PD0332991) only inhibits cyclin D/RB signaling.

Example 9. Synthesis of a Dual BRD4-CDK Inhibitor (Compound 2)

Step 1: (6-Chloro-1-cyclopentyl-1,5,7-triaza-1H-inden-2-yl)(dimethylamino)formaldehyde A stirring solution of 6-chloro-1-cyclopentyl-1,5,7-triaza-1H-indene-2-carboxylic acid (200 mg, 0.75 mmol) and a tertiary amine such as trimethylamine or diisopropylethylamine (788 μL, 4.5 mmol) in DMF (4 mL) was treated with HBTU (427 mg, 1.13 mmol) in one portion. The resulting mixture was stirred at room temperature for 30 minutes. Dimethylamine hydrochloride salt (122 mg, 1.50 mmol) was added in one portion and the resulting solution was stirred at room temperature overnight. The next morning, LCMS analysis indicated clean conversion to product (m/z=293.4). The reaction mixture was diluted with EtOAc, transferred to a separatory funnel and washed with saturated $NaHCO_3$ aqueous solution, 0.1 N HCl aqueous and brine. The organics were dried over anhydrous $MgSO_4$, filtered and concentrated to yield crude product. This crude product was purified on $SiO_2$ column using a hexanes/EtOAc gradient. The fractions containing (6-chloro-1-cyclopentyl-1,5,7-triaza-1H-inden-2-yl)(dimethylamino)formaldehyde were concentrated to yield 165 mg (0.57 mmol, 75%). LC/MS—HPLC (254 nm)—Rt 2.90 min. MS (ESI) m/z 293.4 $[M+H]^+$.

Step 2: tert-Butyl 4-acetyl-1-piperazinecarboxylate: A solution of tert-butyl 1-piperazinecarboxylate (9.3 g, 50.0 mmol) in $CH_2Cl_2$ (167 mL) was treated with triethylamine (21 mL, 150.0 mmol, 3 eq.) and cooled to 0° C. under $N_2$. Acetyl chloride (5.33 mL, 75.0 mmol, 1.5 eq.) was added dropwise over 15 minutes. The reaction mixture was allowed to reach room temperature and was stirred overnight. After overnight stirring the reaction mixture was placed in a separatory funnel, washed twice with 0.1N HCl aqueous. The organics were dried over anhydrous $MgSO_4$, filtered and concentrated in a roto-evaporator. The crude residue was purified by silica-gel chromatography, eluting with a $CH_2Cl_2$/MeOH gradient. The desired product tert-butyl 4-acetyl-1-piperazinecarboxylate was obtained as an oil which solidified upon standing. Yield=10.35 g (45.4 mmol, 91%). LC/MS—HPLC (254 nm)—Rt 2.23 min. MS (ESI) m/z 229.6 $[M+H]^+$.

Step 3: tert-Butyl 4-[3-(4-bromo-3-hydroxy-2-thienyl)-3-oxopropionyl]-1-piperazinecarboxylate: Lithium hexamethyldisilazide (LiHMDS) (13.5 mL of a 1 M solution in THF, 13.5 mmol) was added to a round bottom flask under a $N_2$ atmosphere and cooled to 0° C. A solution of tert-butyl 4-acetyl-1-piperazinecarboxylate (1.54 g, 6.75 mmol, 1.6 eq.) in THF (1.5 mL) was added slowly. The resulting solution was stirred at 0° C. for 1 hour. A solution of methyl 4-bromo-3-hydroxy-2-thiophene (1.0 g, 4.22 mmol) in THF (1.5 mL) was added dropwise. After 1 hour at 0° C., the reaction was warmed to room temperature and stirred overnight. LCMS analysis indicated clean conversion to product. The reaction was quenched with 0.1 N HCl aqueous and then extracted with EtOAc. The organic layer was washed with 0.1 N HCl aqueous and brine, dried over anhydrous $MgSO_4$, filtered and then evaporated in vacuo. The residue was a tan oil, which was used in the next step without further purification. Yield=2.38 g. LC/MS—HPLC (254 nm)—Rt 2.88 min. MS (ESI) m/z 433.2 [M+H]+. Purity=73% by UV (254 nm).

Step 4: tert-Butyl 4-(3-bromo-7-oxo-4-oxa-1-thia-5-indenyl)-1-piperazinecarboxylate: tert-Butyl 4-[3-(4-bromo-3-hydroxy-2-thienyl)-3-oxopropionyl]-1-piperazinecarboxylate (crude from Step 3, 4.22 mmol) was dissolved in $CH_2Cl_2$ (25 mL) and cooled to 0° C. under a $N_2$ atmosphere. Trifluoromethanesulfonic anhydride (1.85 mL, 10.97 mmol, 2.6 eq.) was added dropwise. The reaction was stirred at 0° C. for 1 hour and then warmed to room temperature. After 1 hour at room temperature, the reaction was deemed complete by LCMS however, the Boc protecting group was missing in the cyclized product. The reaction was quenched slowly with $H_2O$ and then poured slowly onto a $NaHCO_3$ saturated solution. The product was extracted with $CH_2Cl_2$. The organic layer was dried over anhydrous $MgSO_4$, filtered and evaporated to yield the crude deprotected material as an orange oil (yield=960 mg).

This was dissolved in $CH_2Cl_2$ (10 mL), treated with diisopropylethylamine (1.6 mL) and $(Boc)_2O$ (770 mg) to re-attach the Boc protecting group. The reaction was then stirred at room temperature overnight. After stirring overnight, the reaction was washed with 0.1 N HCl aqueous, dried over anhydrous $MgSO_4$, filtered and evaporated. The residue was purified by silica-gel chromatography, eluting with a hexanes/EtOAc gradient. The desired tert-butyl 4-(3-bromo-7-oxo-4-oxa-1-thia-5-indenyl)-1-piperazinecarboxylate was obtained as a yellow solid. Yield=632 mg (1.53 mmol, 36%). LC/MS—HPLC (254 nm)—Rt 2.84 min. MS (ESI) m/z 415.5 [M+H]+. Purity=96.6% by UV (254 nm).

Step 5: tert-Butyl 4-[3-(p-aminophenyl)-7-oxo-4-oxa-1-thia-5-indenyl]-1-piperazinecarboxylate: tert-Butyl 4-(3-bromo-7-oxo-4-oxa-1-thia-5-indenyl)-1-piperazinecarboxylate (414 mg, 1.0 mmol) and 4-aminophenylboronic acid hydrochloride (260 mg, 1.5 mmol, 1.5 eq.) were dissolved in dioxane or a mix of toluene:ethanol (2:1 v/v, 10 mL). The mixture was treated with $Na_2CO_3$ 2M aqueous solution (3.3 mL) and deoxygenated by bubbling $N_2$ for 10 minutes. $Pd[PPh_3]_4$ (58 mg, 0.05 mmol) was added and the mixture was heated to 85° C. for 3 hours in a closed vial. The cooled reaction mixture was diluted with EtOAc (50 mL) washed with water and brine. The aqueous layers were extracted once again with a $CH_2Cl_2$/iPrOH mixture (9:1 v/v). The combined organics were dried over anhydrous $MgSO_4$, filtered and evaporated. The crude residue was triturated with $Et_2O$ and EtOAc and filtered to yield the pure title compound tert-butyl 4-[3-(p-aminophenyl)-7-oxo-4-oxa-1-thia-5-indenyl]-1-piperazinecarboxylate as a tan solid. Yield=345 mg (0.81 mmol, 81%).

LC/MS—HPLC (254 nm)—Rt 2.16 min. MS (ESI) m/z 428.2 $[M+H]^+$. Purity=98.3% by UV (254 nm).

Step 6: tert-Butyl 4-(3-{p-[1-cyclopentyl-2-(dimethylamino)carbonyl-1,5,7-triaza-1H-inden-6-ylamino]phenyl}-7-oxo-4-oxa-1-thia-5-indenyl)-1-piperazinecarboxylate In an 8 mL vial, (6-chloro-1-cyclopentyl-1,5,7-triaza-1H-inden-2-yl) (dimethylamino)formaldehyde (44 mg, 0.15 mmol), tert-butyl 4-[3-(p-aminophenyl)-7-oxo-4-oxa-1-thia-5-indenyl]-1-piperazinecarboxylate (64 mg, 0.15 mmol), $Cs_2CO_3$ (70 mg, 0.216 mmol), BINAP (5 mg, 0.0075 mmol) and $Pd(OAc)_2$ (2 mg, 0.0075 mmol) were degassed under $N_2$ for 10 minutes. Degassed 1,4-dioxane (1 mL) was added and the resulting mixture was stirred at 110° C. for 16 hours. After 16 hours LCMS indicated complete consumption of starting material and formation of product. The reaction was cooled, diluted with EtOAc (50 mL) and washed with $H_2O$ (50 mL) and brine. The organic layer was dried over anhydrous $MgSO_4$, filtered and concentrated in vacuo. The crude residue was purified by automated chromatography on silica-gel, eluting with a hexanes/EtOAc gradient. The desired tert-butyl 4-(3-{p-[1-cyclopentyl-2-(dimethylamino)carbonyl-1,5,7-triaza-1H-inden-6-ylamino]phenyl}-7-oxo-4-oxa-1-thia-5-indenyl)-1-piperazinecarboxylate was obtained as a yellow solid. Yield=62 mg (0.09 mmol, LC/MS—HPLC (254 nm)—Rt 2.61 min. MS (ESI) m/z 684.8 [M+H]+. Purity=97.9% by UV (254 nm).

Step 7: (1-Cyclopentyl-6-{p-[7-oxo-5-(1-piperazinyl)-4-oxa-1-thia-3-indenyl]phenylamino}-1,5,7-triaza-1H-inden-2-yl)(dimethylamino)formaldehyde hydrochloride (Compound 2 as HCl salt): A solution of tert-butyl 4-(3-{p-[1-cyclopentyl-2 (dimethylamino)carbonyl-1,5,7-triaza-1H-inden-6-ylamino]phenyl}-7-oxo-4-oxa-1-thia-5-indenyl)-1-piperazinecarboxylate (50 mg, 0.0732 mmol) in $CH_2Cl_2$ (7 mL) was treated with HCl (1 mL of a 4 M solution in dioxane) and the resulting mixture was stirred at room temperature overnight. Upon examination the next morning, LCMS analysis indicated that the reaction was completed. The volatiles were removed in vacuo and the resulting solids were triturated with $Et_2O$ to yield the desired product, compound 2 ((1-cyclopentyl-6-{p-[7-oxo-5-(1-piperazinyl)-4-oxa-1-thia-3-indenyl]phenylamino}-1,5,7-triaza-1H-inden-2-yl)(dimethylamino)formaldehyde hydrochloride) as the hydrochloride salt. Yield=37 mg (0.062 mmol, 84%). LC/MS—HPLC (254 nm)—Rt 2.14 min. MS (ESI) m/z 584.6 [M+H]+. Purity=96.9% by UV (254 nm). $^1$HNMR (500 MHz-DMSO-d6) δ 9.96 (s, 1H); 9.25 (br, 2H); 8.84 (s, 1H); 8.12 (s, 1H); 7.96 (d, J=7.2 Hz, 2H); 7.68 (d, J=7.2 Hz, 2H); 6.67 (s, 1H); 5.68 (s, 1H); 4.75 (m, 1H); 3.73 (m, 4H); 3.24 (m, 4H); 3.06 (br, 6H); 2.00 (br, 6H); 1.69 (br, 2H).

Example 10. Molecular Modeling of Multitarget PI3K/BRD4/CDK Triple Inhibitor

Published crystal structures of human-derived onco-proteins co-crystallized with small-molecule inhibitors, such as CDK6 (e.g, PDB: 2EUF, 4AUA, 5L2T), CDK4 (e.g., PDB: 2W96, 2W99, 2W9F, 2W9), BRD4-BD1 (e.g., PDB: 3MXF, 4CFK), PI3K-alpha (e.g., PDB: 4JPS, 5DXT) were obtained from the Protein Data Bank for the creation of computation models for protein-small molecule binding interactions to design, evaluate, prioritize synthesize, and test compounds in wet-lab tests (i.e., enzymatic, cell-based, in vivo). Proprietary crystal structures of compounds co-crystallized with these onco-targets (e.g., BRD4-BD1, BRD4-BD2) were obtained and also used for the creation of computational models. In addition, a homology model of PI3K-alpha was also created for the creation of computational models.

Three-dimensional (3D) models of the onco-proteins were created by keeping constant the atomic coordinates of the amino acid residues belonging to the amino acid backbone (peptide sequence) of the co-crystallized onco-proteins, removing co-crystallized factors (e.g., DMSO, glycol, water) and small molecules. Only co-crystallized water molecules known, found or suspected to participate in the formation of binding interactions between the onco-protein and a small molecule were kept as part of the computational model.

For the creation of a homology model of human PI3K-alpha, the human PI3K-alpha protein sequence obtained from the Swiss Prot protein sequence database (UniProtKB/Swiss-Prot entry no. P42336, PK3CA-HUMAN) was superimposed over the 3D coordinates of human PI3K-gamma cocrystallized with LY294002 (PDB code: 1E7V) removing both water molecules and LY294002 to create a 3D PI3K-alpha homology model.

A 3D grid of different dimensions (i.e., 10 Å radius) centered on the 3D coordinates of a co-crystallized small molecule in the onco-protein or in an area of interest in the onco-protein was created and used to in silico dock small molecules in the region covered by the 3D grid to test for binding interactions between a small molecule and the amino acid residues within the 3D grid of an onco-protein. Different docking software was used to in silico dock small molecules against the 3D models and 3D grids of onco-proteins (e.g., AutoDock Vina, FlexX) to identify favorable binding conformations of small molecules within a 3D grid and the predicted binding affinities for such conformations (kcal/mol).

For docking, a 3D model was constructed for each small molecule where first a 2D model was created (i.e., using ChemDraw), hydrogen atoms were included, atomic charges and addition/subtraction of hydrogens were applied based on the calculated protonated state of a small molecule at physiological pH 7.4, and the energy minimized (also called energy minimization, energy optimization, geometry minimization, or geometry optimization) to obtain the 3D coordinates of a small molecule.

We devised a broad synthetic scheme to synthesize millions of compounds represented by the Markush structure below (Formula IVa).

Formula IVa

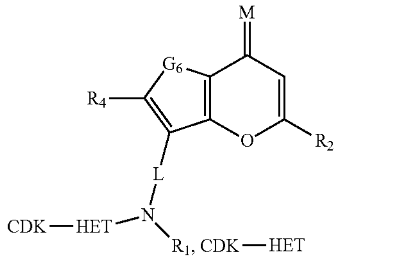

M, $R_4$ and $R_2$ are as defined in Formula I

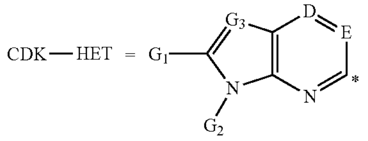

* = Point of attachment

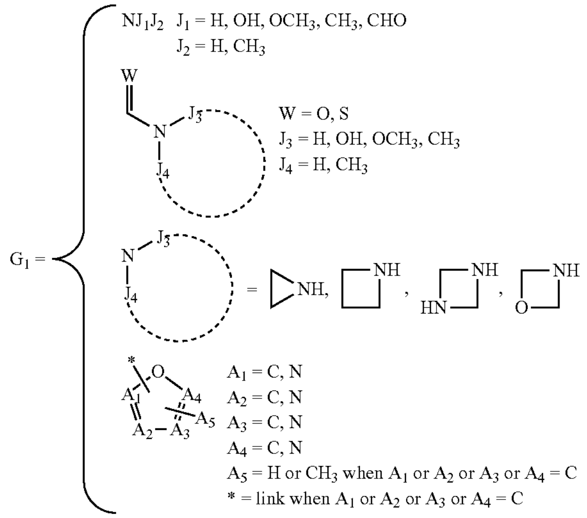

$G_2 = R_1$ ($R_1$ is as defined in Formula I)
$G_3$ = C, N
D = C, N
E = C, N

-continued

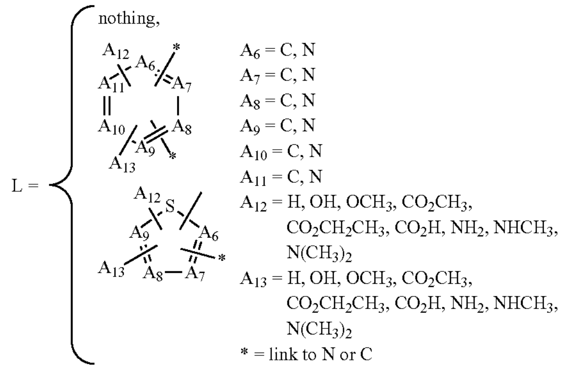

$G_6$ = O, S

The synthetic schemes are shown below as Schemes A, B, and C.

Synthesis Scheme A

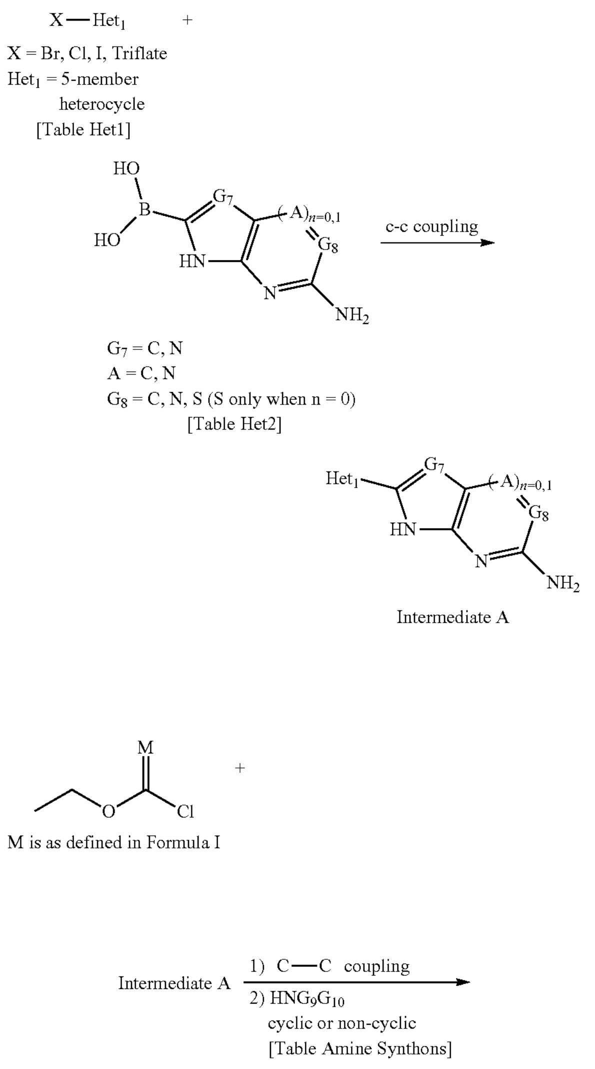

-continued

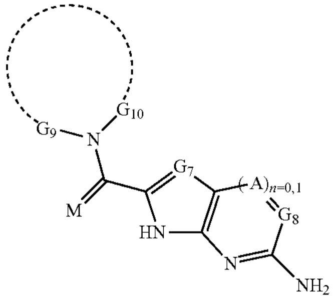

Intermediate B

Intermediate A or B

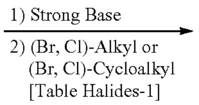

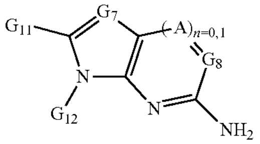

Intermediate C
$G_{11}$ = corresponding substituent
$G_{12}$ = substituent from Table Halides-1

Intermediate C +

Br—$G_{13}$—Cl
or
I—$G_{13}$—Cl

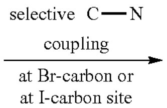

$G_{13}$ = Phenyl analogs,
Heterocycle analogs
[Table Halides-2]

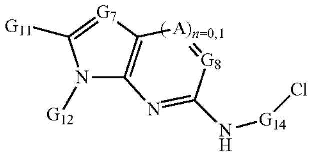

Intermediate D

Synthesis Scheme B

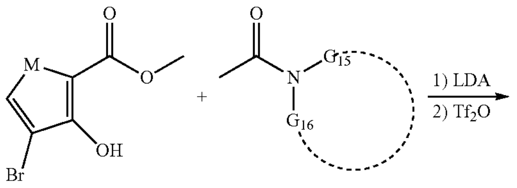

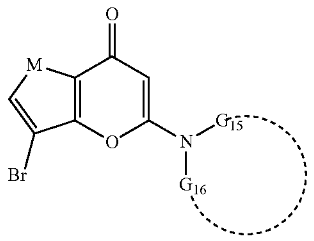

Intermediate E
[Table TP]

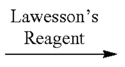

-continued

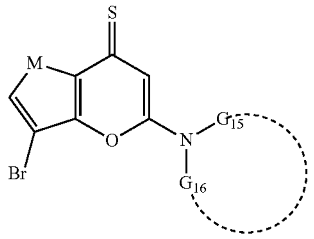

Intermediate F
[Table TP]

Intermediate E
or
Intermediate F

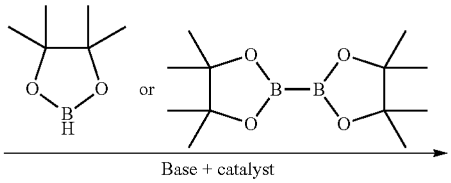

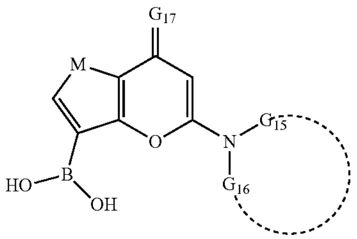

$G_{17}$ = O, S
Intermediate G

M is as defined in Formula I

Synthesis Scheme C

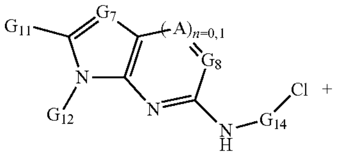

Intermediate D

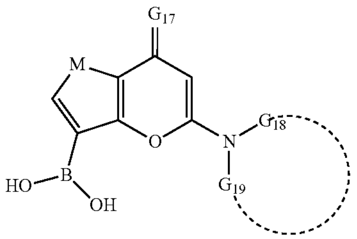

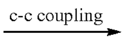

Intermediate G

-continued

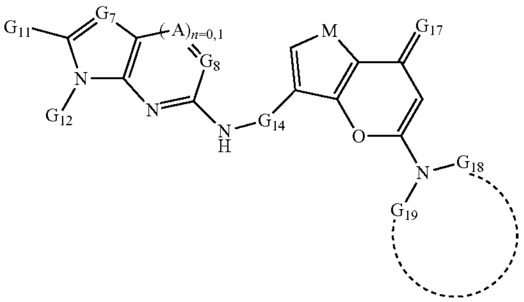

Product A

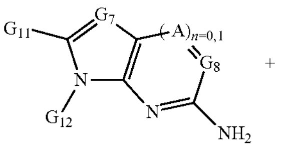

Intermediate C

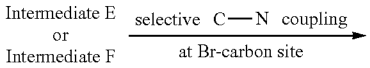

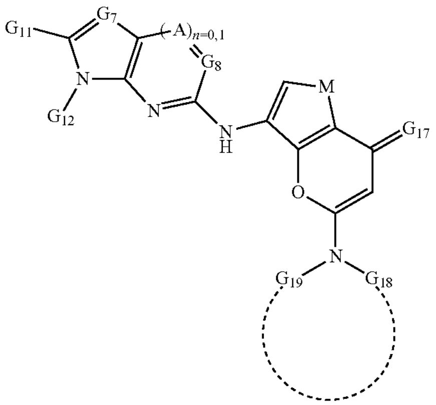

Product B

We selected key reactants (inputs) for each variant of the Markush structure which are listed below in their respective Tables 4-9 (Tables labeled: Het1, Amine Synthon, Halides 1, Het2, Halides 2, and TP, respectively). Selected inputs include reactants that may not be stable as shown and are used for the sole purpose of creating virtual library analogs of compounds encompassed by Formulas IVa, Figure IVb and Figure IVc.

TABLE 4

| Listing of Het1 group. |
| --- |
| 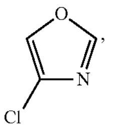 |
| 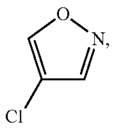 |

TABLE 4-continued

| Listing of Het1 group. |
| --- |
| 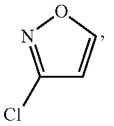 |
| 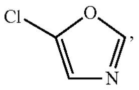 |
| 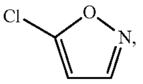 |
| 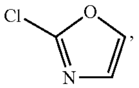 |
| 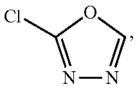 |
| 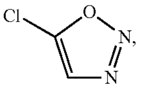 |
| 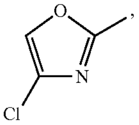 |
| 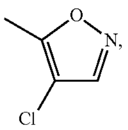 |
| 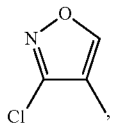 |
| 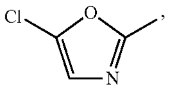 |
| 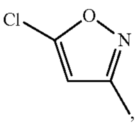 |
| 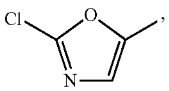 |
| 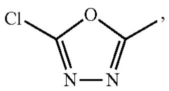 |

TABLE 4-continued
| Listing of Het1 group. |
| --- |
| 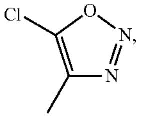, |
| 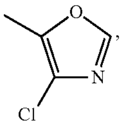, |
| 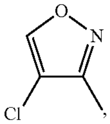, |
| 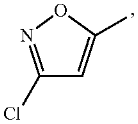, |
| 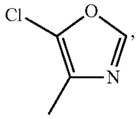, |
| 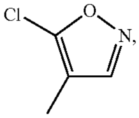, |
| 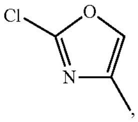, |
| 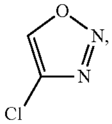, |
| 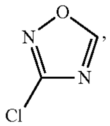, |
| 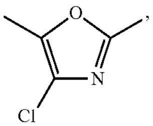, |
| 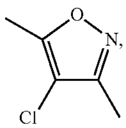, |
| 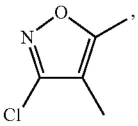, |
| 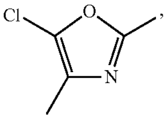, |
| 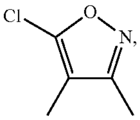, |
| 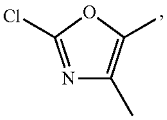, |
| 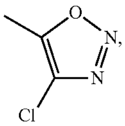, |
| 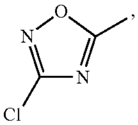, |
| 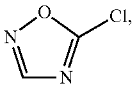, |
| 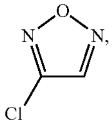, |
| 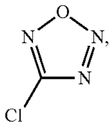, |
| 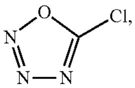, |
| 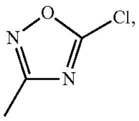, |
| 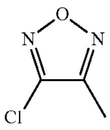 |

TABLE 5
| Listing of Amine Synthon group. |
|---|
| 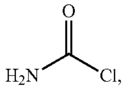 |
| 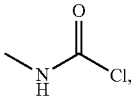 |
| 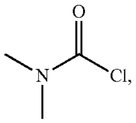 |
| 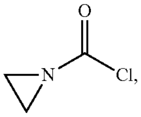 |
| 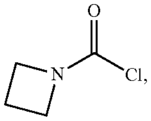 |
| 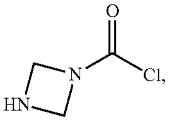 |
| 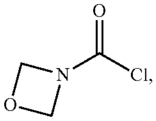 |
| 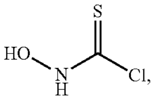 |
| 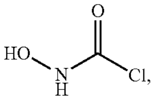 |
| 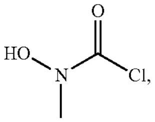 |
| 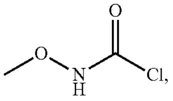 |
| 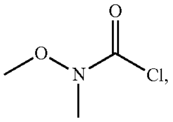 |
TABLE 5-continued
| Listing of Amine Synthon group. |
|---|
| 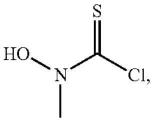 |
| 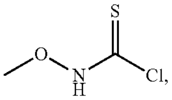 |
| 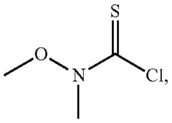 |
| 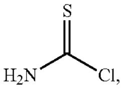 |
| 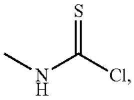 |
| 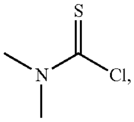 |
| 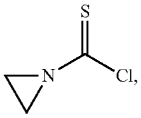 |
| 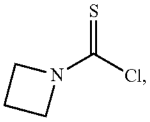 |
| 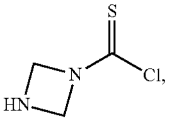 |
| 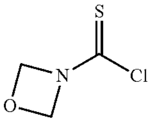 |
TABLE 6
| Listing of Halides 1 group. |
|---|
| 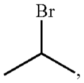 |

TABLE 6-continued
| Listing of Halides 1 group. |
|---|
| 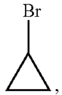, |
| 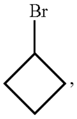, |
| 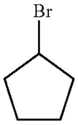 |
TABLE 7
| Listing of Het2 group. |
|---|
| 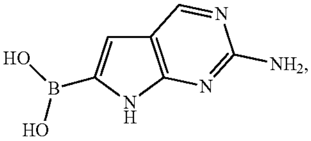 [SMILES: Nc1ncc2cc(B(O)O)[nH]c2n1] |
| 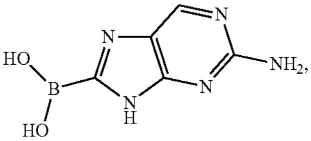 |
| 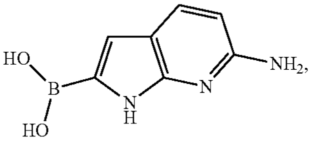 [SMILES: Nc1ccc2cc(B(O)O)[nH]c2n1] |
| 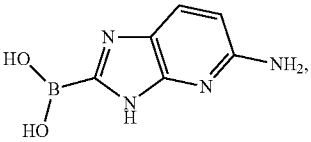 [SMILES: Nc1ccc2nc(B(O)O)[nH]c2n1] |
| 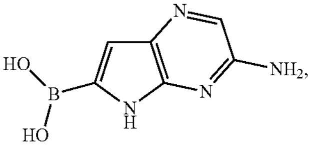 [SMILES: Nc1cnc2cc(B(O)O)[nH]c2n1] |
| 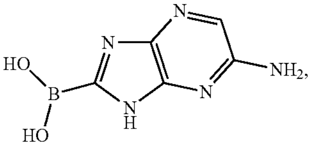 [SMILES: Nc1cnc2nc(B(O)O)[nH]c2n1] |
| 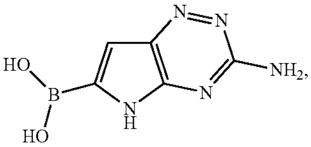 [SMILES: Nc1nnc2cc(B(O)O)[nH]c2n1] |
TABLE 7-continued
| Listing of Het2 group. |
|---|
| 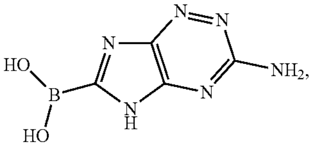 [SMILES: Nc1nnc2nc(B(O)O)[nH]c2n1] |
| 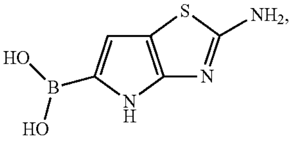 [SMILES: Nc1nc2[nH]c(B(O)O)cc2s1] |
| 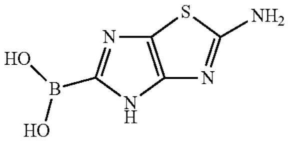 [SMILES: Nc1nc2[nH]c(B(O)O)nc2s1] |
TABLE 8
| Listing of Halides 2 group. |
|---|
| 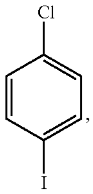 |
| 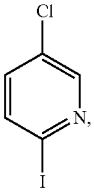 |
| 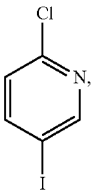 |
| 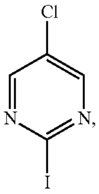 |

TABLE 8-continued
| Listing of Halides 2 group. |
| --- |
| 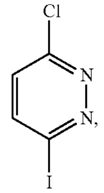 |
| 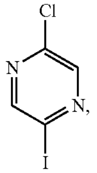 |
| 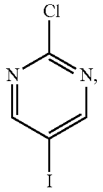 |
| 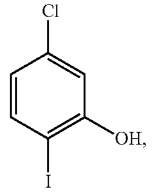 |
| 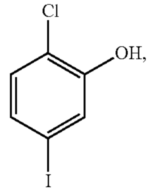 |
| 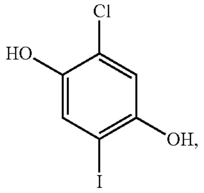 |
| 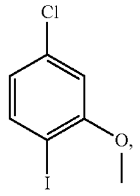 |
| 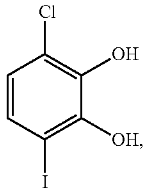 |
TABLE 8-continued
| Listing of Halides 2 group. |
| --- |
| 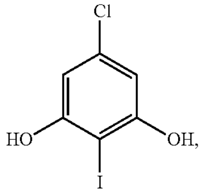 |
| 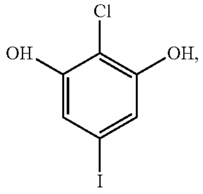 |
| 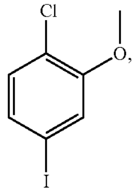 |
| 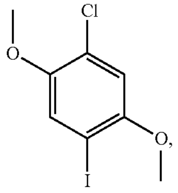 |
| 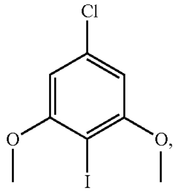 |
| 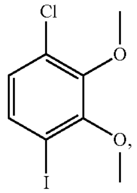 |
| 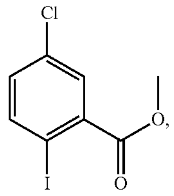 |

TABLE 8-continued
| Listing of Halides 2 group. |
|---|
| 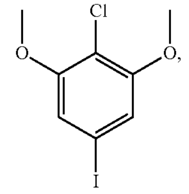 |
| 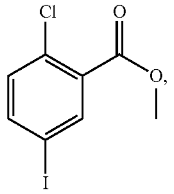 |
| 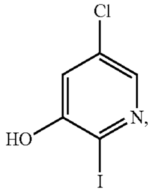 |
| 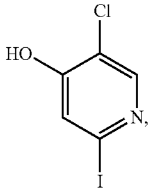 |
| 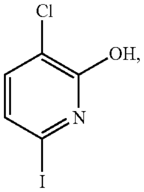 |
| 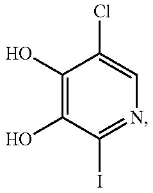 |
| 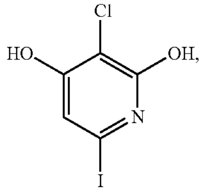 |
TABLE 8-continued
| Listing of Halides 2 group. |
|---|
| 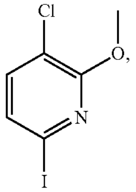 |
| 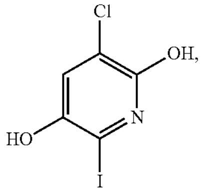 |
| 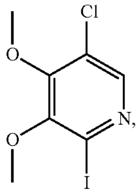 |
| 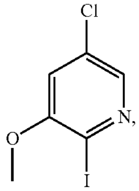 |
| 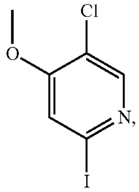 |
| 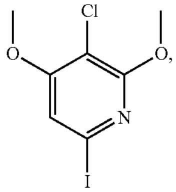 |
| 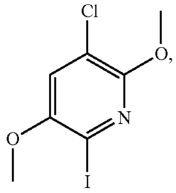 |

TABLE 8-continued
| Listing of Halides 2 group. |
| --- |
| 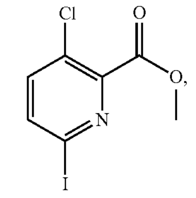 |
| 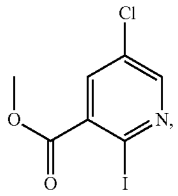 |
| 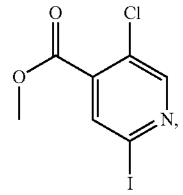 |
| 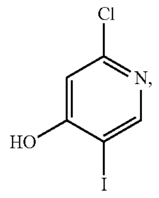 |
| 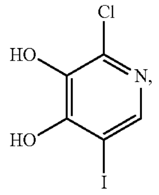 |
| 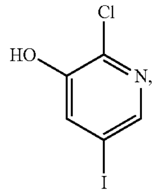 |
| 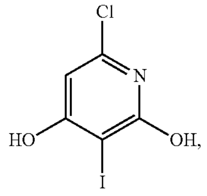 |
TABLE 8-continued
| Listing of Halides 2 group. |
| --- |
| 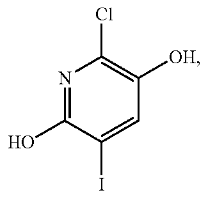 |
| 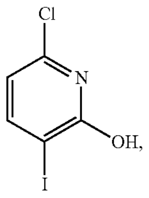 |
| 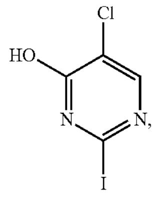 |
| 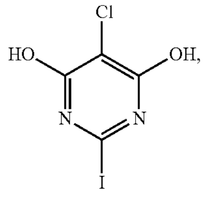 |
| 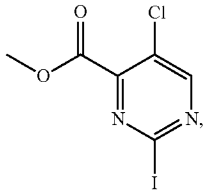 |
| 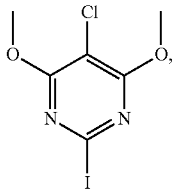 |
| 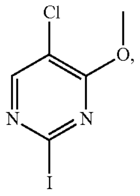 |

TABLE 8-continued
| Listing of Halides 2 group. |
| --- |
| 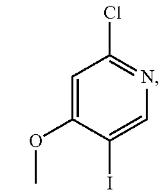 |
| 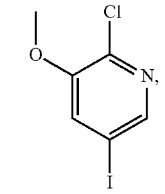 |
| 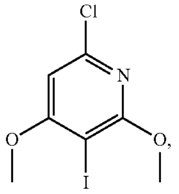 |
| 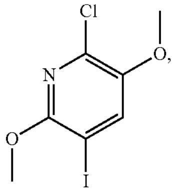 |
| 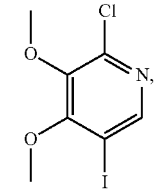 |
| 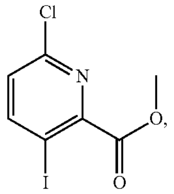 |
| 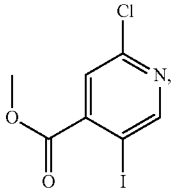 |
TABLE 8-continued
| Listing of Halides 2 group. |
| --- |
| 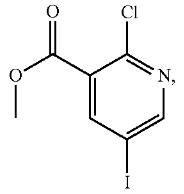 |
| 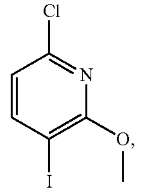 |
| 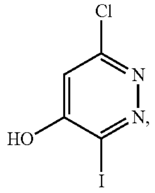 |
| 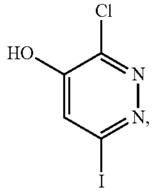 |
| 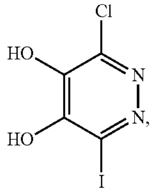 |
| 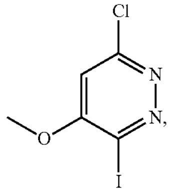 |
| 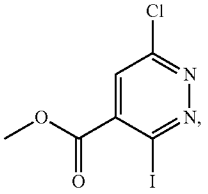 |

TABLE 8-continued
| Listing of Halides 2 group. |
| --- |
| 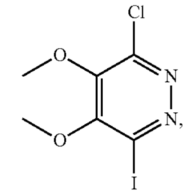 |
| 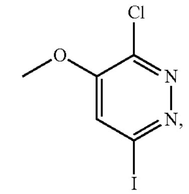 |
| 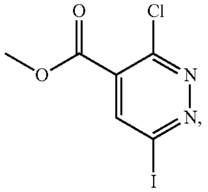 |
| 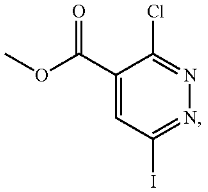 |
| 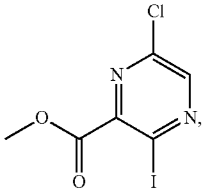 |
| 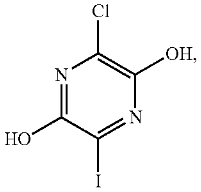 |
| 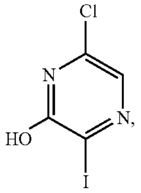 |
TABLE 8-continued
| Listing of Halides 2 group. |
| --- |
| 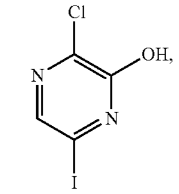 |
| 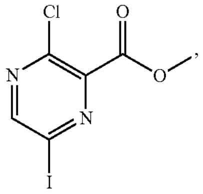 |
| 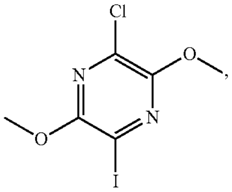 |
| 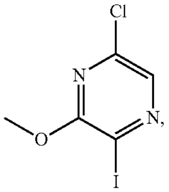 |
| 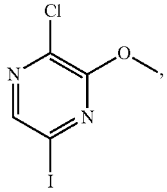 |
| 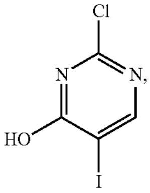 |
| 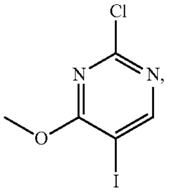 |

TABLE 8-continued
| Listing of Halides 2 group. |
|---|
| 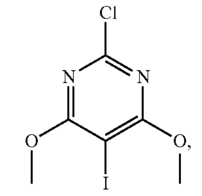 |
| 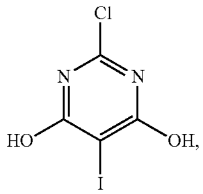 |
| 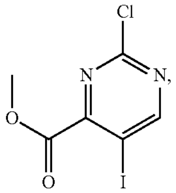 |
| 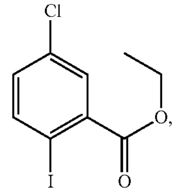 |
| 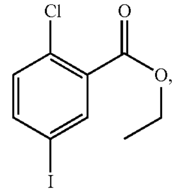 |
| 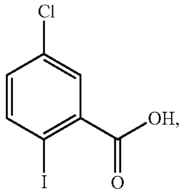 [SMILES: O=C(O)c1cc(Cl)ccc1I] |
| 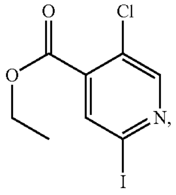 |
TABLE 8-continued
| Listing of Halides 2 group. |
|---|
| 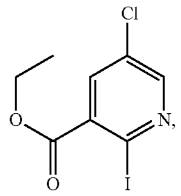 |
| 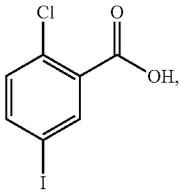 [SMILES: O=C(O)c1cc(I)ccc1Cl] |
| 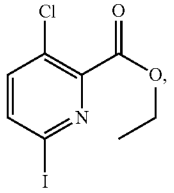 |
| 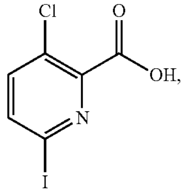 [SMILES: O=C(O)c1nc(I)ccc1Cl] |
| 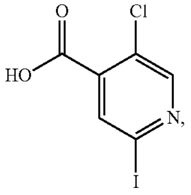 |
| 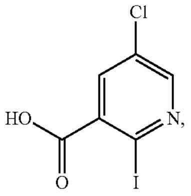 [SMILES: O=C(O)c1cc(Cl)cnc1I] |
| 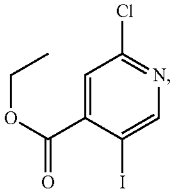 |

TABLE 8-continued
| Listing of Halides 2 group. |
| --- |
| 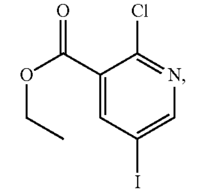 |
| 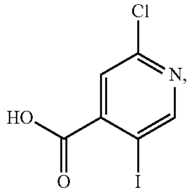 [SMILES: O=C(O)c1cc(Cl)ncc1I] |
| 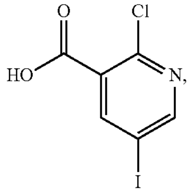 [SMILES: O=C(O)c1cc(I)cnc1Cl] |
| 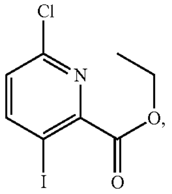 |
| 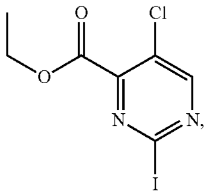 |
| 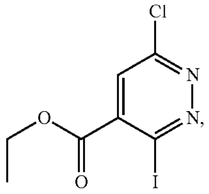 |
| 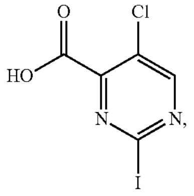 [SMILES: O=C(O)c1nc(I)ncc1Cl] |
TABLE 8-continued
| Listing of Halides 2 group. |
| --- |
| 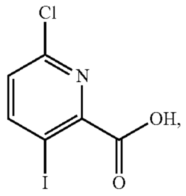 [SMILES: O=C(O)c1nc(Cl)ccc1I] |
| 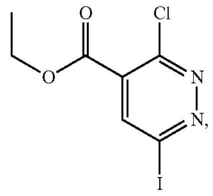 |
| 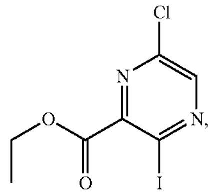 |
| 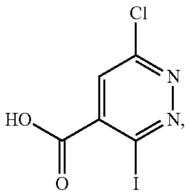 |
| 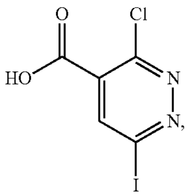 [SMILES: O=C(O)c1cc(I)nnc1Cl] |
| 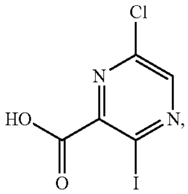 [SMILES: O=C(O)c1nc(Cl)cnc1I] |
| 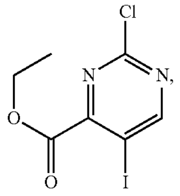 |

TABLE 8-continued
| Listing of Halides 2 group. |
| --- |
| 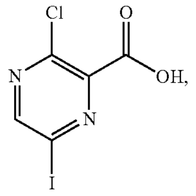 [SMILES: O=C(O)c1nc(I)cnc1Cl] |
| 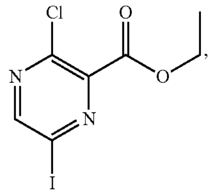 |
| 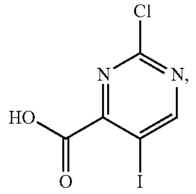 [SMILES: O=C(O)c1nc(Cl)ncc1I] |
| 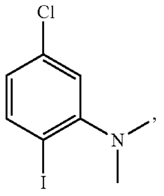 |
| 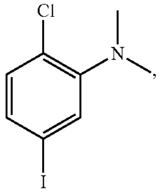 |
| 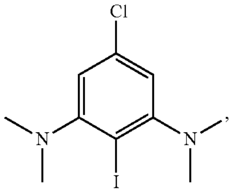 |
| 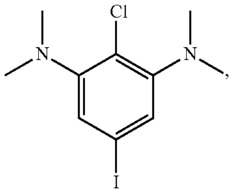 |
TABLE 8-continued
| Listing of Halides 2 group. |
| --- |
| 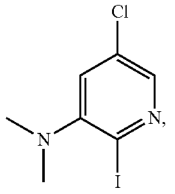 |
| 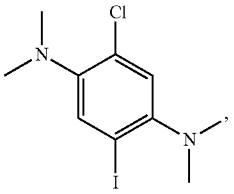 |
| 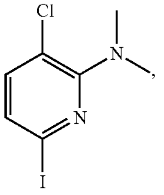 |
| 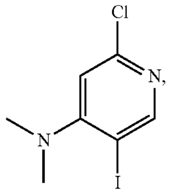 |
| 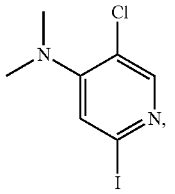 |
| 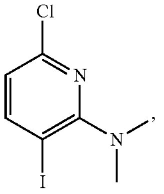 |
| 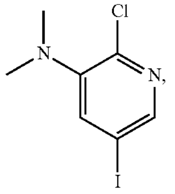 |

TABLE 8-continued
| Listing of Halides 2 group. |
| --- |
| 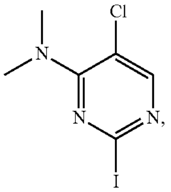 |
| 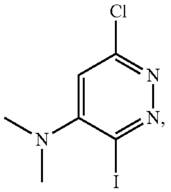 |
| 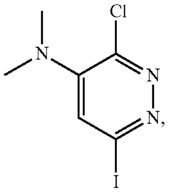 |
| 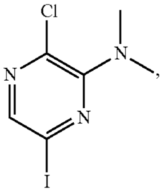 |
| 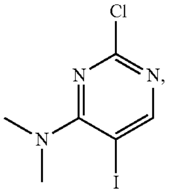 |
| 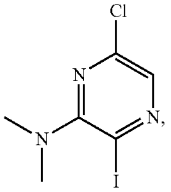 |
| 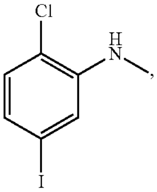 |
| 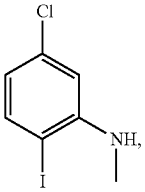 |
| 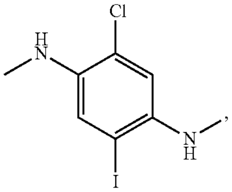 |
| 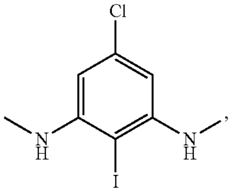 |
| 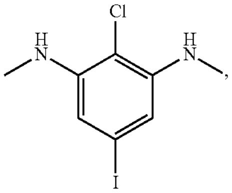 |
| 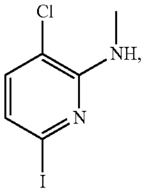 |
| 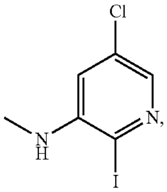 |
| 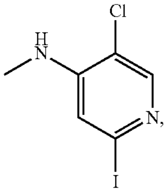 |

TABLE 8-continued
| Listing of Halides 2 group. |
|---|
| 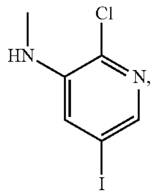 |
| 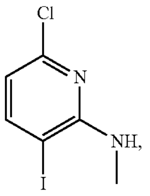 |
| 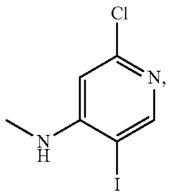 |
| 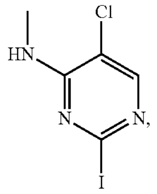 |
| 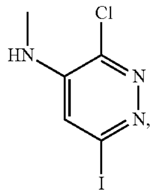 |
| 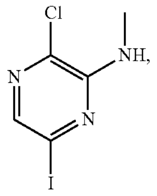 |
| 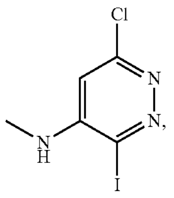 |
TABLE 8-continued
| Listing of Halides 2 group. |
|---|
| 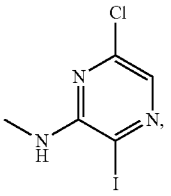 |
| 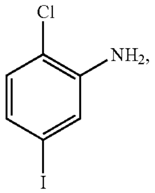 |
| 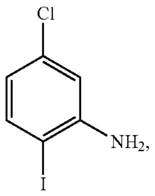 |
| 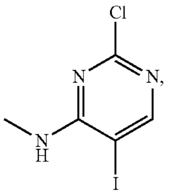 |
| 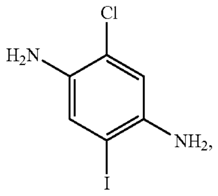 |
| 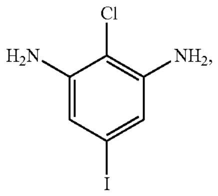 |
| 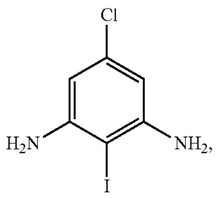 |

TABLE 8-continued
| Listing of Halides 2 group. |
| --- |
| 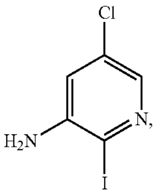 |
| 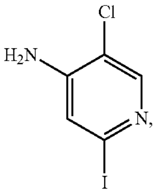 |
| 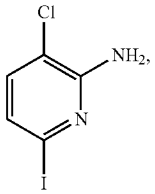 |
| 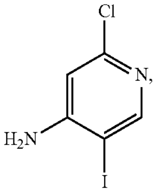 |
| 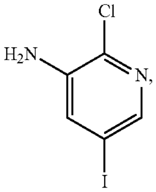 |
| 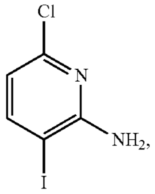 |
| 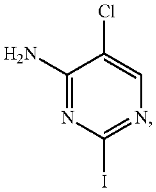 |
TABLE 8-continued
| Listing of Halides 2 group. |
| --- |
| 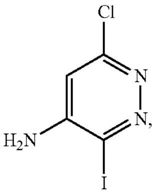 |
| 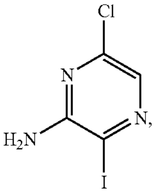 |
| 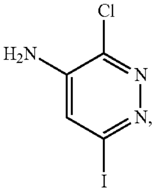 |
| 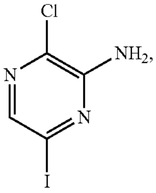 |
| 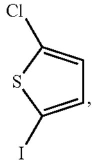 |
| 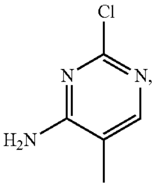 |
| 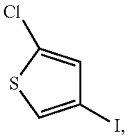 |
| 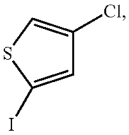 |

TABLE 8-continued
Listing of Halides 2 group.
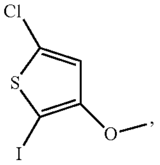
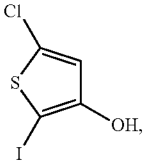
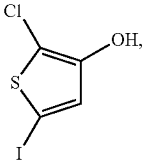
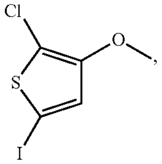
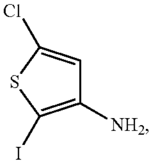
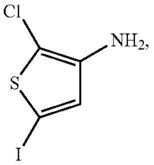
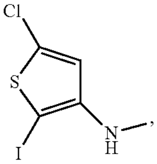
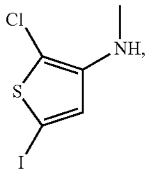
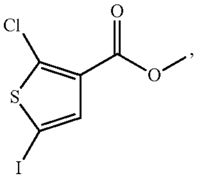
TABLE 8-continued
Listing of Halides 2 group.
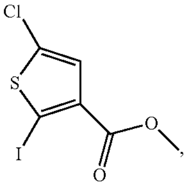
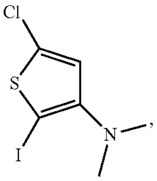
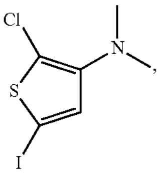
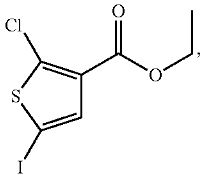
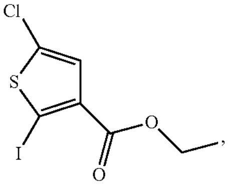
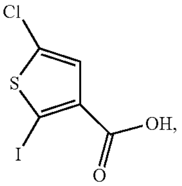
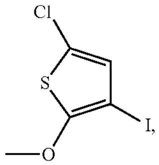
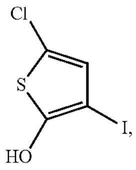

TABLE 8-continued
| Listing of Halides 2 group. |
| --- |
| 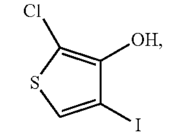 |
| 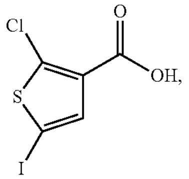 |
| 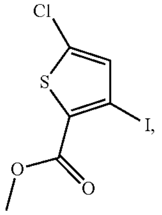 |
| 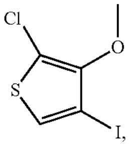 |
| 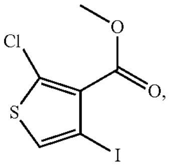 |
| 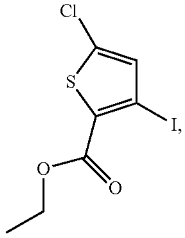 |
| 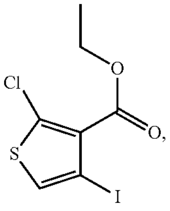 |
| 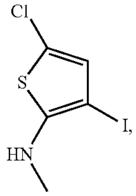 |
TABLE 8-continued
| Listing of Halides 2 group. |
| --- |
| 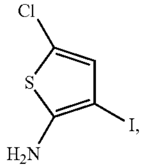 |
| 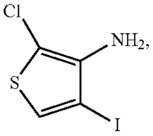 |
| 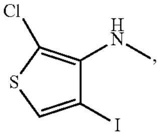 |
| 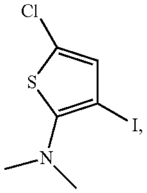 |
| 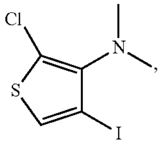 |
| 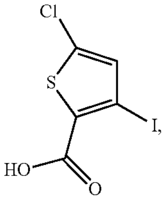 |
| 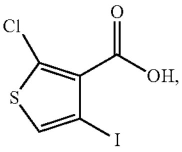 |
| 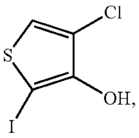 |
| 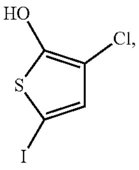 |

TABLE 8-continued
| Listing of Halides 2 group. |
|---|
| 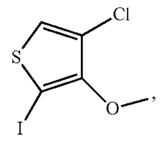 |
| 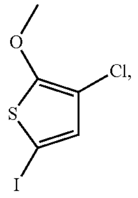 |
| 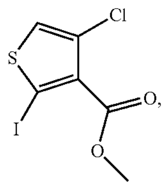 |
| 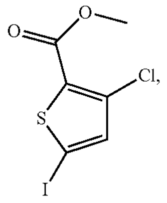 |
| 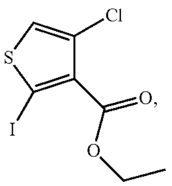 |
| 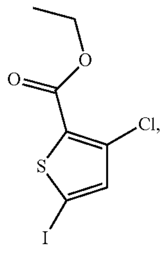 |
| 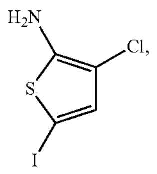 |
| 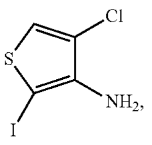 |
TABLE 8-continued
| Listing of Halides 2 group. |
|---|
| 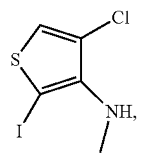 |
| 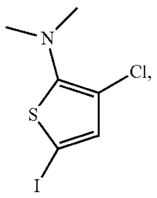 |
| 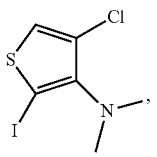 |
| 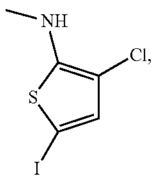 |
| 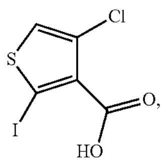 |
| 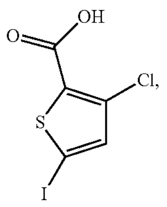 |
| 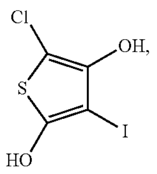 |
| 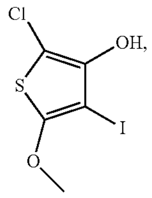 |

TABLE 8-continued
| Listing of Halides 2 group. |
|---|
| 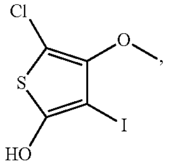 |
| 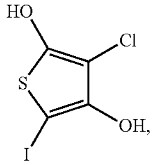 |
| 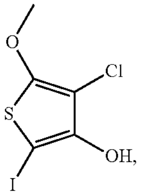 |
| 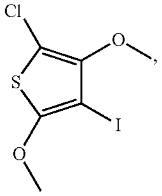 |
| 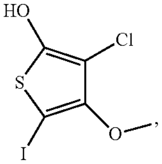 |
| 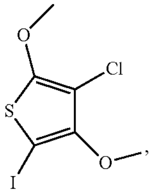 |
| 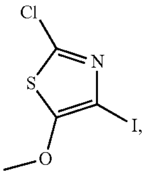 |
| 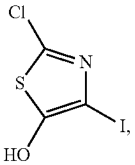 |
| 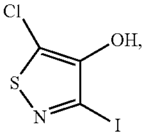 |
| 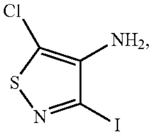 |
| 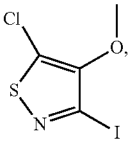 |
| 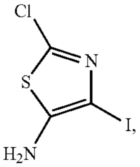 |
| 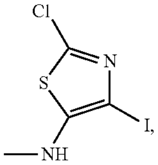 |
| 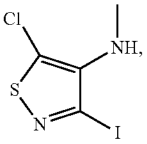 |
| 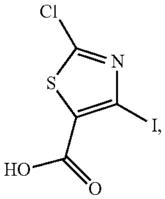 |
| 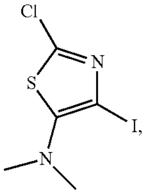 |
| 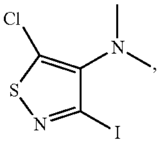 |

TABLE 8-continued
| Listing of Halides 2 group. |
| --- |
| 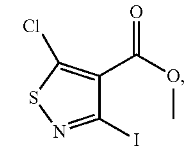 |
| 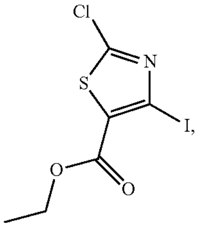 |
| 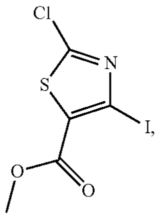 |
| 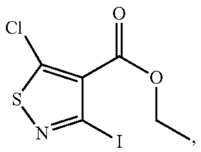 |
| 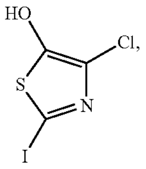 |
| 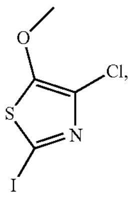 |
| 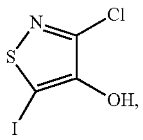 |
| 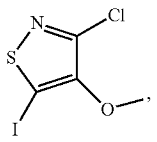 |
TABLE 8-continued
| Listing of Halides 2 group. |
| --- |
| 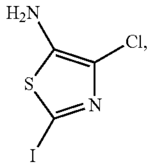 |
| 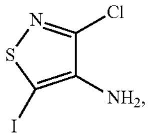 |
| 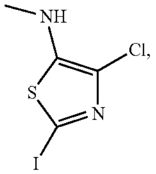 |
| 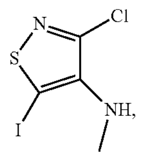 |
| 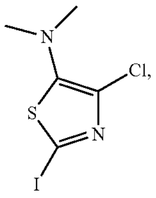 |
| 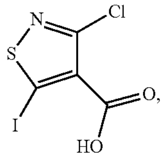 |
| 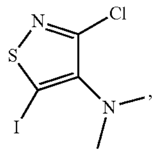 |
| 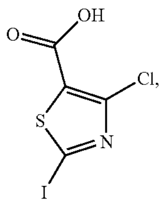 |

TABLE 8-continued
| Listing of Halides 2 group. |
| --- |
| 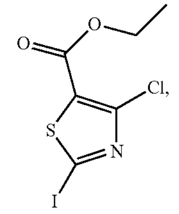 |
| 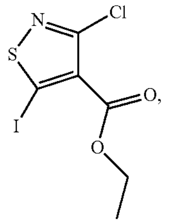 |
| 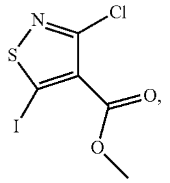 |
| 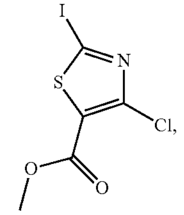 |
| 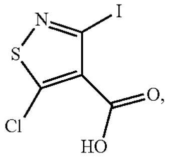 |
| 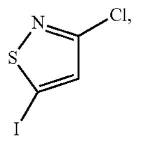 |
| 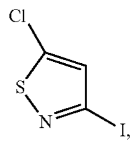 |
| 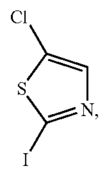 |
TABLE 8-continued
| Listing of Halides 2 group. |
| --- |
| 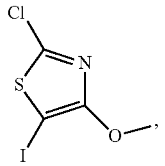 |
| 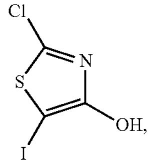 |
| 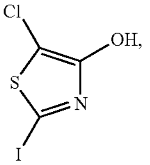 |
| 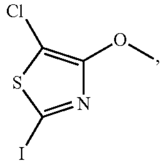 |
| 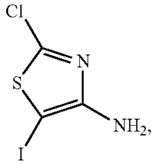 |
| 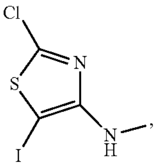 |
| 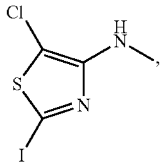 |
| 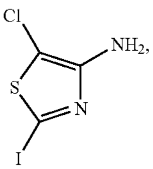 |
| 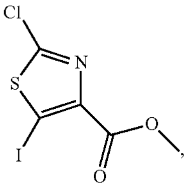 |

TABLE 8-continued
| Listing of Halides 2 group. |
|---|
| 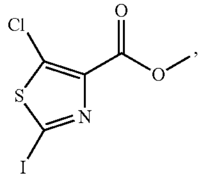 , |
| 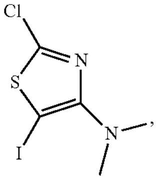 , |
| 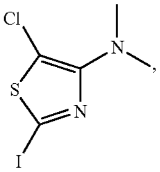 , |
| 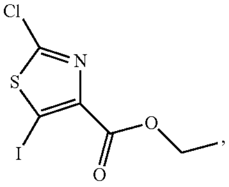 , |
| 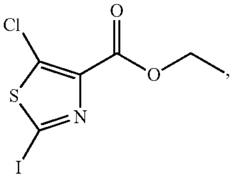 , |
| 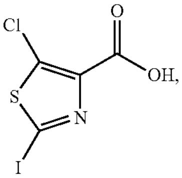 , |
| 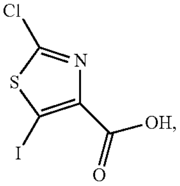 , |
| 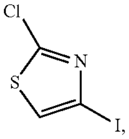 , |
TABLE 8-continued
| Listing of Halides 2 group. |
|---|
| 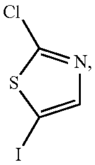 , |
| 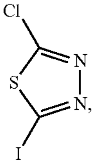 , |
| 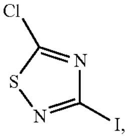 , |
| 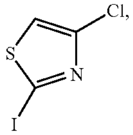 , |
| 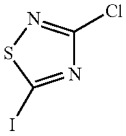 |
TABLE 9
| Listing of TP group. |
|---|
| 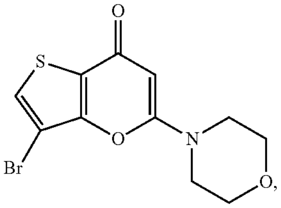 , |
| 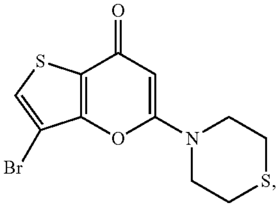 [SMILES: O=c1cc(N2CCOCC2)oc2c(Br)csc12] , |
| 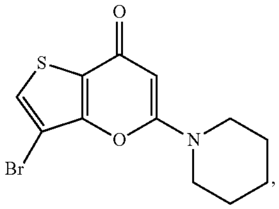 , |

TABLE 9-continued
Listing of TP group.
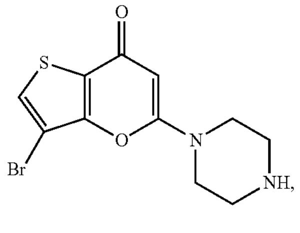
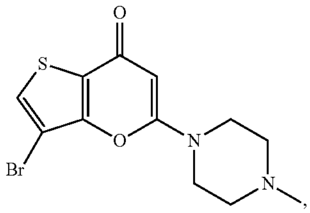
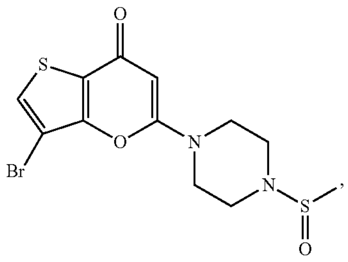
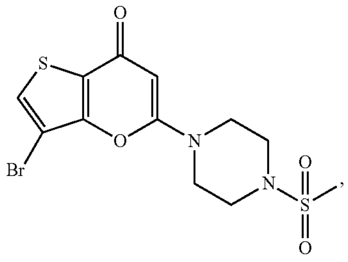
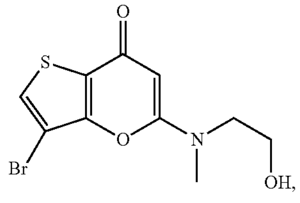
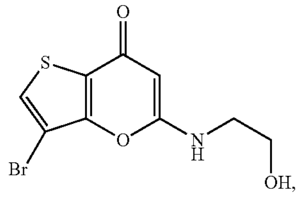 [SMILES: O=c1cc(NCCO)oc2c(Br)csc12]
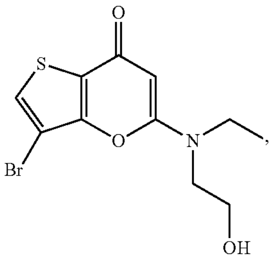
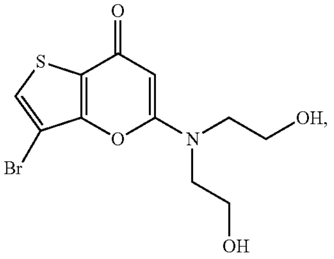 [SMILES: O=c1cc(N(CCO)CCO)oc2c(Br)csc12]
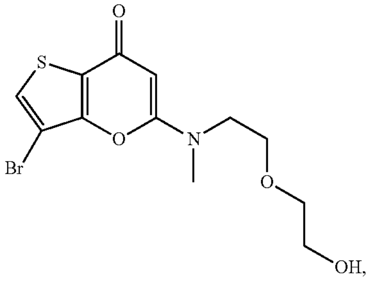 [SMILES: CN(CCOCCO)c1cc(=O)c2scc(Br)c2o1]
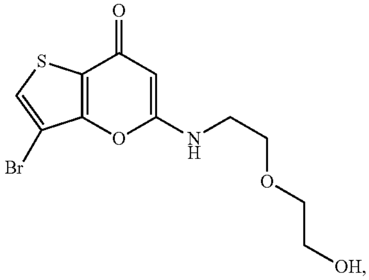 [SMILES: O=c1cc(NCCOCCO)oc2c(Br)csc12]
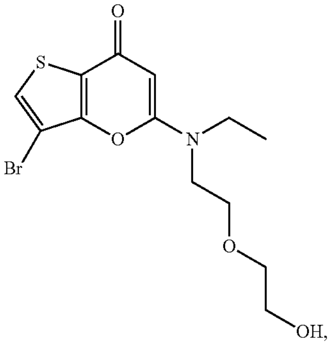 [SMILES: CCN(CCOCCO)c1cc(=O)c2scc(Br)c2o1]

TABLE 9-continued
Listing of TP group.
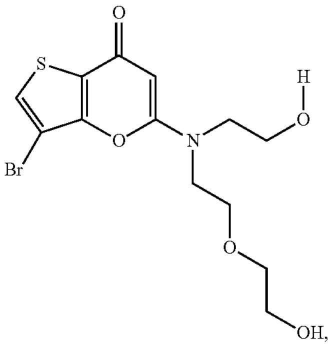 [SMILES: O=c1cc(N(CCO)CCOCCO)oc2c(Br)csc12]
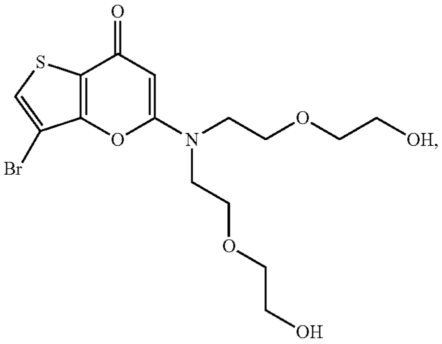 [SMILES: O=c1cc(N(CCOCCO)CCOCCO)oc2c(Br)csc12]
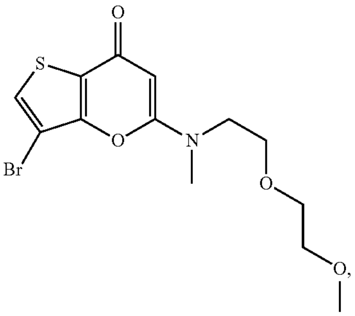
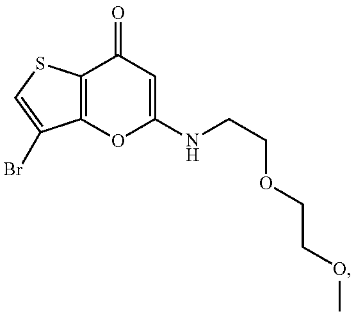 [SMILES: COCCOCCNc1cc(=O)c2scc(Br)c2o1]
TABLE 9-continued
Listing of TP group.
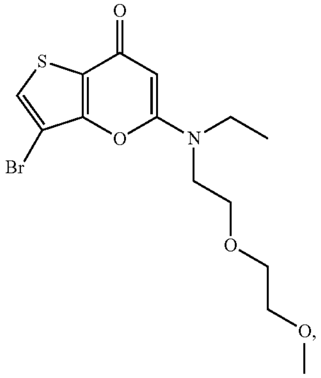 [SMILES: CCN(CCOCCOC)c1cc(=O)c2scc(Br)c2o1]
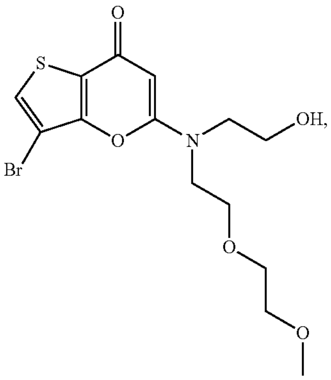 [SMILES: COCCOCCN(CCO)c1cc(=O)c2scc(Br)c2o1]
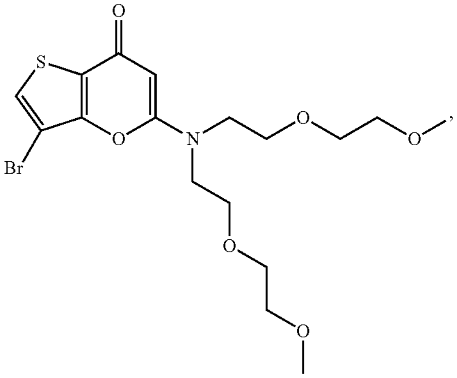
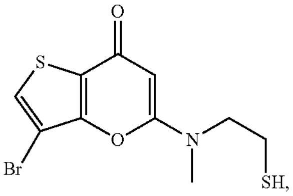
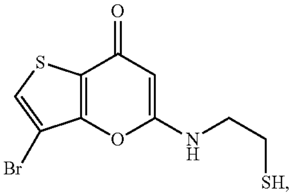

TABLE 9-continued
| Listing of TP group. |
| --- |
| 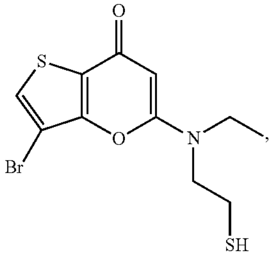 |
| 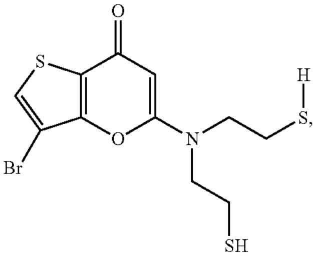 [SMILES: O=c1cc(N(CCS)CCS)oc2c(Br)csc12] |
| 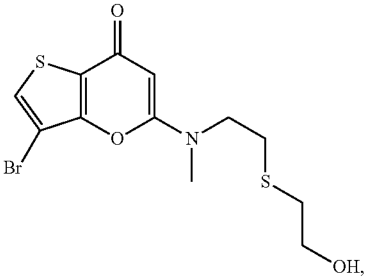 |
| 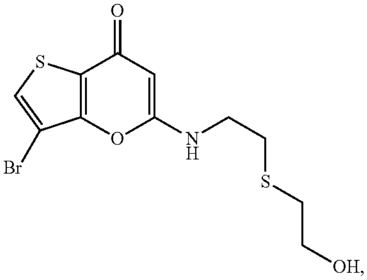 |
| 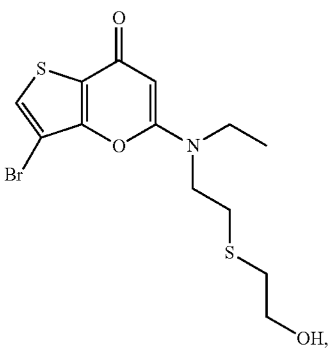 [SMILES: CCN(CCSCCO)c1cc(=O)c2scc(Br)c2o1] |
TABLE 9-continued
| Listing of TP group. |
| --- |
| 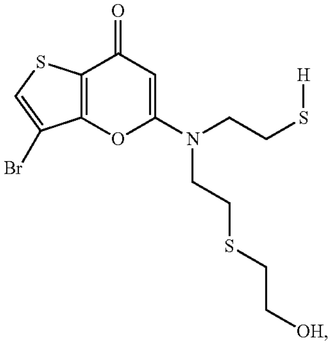 [SMILES: O=c1cc(N(CCS)CCSCCO)oc2c(Br)csc12] |
| 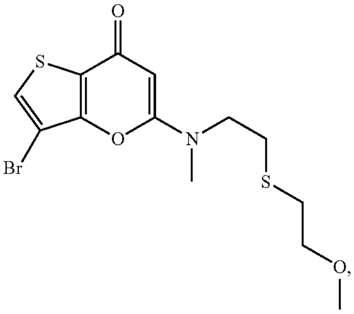 [SMILES: COCCSCCN(C)c1cc(=O)c2scc(Br)c2o1] |
| 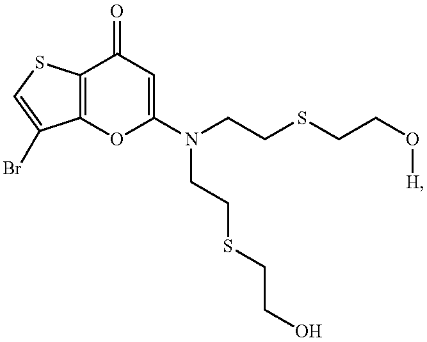 |
| 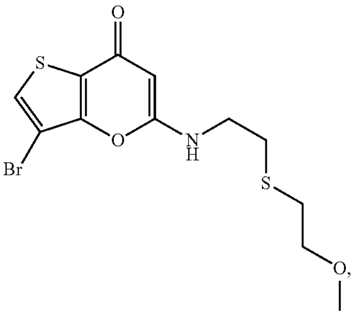 [SMILES: COCCSCCNc1cc(=O)c2scc(Br)c2o1] |

TABLE 9-continued
| Listing of TP group. |
| --- |
| 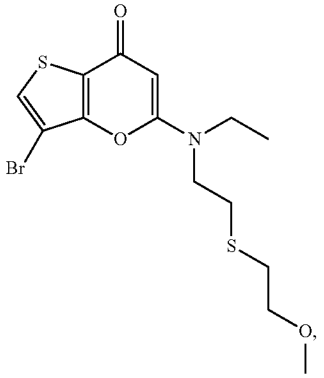 |
| 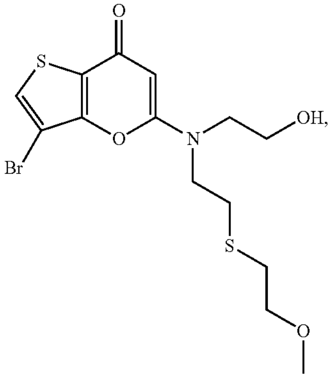 [SMILES: COCCSCCN(CCO)c1cc(=O)c2scc(Br)c2o1] |
| 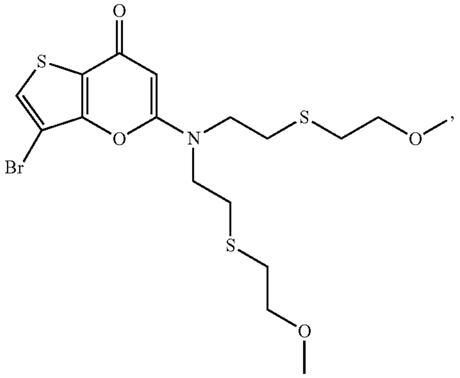 |
| 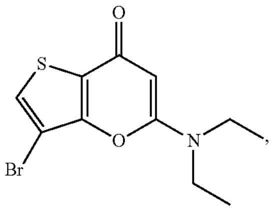 |
| 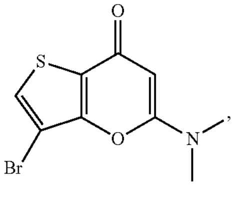 |
TABLE 9-continued
| Listing of TP group. |
| --- |
| 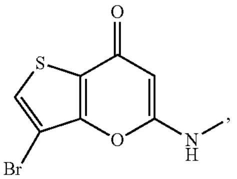 |
| 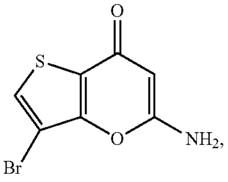 [SMILES: Nc1cc(=O)c2scc(Br)c2o1] |
| 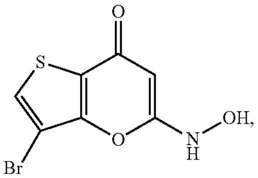 [SMILES: O=c1cc(NO)oc2c(Br)csc12] |
| 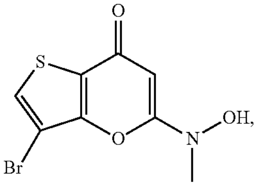 |
| 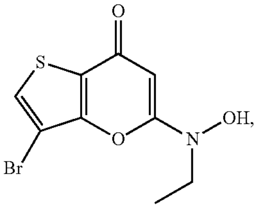 |
| 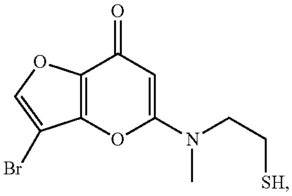 |
| 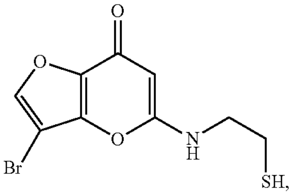 [SMILES: O=c1cc(NCCS)oc2c(Br)coc12] |

TABLE 9-continued
| Listing of TP group. |
|---|
| 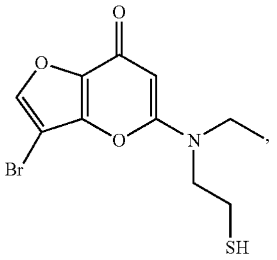, |
| 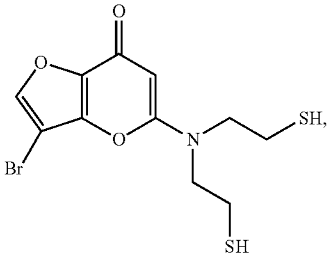, |
| 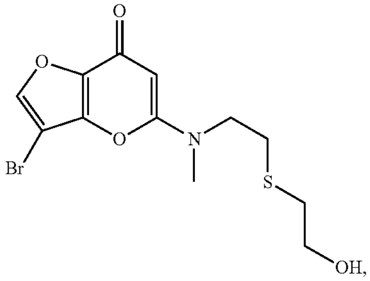 [SMILES: CN(CCSCCO)c1cc(=O)c2occ(Br)c2o1], |
| 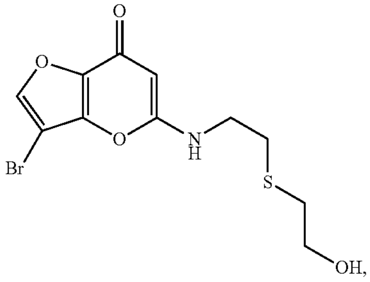 [SMILES: O=c1cc(NCCSCCO)oc2c(Br)coc12], |
| 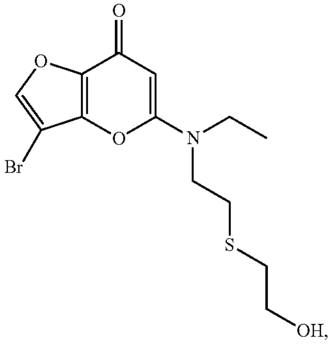 [SMILES: CCN(CCSCCO)c1cc(=O)c2occ(Br)c2o1], |
| 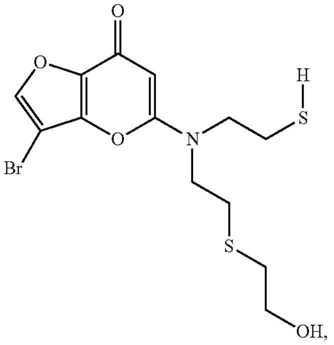, |
| 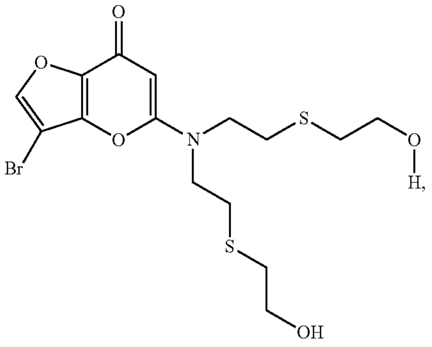, |
| 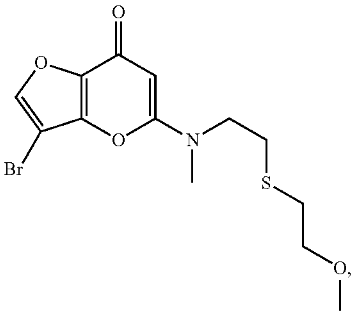 [SMILES: COCCSCCN(C)c1cc(=O)c2occ(Br)c2o1], |
| 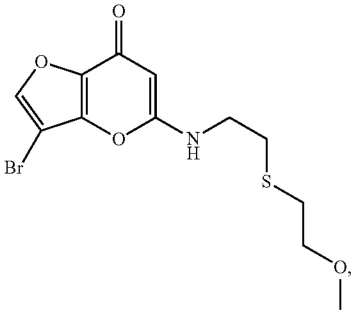 [SMILES: COCCSCCNc1cc(=O)c2occ(Br)c2o1], |

TABLE 9-continued
| Listing of TP group. |
| --- |
| 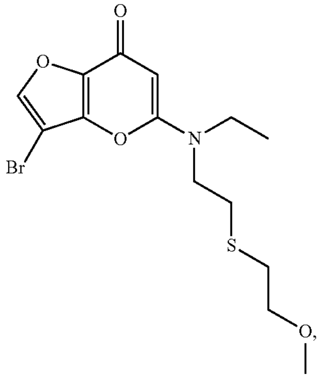 [SMILES: CCN(CCSCCOC)c1cc(=O)c2occ(Br)c2o1] |
| 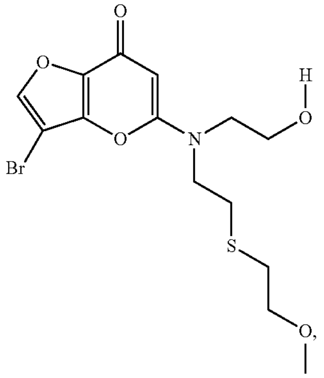 [SMILES: COCCSCCN(CCO)c1cc(=O)c2occ(Br)c2o1] |
| 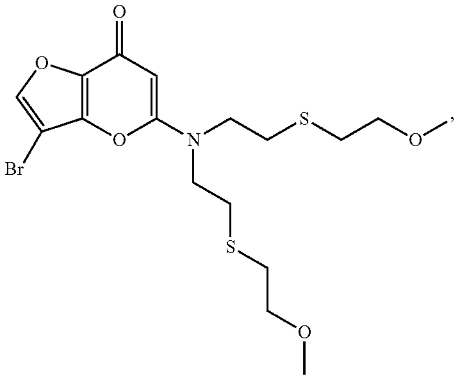 |
| 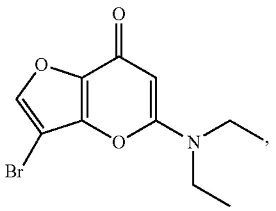 |
| 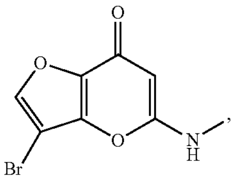 |
TABLE 9-continued
| Listing of TP group. |
| --- |
| 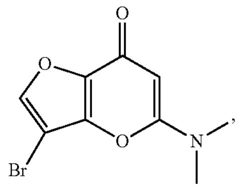 |
| 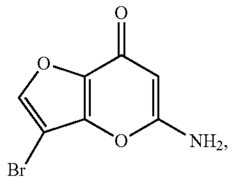 [SMILES: Nc1cc(=O)c2occ(Br)c2o1] |
| 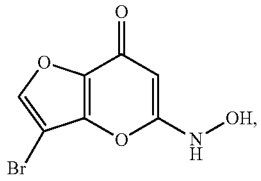 [SMILES: O=c1cc(NO)oc2c(Br)coc12] |
| 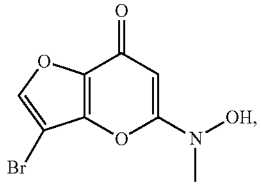 |
| 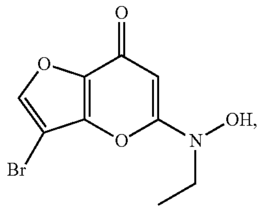 |
| 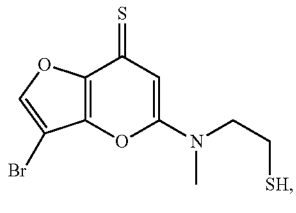 |
| 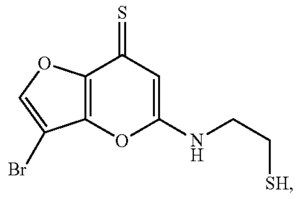 |

TABLE 9-continued
| Listing of TP group. |
| --- |
| 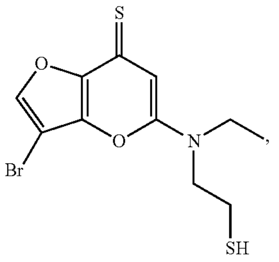 |
| 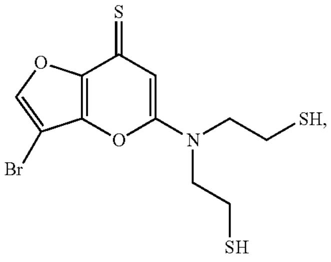 [SMILES: S=c1cc(N(CCS)CCS)oc2c(Br)coc12] |
| 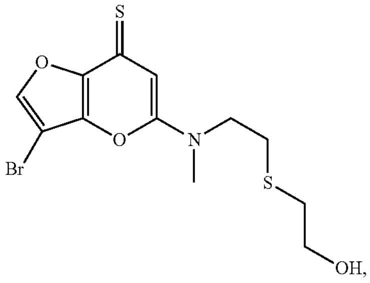 [SMILES: CN(CCSCCO)c1cc(=S)c2occ(Br)c2o1] |
| 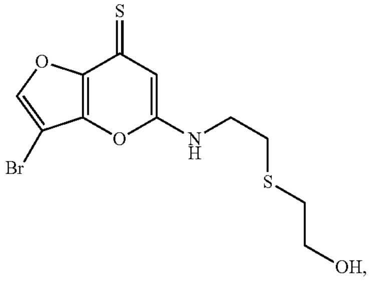 [SMILES: OCCSCCNc1cc(=S)c2occ(Br)c2o1] |
| 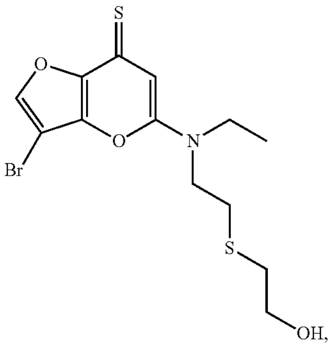 |
| 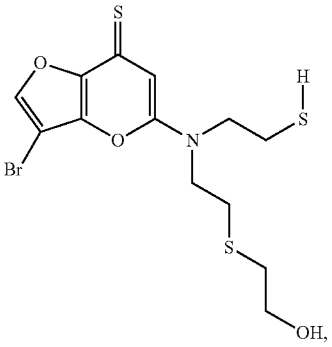 [SMILES: OCCSCCN(CCS)c1cc(=S)c2occ(Br)c2o1] |
| 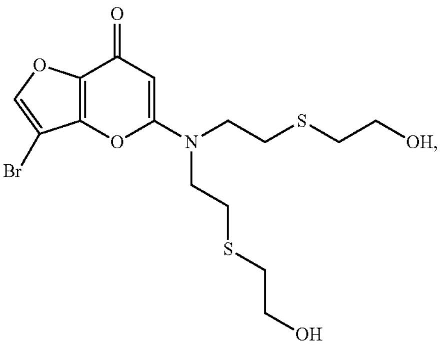 |
| 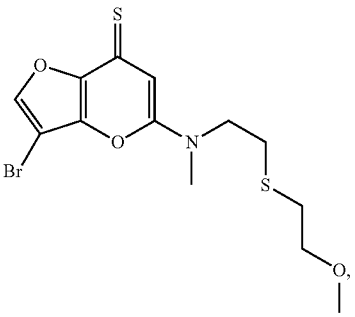 |
| 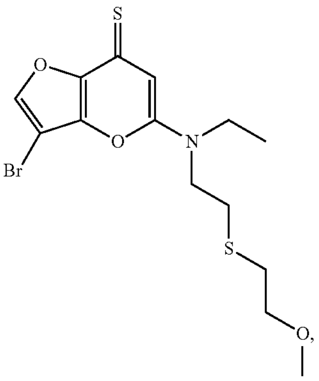 |

TABLE 9-continued
| Listing of TP group. |
|---|
| 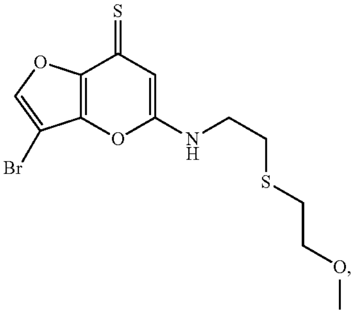 |
| 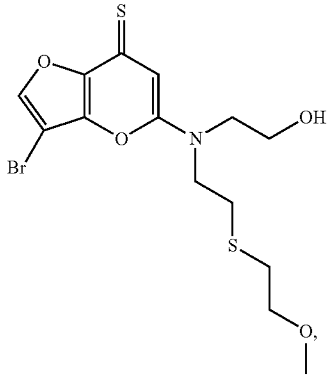 [SMILES: COCCSCCN(CCO)c1cc(=S)c2occ(Br)c2o1] |
| 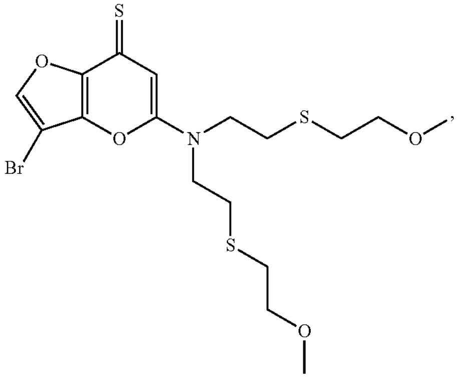 |
| 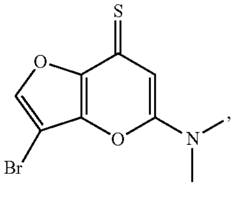 |
| 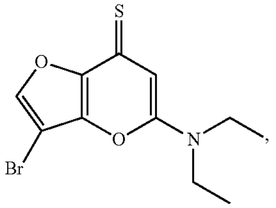 |
TABLE 9-continued
| Listing of TP group. |
|---|
| 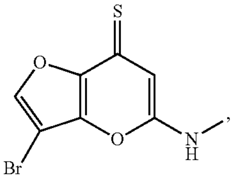 |
| 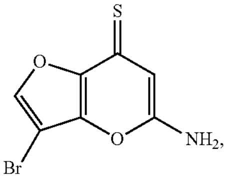 |
| 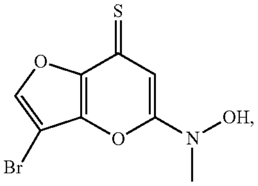 |
| 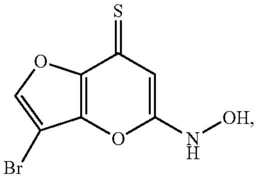 [SMILES: ONc1cc(=S)c2occ(Br)c2o1] |
| 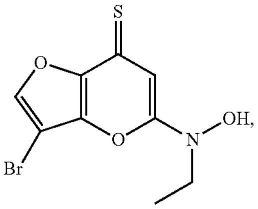 |
| 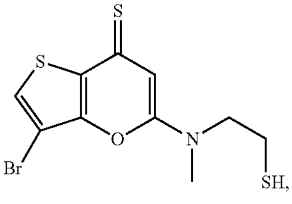 |
| 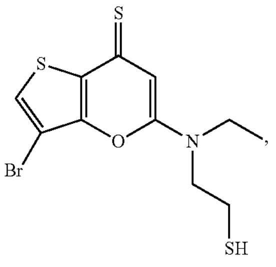 |

TABLE 9-continued
| Listing of TP group. |
|---|
| 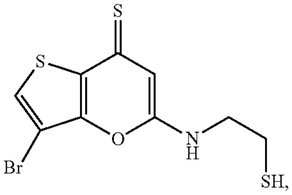, |
| 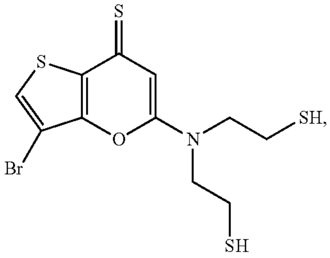 [SMILES: S=c1cc(N(CCS)CCS)oc2c(Br)csc12], |
| 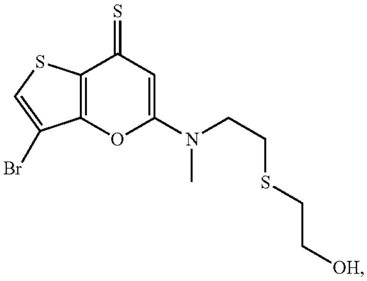, |
| 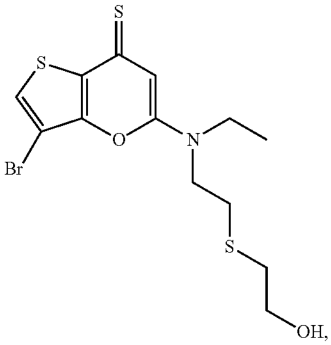 [SMILES: CCN(CCSCCO)c1cc(=S)c2scc(Br)c2o1], |
| 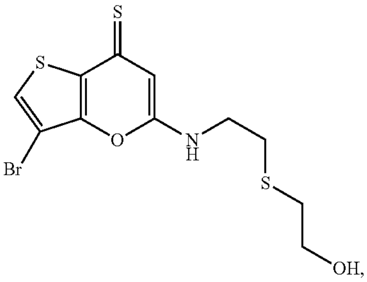 [SMILES: OCCSCCNc1cc(=S)c2scc(Br)c2o1], |
TABLE 9-continued
| Listing of TP group. |
|---|
| 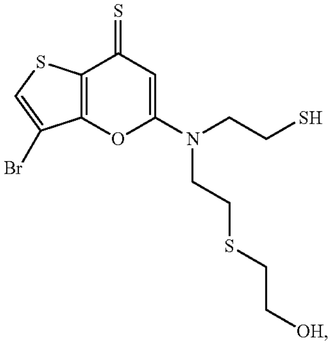 [SMILES: OCCSCCN(CCS)c1cc(=S)c2scc(Br)c2o1], |
| 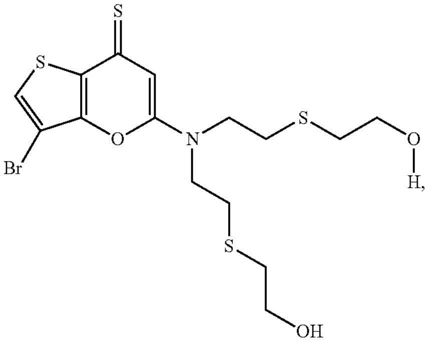, |
| 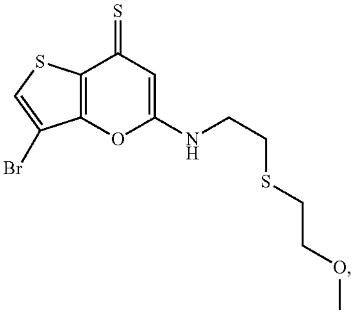 [SMILES: COCCSCCNc1cc(=S)c2scc(Br)c2o1], |
| 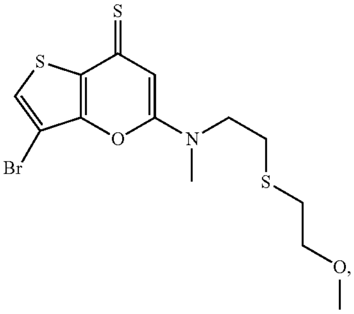 [SMILES: COCCSCCN(C)c1cc(=S)c2scc(Br)c2o1], |

TABLE 9-continued
| Listing of TP group. |
| --- |
| 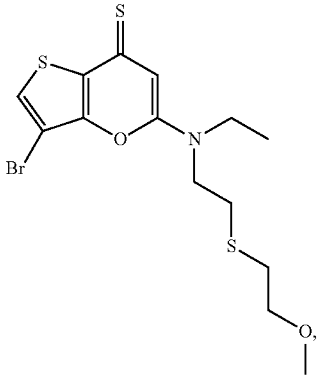 [SMILES: CCN(CCSCCOC)c1cc(=S)c2scc(Br)c2o1] |
| 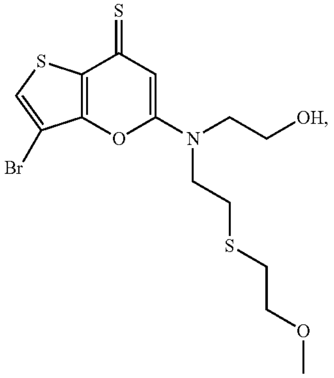 [SMILES: COCCSCCN(CCO)c1cc(=S)c2scc(Br)c2o1] |
| 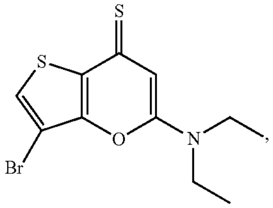 |
| 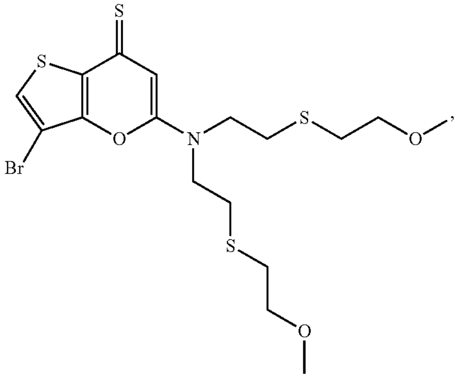 |
| 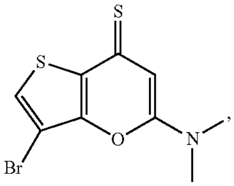 |
| 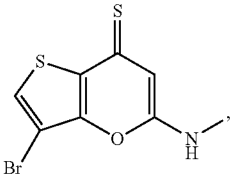 |
| 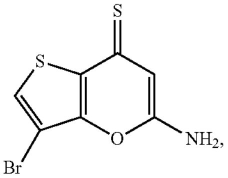 [SMILES: Nc1cc(=S)c2scc(Br)c2o1] |
| 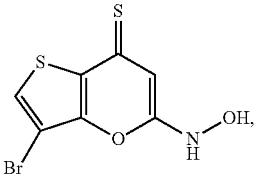 [SMILES: ONc1cc(=S)c2scc(Br)c2o1] |
| 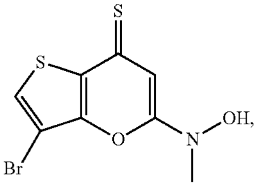 |
| 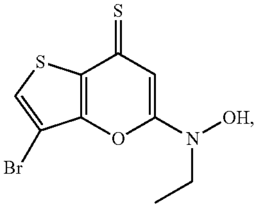 |
| 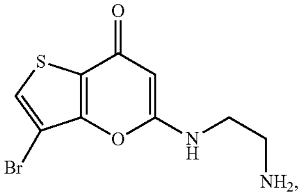 |
| 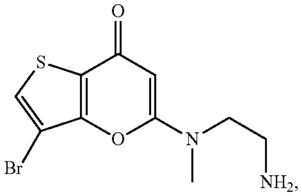 |

TABLE 9-continued
| Listing of TP group. |
| --- |
| 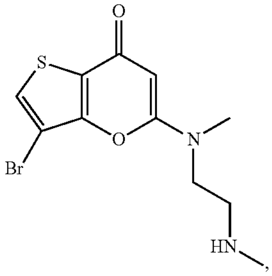 |
| 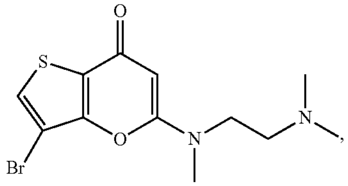 |
| 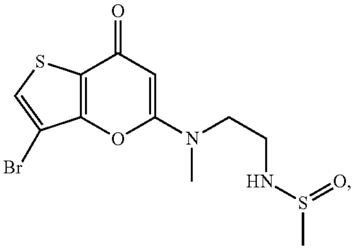 |
| 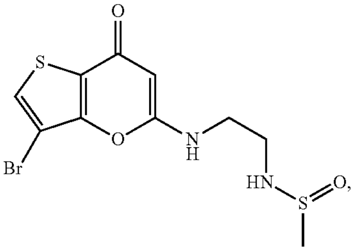 [SMILES: CS(=O)NCCNc1cc(=O)c2scc(Br)c2o1] |
| 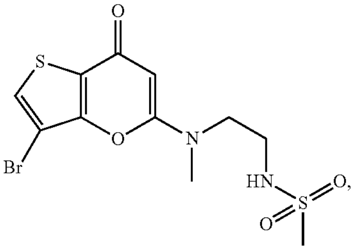 [SMILES: CN(CCNS(C)(=O)=O)c1cc(=O)c2scc(Br)c2o1] |
| 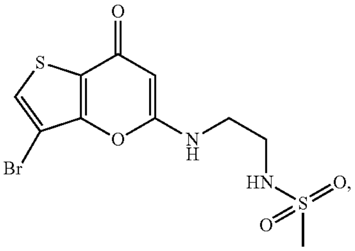 [SMILES: CS(=O)(=O)NCCNc1cc(=O)c2scc(Br)c2o1] |
| 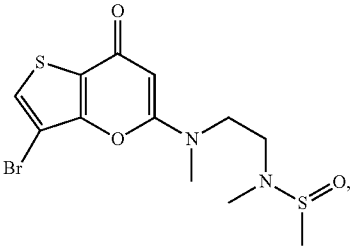 |
| 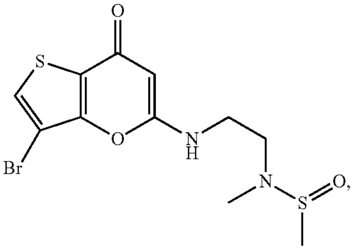 |
| 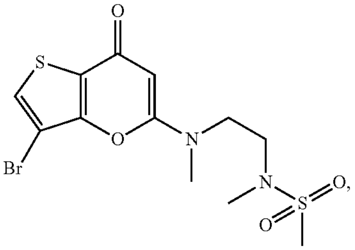 |
| 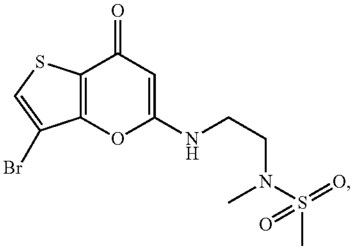 [SMILES: CN(CCNc1cc(=O)c2scc(Br)c2o1)S(C)(=O)=O] |
| 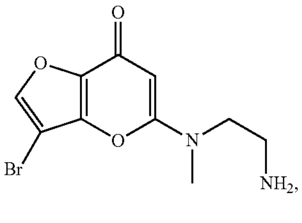 [SMILES: CN(CCN)c1cc(=O)c2occ(Br)c2o1] |
| 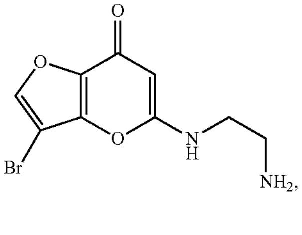 |

TABLE 9-continued
| Listing of TP group. |
| --- |
| 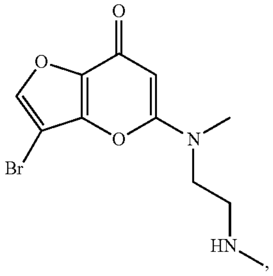 |
| 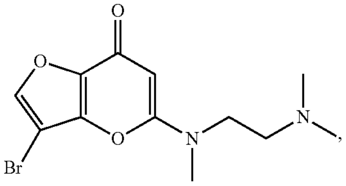 |
| 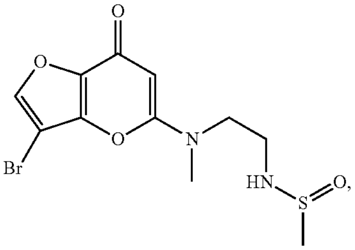 |
| 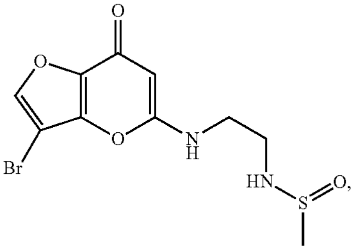 |
| 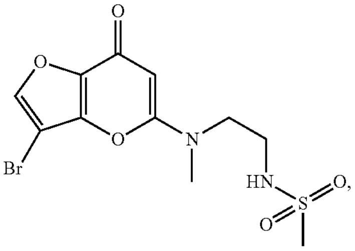 |
| 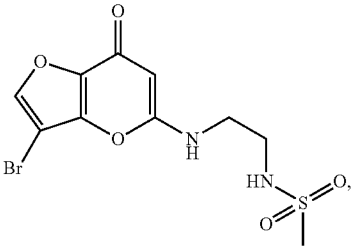 [SMILES: CS(=O)(=O)NCCNc1cc(=O)c2occ(Br)c2o1] |
| 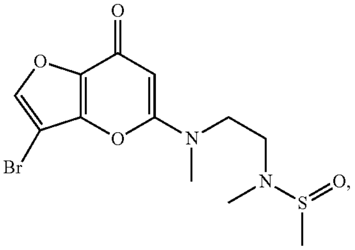 |
| 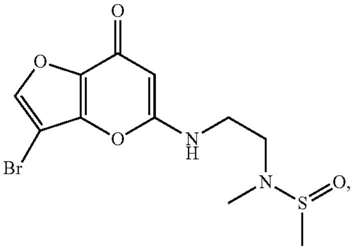 [SMILES: CN(CCNc1cc(=O)c2occ(Br)c2o1)S(C)=O] |
| 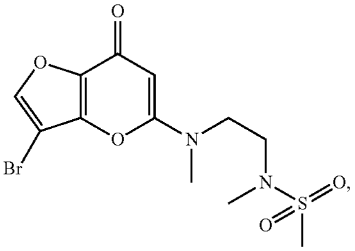 |
| 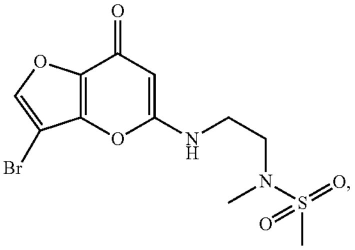 [SMILES: CN(CCNc1cc(=O)c2occ(Br)c2o1)S(C)(=O)=O] |
| 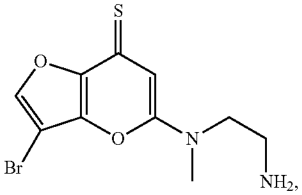 |
| 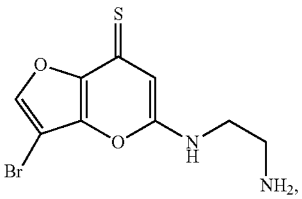 [SMILES: NCCNc1cc(=S)c2occ(Br)c2o1] |

TABLE 9-continued
| Listing of TP group. |
|---|
| 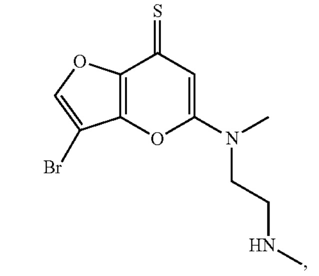 |
| 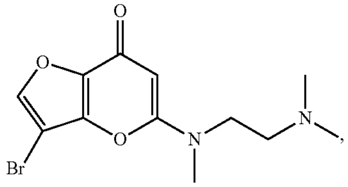 |
| 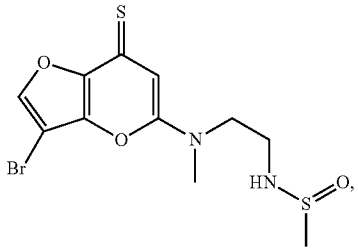 [SMILES: CN(CCNS(C)=O)c1cc(=S)c2occ(Br)c2o1] |
| 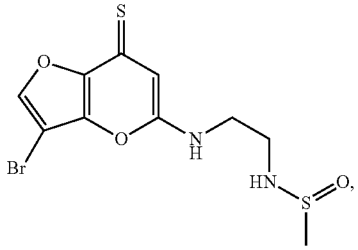 [SMILES: CS(=O)NCCNc1cc(=S)c2occ(Br)c2o1] |
| 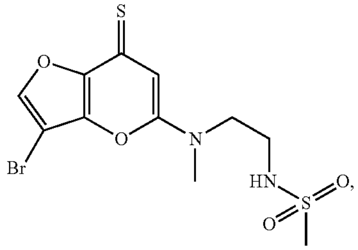 [SMILES: CN(CCNS(C)(=O)=O)c1cc(=S)c2occ(Br)c2o1] |
| 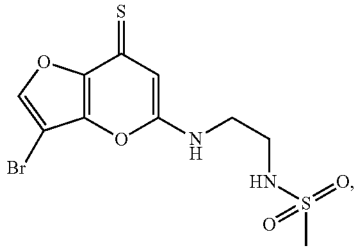 [SMILES: CS(=O)(=O)NCCNc1cc(=S)c2occ(Br)c2o1] |
| 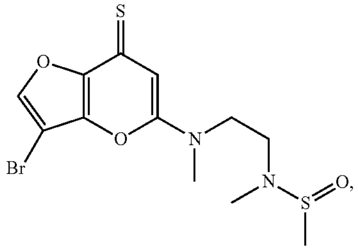 |
| 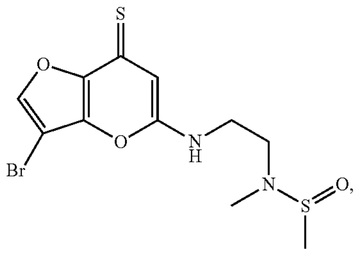 [SMILES: CN(CCNc1cc(=S)c2occ(Br)c2o1)S(C)=O] |
| 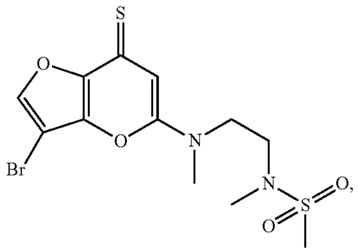 [SMILES: CN(CCN(C)S(C)(=O)=O)c1cc(=S)c2occ(Br)c2o1] |
| 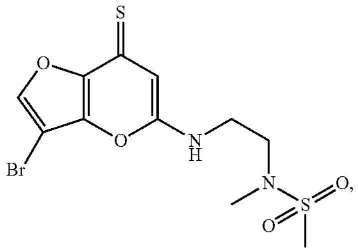 |
| 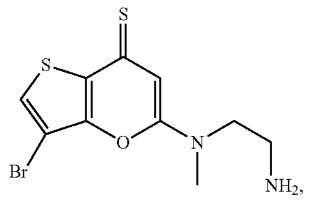 |
| 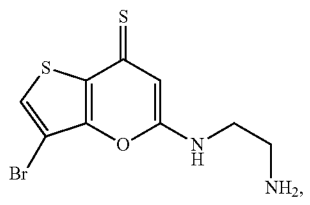 |

TABLE 9-continued
Listing of TP group.
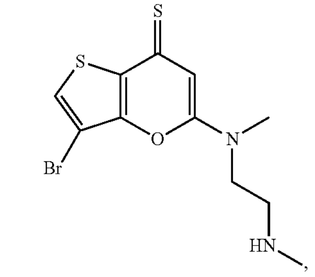
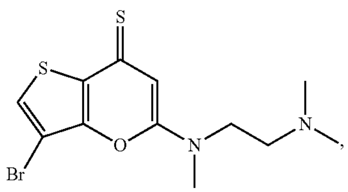
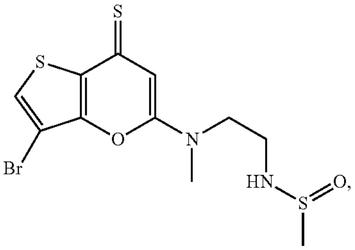 [SMILES: CN(CCNS(C)=O)c1cc(=S)c2scc(Br)c2o1]
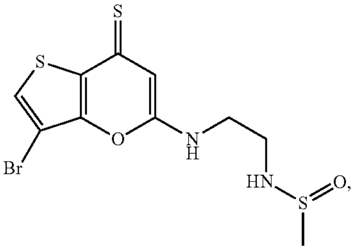 [SMILES: CS(=O)NCCNc1cc(=S)c2scc(Br)c2o1]
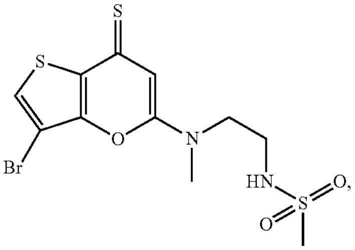
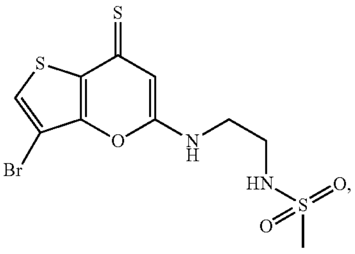
TABLE 9-continued
Listing of TP group.
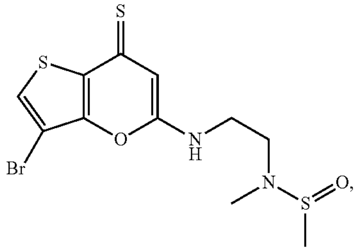
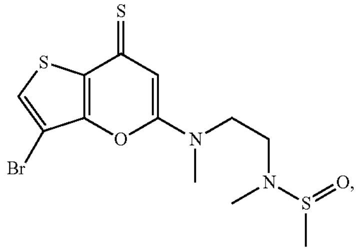 [SMILES: CN(CCN(C)S(C)=O)c1cc(=S)c2scc(Br)c2o1]
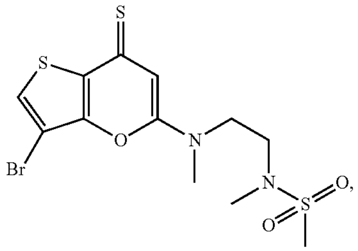 [SMILES: CN(CCN(C)S(C)(=O)=O)c1cc(=S)c2scc(Br)c2o1]
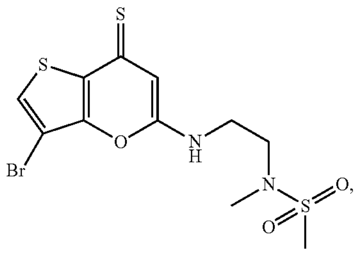 [SMILES: CN(CCNc1cc(=S)c2scc(Br)c2o1)S(C)(=O)=O]
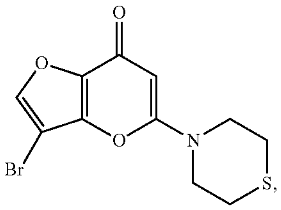
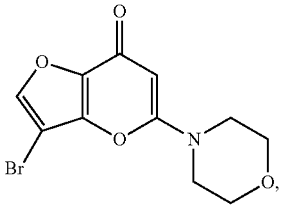

TABLE 9-continued
| Listing of TP group. |
|---|
| 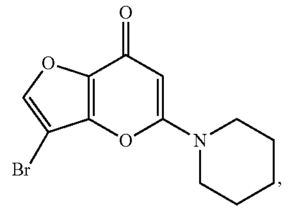 [SMILES: O=c1cc(N2CCSCC2)oc2c(Br)coc12] |
| 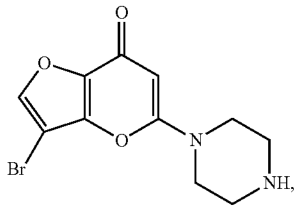 [SMILES: O=c1cc(N2CCNCC2)oc2c(Br)coc12] |
| 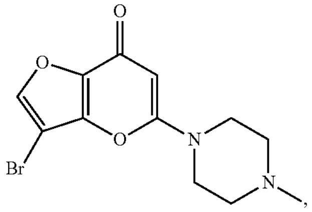 |
| 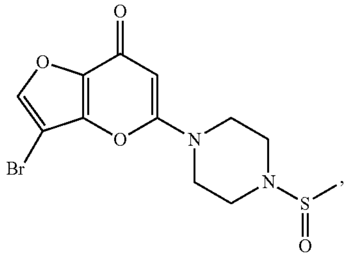 |
| 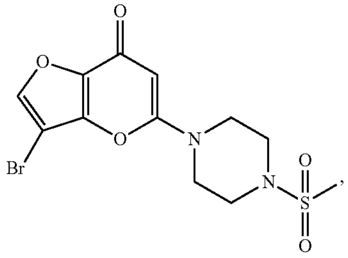 |
| 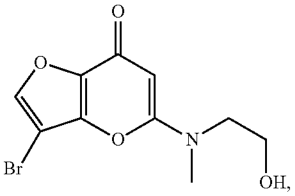 [SMILES: CN(CCO)c1cc(=O)c2occ(Br)c2o1] |
TABLE 9-continued
| Listing of TP group. |
|---|
| 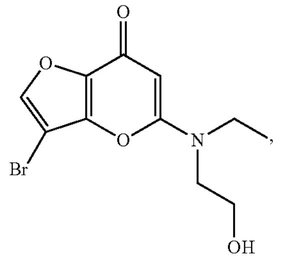 |
| 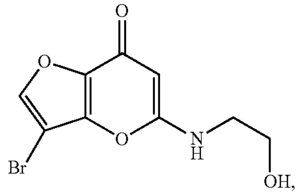 |
| 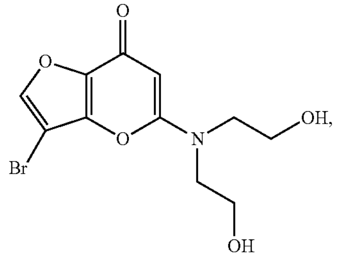 [SMILES: O=c1cc(N(CCO)CCO)oc2c(Br)coc12] |
| 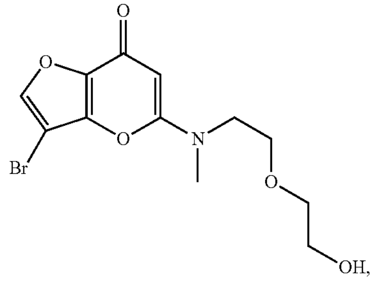 [SMILES: CN(CCOCCO)c1cc(=O)c2occ(Br)c2o1] |
| 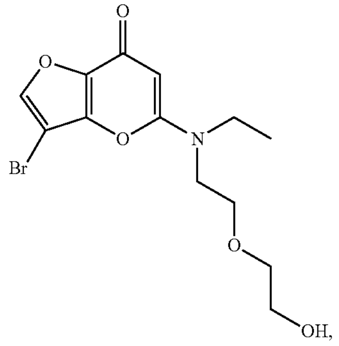 [SMILES: CCN(CCOCCO)c1cc(=O)c2occ(Br)c2o1] |

TABLE 9-continued
| Listing of TP group. |
| --- |
| 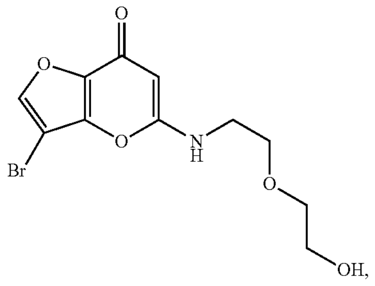 |
| 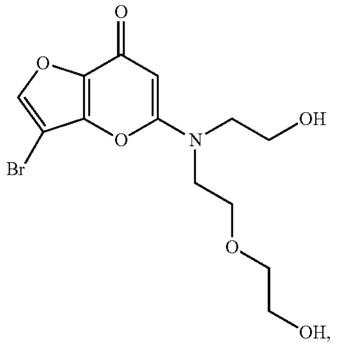 [SMILES: O=c1cc(N(CCO)CCOCCO)oc2c(Br)coc12] |
| 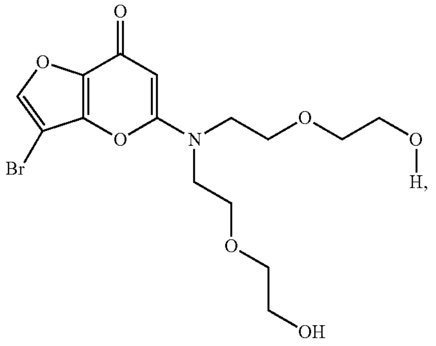 |
| 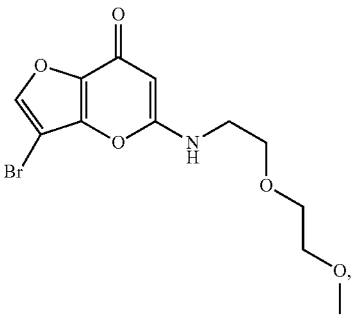 |
TABLE 9-continued
| Listing of TP group. |
| --- |
| 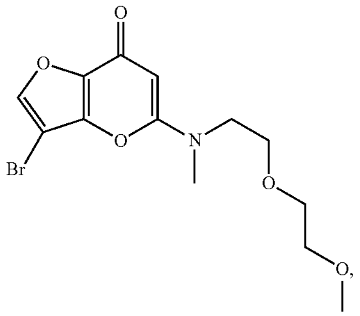 [SMILES: COCCOCCN(C)c1cc(=O)c2occ(Br)c2o1] |
| 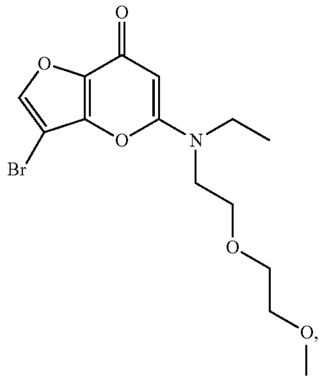 [SMILES: CCN(CCOCCOC)c1cc(=O)c2occ(Br)c2o1] |
| 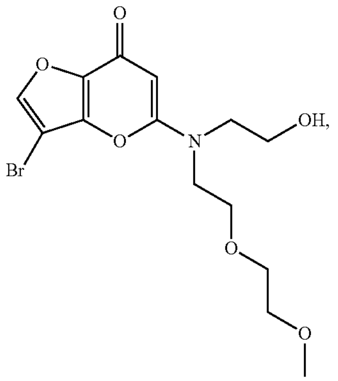 [SMILES: COCCOCCN(CCO)c1cc(=O)c2occ(Br)c2o1] |
| 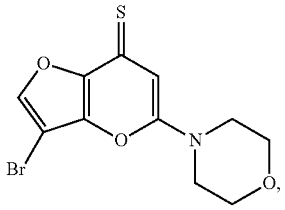 [SMILES: S=c1cc(N2CCOCC2)oc2c(Br)coc12] |

TABLE 9-continued
| Listing of TP group. |
|---|
| 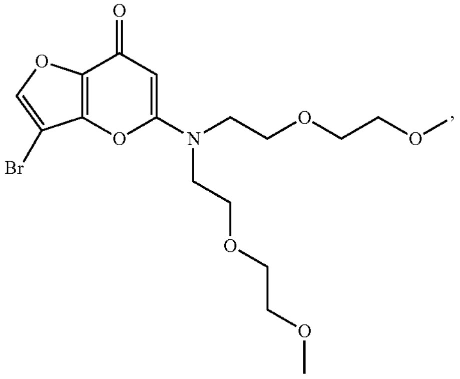 |
| 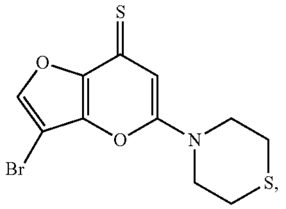 [SMILES: S=c1cc(N2CCSCC2)oc2c(Br)coc12] |
| 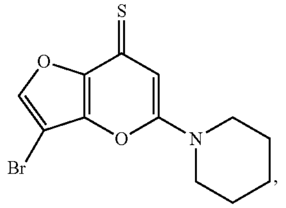 |
| 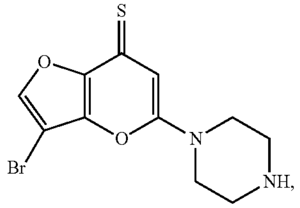 |
| 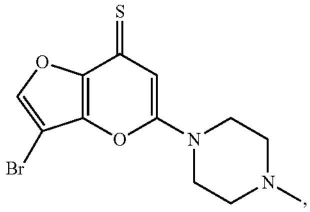 |
| 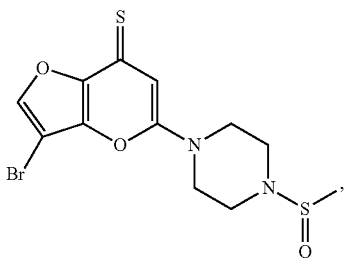 |
TABLE 9-continued
| Listing of TP group. |
|---|
| 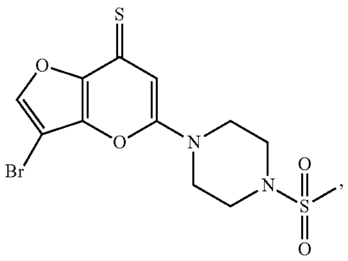 |
| 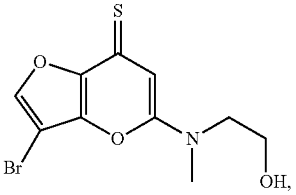 [SMILES: CN(CCO)c1cc(=S)c2occ(Br)c2o1] |
| 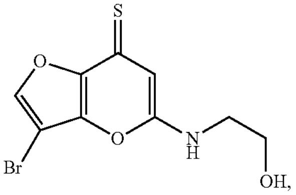 [SMILES: OCCNc1cc(=S)c2occ(Br)c2o1] |
| 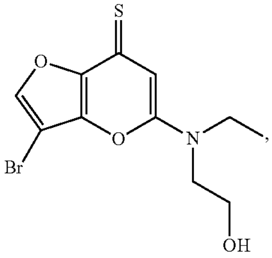 |
| 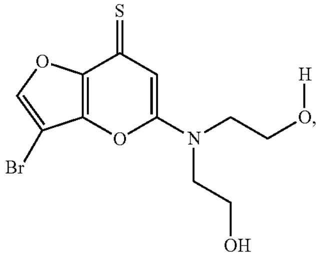 |
| 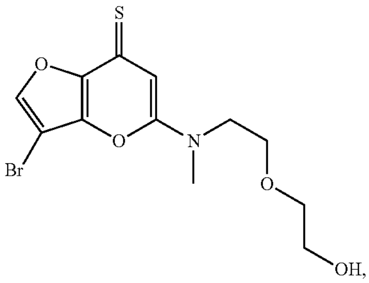 |

TABLE 9-continued
| Listing of TP group. |
|---|
| 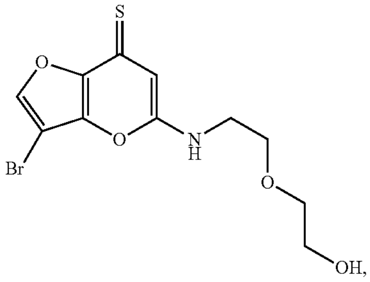 |
| 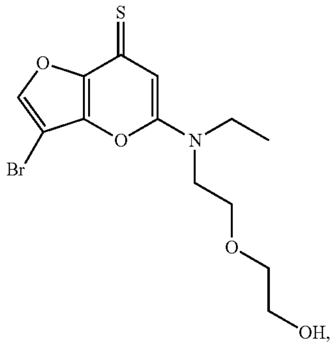 [SMILES: CCN(CCOCCO)c1cc(=S)c2occ(Br)c2o1] |
| 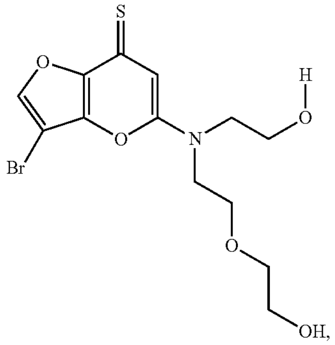 [SMILES: OCCOCCN(CCO)c1cc(=S)c2occ(Br)c2o1] |
| 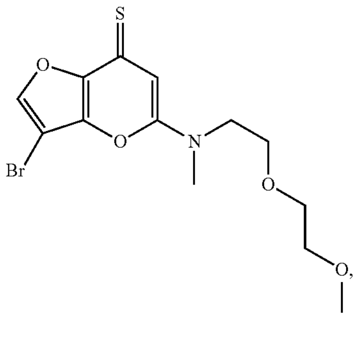 [SMILES: COCCOCCN(C)c1cc(=S)c2occ(Br)c2o1] |
TABLE 9-continued
| Listing of TP group. |
|---|
| 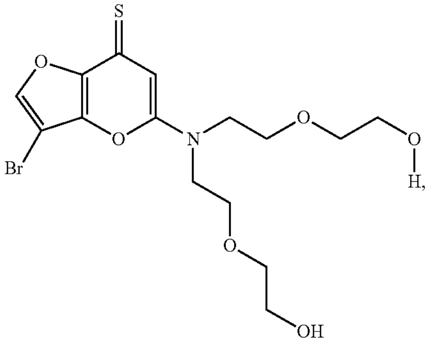 |
| 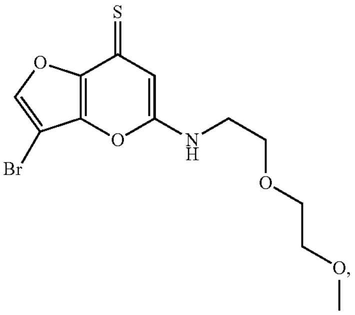 [SMILES: COCCOCCNc1cc(=S)c2occ(Br)c2o1] |
| 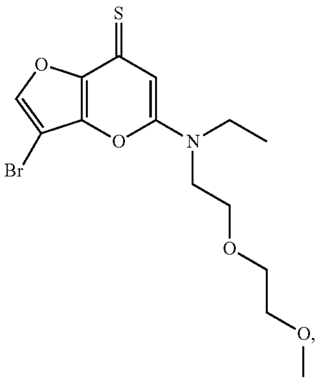 |
| 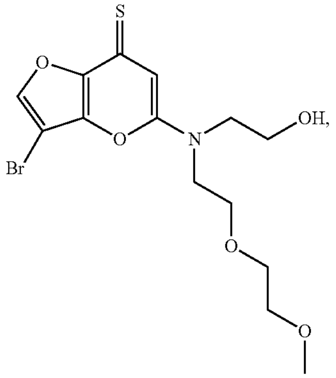 |

TABLE 9-continued
| Listing of TP group. |
| --- |
| 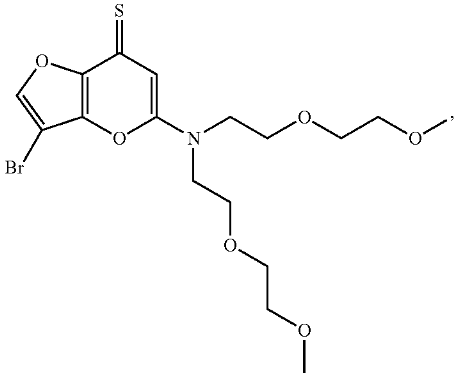 |
| 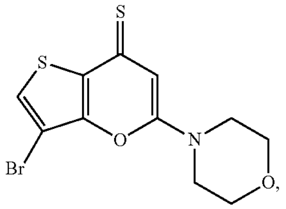 |
| 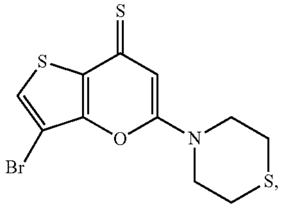 [SMILES: S=c1cc(N2CCOCC2)oc2c(Br)csc12] |
| 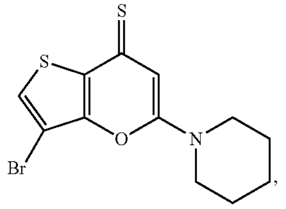 [SMILES: S=c1cc(N2CCCCC2)oc2c(Br)csc12 ; ","] |
| 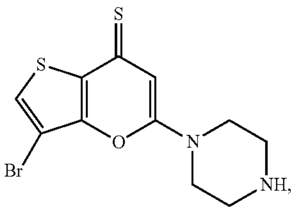 [SMILES: S=c1cc(N2CCNCC2)oc2c(Br)csc12] |
| 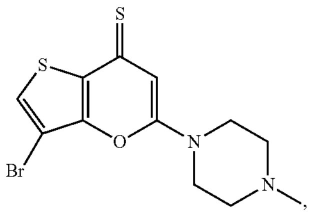 |
TABLE 9-continued
| Listing of TP group. |
| --- |
| 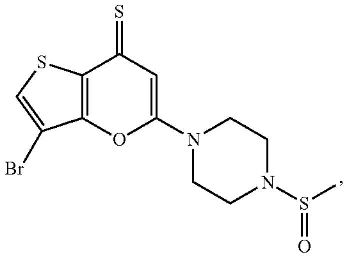 |
| 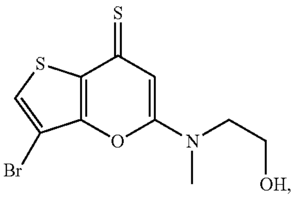 |
| 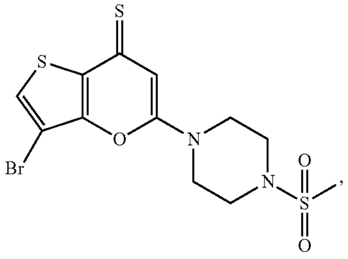 |
| 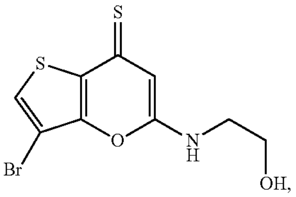 [SMILES: OCCNc1cc(=S)c2scc(Br)c2o1] |
| 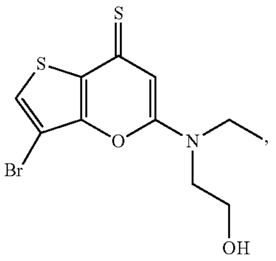 |
| 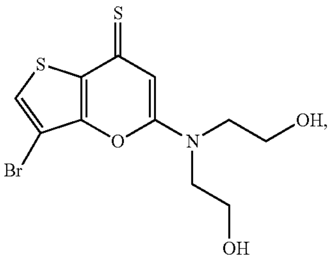 |

TABLE 9-continued

| Listing of TP group. |
| --- |
| 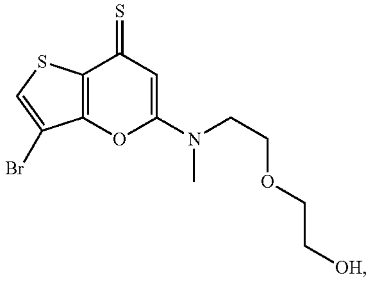 [SMILES: CN(CCOCCO)c1cc(=S)c2scc(Br)c2o1] |
| 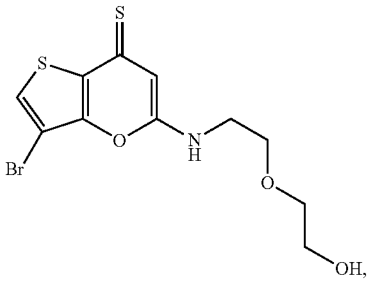 |
| 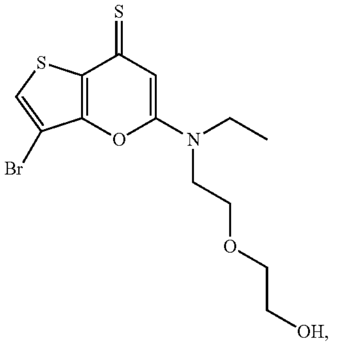 [SMILES: CCN(CCOCCO)c1cc(=S)c2scc(Br)c2o1] |
| 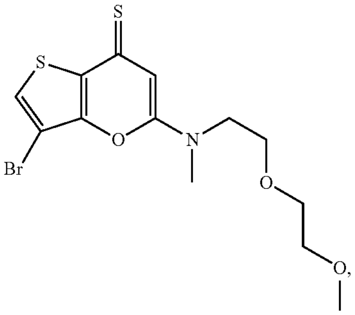 |
| 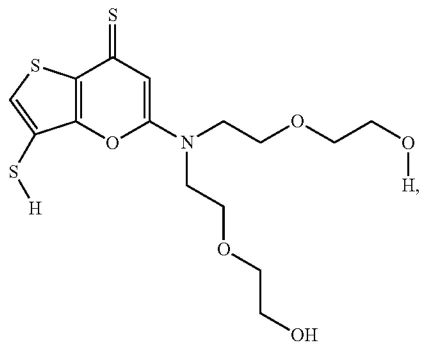 |

TABLE 9-continued

| Listing of TP group. |
| --- |
| 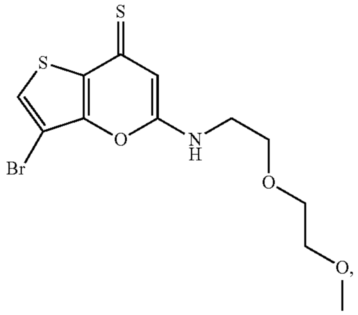 |
| 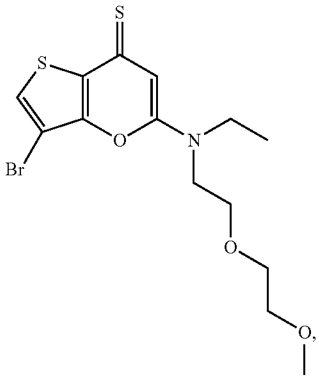 [SMILES: CCN(CCOCCOC)c1cc(=S)c2scc(Br)c2o1] |
| 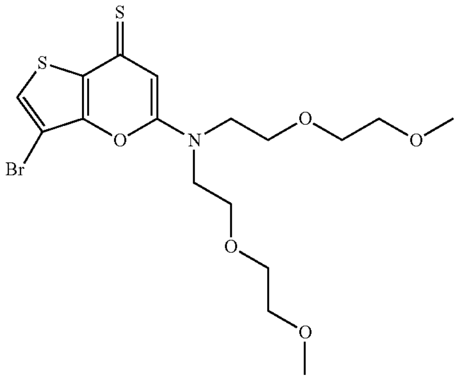 |

A combinatorial enumeration was carried out using all of the reactants to create a virtual compound library of about 140.2 million compounds. From this large collection of compounds, a virtual library subset of about 58,500 compounds was selected by keeping both the CDK as well as the PI3K/BRD4 recognition components constant, only varying the linking moieties between the CDK and PI3K/BRD4 recognition components, including a direct linkage between the CDK and PI3K/BRD4 recognition components (i.e., no chemical moiety).

The virtual library subset was then docked against CDK6, and the compounds sorted based on their calculated binding scores against CDK6 where the more negative a docking score value the higher the affinity a compound is predicted to have towards CDK6. The top-scoring 25 compounds predicted to have the highest affinity towards CDK6 were selected and are shown in Table 10.

TABLE 10
Top-scoring 25 compounds predicted to have highest affinity for CDK6.
| Structure | Mol Weight | CDK6 Score (Kcal/mo) | PI3K-alpha Score (Kcal/mol) | BRD4-BD1 Score (Kcal/mol) |
|---|---|---|---|---|
| 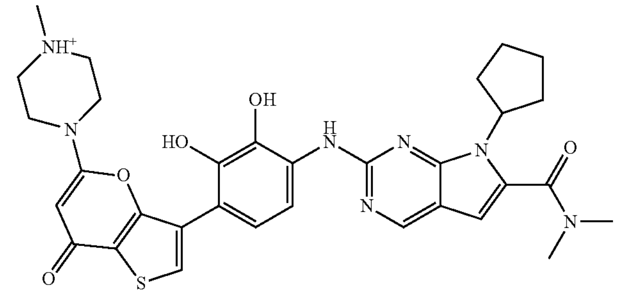 [SMILES: CN(C)C(=O)c1cc2cnc(Nc3ccc(-c4csc5c(=O)cc(N6CC[NH+](C)CC6)oc45)c(O)c3O)nc2n1C1CCCC1] | 630.737 | −12.59 | 6.74 | −7.22 |
| 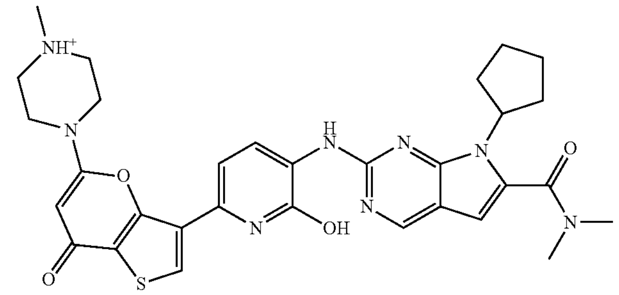 [SMILES: CN(C)C(=O)c1cc2cnc(Nc3ccc(-c4csc5c(=O)cc(N6CC[NH+](C)CC6)oc45)nc3O)nc2n1C1CCCC1] | 615.726 | −12.55 | 10.27 | −7.53 |
| 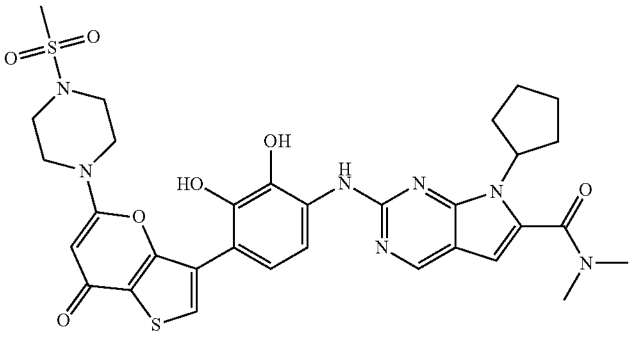 [SMILES: CN(C)C(=O)c1cc2cnc(Nc3ccc(-c4csc5c(=O)cc(N6CCN(S(C)(=O)=O)CC6)oc45)c(O)c3O)nc2n1C1CCCC1] | 693.793 | −12.55 | −6.99 | −6.64 |
| 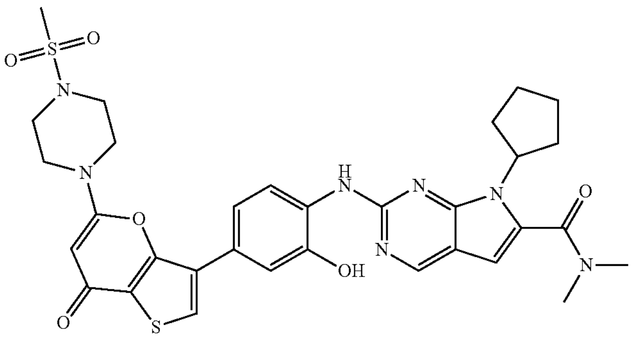 [SMILES: CN(C)C(=O)c1cc2cnc(Nc3ccc(-c4csc5c(=O)cc(N6CCN(S(C)(=O)=O)CC6)oc45)cc3O)nc2n1C1CCCC1] | 677.794 | −12.5 | −3.98 | −7.65 |

TABLE 10-continued
Top-scoring 25 compounds predicted to have highest affinity for CDK6.
| Structure | Mol Weight | CDK6 Score (Kcal/mo) | PI3K-alpha Score (Kcal/mol) | BRD4-BD1 Score (Kcal/mol) |
|---|---|---|---|---|
| 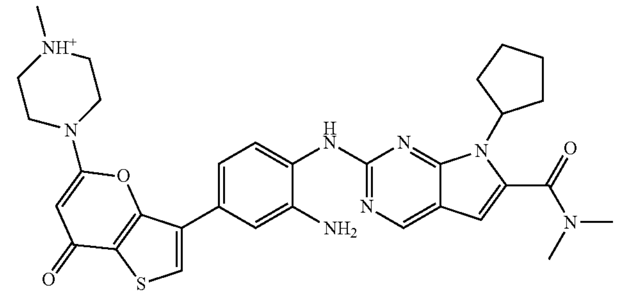 | 613.753 | −12.48 | 6.37 | −8.14 |
| 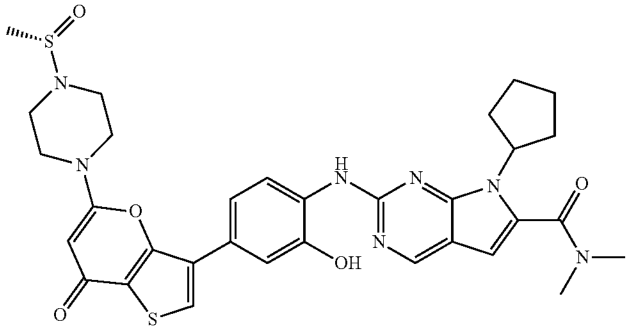 | 661.794 | −12.47 | −9.24 | −7.91 |
| 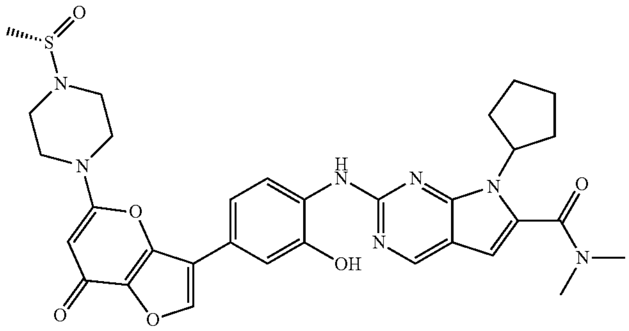 | 645.729 | −12.45 | −6.23 | −7.56 |
| 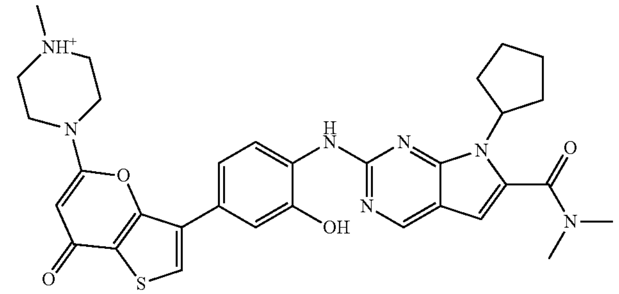 | 614.738 | −12.45 | 9.43 | −7.5 |

TABLE 10-continued
Top-scoring 25 compounds predicted to have highest affinity for CDK6.
| Structure | Mol Weight | CDK6 Score (Kcal/mo) | PI3K-alpha Score (Kcal/mol) | BRD4-BD1 Score (Kcal/mol) |
|---|---|---|---|---|
| 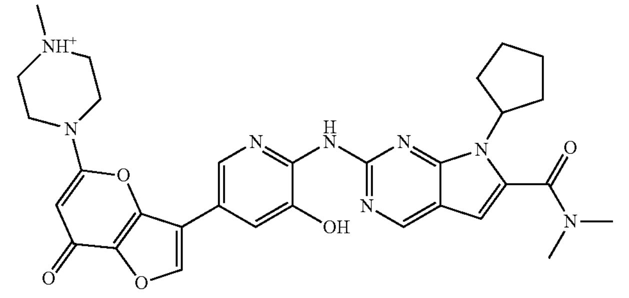 [SMILES: CN(C)C(=O)c1cc2cnc(Nc3ncc(-c4coc5c(=O)cc(N6CC[NH+](C)CC6)oc45)cc3O)nc2n1C1CCCC1] | 599.6602 | −12.44 | 3.96 | −7.48 |
| 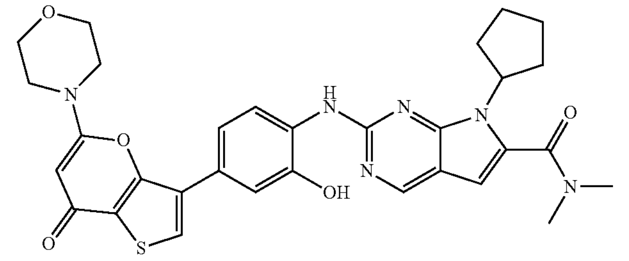 [SMILES: CN(C)C(=O)c1cc2cnc(Nc3ccc(-c4csc5c(=O)cc(N6CCOCC6)oc45)cc3O)nc2n1C1CCCC1] | 600.688 | −12.44 | −18.32 | −8.44 |
| 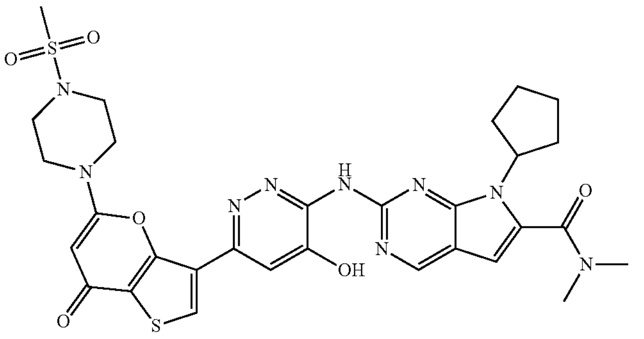 [SMILES: CN(C)C(=O)c1cc2cnc(Nc3nnc(-c4csc5c(=O)cc(N6CCN(S(C)(=O)=O)CC6)oc45)cc3O)nc2n1C1CCCC1] | 679.77 | −12.44 | 0.58 | −6.51 |
| 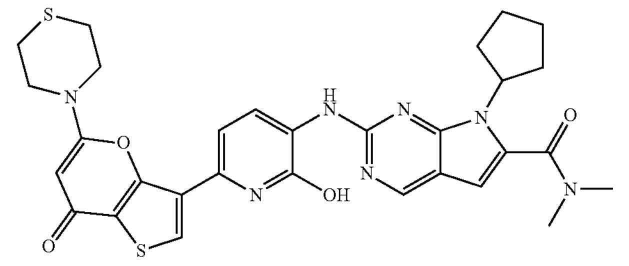 | 617.742 | −12.42 | 1.44 | −8.05 |
| 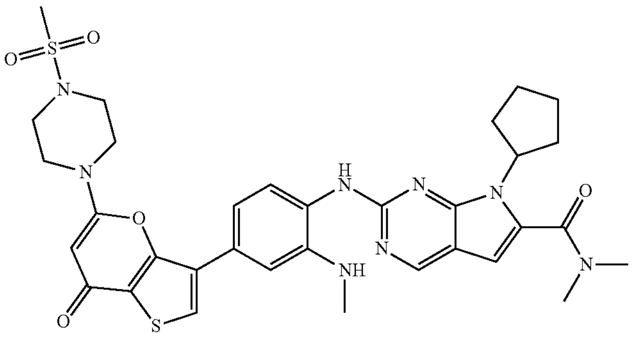 [SMILES: CNc1cc(-c2csc3c(=O)cc(N4CCN(S(C)(=O)=O)CC4)oc23)ccc1Nc1ncc2cc(C(=O)N(C)C)n(C3CCCC3)c2n1] | 690.835 | −12.41 | 1.76 | −7.17 |

TABLE 10-continued
| Top-scoring 25 compounds predicted to have highest affinity for CDK6. | | | | |
|---|---|---|---|---|
| Structure | Mol Weight | CDK6 Score (Kcal/mo) | PI3K-alpha Score (Kcal/mol) | BRD4-BD1 Score (Kcal/mol) |
| 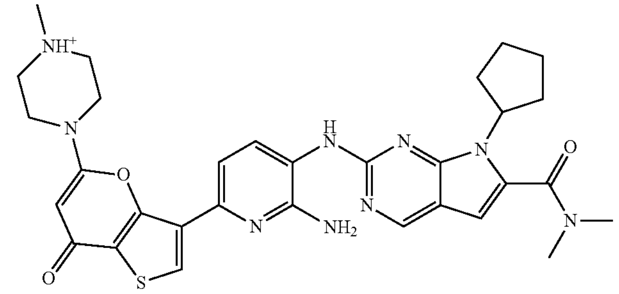 [SMILES: CN(C)C(=O)c1cc2cnc(Nc3ccc(-c4csc5c(=O)cc(N6CC[NH+](C)CC6)oc45)nc3N)nc2n1C1CCCC1] | 614.741 | −12.4 | 2.57 | −7.47 |
| 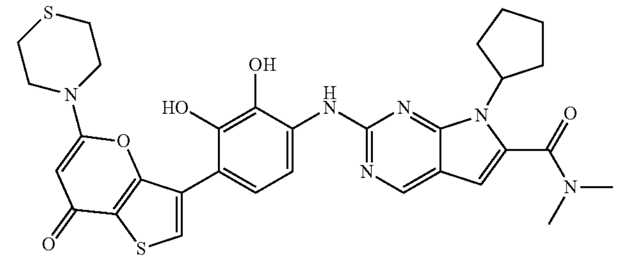 [SMILES: CN(C)C(=O)c1cc2cnc(Nc3ccc(-c4csc5c(=O)cc(N6CCSCC6)oc45)c(O)c3O)nc2n1C1CCCC1] | 632.753 | −12.4 | −3.38 | −7.45 |
| 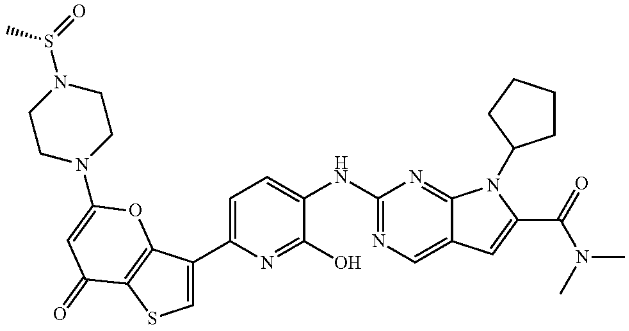 | 662.782 | −12.39 | −13.06 | −8.09 |
| 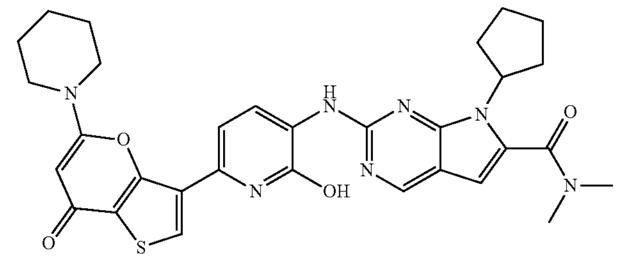 [SMILES: CN(C)C(=O)c1cc2cnc(Nc3ccc(-c4csc5c(=O)cc(N6CCCCC6)oc45)cc3O)nc2n1C1CCCC1] | 599.703 | −12.39 | 2.55 | −7.99 |
| 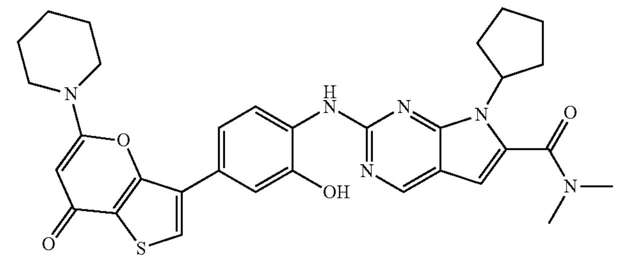 | 598.715 | −12.39 | 2.52 | −8.11 |

TABLE 10-continued
Top-scoring 25 compounds predicted to have highest affinity for CDK6.
| Structure | Mol Weight | CDK6 Score (Kcal/mo) | PI3K-alpha Score (Kcal/mol) | BRD4-BD1 Score (Kcal/mol) |
|---|---|---|---|---|
| 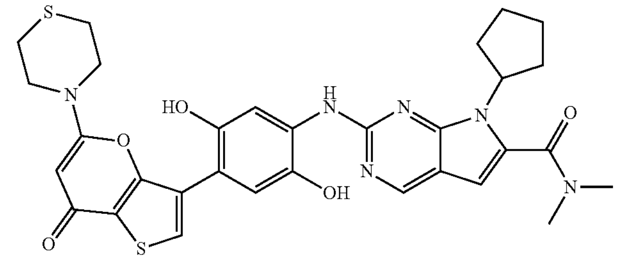 [SMILES: CN(C)C(=O)c1cc2cnc(Nc3cc(O)c(-c4csc5c(=O)cc(N6CCSCC6)oc45)cc3O)nc2n1C1CCCC1] | 632.753 | −12.37 | −3.71 | −7.57 |
| 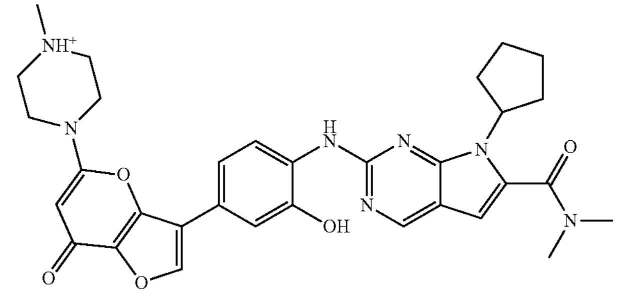 [SMILES: CN(C)C(=O)c1cc2cnc(Nc3ccc(-c4coc5c(=O)cc(N6CC[NH+](C)CC6)oc45)cc3O)nc2n1C1CCCC1] | 598.6721 | −12.37 | 6.39 | −6.88 |
| 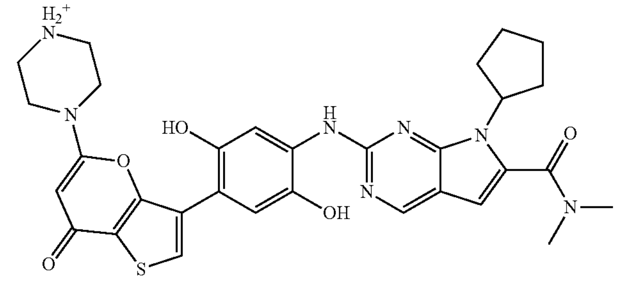 | 616.711 | −12.36 | −4.88 | −8.49 |
| 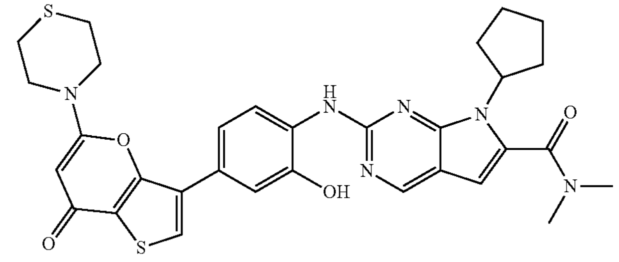 | 616.754 | −12.36 | 3.45 | −8.14 |
| 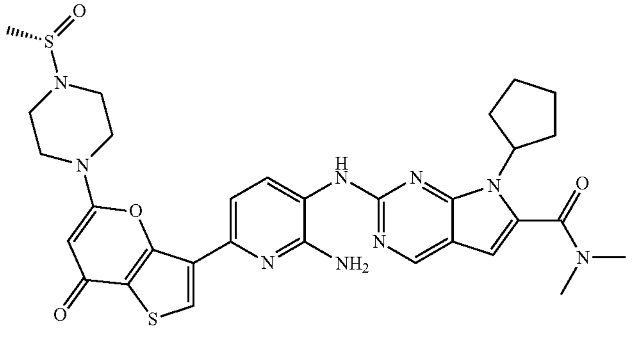 | 661.798 | −12.35 | −15.94 | −7.86 |

TABLE 10-continued

Top-scoring 25 compounds predicted to have highest affinity for CDK6.

| Structure | Mol Weight | CDK6 Score (Kcal/mo) | PI3K-alpha Score (Kcal/mol) | BRD4-BD1 Score (Kcal/mol) |
|---|---|---|---|---|
| 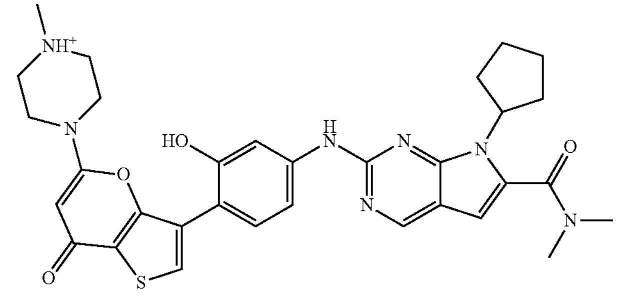 [SMILES: CN(C)C(=O)c1cc2cnc(Nc3ccc(-c4csc5c(=O)cc(N6CC[NH+](C)CC6)oc45)c(O)c3)nc2n1C1CCCC1] | 614.738 | −12.35 | −0.15 | −7.82 |
| 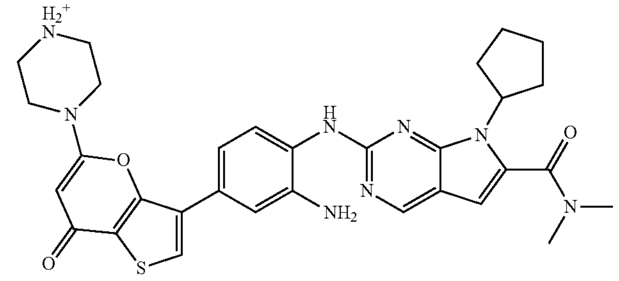 | 599.726 | −12.34 | −3.94 | −8.6 |

Example 11. In Silico Molecular Modeling of Compound 0 and Compound 1 in PI3K Alpha and CDK6 and BRD4

The crystal structure of target protein (CDK6 or BRD4) with inhibitor was obtained from the Protein Database (PDB). Using standard in silico methods the inhibitor molecule was removed and then redocked to show the methodology and model is valid by placing the redocked inhibitor in the same position as was found in the published crystal structure. Compound 1 was then docked in the crystal structure sans inhibitor and the low energy binding orientation was determined as the most likely fit.

In the modeling of compound 1 in human PI3K-alpha (PDB code: 4JPS) the following small molecule-protein interactions were observed:

a. Morpholine oxygen of compound 0 accepts H-bond from amide of valine 851
b. Carbonyl oxygen of compound 0 accepts H-bond from 2 waters in the cavity
c. Hydrophobic π-sigma from chromone ring of compound 0 with isoleucine 932
d. Hydrophobic interactions of morpholine ring of compound 0 with phenyl ring of tyrosine 836 and the methyl group of methionine 922

A comparison was made of compound 1 docking with that of the well-known compound 0 also docked simultaneously in the PI3K-alpha protein and the following observations were made:

a) The phenyl of compound 1 is slightly twisted versus that the phenyl of compound 0
b) Water π interactions are predicted
c) Pyrimidine nitrogen of compound 1 accepts H-bond from amide of glutamine 859
d) Pyrimidine ring of compound 1 forms π-π hydrophobic interactions with the phenyl of tryptophan 780
e) The 5-membered ring of compound 1 forms π-π hydrophobic interactions with histidine 855
f) Cyclopentyl ring of compound 1 forms π-alkyl interaction with histidine 855
g) One methyl of dimethyl group of compound 1 forms apparent π-sigma with water
h) The pyrimidine ring of compound 1 slides between upper lobe (glutamine 859) and flat hydrophobic lower surface formed by a tryptophan amino acid Clearly, the docking results show that the compound 1 molecule is not simply binding PI3K-alpha via only the morpholine-chromone-thiophene group common to compound 0 but is instead fully engaged along it whole length demonstrating multiple interactions with PI3K-alpha. This is different from simple conjugates of two separate inhibitors where one part of the conjugate molecule engages or interacts with one target and a separate part of the molecule (i.e., the other inhibitor of the conjugate) interacts only with a different target. In the compound 1 class of compounds the whole molecule is available and interacts with the protein (PI3K, BRD4, and CDK4/6) that it inhibits.

Inspection of compound 1 docked in the crystal structure of ribociclib with human CDK6 (PDB code 5L2T) suggests that compound 1 fits into CDK6 with the same interactions as ribociclib as noted below:

a) The thiophene of compound 1 has hydrophobic-hydrophobic interaction with isoleucine 19 of CDK6
b) The phenyl ring of compound 1 forms hydrophobic interactions with isoleucine 19 above the ring and pi interaction below with glutamine (GLN103) and non-classical pi interaction with ASP104 of CDK6
c) The morpholine oxygen of compound 1 appears to be forming H bonds with glutamine 149 and/or lysine 147 d) The cyclopentyl group of compound 1 forms hydrophobic-hydrophobic interactions with alanine 162 and valine 27 (same as in known CDK inhibitor in crystal structure)

Additionally, compound 1 appears to also wrap around the mouth of the cavity providing additional interactions which may explain the increased $IC_{50}$ potency.

Compound 1 was similarly modeled in human BRD4 (PDB code 4CFK) showing excellent overlay with the 4CFK's co-crystallized ligand LY294002 in the acetyl-lysine binding cavity.

The 4CFK crystal structure is discussed in more detail in the following reference incorporated herein: "The Commonly Used PI3-Kinase Probe LY294002 is an Inhibitor of BET Bromodomains." Dittmann, A., Werner, T., Chung, C., Savitski, M. M., Falth Savitski, M., Grandi, P., Hopf, C., Lindon, M., Neubauer, G., Prinjha, R. K., Bantscheff, M., Drewes, G. (2014) ACS Chem. Biol. 9: 495-502.

Moreover, compound 1 modeled in BRD4 showed excellent overly with the thienopyrane-morpholine part of the compound 0 molecule which was described in the crystal structure of compound 0 with BRD4 (Andrews et al., PNAS 2017, vol. 114, no. 7, pp E1072-E108; reference incorporated herein).

The fact that compound 1 has better BRD4 inhibition than compound 0 is supported by the molecular modeling which shows the CDK binding headpiece (e.g., the substituted amino-pyrimidine) wrapping around the surface of the BRD4 protein providing additional binding interactions.

Example 12. Synthesis of BRD4-CDK Inhibitor Compound 4

Step 1: (6-Chloro-1-cyclopentyl-1,5,7-triaza-1H-inden-2-yl) (dimethylamino)formaldehyde A stirring solution of 6-chloro-1-cyclopentyl-1,5,7-triaza-1H-indene-2-carboxylic acid (530 mg, 2.0 mmol) and diisopropylethylamine (2.15 mL, 12.0 mmol) in DMF (10 mL) was treated with HBTU (1.14 g, 3.0 mmol) in one portion. The resulting mixture was stirred at room temperature for 30 minutes. Dimethylamine hydrochloride salt (326 mg, 4.0 mmol) was added in one portion and the resulting solution was stirred at room temperature overnight. Next morning, LCMS analysis indicated clean conversion to product (m/z=293.4). The reaction mixture was diluted with EtOAc, transferred to a separatory funnel and washed with saturated $NaHCO_3$ aqueous solution, 0.1 N HCl aqueous and brine. The organics were dried over anhydrous $MgSO_4$, filtered and concentrated to yield the crude product. This was purified by automated silica-gel chromatography eluting with a hexanes/EtOAc gradient. The fractions containing (6-chloro-1-cyclopentyl-1,5,7-triaza-1H-inden-2-yl) (dimethylamino)formaldehyde were concentrated to yield 570 mg (1.95 mmol, 98%).

LC/MS—HPLC (254 nm)—Rt 2.90 min. MS (ESI) m/z 293.4 $[M+H]^+$.

Step 2: Methyl 2-amino-5-(4,4,5,5-tetramethyl-1,3,2-dioxaborolan-2-yl)benzoate: A suspension of methyl 2-amino-5-bromobenzoate (460 mg, 2.0 mmol), potassium acetate (441 mg, 4.5 mmol) and pinacol diborane (1.52 g, 6.0 mmol) in 1,4-dioxane (20 mL) was degassed under a flow of $N_2$ for 15 minutes. $PdCl_2$(dppf) (73 mg, 0.1 mmol) was added and the mixture heated to 95° C. for 16 hours. The reaction was deemed complete by LCMS. After cooling, the contents were partitioned between $CH_2Cl_2$ and water. The organic layer was washed with water, dried over anhydrous $MgSO_4$, filtered and evaporated. The product was purified by automated silica-gel chromatography eluting with a hexanes/EtOAc gradient. The fractions containing methyl 2-amino-5-(4,4,5,5-tetramethyl-1,3,2-dioxaborolan-2-yl)benzoate were concentrated to yield the product as a colorless oil=560 mg (2.00 mmol, quant.).

LC/MS—HPLC (254 nm)—Rt 3.32 min. MS (ESI) m/z 278.3 $[M+H]^+$.

Step 3: Methyl 2-amino-5-(5-morpholino-7-oxo-4-oxa-1-thia-3-indenyl)benzoate: 3-Bromo-5-morpholino-4-oxa-1-thia-7-indenone (158 mg, 0.5 mmol) and methyl 2-amino-5-(4,4,5,5-tetramethyl-1,3,2-dioxaborolan-2-yl)benzoate (208 mg, 0.75 mmol, 1.5 eq.) were dissolved in toluene:ethanol (2:1 v/v, 5 mL). The mixture was treated with $Na_2CO_3$ 2M aqueous solution (1.7 mL) and deoxygenated by bubbling $N_2$ for 10 minutes. $Pd[PPh_3]_4$ (29 mg, 0.025 mmol) was added and the mixture was heated to 85° C. for 1 hour in a closed vial. The cooled reaction mixture was diluted with EtOAc (50 mL) washed with water and brine. The aqueous layers were extracted once again with a $CH_2Cl_2$/iPrOH mixture (9:1 v/v). The combined organics were dried over anhydrous $MgSO_4$, filtered and evaporated. The crude residue was triturated with $Et_2O$ and EtOAc and filtered to yield the pure title compound as a white solid. Yield=140 mg (0.36 mmol, 73%).

LC/MS—HPLC (254 nm)—Rt 2.48 min. MS (ESI) m/z 387.2 [M+H]+. Purity=98.0% by UV (254 nm).

Step 4: Methyl 2-[1-cyclopentyl-2-(dimethylamino)carbonyl-1,5,7-triaza-1H-inden-6-ylamino]-5-(5-morpholino-7-oxo-4-oxa-1-thia-3-indenyl)benzoate (Compound 4) In a 8 mL vial, (6-chloro-1-cyclopentyl-1,5,7-triaza-1H-inden-2-yl) (dimethylamino)formaldehyde (88 mg, 0.30 mmol), methyl 2-amino-5-(5-morpholino-7-oxo-4-oxa-1-thia-3-indenyl)benzoate (77 mg, 0.2 mmol), $Cs_2CO_3$ (130 mg, 0.4 mmol), BINAP (12 mg, 0.02 mmol) and $Pd(OAc)_2$ (2.2 mg, 0.01 mmol) were degassed under $N_2$ for 10 minutes. Degassed 1,4-dioxane (4 mL) was added and the resulting mixture was stirred at 110° C. for 6 hours. LCMS analysis indicated complete consumption of starting material and formation of desired product. The reaction was cooled, diluted with EtOAc (50 mL) and washed with $H_2O$ (50 mL) and brine. The organic layer was dried over anhydrous $MgSO_4$, filtered and concentrated in vacuo. The crude residue was purified by chromatography on silica-gel, eluting with a $CH_2Cl_2$/MeOH gradient. The product, Compound 4, was obtained as a yellow solid. Yield=44 mg (0.07 mmol, 34%).

LC/MS—HPLC (254 nm)—Rt 3.10 min. MS (ESI) m/z 643.3 $[M+H]^+$. Purity=95% by UV (254 nm).

Example 13. Synthesis of CDK Inhibitor Compound 5

Step 1: 3-(p-Aminophenyl)-5-morpholino-4-oxa-1-thia-7-indenone (42CR53): 3-Bromo-5-morpholino-4-oxa-1-thia-7-indenone (280 mg, 0.833 mmol) and 4-aminophenylboronic acid hydrochloride (200 mg, 1.15 mmol, 1.3 eq.) were dissolved in 1,4-dioxane (4 mL). The mixture was treated with $Na_2CO_3$ 2M aqueous solution (1.8 mL) and deoxygenated by bubbling $N_2$ for 10 minutes. $Pd[PPh_3]_4$ (25 mg, 0.09 mmol) was added and the mixture was heated to 85° C. for 4 hours. LCMS analysis indicated conversion to product about 50%. The cooled reaction mixture was diluted with EtOAc (100 mL) washed with water and brine. The crude residue was triturated with MeOH/$Et_2O$ mixture and filtered to yield the pure title compound as a tan solid. Yield=140 mg (0.43 mmol, 51%).

LC/MS—HPLC (254 nm)—Rt 2.11 min. MS (ESI) m/z 329.1 $[M+H]^+$. Purity=98.0% by UV (254 nm).

Step 2: 3-{p-[5-Fluoro-4-(7-fluoro-3-isopropyl-2-methyl-1,3-diaza-3H-inden-5-yl)-2-pyrimidinylamino]phenyl}-5-morpholino-4-oxa-1-thia-7-indenone (Compound 5): In a 8 mL vial, commercially available 6-(2-chloro-5-fluoro-4-pyrimidinyl)-4-fluoro-1-isopropyl-2-methyl-1,3-diaza-1H-indene (73 mg, 0.225 mmol), 3-(p-aminophenyl)-5-morpholino-4-oxa-1-thia-7-indenone (49 mg, 0.15 mmol), $Cs_2CO_3$ (98 mg, 0.30 mmol), BINAP (9 mg, 0.015 mmol) and $Pd(OAc)_2$ (2.0 mg, 0.0075 mmol) were degassed under $N_2$ for 10 minutes. Degassed 1,4-dioxane (3 mL) was added and the resulting mixture was stirred at 110° C. for 6 hours. LCMS indicated complete consumption of starting material and formation of product. The reaction was cooled and directly purified by chromatography on silica-gel, eluting with a $CH_2Cl_2$/MeOH gradient. The product, Compound 5, was obtained as a beige solid, after trituration with EtOAc. Yield=14 mg (0.023 mmol, 14%).

LC/MS—HPLC (254 nm)—Rt 2.60 min. MS (ESI) m/z 615.4 $[M+H]^+$. Purity=97.3% by UV (254 nm).

Example 14. Synthesis of CDK Inhibitor Compound 7

Step 1: (6-Chloro-1-cyclopentyl-1,5,7-triaza-1H-inden-2-yl) (dimethylamino)formaldehyde A stirring solution of commercially available 6-chloro-1-cyclopentyl-1,5,7-triaza-1H-indene-2-carboxylic acid (530 mg, 2.0 mmol) and a tertiary amine such as trimethylamine or diisopropylethylamine (2.15 mL, 12.0 mmol) in DMF (10 mL) was treated with HBTU (1.14 g, 3.0 mmol) in one portion. The resulting mixture was stirred at room temperature for 30 minutes. Dimethylamine hydrochloride salt (326 mg, 4.0 mmol) was added in one portion and the resulting solution was stirred at room temperature overnight. Next morning, LCMS analysis indicated clean conversion to product (m/z=293.4). The reaction mixture was diluted with EtOAc, transferred to a separatory funnel and washed with saturated $NaHCO_3$ aqueous solution, 0.1 N HCl aqueous and brine. The organics were dried over anhydrous $MgSO_4$, filtered and concentrated to yield the crude product. This was purified by automated silica-gel chromatography eluting with a hexanes/EtOAc gradient. The fractions containing the product (6-chloro-1-cyclopentyl-1,5,7-triaza-1H-inden-2-yl) (dimethylamino)formaldehyde) were concentrated to yield 570 mg.

LC/MS—HPLC (254 nm)—Rt 2.90 min. MS (ESI) m/z 293.4 $[M+H]^+$.

Step 2: Methyl 5-amino-2-(4,4,5,5-tetramethyl-1,3,2-dioxaborolan-2-yl)benzoate: A suspension of methyl 5-amino-2-bromobenzoate (1 g, 4.98 mmol), potassium acetate (1.1 g, 11.21 mmol) and pinacol diborane (3.79 g, 14.94 mmol) in 1,4-dioxane (50 mL) was degassed under a flow of $N_2$ for 15 minutes. $PdCl_2$(dppf) $CH_2Cl_2$ (182 mg, 0.25 mmol), and KOAc was added and the mixture heated to 85-95° C. for 3 hours. The reaction was then deemed complete by LCMS analysis. After cooling, the contents were partitioned between $CH_2Cl_2$ and water. The organic layer was washed with water, dried over anhydrous $MgSO_4$, filtered and evaporated. The product was purified by automated silica-gel chromatography eluting with a hexanes/EtOAc gradient. The fractions containing the product were concentrated to yield the title product as a colorless oil, which solidified upon standing. Yield=1.38 g (4.98 mmol, quant.).

LC/MS—HPLC (254 nm)—Rt 3.73 min. MS (ESI) m/z 278.5 $[M+H]^+$.

Step 3: Methyl 5-amino-2-(5-morpholino-7-oxo-4-oxa-1-thia-3-indenyl)benzoate: 3-Bromo-5-morpholino-4-oxa-1-thia-7-indenone (632 mg, 2.0 mmol) and methyl 5-amino-2-(4,4,5,5-tetramethyl-1,3,2-dioxaborolan-2-yl)benzoate (831 mg, 3.0 mmol, 1.5 eq.) were dissolved in dioxane or a mix of toluene:ethanol (2:1 v/v, 20 mL). The mixture was treated with $Na_2CO_3$ 2M aqueous solution (6.7 mL) and deoxygenated by bubbling $N_2$ for 10 minutes. $Pd[PPh_3]_4$ (116 mg, 0.1 mmol) was added and the mixture was heated to 85° C. for 4 hours. LCMS analysis indicated about 50% conversion to product. The cooled reaction mixture was diluted with EtOAc (100 mL), washed with water and then washed with brine. The aqueous layers were extracted once again with a $CH_2Cl_2$/iPrOH mixture (9:1 v/v). The combined organics were dried over anhydrous $MgSO_4$, filtered and evaporated. The crude residue was triturated with $Et_2O$ and EtOAc and filtered to yield the pure title compound as a white solid. Yield=162 mg (0.42 mmol, 21%). LC/MS—HPLC (254 nm)—Rt 2.11 min. MS (ESI) m/z 387.3 $[M+H]^+$. Purity=98.0% by UV (254 nm).

Step 4: Methyl 5-[1-cyclopentyl-2-(dimethylamino)carbonyl-1,5,7-triaza-1H-inden-6-ylamino]-2-(5-morpholino-7-oxo-4-oxa-1-thia-3-indenyl)benzoate Compound 7): In a, 8-mL vial, (6-chloro-1-cyclopentyl-1,5,7-triaza-1H-inden-2-yl) (dimethylamino)formaldehyde (95 mg, 0.327 mmol), methyl 5-amino-2-(5-morpholino-7-oxo-4-oxa-1-thia-3-indenyl)benzoate (84 mg, 0.218 mmol), $Cs_2CO_3$ (142 mg, 0.436 mmol), BINAP (14 mg, 0.022 mmol) and $Pd(OAc)_2$ (2.4 mg, 0.011 mmol) were degassed under $N_2$ for 10 minutes. Degassed 1,4-dioxane (4.4 mL) was added and the resulting mixture was stirred at 110° C. for 4-16 hours. LCMS analysis indicated complete consumption of starting material and formation of product. The reaction was cooled and directly purified by chromatography on silica-gel, eluting with a $CH_2Cl_2$/MeOH gradient. The product was further purified on preparative TLC plates, developing with a 95:5 v/v mixture of $CH_2Cl_2$/MeOH. The product, compound 7, was obtained as a beige solid. Yield=53 mg (0.083 mmol, 38%). LC/MS—HPLC (254 nm)—Rt 2.78 min. MS (ESI) m/z 643.3 $[M+H]^+$. Purity=>95% by UV (254 nm).

Figure 7A:
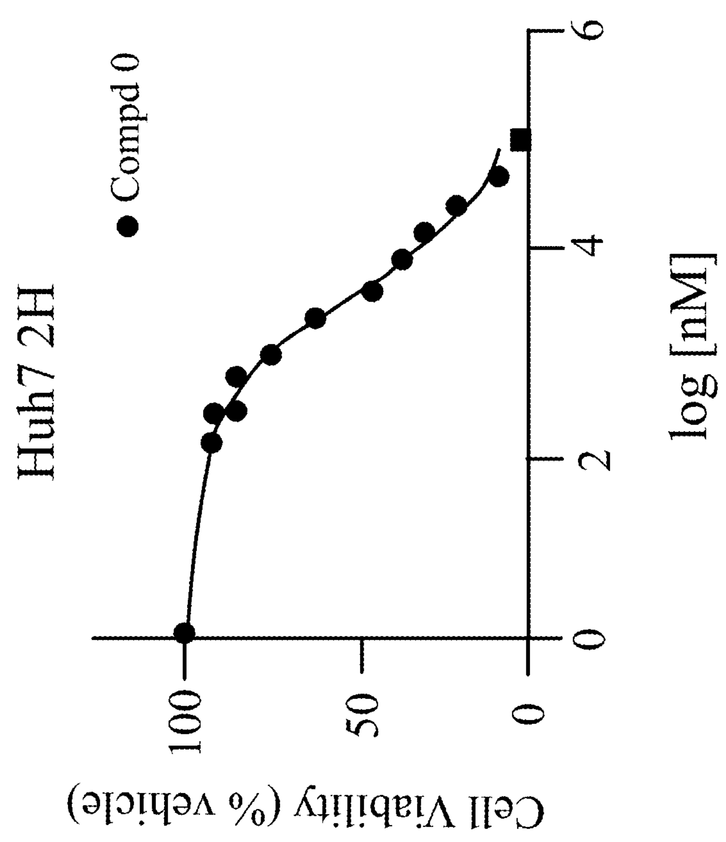
FIG. 7A shows cell viability of Huh7 2H cells exposed to Compound 0.
Figure 7B:
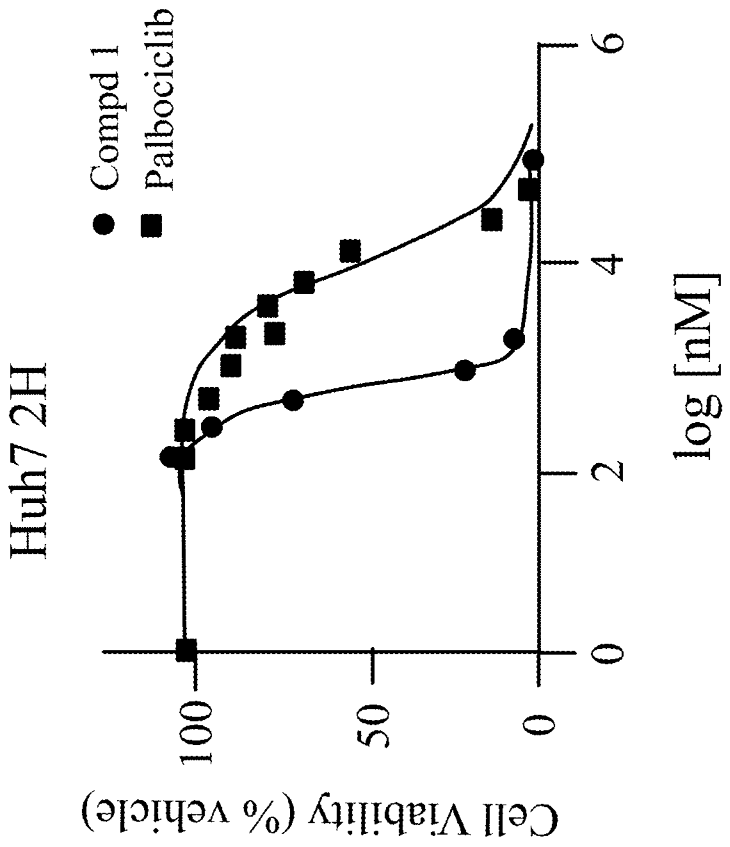
FIG. 7B shows cell viability of Huh7 2H cells exposed to compounds Compound 1 or Palbociclib.

Example 15. Triple Inhibitor Compound 1 Provides Improved Anticancer Activity in Huh 7 Cells The procedures of example 6 were followed except using the Huh7 2H cell line. The cell viability versus concentration results are presented in FIGS. 7A and 7B for compound 0, compound 1, and Pablociclib. In separate cell viability experiments some variability in $IC_{50}$ values was observed for Compound 0 (a potent dual BRD4/PI3K inhibitor) ranging from 2.97 to 5.9 micromolar (M). The potent triple inhibitor Compound 1 (inhibitor of CDK4/6 and PI3K and BRD4) shows potent $IC_{50}$ in cell viability of 0.495 nM, while the FDA-approved Palbociclib (potent CDK4/6 inhibitor) was about 18 times less potent than Compound 1 with an $IC_{50}$ of 9.20 μM.

In conclusion, triple inhibition with Compound 1 provided the most potency in tests using single, double, and triple single-molecule targeting agents. Specifically, inhibition of BRD4-only was less potent than inhibition of CDK-only, which was less potent than dual inhibition of BRD4 and PI3K, which was less potent than triple inhibition of BRD4, PI3K, and CDK4/6. By altering a dual PI3K/BRD4 inhibitor to include inhibition of CDK, a large increase in potency towards blocking cell viability of 6- to 10-fold was observed.

Example 16. Preparation of Compound 10 from Compound 7

5-[1-Cyclopentyl-2-(dimethylamino)carbonyl-1,5,7-triaza-1H-inden-6-ylamino]-2-(5-morpholino-7-oxo-4-oxa-1-thia-3-indenyl)benzoic acid (Compound 10): A stirring solution of 9.5 mg (0.0148 mmol) of compound 7 (methyl 5-[1-cyclopentyl-2-(dimethylamino)carbonyl-1,5,7-triaza-1H-inden-6-ylamino]-2-(5-morpholino-7-oxo-4-oxa-1-thia-3-indenyl)benzoate) made as in example 14 was dissolved in tetrahydrofuran (1 mL) and was then treated with a 1 M aqueous solution of LiOH (1 mL). The resulting mixture was stirred at room temperature for 16 hours. Next morning, the LCMS analysis indicated clean conversion to product (m/z=629.7). The reaction mixture was quenched with 1 N HCl aqueous (5 mL) and the resulting solids were filtered and washed with EtOAc. The solids were air-dried resulting in compound 10 (1 mg, 0.0016 mmol, 11%). LC/MS—HPLC (254 nm)—Rt 2.52 min. MS (ESI) m/z 629.7 $[M+H]^+$, purity assessed by 254 nm—72%.

Example 17. Synthesis of Compound 3

Step 1: (6-Chloro-1-cyclopentyl-1,5,7-triaza-1H-inden-2-yl) (dimethylamino)formaldehyde A stirring solution of 6-chloro-1-cyclopentyl-1,5,7-triaza-1H-indene-2-carboxylic acid (530 mg, 2.0 mmol) and a tertiary amine (such as trimethylamine or diisopropylethylamine) (2.15 mL, 12.0 mmol) in DMF (10 mL) was treated with HBTU (1.14 g, 3.0 mmol) in one portion. The resulting mixture was stirred at room temperature for 30 minutes. Dimethylamine hydrochloride salt (326 mg, 4.0 mmol) was added in one portion and the resulting solution was stirred at room temperature overnight. The next morning, LCMS analysis indicated clean conversion to product (m/z=293.4). The reaction mixture was diluted with EtOAc, transferred to a separatory funnel and washed with saturated $NaHCO_3$ aqueous solution, 0.1 N HCl aqueous and brine. The organics were dried over anhydrous $MgSO_4$, filtered and concentrated to yield the crude title product. This was purified by silica-gel chromatography eluting with a hexanes/EtOAc gradient. The fractions containing the product 2-chloro-8-cyclopentyl-6-(1-ethoxyethenyl)-5-methyl-1,3,8-triaza-8H-naphthalen-7-one were concentrated to yield 570 mg. LC/MS—HPLC (254 nm)—Rt 2.90 min. MS (ESI) m/z 293.4 $[M+H]^+$.

Step 2: 3-(6-Amino-3-pyridyl)-5-morpholino-4-oxa-1-thia-7-indenone

3-Bromo-5-morpholino-4-oxa-1-thia-7-indenone (316 mg, 1.0 mmol) and 5-(4,4,5,5-tetramethyl-1,3,2-dioxaborolan-2-yl)-2-pyridylamine (330 mg, 1.5 mmol, 1.5 eq.) were dissolved in dioxane or a mix of toluene:ethanol (2:1 v/v, 10 mL). The mixture was treated with $Na_2CO_3$ 2M aqueous solution (3.3 mL) and deoxygenated by bubbling $N_2$ for 10 minutes. $Pd[PPh_3]_4$ (58 mg, 0.1 mmol) was added and the mixture was heated to 85° C. for 2 hours. LCMS indicated completed conversion to product. The cooled reaction mixture was diluted with EtOAc (100 mL) washed with water and brine. The aqueous layers were extracted once again with a $CH_2Cl_2$/iPrOH mixture (9:1 v/v). The combined organics were dried over anhydrous $MgSO_4$, filtered and evaporated. The crude residue was triturated with $Et_2O$ and EtOAc and filtered to yield the pure title compound as an orange solid. Yield=201 mg (0.61 mmol, 61%).

LC/MS—HPLC (254 nm)—Rt 1.23 min. MS (ESI) m/z 330.3 $[M+H]^+$. Purity=99.2% by UV (254 nm).

Step 3: {1-Cyclopentyl-6-[5-(5-morpholino-7-oxo-4-oxa-1-thia-3-indenyl)-2-pyridylamino]-1,5,7-triaza-1H-inden-2-yl}(dimethylamino)formaldehyde: In an 8-mL vial, (6-chloro-1-cyclopentyl-1,5,7-triaza-1H-inden-2-yl) (dimethylamino)formaldehyde (93 mg, 0.32 mmol), 3-(6-amino-3-pyridyl)-5-morpholino-4-oxa-1-thia-7-indenone (70 mg, 0.21 mmol), $Cs_2CO_3$ (139 mg, 0.43 mmol), BINAP (53 mg, 0.085 mmol) and $Pd(OAc)_2$ (10 mg, 0.042 mmol) were degassed under $N_2$ for 10 minutes. Degassed 1,4-dioxane (4.3 mL) was added and the resulting mixture was stirred at 110° C. for 6 hours. LCMS analysis indicated complete consumption of starting material and formation of product. The reaction was cooled and directly purified by chromatography on silica-gel, eluting with a $CH_2Cl_2$/MeOH gradient. The fractions containing the product were combined and evaporated to yield a tan solid (80 mg). This was triturated with acetone and filtered and the pure compound 3 was obtained as a white solid. Yield=38 mg (0.065 mmol, 31%). LC/MS—HPLC (254 nm)—Rt 2.08 min. MS (ESI) m/z 586.2 $[M+H]^+$. Purity=97.4% by UV (254 nm).

Example 18. Synthesis of Compound 6

Step 1: 2-Chloro-8-cyclopentyl-6-(1-ethoxyethenyl)-5-methyl-1,3,8-triaza-8H-naphthalen-7-one: A stirred solution of commercially available 6-bromo-2-chloro-8-cyclopentyl-5-methyl-1,3,8-triaza-8H-naphthalen-7-one (1.0 g, 2.92 mmol) in toluene (41 mL) was treated with tributyl(1-ethoxyvinyl)tin (1.0 g, 2.77 g). This mixture was degassed by $N_2$ bubbling for 10 minutes, followed by treatment with $Pd[Ph_3P]_4$ (300 mg, 0.26 mmol). The resulting mixture was heated to 110° C. for 16 hours. LCMS analysis indicated the reaction was completed. The reaction was cooled to room temperature and concentrated in vacuo. The crude residue was purified by automated chromatography on silica-gel, eluting with a hexanes/EtOAc gradient. The product was obtained as a light yellow oil. Yield=516 mg (1.55 mmol, 56%). LC/MS—HPLC (254 nm)—Rt 3.55 min. MS (ESI) m/z 334.4 $[M+H]^+$.

Step 2: 1-(2-Chloro-8-cyclopentyl-5-methyl-7-oxo-1,3,8-triaza-8H-naphth-6-yl)-1-ethanone 2-Chloro-8-cyclopentyl-6-(1-ethoxyethenyl)-5-methyl-1,3,8-triaza-8H-naphthalen-7-one (516 mg, 1.55 mmol) was dissolved in THF or $CH_2Cl_2$ (15 mL) and treated with trifluoroacetic acid (2 mL) and the resulting mixture was stirred at 50° C. for 3 h. LCMS analysis showed clean conversion to product. The reaction was cooled and concentrated in vacuo. The crude residue was purified by chromatography on silica-gel, eluting with a hexanes/EtOAc gradient. The product 1-(2-chloro-8-cyclopentyl-5-methyl-7-oxo-1,3,8-triaza-8H-naphth-6-yl)-1-ethanone was obtained as a white solid. Yield=195 mg (0.64 mmol, 22%). LC/MS—HPLC (254 nm)—Rt 4.23 min. MS (ESI) m/z 306.4 $[M+H]^+$.

Step 3: 1-{8-Cyclopentyl-5-methyl-2-[p-(5-morpholino-7-oxo-4-oxa-1-thia-3-indenyl)phenylamino]-7-oxo-1,3,8-triaza-8H-naphth-6-yl}-1-ethanone. In an 8-mL vial, 1-(2-chloro-8-cyclopentyl-5-methyl-7-oxo-1,3,8-triaza-8H-naphth-6-yl)-1-ethanone (103 mg, 0.34 mmol), 3-(p- aminophenyl)-5-morpholino-4-oxa-1-thia-7-indenone (74 mg, 0.23 mmol), $Cs_2CO_3$ (147 mg, 0.45 mmol), BINAP (56 mg, 0.09 mmol) and $Pd(OAc)_2$ (10 mg, 0.045 mmol) were degassed under $N_2$ for 10 minutes. Degassed 1,4-dioxane (4 mL) was added and the resulting mixture was stirred at 110° C. for 6 hours. LCMS indicated complete consumption of starting material and formation of product. The reaction was cooled and directly purified by automated chromatography on silica-gel, eluting with a $CH_2Cl_2$/MeOH gradient. The fractions containing the product were combined and evaporated. The product was repurified by preparative thin layer chromatography (TLC), eluting with a 95:5 v/v mixture of $CH_2Cl_2$ and MeOH. Product (compound 6; 1-{8-cyclopentyl-5-methyl-2-[p-(5-morpholino-7-oxo-4-oxa-1-thia-3-indenyl)phenylamino]-7-oxo-1,3,8-triaza-8H-naphth-6-yl}-1-ethanone) was obtained as a white solid. Yield=9 mg (0.015 mmol, 7%). LC/MS—HPLC (254 nm)—Rt 3.05 min. MS (ESI) m/z 598.5 [M+H]+. Purity=98% by UV (254 nm).

Example 19. Lack of BRD4 Inhibition for Dual CDK/PI3K Inhibitor ON123300 and Preparation of Compound 8

The dual inhibition of CDK4/Rb and PI3K (delta) has been described in a single molecule designated ON123300 (S K A Divakar et al., Leukemia 2016, volume 30, pages 86-93). ON123300 is reported to inhibit CDK4/Cyclin D1 at 3.87 nM $IC_{50}$, CDK6/Cyclin D1 at 9.82 nM $IC_{50}$, and PI3K-delta isoform at 144 nM $IC_{50}$ along with a few other kinases (see Table 2 in the above reference). The structure and some key aspects of its synthesis are shown below:

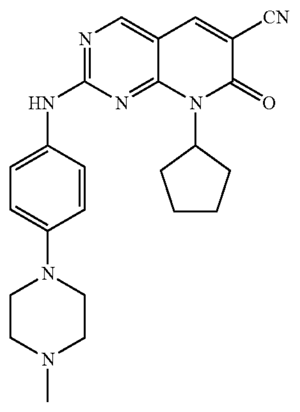

ON123300

Key aspects for synthesizing the core pyrido-pyrimidines have been reports as shown below:

Scheme: Synthesis of Pyrido[2,3-d]pyrimidines

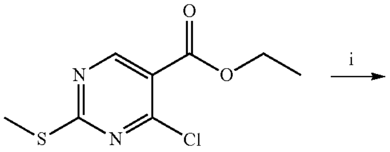

1

-continued

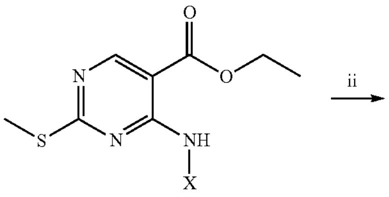

2

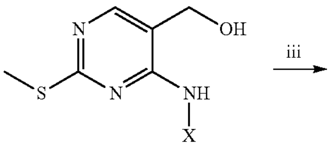

3

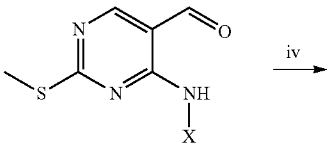

4

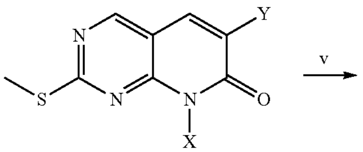

5

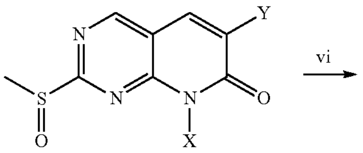

6

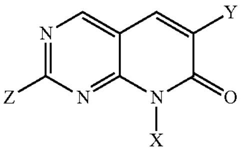

ON123160 to ON1231820

X = Methyl, Propyl, Cyclopentyl, Cyclohexyl

Y=CN, $PhSO_2$, $CH_3SO_2$

Z=Substituted aryl or heteroaryl amine

Reagents and conditions: (i) X—$NH_2$, $Et_3N$, THF, RT, 3 hr. (ii) $LiAlH_4$, THF, −10° C.—RT, 3 hr. (iii) $MnO_2$, $CHCl_3$ RT, 36 hr (iv) Z, DMSO or Toluene, 100° C., 3-10 hr.

Compound 4 in the above synthetic scheme is readily commercially available (LabNetwork, Catalog Number WX687916; Ryan Scientific, Catalog Number 072-28427; Combi-Blocks, Catalog Number QK-1905):

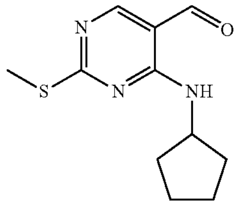

CAS #211245-64-6

ON123300 was tested for inhibition of BRD4 binding domain 1 and binding domain 2 and found to have an $IC_{50}$ of 45,600 nM and >50,000 nM, respectively. Thus, ON123300 does not function as an inhibitor of BRD4 to any meaningful extent.

Compound 8 (see below) is synthesized as an inhibitor of BRD4, PI3K, CDK4 and CDK6 via the following route using the chemistry described for ON123300 intermediates and finally coupling with 3-(p-aminophenyl)-5-morpholino-4-oxa-1-thia-7-indenone (prepared as in step 2 of example 1 and other examples herein). The $NH_2$ of 3-(p-aminophenyl)-5-morpholino-4-oxa-1-thia-7-indenone is reacted via nucleophilic aromatic substitution to replace the good methyl-thione leaving group to form triple BRD4/PI3K/CDK inhibitor Compound 8.

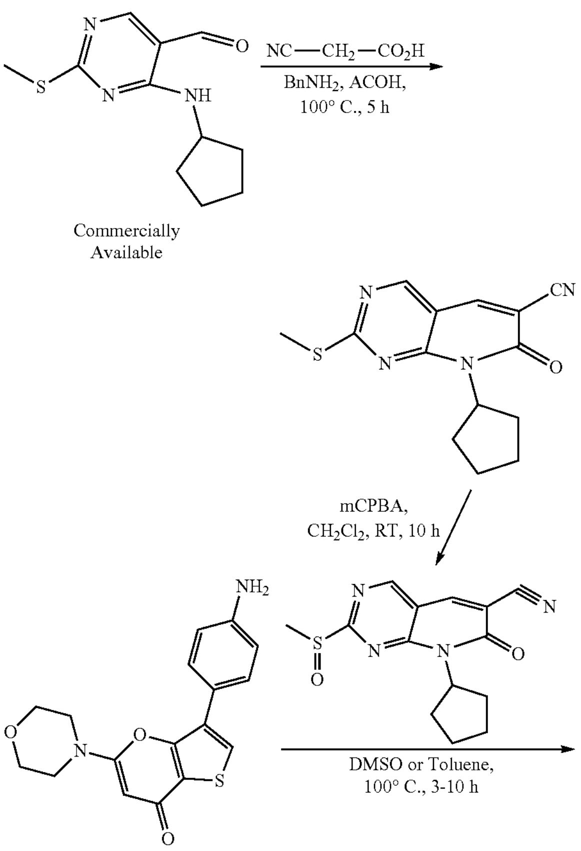

Commercially Available

From step 2 Example 1 3-(p-Aminophenyl)-5-morpholino-4-oxa-1-thia-7-indenone

-continued

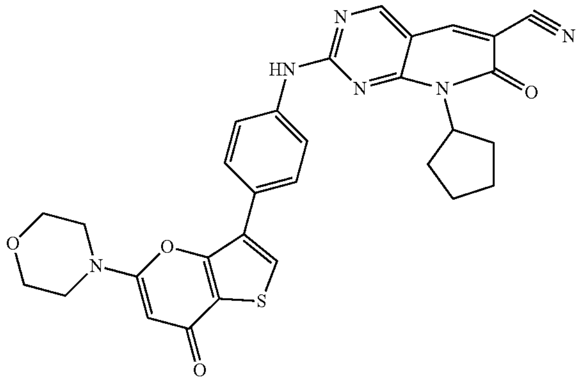

Compound 8

Example 20. Preparation of Compound 19

The preparation of compound 19 is shown in the scheme below:

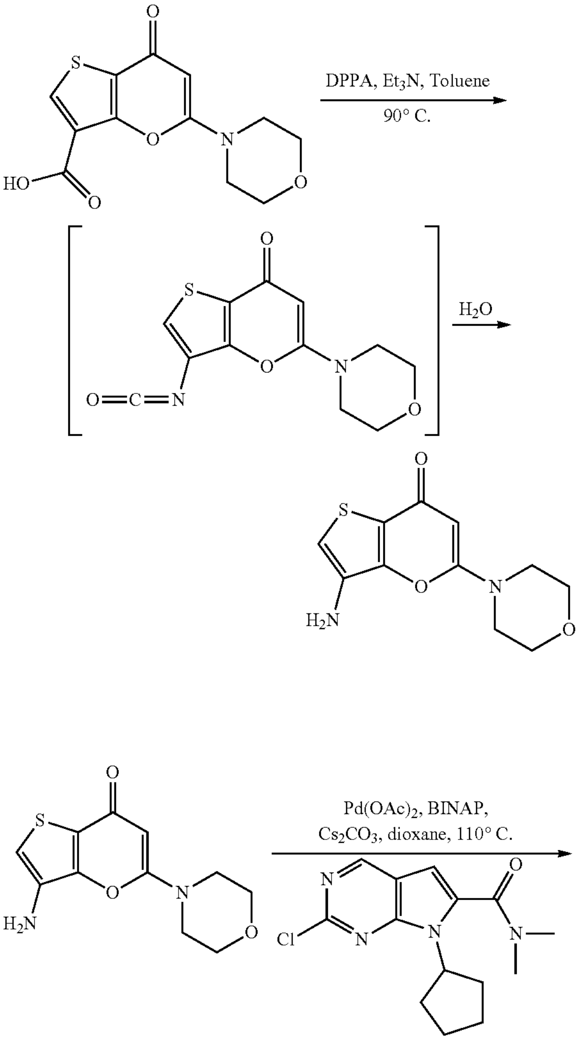

-continued

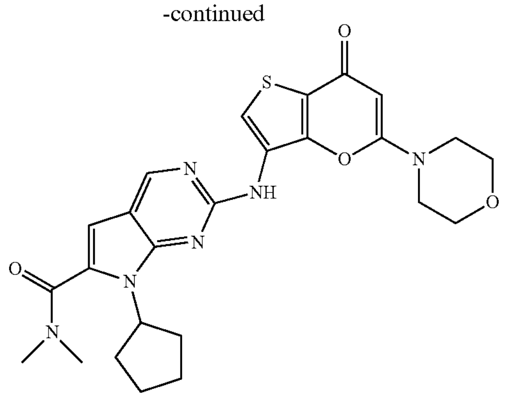

Compound 19

An alternate route is hereby taught by the synthetic methods described in U.S. Pat. No. 8,557,807 patent in columns 43 and 44 section titled "Thiophene amination reaction procedure K". Substituting a primary amine protected as a secondary amine would give the desired amine attachment which can then be deprotected to yield the primary amine attached to the thiophene group which is then reacted with the chloro-pyrimidine to yield compound 19. An example of such an amine starting material would be dibenzyl amine which can then be converted to the primary amine via removal of the 2 benzyl groups for example via standard hydrogenation conditions. Other examples include protecting groups common in peptide chemistry that allow a secondary amine to react to give a tertiary amine and then protecting groups removed to provide a primary amine.

Our synthesis of compound 19 was achieved according to the procedure described in Example 27, step-3, using 0.5 eq of 2-chloro-7-cyclopentyl-N,N-dimethyl-7H-pyrrolo[2,3-d]pyrimidine-6-carboxamide heating the reaction mixture at 110° C. for 4.0 hours. Proton NMR and mass spectra are consistent with the structure of product. Calculated molecular weight: 508.19 Dalton. MS (ESI) m/z=509.44 $[M+H]^+$

Example 21. Compiled Compound $IC_{50}$ Data for BRD4, PI3K, and CDK (Values in nM)

The compounds of the invention were characterized by their ability to inhibit the target proteins using third party vendors offering such services. PI3K-alpha, PI3K-gamma, and PI3K-delta inhibition activity was determined by Thermo Fisher Scientific-Biosciences Life Sciences Solutions, Madison, WI. The bromodomain protein inhibition (binding domain 1 and 2 of BRD4 was determined by Reaction Biology Corp., Malvern, PA. The cyclin dependent kinase inhibition on CDK4 and CDK6 was determined by Reaction Biology Corp., Malvern, PA. Additional information on each of the above testing procedures and services is available at each company's website on the internet. The $IC_{50}$ data presented below in Table 11 is calculated from a 10-point curve and is expressed in nanomolar concentration (nM) and grouped according to potency. Where multiple values have been obtained the range from lowest to highest values is presented. NI=no inhibition detected up to 50 μM or $IC_{50}$ not reached at 50 μM. ND=not done.

TABLE 11

| Compliled $IC_{50}$ data | | | | | | | |
|---|---|---|---|---|---|---|---|
| Cmpd # | BRD4-1 | BRD4-2 | P13K α | P13K δ | P13K γ | CDK4 | CDK6 |
| 1 | * | * | * | * | *** | * | * |
| 2 | ** | ** | **** | **** | **** | * | * |
| 3 | * to ** | ** | ** | * | ** | * | * |
| 4 | ** | *** | ** | ** | *** | NI | NI |
| 5 | NI | NI | **** | *** | NI | * | * |
| 6 | ** | ** | * | * | *** | * | * |
| 7 | ** | ** | ** | * | *** | * | * |
| 8 | ND | ND | ND | ND | ND | ND | ND |
| 9 | ND | ND | ND | ND | ND | ND | ND |
| 10 | * | ** | * | ** | ** | **** | **** |
| 11 | *** | *** | ** | ** | **** | * | * |
| 12 | **** | **** | ** | ** | **** | ** | ** |
| 13 | ND | ND | ND | ND | ND | ND | ND |
| 14 | ND | ND | ND | ND | ND | ND | ND |
| 15 | ND | ND | ND | ND | ND | ND | ND |
| 16 | ND | ND | ND | ND | ND | ND | ND |
| 17 | ND | ND | ND | ND | ND | ND | ND |
| 18 | ** | *** | **** | ** | *** | * | * |
| 19 | ND | ND | ND | ND | ND | ND | ND |

Key for $IC_{50}$ values:
* = <100 nM
** = 100 nM-1000 nM
*** = >1000 nM-<5000 nM
**** = >5000 nM-50000 nM
NI = >50000 nM
ND = not done These results demonstrate a wide variety of compounds of the invention that are potent inhibitors of CDK4 and CDK6 as well as in combination with inhibition of PI3K and/or BRD4.

Example 22. Compound 1 is Superior to Palbociclib

Figure 8A:
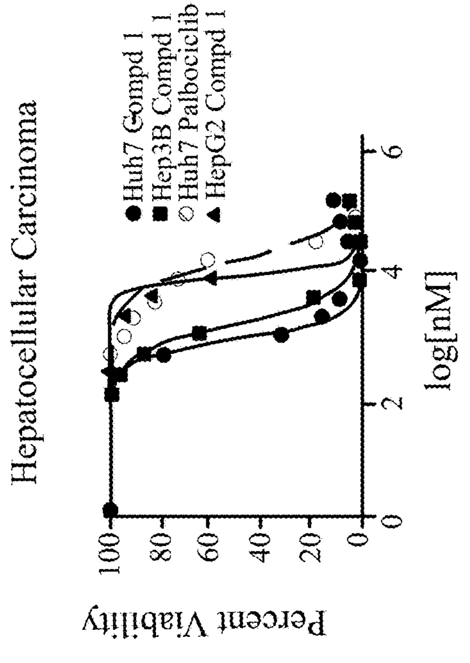
FIG. 8A shows cell viability in Hepatocellular carcinoma cell lines treated with Compound 1 or Palbociclib.
Figure 8B:
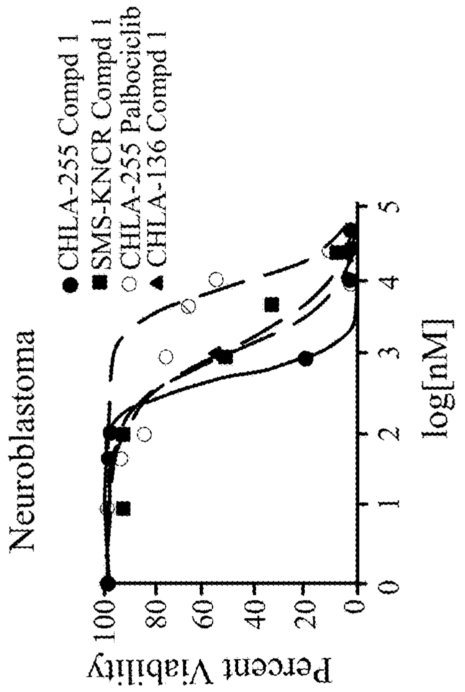
FIG. 8B shows cell viability in Neuroblastoma cell lines treated with Compound 1 or Palbociclib.
Figure 8C:
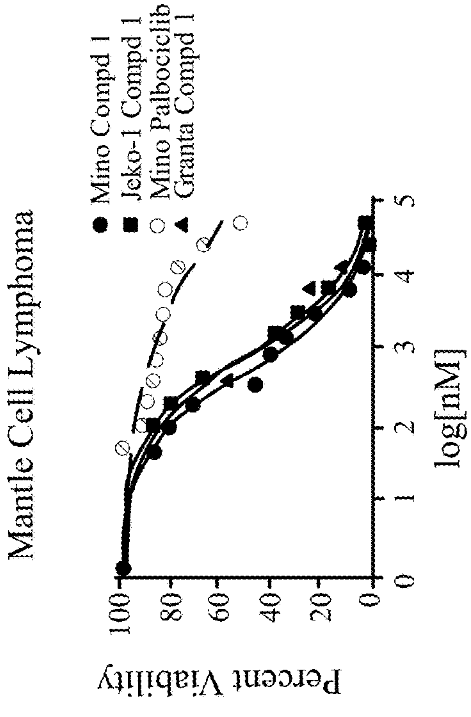
FIG. 8C shows cell viability in Mantle cell lymphoma cell lines treated with Compound 1 or Palbociclib.
Figure 8D:
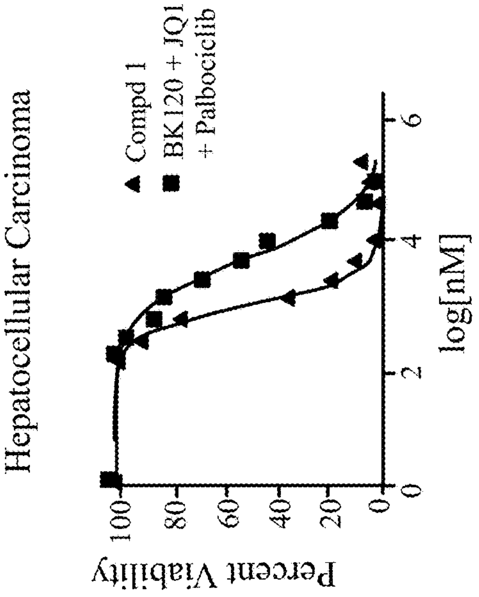
FIG. 8D shows cell viability in Hepatocellular carcinoma cell lines treated with Compound 1 or a combination of BK120, JQ1 and Palbociclib.

The percent viability versus concentration experimental procedures for hepatocellular carcinoma cell lines, neuroblastoma cell lines, and Mantle cell lymphoma cell lines was performed as described in example 6, example 4, and example 5, respectively. The results of these experiments are shown in FIGS. 8A-8D. In general, Compound 1 performed substantially better than Palbociclib against Hepatocellular carcinoma (FIG. 8A), Neuroblastoma (FIG. 8B), and Mantle Cell lymphoma (FIG. 8C) cell lines. The superior results of the triple inhibitor Compound 1 are striking in comparison with the single inhibitor Palbociclib (inhibitor of CDK4/6) and in comparison with a combination of three separate inhibitors directed at the same three targets (FIG. 8D). It is believed that the superior results with Compound 1 are related to simultaneous disruption of multiple inter-related signaling pathways and orthogonal pathways. As shown in FIG. 8D, the single molecule, triple inhibitor Compound 1 performed substantially better against hepatocellular carcinoma cells than a combination of three separate molecule inhibitors targeting PI3K (BKM120), BRD4 (JQ1), and CDK4/6 (Palbociclib).

In further support of the superiority of Compound 1 over Palbociclib an evaluation of apoptosis induced by the two compounds was performed and showed that Compound 1 induced a greater fold-increase in apoptosis at 500 nM concentration than did Palbociclib at either 2000 or 10000 nM.

Example 23. Preparation of Compound 11

{1-Cyclopentyl-6-[p-(5-morpholino-7-thioxo-4-oxa-1-thia-3-indenyl)phenylamino]-1,5,7-triaza-1H-inden-2-yl}

(dimethylamino)formaldehyde. In an 8-mL vial, {1-cyclopentyl-6-[p-(5-morpholino-7-oxo-4-oxa-1-thia-3-indenyl) phenylamino]-1,5,7-triaza-1H-inden-2-yl}(dimethylamino) formaldehyde (Compound 1, 47 mg, 0.08 mmol) was dissolved in pyridine (1 mL) and treated with Lawesson's reagent [2,4-bis(4-methoxyphenyl)-1,3,2,4-dithiadiphosphetane-2,4-dithione] (20 mg, 0.048 mmol, 0.6 eq.) under magnetic stirring. The resulting solution was heated to 130° C. and stirred at that temperature for 2 hours. LCMS analysis indicated approximately a 1:1 mixture of product and starting material. The reaction was cooled, diluted with $CH_2Cl_2$ (50 mL) and washed with $H_2O$ (50 mL). The organic layer was dried over anhydrous $MgSO_4$, filtered and concentrated in vacuo. The crude residue was purified by preparative TLC plate chromatography on silica-gel, eluting with a 95:5 v/v $CH_2Cl_2$/MeOH mixture. The product, compound 11, was obtained as a yellow solid. Yield=8 mg (0.013 mmol, 17%). LC/MS—HPLC (254 nm)—Rt 2.60 min. MS (ESI) m/z 601.7 $[M+H]^+$. Purity=95% by UV (254 nm).

Example 24. Preparation of Compound 12

7-Cyclopentyl-N,N-dimethyl-2-((4-(5-morpholino-7-thioxo-7H-thieno[3,2-b]pyran-3-yl)phenyl)amino)-7H-pyrrolo[2,3-d]pyrimidine-6-carbothioamide. In an 8-mL vial, {1-cyclopentyl-6-[p-(5-morpholino-7-oxo-4-oxa-1-thia-3-indenyl)phenylamino]-1,5,7-triaza-1H-inden-2-yl}(dimethylamino)formaldehyde (Compound 1, 47 mg, 0.08 mmol) was dissolved in pyridine (1 mL) and treated with Lawesson's reagent [2,4-bis(4-methoxyphenyl)-1,3,2,4-dithiadiphosphetane-2,4-dithione] (20 mg, 0.048 mmol, 0.6 eq.) under magnetic stirring. The resulting solution was heated to 130° C. and stirred at that temperature for 2 hours. LCMS analysis indicated approximately a 1:1 mixture of mono sulfurization and starting material. Another portion of Lawesson's reagent (50 mg) was added and the reaction heated for another 2 hours. LCMS analysis then indicated complete conversion to the di-sulfurized product (compound 12). The reaction was cooled, diluted with $CH_2Cl_2$ (50 mL) and washed with $H_2O$ (50 mL) and TN HCl aq (20 mL). The organic layer was dried over anhydrous $MgSO_4$, filtered and concentrated in vacuo. The crude residue was purified by preparative TLC plate chromatography on silica-gel, eluting with a 95:5 v/v $CH_2Cl_2$/MeOH mixture. The title product, compound 12, was obtained as a yellow solid. Yield=33 mg (0.054 mmol, 65%). LC/MS—HPLC (254 nm)—Rt 3.24 min. MS (ESI) m/z 617.0 [M+H]+. Purity=97.1% by UV (254 nm).

Figure 9A:
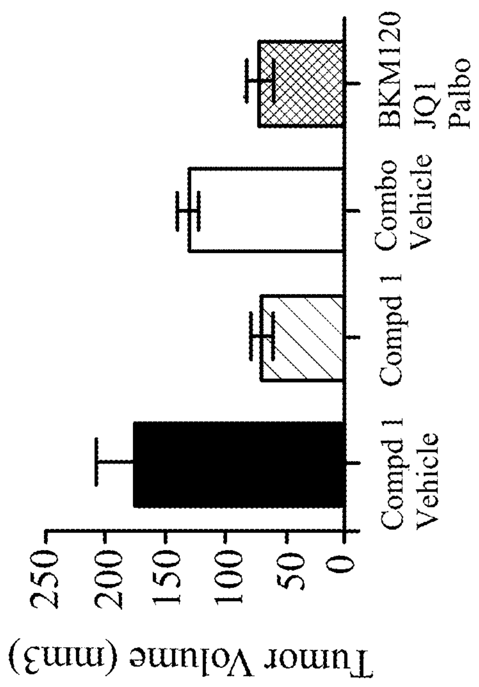
FIG. 9A shows in vivo anticancer activity of Compound 1 versus treatment with three cognate inhibitors.
Figure 9B:
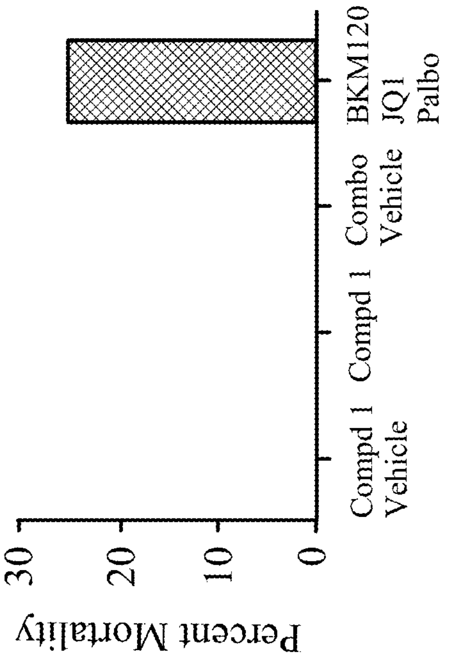
FIG. 9B shows that Compound 1 was not toxic in mice while a combination of three separate inhibitors led to significant mortality.

Example 25. In Vivo Safety and Efficacy of Triple Inhibitor Compound 1 Versus a Combination of Three Cognate Inhibitors $1\times10^7$ Huh7 cells were implanted into NGS mice. When tumors reached ~1400 $mm^3$ after 14 days of tumor implantation, animals were divided into four groups (n=8 per group). Group 1 was treated with compound 1 Vehicle (Hot Rod #8 (Pharmatek), group 2 was treated with compound 1 (30 mg/kg) formulated in Pharmatek Hot Rod formulation solution #8, group 3 was treated with Combo Vehicle (NMP/PEG300 (10/90 v/v) plus lactated Ringer's (pH 4.0) plus 0.5% methylcellulose and 0.2% Tween 80), and group 4 was treated with BKM120 (30 mg/kg) plus palbociclib (30 mg/kg) plus JQ1 (30 mg/kg) dissolved in the Combo Vehicle. Mice were treated by oral gavage, 5 times per week for 2 weeks. The results are shown in FIG. 9. FIG. 9A demonstrates efficacy of triple inhibitor compound 1 (BRD4/PI3K/CDK4 and CDK6) comparable to the efficacy of 3 separate cognate inhibitors (BRD4 inhibitor plus a PI3K inhibitor plus a CDK4/6 inhibitor) administered simultaneously. However, a dramatic difference in toxicity was noted. The toxicity (animal death) in compound 1 treated vs 3-drug combination treated mice is shown in FIG. 9B. The combo treatment resulted in 25% mortality rate versus no animal deaths in the compound 1 treatment group. Thus, compound 1 and other compounds of the invention represent a way to treat mammals with combinations of inhibitors of multiple anticancer mechanisms resulting in at least equal efficacy but dramatically diminished toxicity versus the administration of multiple single agents. While not wishing to be bound to theory this may be the result of less off-target side effects for a multiple inhibitor than would be present for multiple single inhibitors. The statistically significance of the results in FIG. 9 show $p<0.001$ for efficacy of both treatments versus vehicles and mortality comparison for compound 1 to the 3-drug combination in vivo.

Example 26. Compound 1 Shows Broad Anticancer Activity Across Numerous Cancer Cell Line Types Compound 1 was supplied to the National Cancer Institute for evaluation in the NCI 60 cell panel single dose inhibition study.

The number reported for the One-dose assay is growth relative to the no-drug control, and relative to the time zero number of cells. This allows detection of both growth inhibition (values between 0 and 100) and lethality (values less than 0). This is the same as for the 5-dose assay, described below. For example, a value of 100 means no growth inhibition. A value of 40 would mean 60% growth inhibition. A value of 0 means no net growth over the course of the experiment. A value of −40 would mean 40% lethality. A value of −100 means all cells are dead.

For compound 1 the overall mean growth percent inhibition was −32.83 indicating about 33% lethality overall of the cells compared to controls. For compound 2 (dual BRD4/CDK4-6 inhibitor) the mean growth percent inhibition was +16 indicating growth inhibition not lethality. This supports the benefit of the PI3K inhibition component of the triple inhibitor compound 1. For comparison the dual BRD4/PI3K inhibitor compound 0 had also been evaluated and showed a mean growth percent inhibition of +10 indicating growth inhibition not lethality. Thus, for maximum anticancer effect the triple inhibition of BRD4 and PI3K and CDK4/6 is desired as exemplified by compound 1 and other compounds of the invention.

The individual cell line growth percent inhibition for compound 1 is listed below grouped by cancer type:

Leukemia

| | |
|---|---|
| CCRF-CEM | −14.44 |
| HL-60(TB) | −46.74 |
| K-562 | 2.96 |
| MOLT-4 | −31.97 |
| RPMI-8226 | −46.71 |
| SR | 0.02 |

Non-Small Cell Lung Cancer

| | |
|---|---|
| A549/ATCC | −36.82 |
| EKVX | −19.52 |
| HOP-62 | −30.36 |

-continued

| | |
|---|---|
| HOP-92 | −3.68 |
| NCI-H226 | 2.17 |
| NCI-H23 | −10.23 |
| NCI-H322M | −28.97 |
| NCI-H460 | −26.41 |
| NCI-H522 | −65.10 |

Colon Cancer

| | |
|---|---|
| COLO 205 | −84.28 |
| HCC-2998 | −44.57 |
| HCT-116 | −29.20 |
| HCT-15 | −11.42 |
| HT29 | −48.56 |
| KM12 | −86.90 |
| SW-620 | −45.59 |

CNS Cancer

| | |
|---|---|
| SF-268 | −2.94 |
| SF-295 | −36.90 |
| SF-539 | −70.17 |
| SNB-19 | 1.45 |
| SNB-75 | −65.05 |
| U251 | −7.84 |

Melanoma

| | |
|---|---|
| LOX IMVI | −39.35 |
| MALME-3M | −67.87 |
| M14 | −73.37 |
| MDA-MB-435 | −38.71 |
| SK-MEL-2 | −58.60 |
| SK-MEL-28 | −55.86 |
| SK-MEL-5 | −98.03 |
| UACC-257 | −81.54 |
| UACC-62 | −69.59 |

Ovarian Cancer

| | |
|---|---|
| IGROV1 | −7.11 |
| OVCAR-3 | 2.63 |
| OVCAR-4 | 12.39 |
| OVCAR-5 | −9.43 |
| OVCAR-8 | 2.54 |
| NCI/ADR-RES | 0.63 |
| SK-OV-3 | −28.34 |

Renal Cancer

| | |
|---|---|
| 786-0 | −1.22 |
| ACHN | 1.06 |
| CAKI-1 | −50.83 |
| RXF 393 | −85.84 |
| SN12C | 4.35 |
| TK-10 | −10.03 |
| UO-31 | −5.39 |

Prostate Cancer

| | |
|---|---|
| PC-3 | −42.03 |
| DU-145 | −97.13 |

Breast Cancer

| | |
|---|---|
| MCF7 | −46.81 |
| MDA-MB-231/ATCC | −7.21 |
| HS 578T | −8.99 |
| BT-549 | −79.13 |
| T-47D | −4.72 |
| MDA-MB-468 | −5.41 |

Example 27. Preparation of Compound 13

Step-1: 3-((Diphenylmethylene)amino)-5-morpholino-7H-thieno[3,2-b]pyran-7-one. A mixture of 3-bromo-5-morpholino-7H-thieno[3,2-b]pyran-7-one (0.308 g, 0.944 mmol), diphenylmethanimine (0.190 g, 1.04 mmol), BINAP (0.031 g, 0.096 mmol), and cesium carbonate (1.26 g, 3.88 mmol) in 1,4-dioxane (5.0 mL) was degassed under a flow of argon for 15 min. $Pd(OAc)_2$ (0.013 g, 0.055 mmol) was added to the mixture and degassed for 10 min, then the reaction mixture was heated to 95-100° C. for 12 h. The reaction mixture was allowed to cool down to ambient temperature. The solvent was evaporated under reduced pressure. The crude product was purified by flash column chromatography (silica-gel), eluting with EtOAc/MeOH (95:5) gradient. The fractions containing the product were concentrated to yield 89% of the title compound (0.352 g, 0.845 mmol). Physical state: Light brown solid.

Step-2: 3-Amino-5-morpholino-7H-thieno[3,2-b]pyran-7-one hydrochloride. To a solution of the above imine (0.352 g, 0.845 mmol) in dichloromethane (10 mL) was added EtOH HCl (2.0 M, 12 mL) and stirred at ambient temperature for 2.0 h. The solvent was evaporated under reduced pressure and then the crude product was washed with hexanes (2×10 mL), and DCM/hexanes (1:1, 2×10 mL). Finally, the product was dried under vacuum to yield 83% of the title compound as the amine hydrochloride salt (0.201 g, 0.697 mmol). Physical state Light brown solid.

Step-3: Preparation of compound 13. A mixture of the above amine (0.033 g, 0.119 mmol), 2-chloro-7-cyclopentyl-N,N-dimethyl-7H-pyrrolo[2,3-d]pyrimidine-6-carboxamide (0.042 g, 0.142 mmol), BINAP (0.014 g, 0.023 mmol), and cesium carbonate (0.116 g, 0.357 mmol) in 1,4-doxane (1.0 mL) was degassed under a flow of argon for 15 min. $Pd(OAc)_2$ (0.003 g, 0.011 mmol) was added to the mixture and degassed for 10 min. Then, the reaction mixture was heated to 95-100° C. for 12 h. The reaction mixture was cooled to ambient temperature. The crude product, obtained after evaporation of the solvent, was purified by flash column chromatography (silica-gel) eluting with DCM/MeOH (97:3) gradient. The fractions containing the product were concentrated to yield 11% of compound 13 (0.011 g, 0.014 mmol). Physical state: Off white solid. Proton NMR and mass spectra are consistent with the structure of product. Calculated molecular weight: 764.32 Dalton. MS (ESI) m/z=787.01 $[M+Na]^+$ Example 28. Preparation of Compound 14

A solution of 3-(4-aminophenyl)-5-morpholino-7H-thieno[3,2-b]pyran-7-one (as prepared in example 30) (0.065 g, 0.198 mmol), methyl 2-chloro-7-cyclopentyl-7H-pyrrolo[2,3-d]pyrimidine-6-carboxylate (0.046 g, 0.165 mmol), BINAP (0.022 g, 0.033 mmol), and cesium carbonate (0.163 g, 0.495 mmol) in 1,4-doxane (2.0 mL) was degassed under a flow of argon for 15 min. $Pd(OAc)_2$ (0.005 g, 0.016 mmol) was added to the mixture and degassed for 10 min. The reaction mixture was then heated to 95-100° C. for 12 h. The reaction mixture was cooled to the ambient temperature and the solvent was evaporated under reduced pressure. The crude product was purified by flash column chromatography (silica-gel), eluting with DCM/MeOH (95:5) gradient. The fractions containing the product were concentrated to yield 9% of compound 14 (0.007 g, 0.012 mmol). Physical state: Pale yellow solid. $R_f$=0.30 (mobile phase: 10% MeOH/DCM) on silica gel plate. Proton NMR and mass spectra are consistent with the structure of product. Calculated molecular weight: 571.19 Dalton. MS (ESI) m/z=572.38 [M+H]+

Example 29. Preparation of Compound 15

Step-1: 3-((4-Aminophenyl)ethynyl)-5-morpholino-7H-thieno[3,2-b]pyran-7-one. 3-Bromo-5-morpholino-7H-thieno[3,2-b]pyran-7-one (0.608 g, 1.92 mmol), 4-ethynylaniline (0.452 g, 3.84 mmol), copper(I) iodide (0.019 g, 0.096 mmol), and diisopropylethylamine (0.85 mL, 3.93 mmol) were dissolved in dry tetrahydrofuran (10 mL). The mixture was degassed under a flow of argon for 15 min. Then, $PdCl_2(PPh_3)_2$ (0.065 g, 0.096 mmol) was added and the reaction mixture again degassed for 10 min. After degassing, the reaction mixture was heated to 85° C. for 4.0 h in a closed vial. The reaction was cooled to ambient temperature, diluted with dichloromethane (30 mL), washed with water (10 mL), and brine (10 mL). The water layer was extracted with dichloromethane (2×10 mL), the combined organic extracts were dried over sodium sulfate, filtered, and concentrated under reduced pressure. The crude product was purified by flash column chromatography (silica-gel), eluting with DCM/MeOH (95:5) gradient. The fractions containing the product (3-((4-aminophenyl)ethynyl)-5-morpholino-7H-thieno[3,2-b]pyran-7-one) were concentrated to yield 31% of the title compound 0.209 g, 0.593 mmol). Physical state: Brown Solid. $R_f$=0.3 (mobile phase: 5% MeOH/DCM) on silica gel plate Step-2: A solution of the amine from step 1 (0.052 g, 0.142 mmol), 2-chloro-7-cyclopentyl-N,N-dimethyl-7H-pyrrolo[2,3-d]pyrimidine-6-carboxamide (0.053 g, 0.171 mmol), BINAP (0.019 g, 0.028 mmol), and cesium carbonate (0.141 g, 0.426 mmol) in 1,4-doxane (2.0 mL) was degassed under a flow of argon for 15 min. $Pd(OAc)_2$ (0.010 g, 0.025 mmol) was added to the mixture and degassed for 10 min. The reaction mixture was next heated to 95-100° C. for 12 h. The reaction mixture was cooled to ambient temperature, and the solvent was evaporated under reduced pressure. The crude product was purified by flash column chromatography (silica-gel), eluting with DCM/MeOH (95:5) gradient. The fractions containing the product were concentrated to yield 20% of compound 15 (0.017 g, 0.027 mmol).

Physical state: Off white solid. $R_f$=0.25 (mobile phase: 5% MeOH/DCM) on silica gel plate. Proton NMR and mass spectra are consistent with the structure of product. Calculated molecular weight: 608.22 Dalton. MS (ESI) m/z=609.21 [M+H]+

Example 30. Preparation of Compound 16

Step-1: 3-(4-Aminophenyl)-5-morpholino-7H-thieno[3,2-b]pyran-7-one. 3-Bromo-5-morpholino-7H-thieno[3,2-b]pyran-7-one (0.205 g, 0.632 mmol) and 4-aminophenylboronic ester (0.166 g, 0.759 mol) were dissolved in toluene: ethanol (2:1, v/v, 7.0 mL). The mixture was treated with aq 2.0 M $Na_2CO_3$ (3.5 mL) and degassed under a flow of argon for 15 min. $Pd(PPh_3)_4$ (0.036 g, 0.031 mmol) was then added and the reaction mixture again degassed for 10 min. The reaction mixture was then heated to 85° C. for 2.0 h in a closed vial. The reaction mixture was cooled to the ambient temperature, diluted with EtOAc (30 mL), washed with water (10 mL), and brine (10 mL). The water layer was extracted with EtOAc (2×10 mL). The combined organic extracts were dried over sodium sulfate, filtered, and concentrated under reduced pressure. The crude product was purified by flash column chromatography (silica-gel), eluting with hexanes/EtOAc (10:90) gradient. The fractions containing the title product were concentrated to yield 75% of 3-(4-aminophenyl)-5-morpholino-7H-thieno[3,2-b]pyran-7-one (0.156 g, 0.475 mmol). Physical state: Brown Solid. $R_f$=0.2 (Mobile phase: 90% EtOAc/hexane) on silica gel plate.

Step-2: A solution of 3-(4-aminophenyl)-5-morpholino-7H-thieno[3,2-b]pyran-7-one (0.104 g, 0.33 mmol), 2-chloro-7-cyclopentyl-N-methyl-7H-pyrrolo[2,3-d]pyrimidine-6-carboxamide (0.079 g, 0.27 mmol), BINAP (0,036 g, 0.054 mmol), and cesium carbonate (0.269 g, 0.81 mmol) in 1,4-doxane (5.0 mL) was degassed under a flow of argon for 15 min. $Pd(OAc)_2$ (0.010 g, 0.025 mmol) was added to the mixture and degassed for 10 min. Then, the reaction mixture was heated to 95-100° C. for 12 h. The reaction mixture was cooled to the ambient temperature, diluted with EtOAc (10 mL), washed with water (10 mL), and brine (10 mL). The aqueous solution was extracted with EtOAc (15 mL×2). The combined organic extracts were dried over sodium sulfate, filtered, and concentrated under reduced pressure. The crude product was purified by flash column chromatography (silica-gel), eluting with EtOAc gradient. The fractions containing the desired product were concentrated to yield 55% of compound 16 (0.356 g, 1.62 mmol). Physical state: Pale yellow solid. $R_f$=0.25 (Mobile phase: 10% MeOH/EtOAc) on silica gel plate. Proton NMR and mass spectra are consistent with the structure of product. Calculated molecular weight: 570.2 Dalton. MS (ESI) m/z=571.39 [M+H]+

Example 31. Preparation of Compound 17

Step-1: 3-(3-Aminophenyl)-5-morpholino-7H-thieno[3,2-b]pyran-7-one. A mixture of 3-bromo-5-morpholino-7H-thieno[3,2-b]pyran-7-one (0.404 g, 1.26 mmol) and 3-aminophenyl boronic ester (0.336 g, 1.51 mmol) was dissolved in toluene:ethanol (2:1, v/v, 30 mL). The mixture was treated with aqueous 2.0 M $Na_2CO_3$ (5.0 mL) and degassed under a flow of argon for 15 min. $Pd(PPh_3)_4$ (0.073 g, 0.063 mmol) was added, and the mixture again degassed for 10 min. The reaction mixture was next heated to 85° C. for 2.0 h in a closed vial. The reaction mixture was cooled to the ambient temperature, diluted with DCM (30 mL), washed with water (10 mL), and brine (10 mL). The water layer was extracted with DCM (2×10 mL). The combined organic extracts were dried over sodium sulfate, filtered, and concentrated under reduced pressure. The crude product was purified by flash column chromatography (silica-gel), eluting with DCM/MeOH (95:5) gradient. The fractions containing the product were concentrated to yield 50% of 3-(3-aminophenyl)-5-morpholino-7H-thieno[3,2-b]pyran-7-one (0.206 g, 0.627 mmol). Physical state: Brown Solid. $R_f$=0.4 (mobile phase: 10% MeOH/DCM).

Step 2: A solution of 3-(3-aminophenyl)-5-morpholino-7H-thieno[3,2-b]pyran-7-one from step 1 (0.050 g, 0.152 mmol), 2-chloro-7-cyclopentyl-N,N-dimethyl-7H-pyrrolo[2,3-d]pyrimidine-6-carboxamide (0.055 g, 0.182 mmol), BINAP (0.017 g, 0.029 mmol), and cesium carbonate (0.151 g, 0.458 mmol) in 1,4-doxane (2.0 mL) was degassed under a flow of argon for 15 min. $Pd(OAc)_2$ (0.010 g, 0.025 mmol) was added to the mixture and degassed for 10 min. Then, the reaction mixture was heated to 95-100° C. for 12 h. The reaction mixture was next cooled to the ambient temperature and concentrated under reduced pressure. The crude product was purified by flash column chromatography (silica-gel), eluting with DCM/MeOH (97:3) gradient. The fractions containing the product were concentrated to yield 28% of compound 17 (0.024 g, 0.041 mmol). Physical state: Pale yellow solid. $R_f$=0.30 (mobile phase: 5% MeOH/DCM) on silica gel plate. Proton NMR and mass spectra are consistent with the structure of product. Calculated molecular weight: 584.2 Dalton. MS (ESI) m/z=585.42 [M+H]$^+$.

Example 32. Synthesis of Analogs of Compound 1

Analog 1: 2,2'-((5-(5-Morpholino-7-oxo-7H-thieno[3,2-b]pyran-3-yl)pyridin-3-yl)azanediyl)bis(7-cyclopentyl-N,N-dimethyl-7H-pyrrolo[2,3-d]pyrimidine-6-carboxamide)

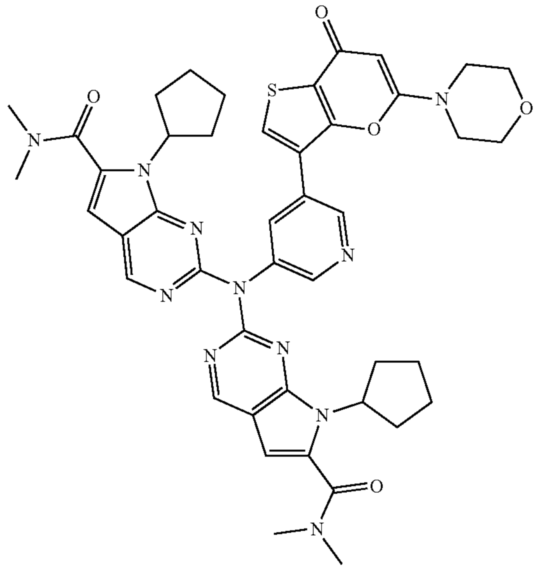 [SMILES: CN(C)C(=O)c1cc2cnc(N(c3cncc(-c4csc5c(=O)cc(N6CCOCC6)oc45)c3)c3ncc4cc(C(=O)N(C)C)n(C5CCCC5)c4n3)nc2n1C1CCCC1]

Analog 1 was made according to the experimental procedure described in Example 27, step-3, using 3-(5-aminopyridin-3-yl)-5-morpholino-7H-thieno[3,2-b]pyran-7-one as the amine and carrying out the reaction at 110° C. Analog 1 was obtained with 83% conversion. Calculated molecular weight: 841.35 Dalton. MS (ESI) m/z=842.3 [M+H]$^+$ Analog 2: 7-Cyclopentyl-N,N-dimethyl-2-((5-(5-morpholino-7-oxo-7H-thieno[3,2-b]pyran-3-yl)pyridin-3-yl)amino)-7H-pyrrolo[2,3-d]pyrimidine-6-carboxamide

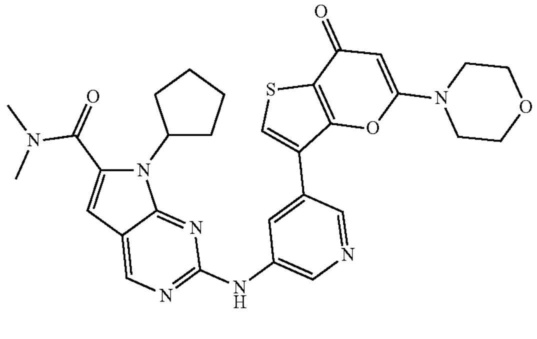 [SMILES: CN(C)C(=O)c1cc2cnc(Nc3cncc(-c4csc5c(=O)cc(N6CCOCC6)oc45)c3)nc2n1C1CCCC1]

Analog 2 was made according to the experimental procedure described in Example 27, step-3, using 3-(5-aminopyridin-3-yl)-5-morpholino-7H-thieno[3,2-b]pyran-7-one as the amine and carrying out the reaction at 110° C. Analog 2 was obtained with 7% conversion. Calculated molecular weight: 585.22 Dalton. MS (ESI) m/z=586.3 [M+H]$^+$ Analog 3: tert-Butyl (7-cyclopentyl-2-((4-(5-morpholino-7-oxo-7H-thieno[3,2-b]pyran-3-yl)phenyl)amino)-7H-pyrrolo[2,3-d]pyrimidin-6-yl)carbamate

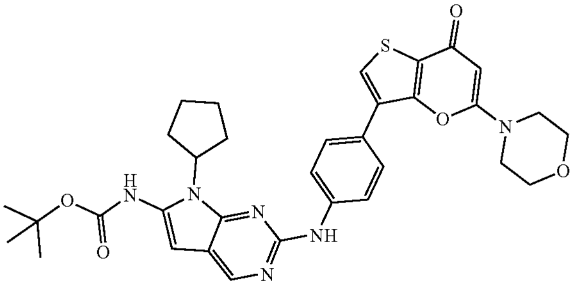 [SMILES: CC(C)(C)OC(=O)Nc1cc2cnc(Nc3ccc(-c4csc5c(=O)cc(N6CCOCC6)oc45)cc3)nc2n1C1CCCC1]

Analog 3 was made according to the experimental procedure described in Example 27, step-3, using tert-butyl (2-chloro-7-cyclopentyl-7H-pyrrolo[2,3-d]pyrimidin-6-yl) carbamate, 3-(4-aminophenyl)-5-morpholino-7H-thieno[3,2-b]pyran-7-one as the amine and carrying out the reaction at 110° C. Analog 3 was obtained with 16% yield (30 mg). Calculated molecular weight: 628.25 Dalton. MS (ESI) m/z=629.27 [M+H]$^+$ Analog 4: tert-Butyl 3-((7-cyclopentyl-6-(dimethylcarbamoyl)-7H-pyrrolo[2,3-d]pyrimidin-2-yl)amino)-5-(5-morpholino-7-oxo-7H-thieno[3,2-b]pyran-3-yl)benzoate

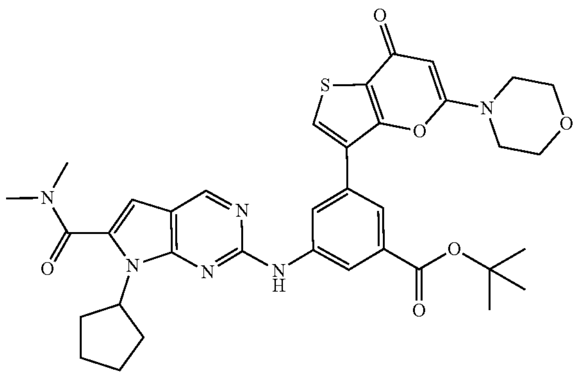 [SMILES: CN(C)C(=O)c1cc2cnc(Nc3cc(C(=O)OC(C)(C)C)cc(-c4csc5c(=O)cc(N6CCOCC6)oc45)c3)nc2n1C1CCCC1]

Analog 4 was made according to the experimental procedure described in Example 27, step-3, using tert-butyl 3-amino-5-(5-morpholino-7-oxo-7H-thieno[3,2-b]pyran-3-yl)benzoate as the amine and carrying out the reaction at 110° C. Calculated molecular weight: 684.27 Dalton. MS (ESI) m/z=685.45 [M+H]+

Analog 5: 3-((7-Cyclopentyl-6-(dimethylcarbamoyl)-7H-pyrrolo[2,3-d]pyrimidin-2-yl)amino)-5-(5-morpholino-7-oxo-7H-thieno[3,2-b]pyran-3-yl)benzoic acid

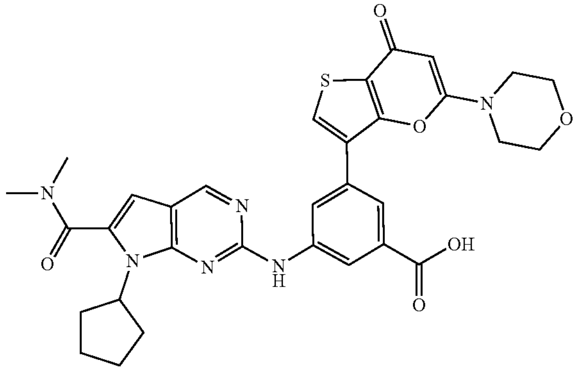 [SMILES: CN(C)C(=O)c1cc2cnc(Nc3cc(C(=O)O)cc(-c4csc5c(=O)cc(N6CCOCC6)oc45)c3)nc2n1C1CCCC1]

Analog 5 (20 mg) was treated with TFA in DCM for 2 hours at room temperature. The volatiles were removed under reduced pressure and the resulting residue was repeatedly washed with methyl tert-butyl ether (MTBE) and 50% DCM in MTBE. Analog 5 was obtained as an off-white solid. Calculated molecular weight: 628.21 Dalton. MS (ESI) m/z=626.99 $[M-H]^-$ Analog 6: 7-cyclopentyl-N-hydroxy-N-methyl-2-((4-(5-morpholino-7-oxo-7H-thieno[3,2-b]pyran-3-yl)phenyl)amino)-7H-pyrrolo[2,3-d]pyrimidine-6-carboxamide

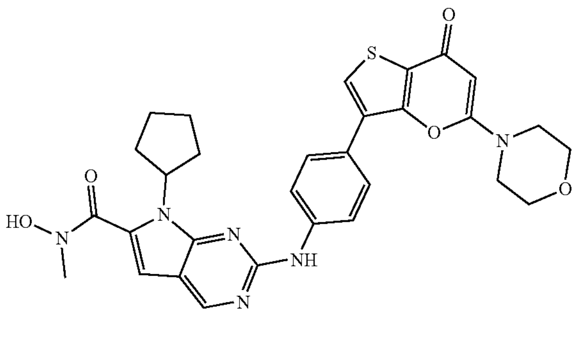 [SMILES: CN(O)C(=O)c1cc2cnc(Nc3ccc(-c4csc5c(=O)cc(N6CCOCC6)oc45)cc3)nc2n1C1CCCC1]

A microwave reaction vessel was charged with compound 14 (25 mg), $Cs_2CO_3$ (171 mg, 12 equivalents), MeNHOH hydrochloride (25 mg, 7 equivalents) and EtOH (3.0 mL). The vessel was closed and the mixture was heated at 150° C. under microwave irradiation conditions for 10 minutes. Mass spectrum analysis of the crude reaction mixture confirms the formation of Analog 6. Calculated molecular weight: 586.66 Dalton. MS (ESI) m/z=587.2 $[M+H]^+$

The invention claimed is:

1. A compound or a pharmaceutically acceptable salt thereof having the Formula IVc:

Formula IVc

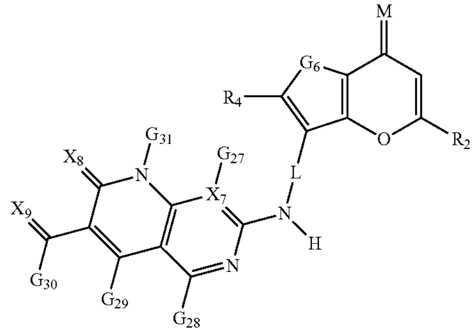

wherein,

M is independently sulfur(S) or oxygen (O);

$R_2$ is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, or substituted carbamate;

$R_4$ is selected from $R_2$;

$G_6$ is selected from sulfur(S) or oxygen (O);

$X_7$=C, N $X_8$=O, S $X_9$=O, S $G_{27}$=null (when $X_7$=N), H, F, Cl, Br, $CF_3$, $CH_3$, $CH_2CH_3$, $CH(CH_3)_2$ $G_{28}$=H, F, Cl, Br, $CF_3$, $CH_3$, $CH_2CH_3$, $CH(CH_3)_2$ $G_{29}$=H, F, Cl, Br, $CF_3$, $CH_3$, $CH_2CH_3$, $CH(CH_3)_2$ $G_{30}$=H, $CF_3$, $CH_2CH_3$, $CH(CH_3)_2$, $CF_3$, $NH_2$, $NHCH_3$, $N(CH_3)_2$, $G_{31}$ $G_{31}$=alkyl,

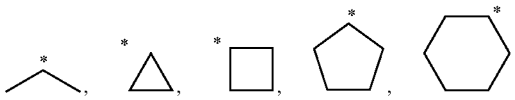

where *=point of attachment

L =

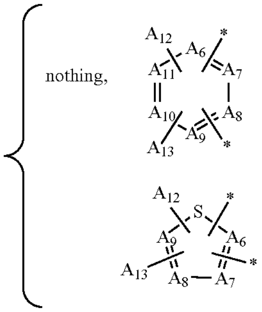

$A_6$ = C, N $A_7$ = C, N $A_8$ = C, N $A_9$ = C, N $A_{10}$ = C, N $A_{11}$ = C, N $A_{12}$ = H, OH, $OCH_3$, $CO_2CH_3$, $CO_2CH_2CH_3$, $CO_2H$, $NH_2$, $NHCH_3$, $N(CH_3)$;

$A_{13}$ = H, OH, $OCH_3$, $CO_2CH_3$, $CO_2CH_2CH_3$, $CO_2H$, $NH_2$, $NHCH_3$, $N(CH_3)$;

* = link to N or C

2. A pharmaceutical formulation comprising a compound of claim 1 in association with a pharmaceutically acceptable carrier, diluent, or excipient.

3. A method for treating a disease in a mammal comprising administering a therapeutically effective amount of a compound of claim 1 wherein said disease is hepatocellular cancer.

4. A compound of claim 1 or a pharmaceutically acceptable salt thereof having a molecular weight greater than 500 daltons.

5. A compound or a pharmaceutically acceptable salt thereof having the formula of Compound 6:

Compound 6

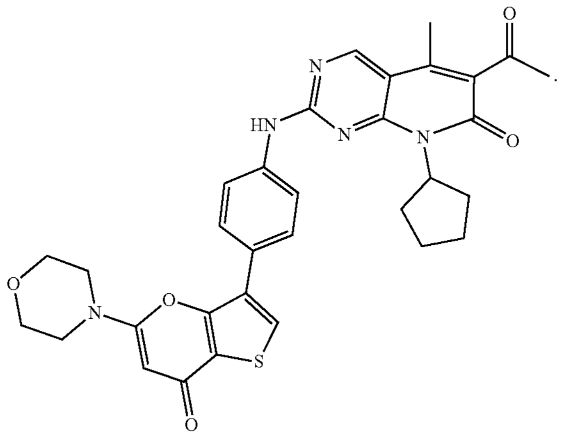

6. A compound or a pharmaceutically acceptable salt thereof having the formula of Compound 8:

Compound 8

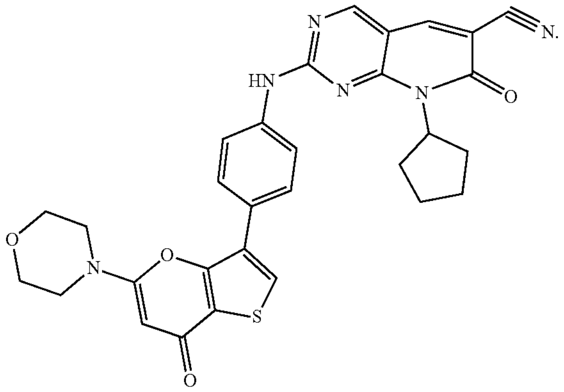

* * * * *